(12) United States Patent
Beaulieu et al.

(10) Patent No.: US 7,888,363 B2
(45) Date of Patent: Feb. 15, 2011

(54) VIRAL POLYMERASE INHIBITORS

(75) Inventors: Pierre Louis Beaulieu, Rosemére (CA); Christian Brochu, Blainville (CA); Catherine Chabot, Terrebonne (CA); Eric Jolicoeur, Laval (CA); Stephen Kawai, Montréal (CA); Marc-André Poupart, Laval (CA); Youla S. Tsantrizos, St. Laurent (CA)

(73) Assignee: Boehringer Ingelheim International GmbH (DE)

( * ) Notice: Subject to any disclaimer, the term of this patent is extended or adjusted under 35 U.S.C. 154(b) by 247 days.

(21) Appl. No.: 11/672,293

(22) Filed: Feb. 7, 2007

(65) Prior Publication Data

US 2007/0142380 A1    Jun. 21, 2007

Related U.S. Application Data

(62) Division of application No. 10/755,256, filed on Jan. 12, 2004, now Pat. No. 7,223,785.

(60) Provisional application No. 60/441,871, filed on Jan. 22, 2003.

(51) Int. Cl.
*A61K 31/497* (2006.01)
*C07D 403/00* (2006.01)

(52) U.S. Cl. .................... 514/254.09; 544/373
(58) Field of Classification Search ............ 514/254.09; 544/373
See application file for complete search history.

(56) References Cited

U.S. PATENT DOCUMENTS

| | | |
|---|---|---|
| 3,565,912 A | 2/1971 | Szmuszkovicz |
| 4,003,908 A | 1/1977 | Denzel et al. |
| 4,146,725 A | 3/1979 | Meyer et al. |
| 4,250,317 A | 2/1981 | Meyer et al. |
| 4,252,803 A | 2/1981 | Webb |
| 4,264,325 A | 4/1981 | Meyer et al. |
| 4,360,679 A | 11/1982 | Meyer et al. |
| 4,384,121 A | 5/1983 | Meyer |
| 4,432,886 A | 2/1984 | Meyer |
| 4,433,975 A | 2/1984 | Meyer |
| 4,590,200 A | 5/1986 | Cross et al. |
| 4,740,519 A | 4/1988 | Shroot et al. |
| 4,859,684 A | 8/1989 | Raeymaekers et al. |
| 4,898,863 A | 2/1990 | Brown et al. |
| 4,920,140 A | 4/1990 | Shroot et al. |
| 5,059,621 A | 10/1991 | Shroot et al. |
| 5,216,003 A | 6/1993 | Vazquez |
| 5,410,061 A | 4/1995 | Gilmore et al. |
| 5,482,956 A | 1/1996 | Lunkenheimer et al. |
| 5,527,819 A | 6/1996 | Williams et al. |
| 5,661,159 A | 8/1997 | Matsuo et al. |
| 5,817,689 A | 10/1998 | Kato et al. |
| 5,866,594 A | 2/1999 | Endo et al. |
| 5,912,260 A | 6/1999 | Kalindjian et al. |
| 5,932,743 A | 8/1999 | Collini et al. |
| 6,063,806 A | 5/2000 | Kamiya et al. |
| 6,069,156 A | 5/2000 | Oku et al. |
| 6,169,107 B1 | 1/2001 | Kitano et al. |
| 6,184,238 B1 | 2/2001 | Takano et al. |
| 6,228,868 B1 | 5/2001 | Gwaltney, II et al. |
| 6,358,992 B1 | 3/2002 | Pamukcu et al. |
| 6,399,644 B1 | 6/2002 | Wexler et al. |
| 6,407,102 B1 | 6/2002 | Mahboobi et al. |
| 6,448,281 B1 | 9/2002 | Beaulieu et al. |
| 6,455,525 B1 | 9/2002 | Singh et al. |
| 6,479,508 B1 | 11/2002 | Beaulieu et al. |
| 6,579,882 B2 | 6/2003 | Stewart et al. |
| 6,608,070 B1 | 8/2003 | Nakao et al. |
| 6,770,643 B2 | 8/2004 | Cox et al. |
| 6,770,666 B2 | 8/2004 | Hashimoto et al. |
| 6,794,404 B2 | 9/2004 | Beaulieu et al. |
| 6,841,566 B2 | 1/2005 | Beaulieu et al. |
| 6,897,207 B2 | 5/2005 | Cox et al. |
| 7,098,231 B2 | 8/2006 | Poupart et al. |
| 7,112,600 B1 | 9/2006 | Hashimoto et al. |
| 7,141,574 B2 | 11/2006 | Beaulieu et al. |
| 7,157,486 B2 | 1/2007 | Beaulieu et al. |
| 7,223,785 B2 * | 5/2007 | Beaulieu et al. ............. 514/419 |
| 7,241,801 B2 | 7/2007 | Beaulieu et al. |
| 7,323,470 B2 | 1/2008 | Poupart et al. |
| 7,332,614 B2 | 2/2008 | Khodabocus et al. |

(Continued)

FOREIGN PATENT DOCUMENTS

CA    1111695    11/1981

(Continued)

OTHER PUBLICATIONS

Zhang, H.-C., et al. "Efficient Synthesis of 3-substituted 2-arylindoles via Suzuki coupling reactions on the solid phase"; Tetrahedron Leters 42, 2001, p. 4751-4754.

(Continued)

*Primary Examiner*—Rei-tsang Shiao
(74) *Attorney, Agent, or Firm*—Michael P. Morris; David A. Dow

(57) ABSTRACT

An isomer, enantiomer, diastereoisomer or tautomer of a compound, represented by formula I:

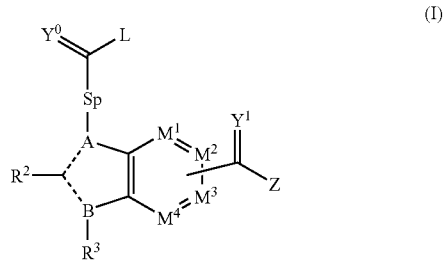

wherein A, B, $R^2$, $R^3$, L, $M^1$, $M^2$, $M^3$, $M^4$, $Y^1$, $Y^0$, Z and Sp are as defined in claim 1, or a salt thereof, as an inhibitor of HCV NS5B polymerase.

52 Claims, No Drawings

U.S. PATENT DOCUMENTS

| | | |
|---|---|---|
| 2001/0039286 A1 | 11/2001 | Dinnell et al. |
| 2002/0173527 A1 | 11/2002 | Astles |
| 2003/0050320 A1 | 3/2003 | Hashimoto et al. |
| 2003/0108862 A1 | 6/2003 | Kukolj et al. |
| 2003/0134853 A1 | 7/2003 | Priestley et al. |
| 2003/0176433 A1 | 9/2003 | Beaulieu et al. |
| 2003/0232816 A1 | 12/2003 | Beaulieu et al. |
| 2004/0024190 A1 | 2/2004 | Beaulieu et al. |
| 2004/0082635 A1 | 4/2004 | Hashimoto et al. |
| 2004/0097438 A1 | 5/2004 | Hashimoto et al. |
| 2004/0110126 A1 | 6/2004 | Kukolj et al. |
| 2004/0171833 A1 | 9/2004 | Buchwald et al. |
| 2004/0224955 A1 | 11/2004 | Beaulieu et al. |
| 2005/0032875 A1 | 2/2005 | Wolleb et al. |
| 2005/0209465 A1 | 9/2005 | Li et al. |
| 2005/0222236 A1 | 10/2005 | Tsantrizos et al. |
| 2006/0160798 A1 | 7/2006 | Beaulieu et al. |
| 2006/0183752 A1 | 8/2006 | Khodabocus et al. |
| 2006/0293306 A1 | 12/2006 | Beaulieu et al. |
| 2007/0142380 A1 | 6/2007 | Beaulieu et al. |
| 2007/0249629 A1 | 10/2007 | Beaulieu et al. |
| 2008/0119490 A1 | 5/2008 | Poupart et al. |
| 2009/0087409 A1 | 4/2009 | Beaulieu et al. |
| 2009/0170859 A1 | 7/2009 | Tsantrizos et al. |

FOREIGN PATENT DOCUMENTS

| | | |
|---|---|---|
| CA | 2150812 | 6/1994 |
| CA | 2158996 | 10/1994 |
| CA | 2143040 | 8/1995 |
| CA | 2124169 | 11/1995 |
| CA | 2164394 | 6/1996 |
| CA | 2223585 | 12/1996 |
| CA | 2241186 | 6/1997 |
| CA | 2389165 | 5/2001 |
| CA | 2363274 | 7/2001 |
| CA | 2412718 | 1/2002 |
| CA | 2448737 | 1/2003 |
| CA | 2449180 | 2/2003 |
| CH | 511873 | 8/1971 |
| DE | 2641060 | 3/1978 |
| DE | 3522230 | 1/1987 |
| DE | 19507913 | 9/1996 |
| EP | 10063 | 4/1980 |
| EP | 0011824 | 6/1980 |
| EP | 12291 | 6/1980 |
| EP | 14411 | 8/1980 |
| EP | 50957 | 5/1982 |
| EP | 73663 | 3/1983 |
| EP | 209707 | 1/1987 |
| EP | 242167 | 10/1987 |
| EP | 318084 | 5/1989 |
| EP | 353606 | 2/1990 |
| EP | 429240 | 5/1991 |
| EP | 439356 | 7/1991 |
| EP | 459334 | 12/1991 |
| EP | 539117 | 4/1993 |
| EP | 546713 | 6/1993 |
| EP | 549175 | 6/1993 |
| EP | 563910 | 10/1993 |
| EP | 583665 | 2/1994 |
| EP | 607439 | 7/1994 |
| EP | 615159 | 9/1994 |
| EP | 750226 | 12/1996 |
| EP | 0801059 | 10/1997 |
| EP | 987250 | 3/2000 |
| EP | 1142880 | 10/2001 |
| EP | 1 162 196 A1 | 12/2001 |
| EP | 1 256 628 A2 | 11/2002 |
| EP | 1256628 A2 | 11/2002 |
| FR | 1604809 | 4/1972 |
| FR | 2291749 | 6/1976 |
| GB | 602426 A | 5/1948 |
| GB | 1094903 | 12/1967 |
| GB | 1186504 | 4/1970 |
| GB | 1436089 | 5/1976 |
| GB | 1509527 | 5/1978 |
| GB | 2118552 | 11/1983 |
| GB | 2164648 | 3/1986 |
| GB | 2197320 | 5/1988 |
| GB | 2203420 | 10/1988 |
| JP | 60149502 | 8/1985 |
| JP | 61085360 | 4/1986 |
| JP | 3156444 | 7/1991 |
| JP | 5239036 | 9/1993 |
| JP | 6161064 | 6/1994 |
| JP | 6186703 | 7/1994 |
| JP | 6186705 | 7/1994 |
| JP | 6186706 | 7/1994 |
| JP | 6194794 | 7/1994 |
| JP | 6239841 | 8/1994 |
| JP | 6297858 | 10/1994 |
| JP | 7140604 | 6/1995 |
| JP | 7228530 | 8/1995 |
| JP | 9124632 | 5/1997 |
| JP | 09124632 A | 5/1997 |
| JP | 9328678 | 12/1997 |
| JP | 10067682 | 3/1998 |
| JP | 10114654 | 5/1998 |
| JP | 10204059 | 8/1998 |
| JP | 10265478 | 10/1998 |
| JP | 11021693 | 1/1999 |
| JP | 115003445 | 3/1999 |
| JP | 11177218 | 7/1999 |
| JP | 2001122855 | 5/2001 |
| WO | 9116313 | 10/1991 |
| WO | 9210097 | 6/1992 |
| WO | 9306828 | 4/1993 |
| WO | 9411349 | 5/1994 |
| WO | 9507263 | 3/1995 |
| WO | 9616938 | 6/1996 |
| WO | 9632379 | 10/1996 |
| WO | 9639391 | 12/1996 |
| WO | 9712613 | 4/1997 |
| WO | 9744319 | 11/1997 |
| WO | 9748697 | 12/1997 |
| WO | 9801436 | 1/1998 |
| WO | 9808847 | 3/1998 |
| WO | 9829408 | 7/1998 |
| WO | 9837069 | 8/1998 |
| WO | 9837079 | 8/1998 |
| WO | 9839287 A1 | 9/1998 |
| WO | 9928297 | 6/1999 |
| WO | 9929660 | 6/1999 |
| WO | 9929661 | 6/1999 |
| WO | 9929843 A1 | 6/1999 |
| WO | 9935130 A1 | 7/1999 |
| WO | 9951781 | 10/1999 |
| WO | 9957117 A2 | 11/1999 |
| WO | 9961020 | 12/1999 |
| WO | 9965886 | 12/1999 |
| WO | 0006556 | 2/2000 |
| WO | 0006566 | 2/2000 |
| WO | WO 00/06529 | 2/2000 |
| WO | 0010573 | 3/2000 |
| WO | 0013708 | 3/2000 |
| WO | 0018231 | 4/2000 |
| WO | 0026202 | 5/2000 |
| WO | 0027846 | 5/2000 |
| WO | 0034277 A1 | 6/2000 |
| WO | 0130774 | 5/2001 |
| WO | 0132653 | 5/2001 |
| WO | 0147883 | 7/2001 |
| WO | 0147922 | 7/2001 |

| | | |
|---|---|---|
| WO | 0151487 | 7/2001 |
| WO | 0187885 | 11/2001 |
| WO | WO 01/85172 A1 | 11/2001 |
| WO | WO 01/90121 A2 | 11/2001 |
| WO | WO 02/04425 A2 | 1/2002 |
| WO | WO 02/06246 A1 | 1/2002 |
| WO | 0226228 A1 | 4/2002 |
| WO | WO 02/057287 A2 | 7/2002 |
| WO | WO 02/057425 A2 | 7/2002 |
| WO | 02059118 | 8/2002 |
| WO | 02070739 | 9/2002 |
| WO | WO 02/069903 A2 | 9/2002 |
| WO | WO 02/098424 A1 | 12/2002 |
| WO | WO 02/100846 A1 | 12/2002 |
| WO | WO 02/100851 A2 | 12/2002 |
| WO | 03/007945 | 1/2003 |
| WO | 03000254 | 1/2003 |
| WO | 03/010140 | 2/2003 |
| WO | 03014377 | 2/2003 |
| WO | WO 03/010141 A2 | 2/2003 |
| WO | 03/018555 | 3/2003 |
| WO | 03026587 | 4/2003 |
| WO | WO 03/040112 A1 | 5/2003 |
| WO | 03101993 | 12/2003 |
| WO | 2004005286 | 1/2004 |
| WO | 2004/064925 | 8/2004 |
| WO | 2004/065367 | 8/2004 |
| WO | WO 2004/087714 A1 | 10/2004 |
| WO | 2005/012288 | 2/2005 |
| WO | WO 2005/014543 | 2/2005 |
| WO | 2005/080388 | 9/2005 |

OTHER PUBLICATIONS

Afdhal, N, O'Brien C, Godofsky E, et al. Valpicitabine (NM283), alone or with PEG-interferon, compared to PEG interferon/ribavirin (PEGIFN/RBV) retreatment in patients with HCV-1 infection and prior non-response to PEBIFN/RBV: One-year results. Presented at the 42nd annual EASL meeting, Apr. 11-15, 2007, Barcelona, Spain.
Ago, H., et al., "Crystal structure of the RNA-dependent RNA polymerase of hepatitis C virus". Structure, 1999, V.7, No. 11, Research Article, pp. 1417-1426.
Amat, Mercedes, et al, "An Efficient Synthesis of 2-(2-Pyridyl)indoles by Palladium (0)-catalyzed heteroarylation", Tetrahedron Letters, vol. 34, No. 31, 1993, p. 5005.
Baba et al.; "A Novel Stereospecific Alkenyl'Alkenyl Cross-Coupling by a Palladium or Nickel-Catalyzed Reaction of Alkenylalanes with Alkenyl Halides" J. Am. Chem. Soc., 1976, 98, 6729-6731.
Bartenschlager, R.,et al., "Nonstructural protein 3 of the hepatitis C virus encodes a serine-type proteinase required for cleavage at the NS3/4 and NS4/5 junctions". Journal of Virology, Jul. 1993, p. 3835-3844.
Beaulieu et al. "Non-nucleoside inhibitors of the hepatitis C virus NS5B polymerase: discovery and preliminary SAR of benzimidazole derivatives." Bioorganic and Medicinal Chemistry Letters, 14 (2004) 119-124.
Beaulieu, P.L. et al; "Therapies for Hepatitis C Infection: Targeting the Non-Structural Proteins of HCV"; Curr. Med. Chem.-Anti-Infective Agents, 2002, vol. 1, No. 2, pp. 1-14.
Behrens, S-E., et al., "Identification and properties of the RNA-dependent RNA polymerase of hepatitis C virus". The EMBO Journal, vol. 15, No. 1, 1996, pp. 12-22.
Bressanelli, S., et al., "Crystal structure of the RNA-dependent RNA polymerase of hepatitis C virus". PNAS, Nov. 1999, Vo. 96, No. 23. pp. 13034-13039.
Bukh, J. et al., "Toward a surrogate model for hepatitis C virus: an infectious molecular clone of the GB virus-B hepatitis agent" Virology, vol. 262, 1999, pp. 470-478.
CA Abstract, CA 123: 33085, 1995.
CA Abstract, CA 126: 305540, 1997.
CA Abstract. Zimmermann, et al., Archiv der Pharmazie (Weinheim, Germany) (1976), 309(7), p. 597-600; CA 86:43587, 1977.

Carroll, S. S., et al., "Only a small fraction of purified hepatitis C RNA-dependent RNA polymerase is catalytically compentent: implications for viral replication and in vitro assays". Biochemistry, 2000, 39, pp. 8243-8249.
CAS Registry No. 115577-24-7 Registry Copyright 2001 ACS.
CAS Registry No. 214150-90-0 Registry Copyright 2001 ACS.
CAS Registry No. 214150-93-3 Registry Copyright 2001 ACS.
CAS Registry No. 66315-47-7 Registry Copyright 2001 ACS.
CAS Registry No. 66315-51-3 Registry Copyright 2001 ACS.
CAS Registry No. 66315-52-4 Registry Copyright 2001 ACS.
CAS Registry No. 66630-73-7 Registry Copyright 2001 ACS.
Danieli, B. et al. "Application of the PD-catalyzed hetroarylation to the synthesis of 5-(indol2'-yl)pyridin-2-one and 5-(indol-2'yl) pyran-2-one" Tetrahedron, vol. 54, No. 46, 1998, p. 14081.
DeFrancesco, R., et al., "RNA-dependent RNA polymerase of hepatitis C virus". Methods in Enzymology, vol. 275, 1998, pp. 58-67.
Deutsch, M. et al; "Old and emerging therapies in chronic hepatitis C: an update;" 2008, J. of Viral Hepatitis, 15, p. 2-11.
Erhardt et al, "Safety, Pharmacokinetics and Antiviral effects of Boehringer Ingelheim BILB 1941, a Novel HCV RNA Polymerase, After 5 days Oral treatment in Patients with Chronic Hepatitis C", Poster from EASL 42nd Mtg. of Euruopean Association for the Study of Liver Diseases, Barcelona, Spain Apr. 11-15, 2007.
Ferrari, E., et al., "Characterization of soluble hepatitis C virus RNA-dependent RNA polymerase expressed in *Escherichia coli*". Journal of Virology, 1990, vol. 73, No. 2., pp. 1649-1654.
Fuerstner, A. et al; "Titanium-Induced Zipper Reactions"; Angewandte Chemie, International Edition in English (1995), 34(6),pp. 678-681 (XP-002233857).
Gale, M.J.et al., "Evidence that hepatitis C virus resistance to interferon is mediated through repression of the PKR protein kinase by the nonstructural 5A protein". Virology, 230, 1997, Article No. VY978493, pp. 217-227.
Grakoui, A., et al., "A second hepatitis C virus-encoded proteinase". Proc. Natl. Acad. Sci, USA, vol. 90, Nov. 1993, Biochemistry, pp. 10583-10587.
Hashimoto, et al., WO 2001047883; CA 135:76874,2001.
Hijkata, M., et al., "Gene mapping of the putative structural region of the hepatitis C virus genome by in vitro processing analysis". Proc. Natl. Acad. Sci. USA, vol. 88, Jul. 1991, Biochemistry, pp. 5547-5551.
Hijkata, M., et al., "Two distinct proteinase activities required for the processing of a putative nonstructural precursor protein of hepatitis C virus". Journal of Virology, Aug. 1993, Vo. 67, No. 8, pp. 4665-4675.
Hishmat, O. H., et al; "Synthesis of Pharmacologically Active Indoles"; Bolletino Chimico Farmaceutico (1999), 183 (6), pp. 259-266 (XP-002233311).
Hoofnagle, J.H.; 1997; Hepatology 26: 15S-20S.
Hulme, C., et al; "The Synthesis and Biological Evaluation of a Novel Series of Indole PDE4 Inhibitors I"; Bioorganic & Medicinal Chemistry Letters 8 (1998), pp. 1867-1872 (XP-002233861).
Ishiyama, T., Murata, M., Miyaura, N.; "Palladium(0)-Catalyzed Cross-Coupling Reaction of Alkoxydiboron with Haloarenes: A Direct Procedure for Arylboronic Esters;" J. Org. Chem. 1995, 60, 7508.
Kim, D. W., et al., "C-terminal domain of the hepatitis C virus NS3 protein contains an RNA helicase activity". Biochemical & Biophysical Research Communications, vol. 215, No. 1, 1995, pp. 160-166.
Kim, J.E., et al., "Subcellular localization of hepatitis C viral proteins in mammalian cells". Arch Virol., 1999, 144, pp. 329.343.
Kolykhalov, A.A. et al,"Hepatitis C Virus-Encoded Enzymatic Activities and Conserved RNA Elements in the 3' nontranslated Region are Essential for Virus Replication in Vivo", J. Virology, 2000, 74(4): 2046-2051.
Kwong, A. D., et al., "Hepatitis C virus NS3/4A protease". Antiviral Research, 40, 1998, pp. 1-18.
Lauer, G. and Walker, B., "Hepatitis C Virus Infection," N. Engl. J. Med., vol. 345(1), pp. 41-52 (Jul. 2001), at p. 46, col. 1, lines 23-25.
Lemon, S.H.; Honda, M.; "Internal Ribosome Entry Sites within the RNA Genomes of Hepatitis C Virus and Other Flaviviruses;" 1997; Semin. Virol. 8: 274-288.

Lesburg, C.A., et al., "Crystal structure of the RNA-dependent RNA polymerase from hepatitis C virus reveals a fully encircled active site". Nature Sructural Biology, vol. 6, No. 10, 1999, p. 937-943.

Levin, Jules, "Safety, Pharmacokinetics and Antiviral effects of Boehringer Ingelheim BILB 1941, a Novel HCV RNA Polymerase, After 5 days Oral treatment in Patients with Chronic Hepatitis C", www.natap.org/2007/EASL/EASL_48. htm EASL 42nd Mtg. of Euruopean Association for the Study of Liver Diseases, Barcelona, Spain Apr. 11-15, 2007.

Lindsay, K.L.; "Therapy of Hepatitis C: Overview;" 1997; Hepatology 26: 71S-77S.

Lohmann, V. et al., "Replication of Subgenomic Hepatitis C Virus RNAs in a Hepatoma Cell Line" Science, 1999, 285: 110-113.

Lohmann, V., et al., "Biochemical and kinetic analyses of NS5B RNA-dependent RNA polymerase of the hepatitis C virus". Virology, Article No. VY989311, Vo. 249, 1998, pp. 108-118.

Lohmann, V., et al., "Biochemical Properties of hepatitis C virus NS5B RNA-dependent RNA polymerase and identification of amino acid sequence motifs essential for enzymatic activity". Journal of Virology, Nov. 1997, Vo. 71, No. 11, pp. 8416-8428.

Love, R. A., et al., "The crystal structure of hepatitis C virus NS3 proteinase reveals a trypsin-like fold and a structural zinc binding site". Cell, vol. 87, 1996, pp. 331-342.

Luo, G. et al., "DeNovo initiation of RNA synthesis by the RNA-dependent RNA polymerase (NS5B) of hepatitis C virus". Journal of Virology, Jan. 2000, vol. 74, No. 2, pp. 851-863.

Mayer et al, "Solid-Phase Synthesis of Benzimidazoles"; Tetrahedron Letters 39 (1998) 6655-6658.

McKercher, G., et al., "Specific inhibitors of HCV polymerase identified using an NS5B with lower affinity for template/primer substrate". Nucleic Acids Research, 2004, vol. 32, No. 2, pp. 422-431.

Merlic, C.A. et al. "Benzannulation reactions of Fischer carbene compleses for the synthesis of indolocarbozoles" Tetrahedron, vol. 57, No. 24, p. 5199-5212, 2001.

Miller, J.A. et al, "Preparation of Unsymmetrical Biaryls via Ni-or Pd-Catalyzed Coupling of Aryl chlorides with Arylzincs". Tetrandron Letters, vol. 39 (36), 1998, pp. 6441-6444.

Minato, Akio et al, "Palladium-Phosphine Complex Catalyzed Cross-Coupling Reaction of 1-Methyl-2-pyrrolyl-magnesium Bromide and -zinc chloride with organic halides" Tetrahedron Letters, vol. 22, No. 52, 1981 p. 5319.

Miyaura, N. et al. "Palladium Catalyzed Cross-Coupling Reactions of Organoboron Compounds", Chem. Rev. 1995, vol. 95, pp. 2457-2483.

Murata, M.; Oyama, T.; Watanabe, S., Masuda, Y. "Palladium-Catalyzed Borylation of Aryl Halides or Triflates with Dialkoxyborne: A Novel and Facile Synthetic Route to Arylboronates;" J. Org. Chem. 2000, 65, 164.

Negishi, S. Baba, "Novel Stereoselective Alkenyl-Aryl Coupling via Nickel-catalysed Reaction of Alkenylalanes with Aryl Halides;" J. Chem. Soc. Chem. Communications, 1976, 596-597.

Oh, J-W, et al., "A recombinant hepatitis C virus RNA-dependent RNA polymerase capable of copying the full-length viral RNA". Journal of Virology, Sep. 1999, Vo. 73, No. 9, pp. 7694-7702.

Perandones, F. et al; Synthesis of imidazol[4,5-b]pyridines from aminoimidazolecarbaldehydes, J. heterocyc. Chem. vol. 34, pp. 107-112, 1997.

Qin, W. et al., "Mutational analysis of the structure and function of hepatitis C virus RNA-dependent RNA polymerase". American Assoc. for the Study of Liver Diseases. Hepatology, vol. 33, No. 3, 2001, pp. 728,737.

Reed, K.E., et al., "Phosphorylation of the hepatitis C virus NS5A protein in vitro and in vivo: properties of the NS5A-associated kinase". Journal of Virology, Oct. 1997, vol. 71, No. 10, pp. 7187-7197.

Reed, K.E.; Rice, C.M.; "Overview of Hepatitis C Virus Genome Structure, Polyprotein Processing, and Protein Properties;" 1999; Curr. Top. Microbiol. Immunol. 242: pp. 55-84.

Reichard, O. et al, "Therapy of Hepatitis C: Alpha Interferon and Ribavirin;" 1997 Hepatology 26; pp. 108S-111S.

Rice, C.M.; 1996; "Flavivindae: the viruses and their replication"; pp. 931-960 in Fields Virology; Fields, B.N.; Knipe, D.M.; Howley, P.M. (eds.); Lippincott-Raven Publishers, Philadelphia, PA.

Rorrer, L.C. et al. "Convenient New Route to Tetradentate and Pentadentate Macrocyclic Tetraamide Ligands", Organic Letters, 1999, vol. 1, No. 8, pp. 1157-1159.

Roth, H. J., et al; "Synthesis of Indole and Carbazole Derivatives by Condensation of Alpha-hydroxyketones and Aromatic Amines"; Archiv der Pharmazie and Berichte der Deutschen Pharmazeutischen Gesellschaft (1972), 305(3), pp. 159-171 (XP-002233858).

Sakamoto, T., et al, "Indolylzinc Iodides by Oxidative addition of activ zinc to Iodoindoles" Tetrahedron Letters, vol. 34, No. 37, 1993, p. 5955.

Sarisky, R.T. "Non-nucleoside inhibitors of the HCV polymerase". Journal of Antimicrobial Chemotherapy, 2004, 54, pp. 14-16.

Sarrazin, C., et al., "SCH 503034, a Novel hepatitis C virus protease inhibitor, plus pegylated inteferon a-2b for genotype 1 nonresponders". Gastroenterolgy, 2007, 132, pp. 1270-1278.

Simons, J. N., et al., "Identification of two flavivirus-like genomes in the GB hepatitis agent". Proc. Natl, Acad. Sci, Medical Sciences, Vo. 92, Apr. 1995, pp. 3401-3405.

Stanforth, S.P. "Catalytic Cross-coupling Reactions in Biaryl Synthesis" Tetrahedron, vol. 54(3-4), 1998, pp. 263-303.

Sun, X-L., et al., "De Novo RNA synthesis catalyzed by HCV RNA-dependent RNA polymerase". Biochemical and Biophysical Research Communications, vol. 268, 2000, pp. 798-803.

Takehide, N. et al; "Benzo-Heterocyclic Derivative"; Patent Abstracts of Japan; Publication No. 09124632 A; May 13, 1997.

Tomei, L., et al., "Biochemical characterization of a hepatitis C virus RNA-dependent RNA polymerse mutant lacking the C-terminal hydrophobic sequence". Journal of General Virology, 2000, 81, pp. 759,767.

Watanabe, T. et al, "Synthesis of sterically hindered blaryis via the palladium-catalyzed cross-coupling reaction of aryliboronic acids of their esters with haloarenes" SYNLETT, vol. 3, p. 207-210, 1992.

Wu et al; "One-pot' nitro reduction-cyclisation solid phase route to benzimidazoles"; Tetrahedron Letters 41 (2000) 9871-9874.

Yamashita, T., et al., "RNA-dependent RNA polymerase activity of the soluble recombinant hepatitis C virus NS5B protein truncated at the C-terminal region". The Journal of Biological Chemistry, vol. 273, No. 25, Jun. 1999, pp. 15479-15486.

Yanagi, M., et al., "Transcripts from a single full-length cDNA clone of hepatitis C virus are infectious when directly transfected into the liver of a chimpanzee". PNAS, Vo. 94, Aug. 1997, pp. 8738-8743.

Youngdale, G. A. et al; "Synthesis and Antiinflammatory Activity of 5-Substituted 2,3-bis(p-methoxyphenyl) indoles"; J Med Chem (1969) 12, pp. 948-949 (XP-002233859).

Yuan, Z-H, et al., "Expression, purfication, and partial characterization of HCV RNA polymerase". Biochemical and Biophysical Research Communications, vol. 232, 1997, pp. 231-235.

Zhang, J-H, et al., "A simple statistical parameter for use in evaluation and validation of high throughput screening assays". Journal of Biomolecular Screening, vol. 4, Nov. 1999, pp. 67-73.

Zhong, W., et al., "De Novo initiation of RNA synthesis by hepatitis C virus nonstructural protein 5B polymerase". Journal of Virology, Feb. 2000, Vo. 74, No. 4, pp. 2017-2022.

Zhong, W., et al., "Template/primer requirements and single nucleotide incorporation by hepatitis C virus nonstructural protein 5B polymerase". Journal of Virology, Oct. 2000, vol. 74, No. 19, pp. 9134-9143.

Chemical Abstract for DE 2642877: CA1977:453062, Copyright 2002.

Chemical Abstract for EP50957: CA1982:509865, Copyright 2002.

Chemical Abstract for EP73663: CA 1983:505247, Copyright 2002.

Chemical Abstract for WO 2000026202 A1: CA2000:314687. Copyright 2002.

Chemical Abstract for WO 2000027846 A2: CA2000:335410, Copyright 2002.

Chemical Abstract for WO 2001/047883: CA2001:489367, Copyright 2002.

Chemical Abstract for WO 2001/087885: CA2001:851160, Copyright 2002.

Chemical Abstract for WO 9808847 A1: CA1998163594, Copyright 2002.

Chemical Abstract for WO 9829408 A1: CA1998:485053, Copyright 2002.

Chemical Abstract: CA 128:275074 for JP 10-067682, Copyright 2003.
Chemical Abstract: CA 129:45274 for JP 10 114654, Copyright 2003.
Chemical Abstract: CA 134:340435 for JP 2001 122855, Copyright 2003.
Chemical Abstract: CA 1968:418961, Copyright 2002.
Chemical Abstract: CA 1969:68209, Copyright 2002.
Chemical Abstract: CA 1986:514976, Copyright 2002.
Chemical Abstract: CA 1987:458985, Copyright 2002.
Chemical Abstract: CA 1990:234572, Copyright 2002.
Chemical Abstract: CA 384846-70-2, Copyright 2002.
Grakoiu, A., et al., "Expression and identification of hepatitis C virus polyprotein cleavage products". Journal of Virology, 1993, vol. 67, No. 3, pp. 1385-1395.

* cited by examiner

VIRAL POLYMERASE INHIBITORS

RELATED APPLICATIONS

This application is a Divisional application of U.S. Ser. No. 10/755,256, filed Jan. 12, 2004, which claims priority benefit of U.S. Provisional Application Ser. No. 60/441,871, filed on Jan. 22, 2003; said applications are herein incorporated by reference in their entirety.

TECHNICAL FIELD OF THE INVENTION

The invention relates to inhibitors of RNA dependent RNA polymerases, particularly those viral polymerases within the Flaviviridae family, more particularly to HCV polymerase.

BACKGROUND OF THE INVENTION

About 30,000 new cases of hepatitis C virus (HCV) infection are estimated to occur in the United States each year (Kolykhalov, A. A.; Mihalik, K.; Feinstone, S. M.; Rice, C. M.; 2000; *J. Virol.* 74: 2046-2051). HCV is not easily cleared by the hosts' immunological defenses; as many as 85% of the people infected with HCV become chronically infected. Many of these persistent infections result in chronic liver disease, including cirrhosis and hepatocellular carcinoma (Hoofnagle, J. H.; 1997; *Hepatology* 26: 15S-20S*). There are an estimated 170 million HCV carriers world-wide, and HCV-associated end-stage liver disease is now the leading cause of liver transplantation. In the United States alone, hepatitis C is responsible for 8,000 to 10,000 deaths annually. Without effective intervention, the number is expected to triple in the next 10 to 20 years. There is no vaccine to prevent HCV infection. Prolonged treatment of chronically infected patients with interferon or interferon and ribavirin is the only currently approved therapy, but it achieves a sustained response in fewer than 50% of cases (Lindsay, K. L.; 1997; *Hepatology* 26: 71S-77S*, and Reichard, O.; Schvarcz, R.; Weiland, O.; 1997 *Hepatology* 26: 108S-111S*).

HCV belongs to the family Flaviviridae, genus *hepacivirus*, which comprises three genera of small enveloped positive-strand RNA viruses (Rice, C. M.; 1996; "Flaviviridae: the viruses and their replication"; pp. 931-960 in *Fields Virology*; Fields, B. N.; Knipe, D. M.; Howley, P. M. (eds.); Lippincott-Raven Publishers, Philadelphia Pa. *). The 9.6 kb genome of HCV consists of a long open reading frame (ORF) flanked by 5' and 3' non-translated regions (NTR's). The HCV 5'NTR is 341 nucleotides in length and functions as an internal ribosome entry site for cap-independent translation initiation (Lemon, S. H.; Honda, M.; 1997; *Semin. Virol.* 8: 274-288). The HCV polyprotein is cleaved co- and post-translationally into at least 10 individual polypeptides (Reed, K. E.; Rice, C. M.; 1999; *Curr. Top. Microbiol. Immunol.* 242: 55-84*). The structural proteins result from signal peptidases in the N-terminal portion of the polyprotein. Two viral proteases mediate downstream cleavages to produce non-structural (NS) proteins that function as components of the HCV RNA replicase. The NS2-3 protease spans the C-terminal half of the NS2 and the N-terminal one-third of NS3 and catalyses cis cleavage of the NS2/3 site. The same portion of NS3 also encodes the catalytic domain of the NS3-4A serine protease that cleaves at four downstream sites. The C-terminal two-thirds of NS3 is highly conserved amongst HCV isolates, with RNA-binding, RNA-stimulated NTPase, and RNA unwinding activities. Although NS4B and the NS5A phosphoprotein are also likely components of the replicase, their specific roles are unknown. The C-terminal polyprotein cleavage product, NS5B, is the elongation subunit of the HCV replicase possessing RNA-dependent RNA polymerase (RdRp) activity (Behrens, S. E.; Tomei, L.; DeFrancesco, R.; 1996; *EMBO J.* 15: 12-22*; and Lohmann, V.; Körner, F.; Herian, U.; Bartenschlager, R.; 1997; *J. Virol.* 71: 8416-8428*). It has been recently demonstrated that mutations destroying NS5B activity abolish infectivity of RNA in a chimp model (Kolykhalov, A. A.; Mihalik, K.; Feinstone, S. M.; Rice, C. M.; 2000; *J. Virol.* 74: 2046-2051*).

The development of new and specific anti-HCV treatments is a high priority, and virus-specific functions essential for replication are the most attractive targets for drug development. The absence of RNA dependent RNA polymerases in mammals, and the fact that this enzyme appears to be essential to viral replication, would suggest that the NS5B polymerase is an ideal target for anti-HCV therapeutics.

WO 00/06529, WO 00/13708, WO 00/10573, WO 00/18231, WO 01/47883, WO 01/85172 and WO 02/04425 report inhibitors of NS5B proposed for treatment of HCV.

SUMMARY OF THE INVENTION

It is therefore an object of the invention to provide a novel series of compounds having good to very good inhibitory activity against HCV polymerase.

Further objects of this invention arise for the one skilled in the art from the following description and the examples.

In a first aspect of the invention, there is provided an isomer, enantiomer, diastereoisomer or tautomer of a compound, represented by formula I:

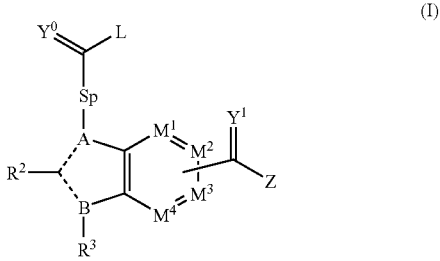

wherein:

either A or B is N and the other B or A is C, wherein ----- between two C-atoms represents a double bond and ----- between a C-atom and a N-atom represents a single bond, the group —C(=Y$^1$)—Z is covalently linked to either M$^2$ or M$^3$, M$^1$ is CR$^{4a}$, M$^2$ or M$^3$, when not linked to —C(=Y$^1$)—Z, is CR$^5$, M$^4$ is CR$^{4b}$, and in addition one or two of the groups selected from M$^1$, M$^2$, M$^3$ and M$^4$ may also be N, with the proviso that the group M$^2$ or M$^3$ to which —C(=Y$^1$)—Z is linked is an C-atom, Sp is a spacer group selected from —(CR$^{51}$R$^{52}$)$_{k1}$—, wherein k1 is 1, 2 or 3;

R$^{51}$, R$^{52}$ are independently H, (C$_{1-6}$)alkyl, (C$_{3-7}$)cycloalkyl or (C$_{1-3}$)alkyl-(C$_{3-7}$)cycloalkyl, or R$^{51}$ and R$^{52}$ are covalently bonded together and to the carbon-atom to which they are attached to form a 3, 4, 5, 6 or 7-membered saturated or 5, 6 or 7-membered unsaturated cyclic system whereby the 5, 6 or 7-membered saturated or unsaturated cyclic system optionally contains 1 to 3 heteroatoms selected from N, O, or S;

said alkyl, cycloalkyl, alkyl-cycloalkyl or cyclic system being optionally substituted by halogen, hydroxy, $(C_{1-6})$alkoxy, cyano, amino, —NH$(C_{1-4}$-alkyl) and/or —N$(C_{1-4}$-alkyl)$_2$;

$Y^0$ is O, S, NR$^{11}$ or CR$^{12}$R$^{13}$, wherein
  $R^{11}$, $R^{12}$, $R^{13}$ are each independently defined as $R^O$;
  $R^{13}$ may also be COOR$^O$ or SO$_2$R$^C$;
  wherein $R^C$ and each $R^O$ is optionally substituted with $R^{150}$;
  or both $R^{12}$ and $R^{13}$ are covalently bonded together and to the carbon-atom to which they are attached to form a 3, 4, 5, 6 or 7-membered saturated or 5, 6 or 7-membered unsaturated cyclic system whereby the 5, 6 or 7-membered saturated or unsaturated cyclic system may contain 1 to 3 heteroatoms selected from N, O, or S; said cyclic systems being optionally substituted with $R^{150}$;

L is $C_{1-6}$alkyl, $(C_{3-6})$cycloalkyl, $C_{1-6}$alkyl-$(C_{3-6})$cycloalkyl, $(C_{2-6})$alkenyl, aryl, $(C_{1-6}$alkyl)aryl, Het, $(C_{1-6})$alkyl-Het, all of which being optionally substituted with $R^{60}$;

or $Y^0$ and L are covalently bonded to form a 5, 6, 7 or 8-membered mono- or a 8, 9, 10 or 11-membered bicyclic group which is optionally unsaturated or aromatic and which optionally contains 1, 2 or 3 heteroatoms selected from N, O, and S, wherein the mono- or bicyclic group is optionally substituted with $R^{60}$;

or if $Y^0$ is CR$^{12}$R$^{13}$ then L may also be H;

or if $Y^0$ is O, then L may also be OR$^C$,
  wherein $R^C$ is optionally substituted with $R^{60}$;

or if $Y^0$ is O, S or NR$^{11}$, then L may also be N(R$^{N2}$)R$^{N1}$, NR$^{N3}$—N(R$^{N2}$)R$^{N1}$, NR$^{N3}$—NR$^{N2}$—CO—R$^C$, NR$^{N4}$—NR$^{N3}$—CO—N(R$^{N2}$)R$^{N1}$, NR$^{N2}$—SO$_2$—R$^C$, NR$^{N2}$—CO—R$^C$, NR$^{N3}$—CO—N(R$^{N2}$)R$^{N1}$ or N(R$^{N1}$)OR$^O$;
  said $R^{N1}$, including any heterocycle or heterobicycle formed by $R^{N1}$, $R^{N2}$ and/or $R^{N3}$, and $R^C$ and $R^O$ being optionally substituted with $R^{60}$;

or if $Y^0$ is O, or S, then L may also be OR$^{6a}$ or N(R$^{5a}$)R$^{6a}$, wherein $R^{5a}$ is defined as $R^{N2}$,
  and wherein $R^{6a}$ is:

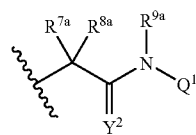

or $R^{6a}$ is:

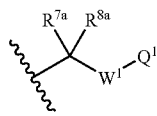

wherein $R^{7a}$ and $R^{8a}$ are each independently defined as $R^O$, COOR$^O$ or CON(R$^{N2}$)R$^{N1}$, wherein said $R^O$ is optionally substituted with $R^{60}$; or
$R^{7a}$ and $R^{8a}$ are covalently bonded together to form a $(C_{3-7})$cycloalkyl or a 4, 5- or 6-membered heterocycle having from 1 to 3 heteroatom selected from O, N, and S;
and when L is N(R$^{5a}$)R$^{6a}$, either of $R^{7a}$ or $R^{8a}$ may be covalently bonded to R$^{5a}$ to form a nitrogen-containing 5- or 6-membered heterocycle, wherein said cycloalkyl or heterocycle being optionally substituted by $R^{150}$; and $W^1$ is selected from
  a) a single bond;
  b) —CH$_2$—;
  c) —CH$_2$—CH$_2$—; and
  d) —CH═CH—;
  wherein the alkylene and alkenylene groups according to b), c) and d) may be substituted with $(C_{1-3})$ alkyl;

$Y^2$ is O or S;

$R^{9a}$ is defined as $R^O$, wherein said $R^O$ is optionally substituted with $R^{60}$; or
$R^{9a}$ is covalently bonded to either of $R^{7a}$ or $R^{8a}$ to form a 5- or 6-membered heterocycle;

$Q^1$ is aryl, Het, $(C_{1-6})$ alkyl-aryl, $(C_{1-6})$ alkyl-Het, $(C_{1-6})$ alkyl-CONH-aryl or $(C_{1-6})$ alkyl-CONH-Het, all of which being optionally substituted with $R^{60}$;

$Y^1$ is O, S or NR$^{14}$, wherein $R^{14}$ is H or $(C_{1-6})$ alkyl;

Z is defined as
  a) OR$^O$;
  b) SO$_2$R$^C$;
  c) N(R$^{N2}$)R$^{N1}$;
  d) NR$^{N3}$—N(R$^{N2}$)R$^{N1}$;
  e) NR$^{N3}$—NR$^{N2}$—CO—R$^C$;
  f) NR$^{N4}$—NR$^{N3}$—CO—N(R$^{N2}$)R$^{N1}$;
  g) NR$^{N2}$—SO$_2$—R$^C$ or
  h) NR$^{N3}$—SO$_2$—N(R$^{N2}$)R$^{N1}$;
  i) NR$^{N2}$—CO—R$^C$;
  j) COOR$^O$;
  k) N(R$^{N1}$)OR$^O$;
  wherein $R^O$ and $R^C$ are optionally substituted with $R^{60}$; and
  said $R^{N1}$, including any heterocycle or heterobicycle formed by $R^{N1}$, $R^{N2}$, and/or $R^{N3}$, being optionally substituted with $R^{60}$;

or Z is OR$^{6b}$ or N(R$^{5b}$)R$^{6b}$ wherein $R^{5b}$ is defined as $R^{N2}$ and $R^{6b}$ is:

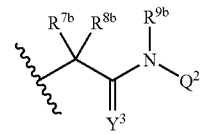

or $R^{6b}$ is:

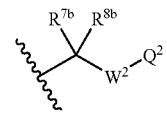

wherein $R^{7b}$, $R^{8b}$, $Y^3$, $R^{9b}$, $W^2$ are defined as $R^{7a}$, $R^{8a}$, $Y^2$, $R^{9a}$, $W^1$ respectively; and $Q^2$ is aryl, Het, $(C_{1-6})$alkyl-aryl, $(C_{1-6})$alkyl-Het, $(C_{1-6})$ alkyl-CONH-aryl or $(C_{1-6})$ alkyl-CONH-Het, all of which being optionally substituted with $R^{60}$
or $Q^2$ is $R^{160}$
or $Q^2$ is selected from the group consisting of O—$C_{1-4}$-alkyl, S—$C_{1-4}$-alkyl, $C_{1-4}$-alkyl, $C_{2-4}$-alkenyl and $C_{2-4}$-alkynyl, all of which being optionally substituted with $R^{160}$; and $R^2$ is selected from: halogen or $R^{21}$, wherein $R^{21}$ is aryl or Het, said $R^{21}$ is optionally substituted with $R^{150}$;

$R^3$ is selected from $(C_{1-6})$alkyl, $(C_{3-7})$cycloalkyl, $(C_{1-3})$alkyl-$(C_{3-7})$cycloalkyl, $(C_{5-7})$cycloakenyl, $(C_{1-3})$alkyl-$(C_{5-7})$cycloalkenyl, $(C_{6-10})$bicycloalkyl, $(C_{1-3})$alkyl-$(C_{6-10})$bicycloalkyl, $(C_{6-10})$bicycloalkenyl, $(C_{1-3})$alkyl-$(C_{6-10})$bicycloalkenyl, HCy or $(C_{1-3})$alkyl-HCy, wherein HCy is a saturated or unsaturated 4 to 7-membered heterocyclic group with 1 to 3 heteroatoms selected from O, S and N;

said alkyl, cycloalkyl, cycloalkenyl, bicycloalkyl, bicycloalkenyl, HCy and alkyl-HCy being optionally substituted with from 1 to 4 substituents selected from: a) halogen;
b) $(C_{1-6})$alkyl optionally substituted with:
  1 to 3 substituents selected from halogen;
  $OR^{31}$ or $SR^{31}$ wherein $R^{31}$ is H, $(C_{1-6}$alkyl), $(C_{3-7})$cycloalkyl or $(C_{1-3})$alkyl-$(C_{3-7})$cycloalkyl; or
  $N(R^{32})_2$ wherein each $R^{32}$ is independently H, $(C_{1-6})$alkyl, $(C_{3-7})$cycloalkyl or $(C_{1-3})$alkyl-$(C_{3-7})$cycloalkyl; or both $R^{32}$ are covalently bonded together and to the nitrogen to which they are attached to form a 5, 6 or 7-membered saturated heterocycle;
c) $OR^{33}$ or $SR^{33}$ wherein $R^{33}$ is H, $(C_{1-6})$alkyl, $(C_{3-7})$cycloalkyl or $(C_{1-3})$alkyl-$(C_{3-7})$cycloalkyl;
d) $N(R^{35})_2$ wherein each $R^{35}$ is independently H, $(C_{1-6})$alkyl, $(C_{3-7})$cycloalkyl or $(C_{1-3})$alkyl-$(C_{3-7})$cycloalkyl; or both $R^{35}$ are covalently bonded together and to the nitrogen to which they are attached to form a 5, 6 or 7-membered saturated heterocycle;

$R^{4a}$, $R^{4b}$, $R^5$ each are independently H or defined as $R^{150}$;
$R^{60}$ is each defined as 1 to 4 substituents independently selected from:
  1 to 3 substituents selected from halogen;
  one of each substituent selected from: $OPO_3H$, $NO_2$, cyano, azido, $C(=NH)NH_2$, $C(=NH)NH(C_{1-6})$alkyl or $C(=NH)NHCO(C_{1-6})$alkyl, $SO_3H$; and
  1 to 3 substituents selected from:
  a) $(C_{1-6})$alkyl, $(C_{3-7})$cycloalkyl, $C_{3-7}$ spirocycloalkyl optionally containing 1 or 2 heteroatoms selected from N, O, and S; $(C_{2-6})$alkenyl, $(C_{2-8})$alkynyl, $(C_{1-6})$alkyl-$(C_{3-7})$cycloalkyl, all of which optionally being substituted with $R^{150}$;
  b) $OR^O$;
  c) $OC(O)R^O$;
  d) $SR^O$, $SO_2R^C$, $SO_2N(R^{N2})R^{N1}$, $SO_2N(R^{N2})C(O)R^C$, $CONR^{N3}SO_2N(R^{N2})R^{N1}$, or $CONR^{N2}SO_2R^C$;
  e) $N(R^{N2})R^{N1}$, $N(R^{N2})COOR^C$, $N(R^{N2})SO_2R^C$ or $N(R^{N1})R^O$;
  f) $N(R^{N2})COR^C$;
  g) $N(R^{N3})CON(R^{N2})R^{N1}$;
  h) $N(R^{N3})COCOR^C$, $N(R^{N3})COCOOR^O$ or $N(R^{N3})COCON(R^{N2})R^{N1}$;
  i) $COR^O$;
  j) $COOR^O$;
  k) $CON(R^{N2})R^{N1}$;
  l) aryl, Het, $(C_{1-4}$alkyl)aryl or $(C_{1-4}$alkyl)Het, all of which optionally being substituted with $R^{150}$;
  wherein said $R^{N1}$, $R^C$ and $R^O$ are each independently optionally substituted with $R^{150}$ as defined,
$R^{150}$ is each defined as 1 to 4 substituents independently selected from:
  1 to 3 substituents selected from halogen;
  one of each substituent selected from: $OPO_3H$, $NO_2$, cyano, azido, $C(=NH)NH_2$, $C(=NH)NH(C_{1-6})$alkyl or $C(=NH)NHCO(C_{1-6})$alkyl; and
  1 to 3 substituents selected from:
  a) $(C_{1-6})$ alkyl, $(C_{3-7})$cycloalkyl, $C_{3-7}$ spirocycloalkyl optionally containing 1 or 2 heteroatoms selected from N, O and S; $(C_{2-6})$alkenyl, $(C_{2-8})$alkynyl, $(C_{1-3})$alkyl-$(C_{3-7})$cycloalkyl, all of which optionally substituted with $R^{160}$;
  b) $OR^O$;
  c) $OC(O)R^O$;
  d) $SR^O$, $SO_2R^C$, $SO_2N(R^{N2})R^{N1}$, $SO_2N(R^{N2})C(O)R^C$ or $CON(R^{N2})SO_2R^C$;
  e) $N(R^{N2})R^{N1}$, $N(R^{N2})COOR^C$, $N(R^{N2})SO_2R^C$ or $N(R^{N1})R^O$;
  f) $N(R^{N2})COR^C$;
  g) $N(R^{N3})CON(R^{N2})R^{N1}$;
  h) $N(R^{N3})COCOR^C$, $N(R^{N3})COCOOR^O$, $N(R^{N3})COCON(R^{N2})OH$, $N(R^{N3})COCON(R^{N2})OC_{1-4}$-alkyl or $N(R^{N3})COCON(R^{N2})R^{N1}$;
  i) $COR^O$;
  j) $COOR^O$;
  k) tetrazole, triazole, $CONR^{N3}$—$SO_2N(R^{N2})R^{N1}$; or $CON(R^{N2})R^{N1}$;
  wherein said $R^{N1}$, $R^C$ and/or $R^O$ are optionally substituted with $R^{160}$ as defined;
$R^{160}$ is each defined as 1, 2 or 3 substituents independently selected from:
  1, 2 or 3 fluorine substituents; and
  one of each substituent selected from tetrazole, triazole, chlorine, bromine, iodine, CN, nitro, $C_{1-4}$alkyl, $CF_3$, $COOR^{161}$, $SO_3H$, $SR^{161}$, $SCF_3$, $SO_2R^{163}$, $OR^{161}$, $OCF_3$, $N(R^{162})_2$, $SO_2N(R^{162})_2$, $NR^{162}SO_2R^C$, $NR^{162}COR^{162}$, $CON(R^{162})_2$, —$NR^{161}$—CO—$COOR^{161}$, —$NR^{161}$—CO—CO($NR^{162})_2$, —$CONR^{161}SO_2R^C$, $CONR^{161}$—$SO_2N(R^{162})_2$ or $SO_2$—$NR^{161}$—$COR^C$, wherein $R^{161}$, $R^{163}$ and each $R^{162}$ is independently $(C_{1-4})$alkyl, $(C_{3-7})$cycloalkyl or $(C_{1-3})$alkyl-$(C_{3-7})$cycloalkyl; and $R^{161}$ and each $R^{162}$ may each independently also be H; or both $R^{162}$ are covalently bonded together and to the nitrogen to which they are attached to form a 5, 6 or 7-membered saturated heterocycle;

$R^O$, $R^C$ are independently defined as $(C_{1-6})$alkyl, $(C_{3-6})$cycloalkyl, $(C_{1-4})$alkyl-$(C_{3-6})$cycloalkyl, $(C_{2-6})$alkenyl, aryl, Het, $(C_{1-4})$alkyl-aryl and $(C_{1-4})$alkyl-Het; and $R^O$ may also be H;

$R^{N1}$ is independently selected from H, $(C_{1-6})$alkyl, $(C_{3-7})$cycloalkyl, $(C_{1-4})$alkyl-$(C_{3-6})$cycloalkyl, $(C_{2-6})$alkenyl, aryl, Het, $(C_{1-4})$alkyl-aryl, $(C_{1-4})$alkyl-Het; or $R^{N2}$, $R^{N3}$, $R^{N4}$ are independently H, $CH_3$, $(C_{2-6})$alkyl, $(C_{3-6})$cycloalkyl, $(C_{1-4})$alkyl-$(C_{3-6})$cycloalkyl; wherein said alkyl, cycloalkyl or alkylcycloalkyl is optionally substituted with hydroxy, halogen, carboxy, $C_{1-6}$-alkoxycarbonyl, $C_{1-6}$-alkyl, $C_{1-6}$-alkoxy, amino, —$NH(C_{1-4}$-alkyl) and/or —$N(C_{1-4}$-alkyl)$_2$; and wherein said $CH_3$ is optionally substituted with halogen, carboxy or $C_{1-6}$-alkoxycarbonyl; and
in the case
  a) of a group $N(R^{N2})R^{N1}$ the substituents $R^{N2}$ and $R^{N1}$; or
  b) of a group $NR^{N3}$—$N(R^{N2})R^{N1}$ the substituents $R^{N3}$ and $R^{N1}$, or $R^{N2}$ and $R^{N1}$;
  may be covalently bonded together to form a 4-, 5-, 6- or 7-membered saturated or unsaturated N-containing heterocycle or a 8-, 9-, 10- or 11-membered N-containing heterobicycle each may have additionally from 1 to 3 heteroatoms selected from O, N, and S;

wherein Het is defined as a 4-, 5-, 6- or 7-membered heterocycle having 1 to 4 heteroatoms selected from O, N and S, or a 8-, 9-, 10- or 11-membered heterobicycle having 1 to 5 heteroatoms selected from O, N and S;

or a salt thereof.

Included within the scope of this invention are compounds of the formula (I) as described hereinbefore, to which a "detectable label", "affinity tag" or "photoreactive group" is linked.

The compounds according to this invention generally show a good to very good inhibitory activity against HCV polymerase. In particular compounds according to this invention inhibit RNA synthesis by the RNA dependent RNA polymerase of HCV, especially of the enzyme NS5B encoded by HCV. A further advantage of compounds provided by this invention is their low to very low or even non-significant activity against other polymerases.

In a second aspect of the invention, there is provided a use of a compound of formula I according to this invention, or a pharmaceutically acceptable salt thereof, as an HCV polymerase inhibitor.

In a third aspect of the invention, there is provided a use of a compound of the formula I according to this invention, or a pharmaceutically acceptable salt thereof, as an inhibitor of RNA dependent RNA polymerase activity of the enzyme NS5B, encoded by HCV.

In a fourth aspect of the invention, there is provided a use of a compound of the formula I according to this invention, or a pharmaceutically acceptable salt thereof, as an inhibitor of HCV replication.

In a fifth aspect of the invention, there is provided a method of treating or preventing HCV infection in a mammal, comprising administering to the mammal an effective amount of a compound of formula I according to this invention, or a pharmaceutically acceptable salt thereof.

In a sixth aspect of the invention, there is provided a method of treating or preventing HCV infection in a mammal, comprising administering to the mammal an effective amount of a compound of formula I, or a pharmaceutically acceptable salt thereof in combination with another antiviral agent.

In a seventh aspect of the invention, there is provided a pharmaceutical composition for the treatment or prevention of HCV infection, comprising an effective amount of a compound of formula I according to this invention, or a pharmaceutically acceptable salt thereof, and a pharmaceutically acceptable carrier.

According to a specific embodiment, the pharmaceutical compositions of this invention comprise a therapeutically effective amount of one or more antiviral agents. Examples of antiviral agents include, ribavirin and amantadine.

According to a further specific embodiment, the pharmaceutical compositions of this invention comprise an other anti-HCV agent as an antiviral agent.

According to a more specific embodiment, the pharmaceutical compositions of this invention comprise an additional immunomodulatory agent as an other anti-HCV agent. Examples of additional immunomodulatory agents include but are not limited to, α-, β-, δ- γ-, tau- and ω-interferons.

According to another more specific embodiment, the pharmaceutical compositions of this invention comprise another inhibitor of HCV polymerase as an other anti-HCV agent.

According to another more specific embodiment, the pharmaceutical compositions of this invention comprise an inhibitor of HCV NS3 protease as an other anti-HCV agent.

According to yet another more specific embodiment, the pharmaceutical compositions of this invention comprise an inhibitor of another target in the HCV life cycle as an other anti-HCV agent. Examples of such other targets are HCV helicase, HCV NS2/3 protease or HCV IRES.

In an eighth aspect of the invention, there is provided a use of a compound of formula I according to this invention, or of a pharmaceutically acceptable salt thereof, for the manufacture of a medicament for the treatment and/or the prevention of a Flaviviridae viral infection, preferably an HCV infection.

In a ninth aspect of the invention, there is provided an intermediate compound represented by the formula 2(v) and 2'(v)

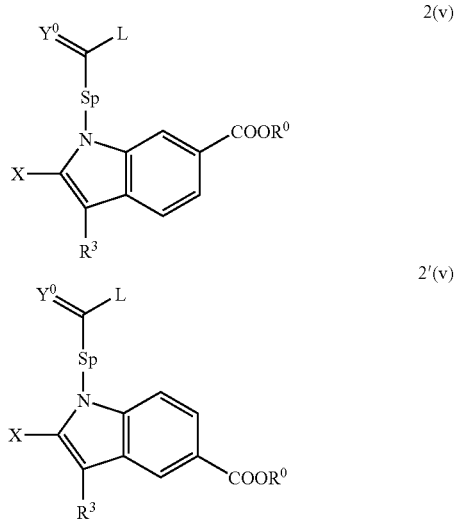

wherein $Y^0$, L, Sp, $R^0$ and $R^3$ are defined as hereinbefore; and X is Cl, Br or I.

Furthermore in a tenth aspect of this invention an intermediate compound represented by the formula

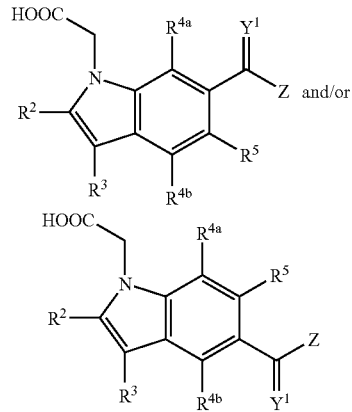

wherein $Y^1$, Z, $R^2$, $R^3$, $R^{4a}$, $R^{4b}$ and $R^5$ are defined as hereinbefore;

not including compounds P1, P2, P3 and P4 of the following formula

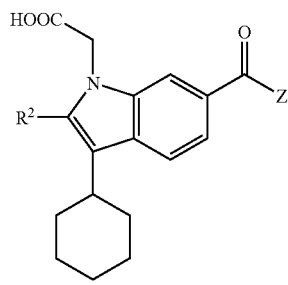

wherein

| Cpd. | R² | Z |
|---|---|---|
| P1 | 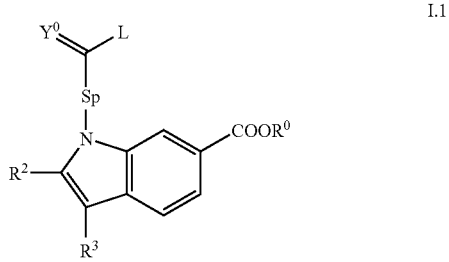 (3-furyl, methyl-substituted) | —O—CH3 |
| P2 | (3-furyl) | —OH |
| P3 | (2-pyridyl) | —OH |
| P4 | (5-bromo-2-pyridyl) | —OH |

In a eleventh aspect of the invention, there is provided a use of the intermediate compounds as defined above for the manufacture of compounds according to this invention.

A twelfth aspect of this invention is related to a process for producing compounds of formula I.1

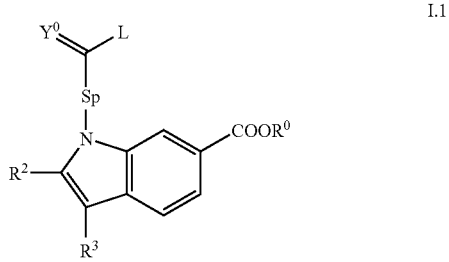

I.1 wherein Y⁰, L, Sp, R⁰, R² and R³ are defined as before, comprising the reaction of an indole derivative of the formula 2(iv)

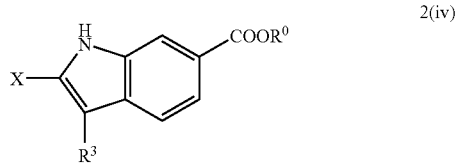

2(iv)

wherein R⁰ and R³ are defined as hereinbefore and X is Cl, Br or I; according to one of the following methods a), b), c) or d):

a) 1.) cross-coupling of the indole derivative of the formula 2(iv) with an organometallic species such as, but not limited to
   i) a stannane derivative of the formula R²—SnR'₃, wherein R² is defined as hereinbefore and R' is a $C_{1-8}$-alkyl or aryl group; or
   ii) a boronic acid derivative R²—B(OH)₂ and R²—B(OR')₂, wherein R² and R' are defined as hereinbefore; under transition metal catalysis to yield an indole derivative of the formula 2(vii)

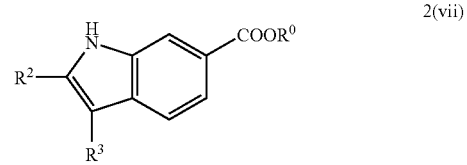

2(vii)

wherein R⁰, R² and R³ are defined as hereinbefore;

2.) the indole derivative of the formula 2(vii) is further processed by N-alkylation using the electrophilic reagent X—Sp-C(=Y⁰)-L, wherein X is a leaving group, like e.g. Cl, Br, I, mesylate, triflate, tosylate; and Sp, Y⁰ and L are as defined hereinbefore, in the presence of a strong base, yielding the product of the formula I.1; or b) 1.) halogen-metal exchange of the indole derivative of the formula 2(iv) using an alkyllithium reagent or lithium metal; and 2.) trans-metallation of the reaction product yielded by the previous step using:
   i) a trialkyl tin halide;
   ii) a trialkyl borate; or
   iii) zinc chloride; and 3.) cross-coupling of the reaction product yielded by the previous step using R²—X, wherein R² is defined as hereinbefore and X is F, Cl, Br, I or triflate, under transition metal catalysis to yield an indole derivative of the formula 2(vii) as defined hereinbefore; and 4.) the indole derivative of the formula 2(vii) is further processed by N-alkylation using the electrophilic reagent X—Sp-C(=Y⁰)-L, wherein X is a leaving group, like e.g. Cl, Br, I, mesylate, triflate, tosylate; and Sp, Y⁰ and L are as defined hereinbefore, in the presence of a strong base, yielding the product of the formula I.1; or c) 1.) N-alkylation of the indole derivative of the formula 2(iv) using the electrophilic reagent X—Sp-C(=Y⁰)-L, wherein X is a leaving group, like e.g. Cl, Br, I, mesylate, triflate, tosylate; and Sp, Y⁰ and L are as defined hereinbefore, in the presence of a strong base, yielding the indole derivative of the formula 2(v)

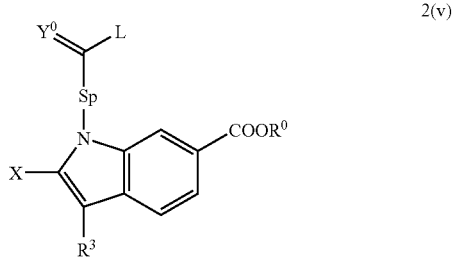

2(v)

2.) 1.) halogen-metal exchange of the derivative of the formula 2(v) using an alkyllithium reagent or lithium metal; and 2.) trans-metallation of the reaction product according to the previous step using:
i) a trialkyl tin halide;
ii) alkyl borate; or
iii) zinc chloride; and 3.) cross-coupling of the reaction product according to the previous step using $R^2$—X, wherein $R^2$ is defined as hereinbefore and X is F, Cl, Br, I or triflate, under transition metal catalysis yielding the product of the formula I.1; or d) 1.) N-alkylation of the indole derivative of the formula 2(iv) using the electrophilic reagent X—Sp-C(=$Y^0$)-L, wherein X is a leaving group, like e.g. Cl, Br, I, mesylate, triflate, tosylate; and Sp, $Y^0$ and L are as defined hereinbefore, in the presence of a strong base, yielding the indole derivative of the formula 2(v) as defined hereinbefore; and 2.) cross-coupling of the indole derivative of the formula 2(v) with an organometallic species such as, but not limited to
i) a stannane derivative of the formula $R^2$—SnR'$_3$, wherein $R^2$ is defined as hereinbefore and R' is a $C_{1-8}$-alkyl or aryl group; or
ii) a boronic acid derivative $R^2$—B(OH)$_2$ and $R^2$—B(OR')$_2$, wherein $R^2$ and R' are defined as hereinbefore; under transition metal catalysis yielding the product of the formula I.1.

DETAILED DESCRIPTION OF THE INVENTION

Definitions

The following definitions apply unless otherwise noted:

As used herein, the term $(C_{1-n})$ alkyl or $C_{1-n}$-alkyl, wherein n is an integer, either alone or in combination with another radical, are intended to mean acyclic straight or branched chain alkyl radicals containing 1 to n carbon atoms respectively. Examples of such radicals include methyl, ethyl, n-propyl, 1-methylethyl (i-propyl), n-butyl, 1-methylpropyl, 2-methylpropyl, 1,1-dimethylethyl (tert.-butyl), n-pentyl, etc. In the following the term Me denotes a methyl group.

If an alkyl group is substituted by halogen, it is preferably mono-, di- or trisubstituted with fluorine or monosubstituted by chlorine or bromine. Preferred alkyl-groups which are trisubstituted with fluorine have a terminal $CF_3$ group.

As used herein, the term $(C_{2-n})$ alkenyl, wherein n is an integer, either alone or in combination with another radical, is intended to mean an unsaturated, acyclic straight chain radical containing two to n carbon atoms, at least two of which are bonded to each other by a double bond. Examples of such radicals are ethenyl (vinyl), 1-propenyl, 2-propenyl, 1-butenyl, etc.

As used herein, the term $(C_{2-n})$ alkynyl, wherein n is an integer, either alone or in combination with another group, is intended to mean an unsaturated, acyclic straight chain radical containing 2 to n carbon atoms, at least two of which are bonded to each other by a triple bond. Examples of such radicals are ethynyl, 1-propynyl, 2-propynyl, etc.

As used herein, the term $(C_{3-n})$cycloalkyl, wherein n is an integer, either alone or in combination with another radical, means a cycloalkyl radical containing from three to n carbon atoms and includes cyclopropyl, cyclobutyl, cyclopentyl, cyclohexyl and cycloheptyl.

As used herein, the term $(C_{5-n})$cycloalkenyl, wherein n is an integer, either alone or in combination with another radical, means an unsaturated cyclic radical containing five to n carbon atoms. Examples are cyclopentenyl and cyclohexenyl.

As used herein the term $(C_{1-n})$alkyl-$(C_{3-m})$cycloalkyl, wherein n and m are integers, either alone or in combination with another radical, means a branched or straight chain alkyl radical having 1 to n C-atoms to which a cycloalkyl radical containing from three to m C-atoms is covalently bonded. Preferably the alkyl radical is a straight chain and the cycloalkyl radical is linked to its terminal C-atom. Examples of $(C_{1-3})$alkyl-$(C_{3-6})$cycloalkyl include cyclopropylmethyl, cyclobutylmethyl, cyclopentylmethyl, cyclohexylmethyl, 2-cyclopropylethyl, 2-cyclobutylethyl, 2-cyclopentylethyl, 2-cyclohexylethyl, 3-cyclopropylpropyl, 3-cyclobutylpropyl, 3-cyclopentylpropyl, 3-cyclohexylpropyl, etc.

As used herein, the terms alkyl-aryl, alkyl-HCy, alkyl-Hetaryl, alkyl-Het, etc. mean an alkyl radical to which an aryl, HCy, Hetaryl, Het group is bonded, respectively. Examples of $(C_{1-3})$alkyl-aryl are benzyl (phenylmethyl), phenylethyl and phenylpropyl.

As used herein, the term "carboxy protecting group" (CPG) defines protecting groups that can be used during synthetic transformation and are listed in Greene, "Protective Groups in Organic Chemistry", John Wiley & Sons, New York (1981) and "The Peptides: Analysis, Synthesis, Biology", Vol. 3, Academic Press, New York (1981), the disclosures of which are hereby incorporated by reference.

A-carboxyl group is usually protected as an ester that can be cleaved to give the carboxylic acid. Protecting groups that can be used include: 1) alkyl esters such as methyl, trimethylsilylethyl and t-butyl, 2) aralkyl esters such as benzyl and substituted benzyl, or 3) esters that can be cleaved by mild base treatment or mild reductive means such as trichloroethyl and phenacyl esters.

As used herein, the term "aryl" either alone or in combination with another radical means a 6- or 10-membered aryl, i.e. an aromatic radical containing six or ten carbon atoms, for example phenyl, 1-naphthyl or 2-naphthyl. The most preferred meaning of aryl is phenyl.

As used herein the term heteroatom means O, S or N.

As used herein, the term "heterocycle", either alone or in combination with another radical, means a monovalent radical derived by removal of a hydrogen from a four-, five-, six-, or seven-membered saturated or unsaturated (including aromatic) heterocycle containing from one to four heteroatoms selected from nitrogen, oxygen and sulfur. Examples of such heterocycles include, but are not limited to, azetidine, pyrrolidine, tetrahydrofuran, thiazolidine, pyrrole, thiophene, hydantoin, diazepine, 1H-imidazole, isoxazole, thiazole, tetrazole, piperidine, piperazine, homopiperidine, homopiperazine, 1,4-dioxane, 4-morpholine, 4-thiomorpholine, pyridine, pyridine-N-oxide or pyrimidine, or the following heterocycles:

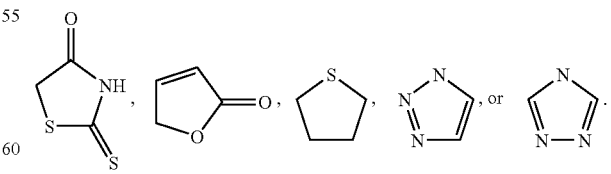

As used herein, the term "9- or 10-membered heterobicycle" or "heterobicycle" either alone or in combination with another radical, means a heterocycle as defined above fused to one or more other cycle, be it a heterocycle or any other cycle. Examples of such heterobicycles include, but are not limited to, indole, benzimidazole, thiazolo[4,5-b]-pyridine, quinoline, or coumarin, or the following:

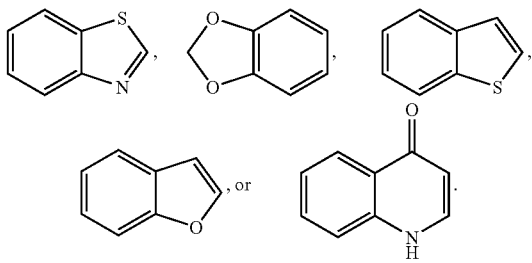

As used herein, the term "Het" defines a 4-, 5-, 6- or 7-membered heterocycle having 1 to 4 heteroatoms selected from O, N and S, which may be saturated, unsaturated or aromatic, or a 8-, 9-, 10- or 11-membered heterobicycle having 1 to 5 heteroatoms wherever possible, selected from O, N and S, which may be saturated, unsaturated or aromatic, unless specified otherwise.

As used herein, the term "HCy" defines a saturated or unsaturated 4-, 5-, 6- or 7-membered monocyclic heterocycle having 1 to 3 heteroatoms selected from O, N and S, unless specified otherwise.

As used herein, the term "Hetaryl" defines an aromatic 5- or 6-membered monocyclic heterocycle having 1 or 2 heteroatoms selected from O, N and S, or a 9- or 10-membered aromatic heterobicycle having 1 to 4 heteroatoms selected from O, N, and S, unless specified otherwise.

As used herein, the term "halo" means a halogen atom and includes fluorine, chlorine, bromine and iodine.

As used herein, the term "OH" refers to a hydroxyl group. It is well known to one skilled in the art that hydroxyl groups may be substituted by functional group equivalents. Examples of such functional group equivalents that are contemplated by this invention include, but are not limited to, ethers, sulfhydryls, and primary, secondary or tertiary amines.

As used herein, the term "SH" refers to a sulfhydryl group. It is intended within the scope of the present invention that, whenever a "SH" or "SR" group is present, it can also be substituted by any other appropriate oxidation state such as SOR, $SO_2R$, or $SO_3R$.

It is intended that the term "substituted" when applied in conjunction with a radical having more than one moiety such as $C_{1-6}$alkyl-aryl, or $C_{1-6}$alkyl-Het, such substitution applies to both moieties i.e. both the alkyl and aryl or Het moieties can be substituted with the defined substituents.

As used herein, the term "COOH" refers to a carboxylic acid group. It is well known to one skilled in the art that carboxylic acid groups may be substituted by functional group equivalents. Examples of such functional group equivalents that are contemplated by this invention include, but are not limited to, esters, amides, imides, boronic acids, tetrazoles, triazoles, N-acylsulfonyldiamides ($RCONHSO_2NR_2$), and N-acylsulfonamides ($RCONHSO_2R$).

As used herein, the term "functional group equivalent" is intended to mean an element or a substituted derivative thereof, that is replaceable by another element that has similar electronic, hybridization or bonding properties.

As used herein, the term "metal catalyst" is intended to mean a metal such as palladium (0) or palladium (2) for use in a cross-coupling reaction. Examples of such palladium catalysts include, but are not limited to, $Pd(Ph_3)_4$, Pd/C, $Pd(OAc)_2$, $PdCl_2$, and the like. Alternative metals that can catalyze cross-coupling reactions include, but are not limited to, complexes of Ni, Rh, Ru and Ir, like for example: $Ni(acac)_2$, $Ni(OAc)_2$, or $NiCl_2$.

The term "detectable label" refers to any group that may be linked to the polymerase or to a compound of the present invention such that when the compound is associated with the polymerase target, such label allows recognition either directly or indirectly of the compound such that it can be detected, measured and quantified. Examples of such "labels" are intended to include, but are not limited to, fluorescent labels, chemiluminescent labels, colorimetric labels, enzymatic markers, radioactive isotopes and affinity tags such as biotin. Such labels are attached to the compound or to the polymerase by well known methods.

The term "affinity tag" means a ligand (that is linked to the polymerase or to a compound of the present invention) whose strong affinity for a receptor can be used to extract from a solution the entity to which the ligand is attached. Examples of such ligands include biotin or a derivative thereof, a histidine polypeptide, a polyarginine, an amylose sugar moiety or a defined epitope recognizable by a specific antibody. Such affinity tags are attached to the compound or to the polymerase by well-known methods.

The term "photoreactive group" means a group that is transformed, upon activation by light, from an inert group to a reactive species, such as a free radical. Examples of such groups include, but are not limited to, benzophenones, azides, and the like.

The term "salt thereof" means any acid and/or base addition salt of a compound according to the invention; preferably a pharmaceutically acceptable salt thereof.

The term "pharmaceutically acceptable salt" means a salt of a compound of formula (I) which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. Lists of suitable salts are found in, e.g., S. M. Birge et al., J. Pharm. Sci., 1977, 66, pp. 1-19, which is hereby incorporated by reference in its entirety.

The term "pharmaceutically-acceptable acid addition salt" means those salts which retain the biological effectiveness and properties of the free bases and which are not biologically or otherwise undesirable, formed with inorganic acids such as hydrochloric acid, hydrobromic acid, sulfuric acid, sulfamic acid, nitric acid, phosphoric acid, and the like, and organic acids such as acetic acid, trifluoroacetic acid, adipic acid, ascorbic acid, aspartic acid, benzenesulfonic acid, benzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, hexanoic acid, formic acid, fumaric acid, 2-hydroxyethanesulfonic acid (isethionic acid), lactic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, pivalic acid, propionic acid, pyruvic acid, salicylic acid, stearic acid, succinic acid, sulfanilic acid, tartaric acid, p-toluenesulfonic acid, undecanoic acid, and the like.

The term "pharmaceutically-acceptable base addition salt" means those salts which retain the biological effectiveness and properties of the free acids and which are not biologically or otherwise undesirable, formed with inorganic bases such as ammonia or hydroxide, carbonate, or bicarbonate of ammonium or a metal cation such as sodium, potassium, lithium, calcium, magnesium, iron, zinc, copper, manganese, aluminum, and the like. Particularly preferred are the ammonium, potassium, sodium, calcium, and magnesium salts. Salts derived from pharmaceutically-acceptable organic non-toxic bases include salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins, and the like. Particularly preferred organic nontoxic bases are isopropylamine, diethylamine, ethanolamine, trimethylamine, dicyclohexylamine, choline, and caffeine.

The term "antiviral agent" as used herein means an agent (compound or biological) that is effective to inhibit the formation and/or replication of a virus in a mammal. This includes agents that interfere with either host or viral mechanisms necessary for the formation and/or replication of a virus in a mammal. Antiviral agents include, for example, ribavirin, amantadine, VX-497 (merimepodib, Vertex Pharmaceuticals), VX-498 (Vertex Pharmaceuticals), Levovirin, Viramidine, Ceplene (maxamine), XTL-001 and XTL-002 (XTL Biopharmaceuticals).

The term "other anti-HCV agent" as used herein means those agents that are effective for diminishing or preventing the progression of hepatitis C related symptoms of disease. Such agents can be selected from: immunomodulatory agents, inhibitors of HCV NS3 protease, other inhibitors of HCV polymerase or inhibitors of another target in the HCV life cycle.

The term "immunomodulatory agent" as used herein means those agents (compounds or biologicals) that are effective to enhance or potentiate the immune system response in a mammal. Immunomodulatory agents include, for example, class I interferons (such as α-, β-, δ- and omega interferons, tau-interferons, consensus interferons and asialo-interferons), class II interferons (such as γ-interferons) and pegylated interferons.

The term "inhibitor of HCV NS3 protease" as used herein means an agent (compound or biological) that is effective to inhibit the function of HCV NS3 protease in a mammal. Inhibitors of HCV NS3 protease include, for example, those compounds described in WO 99/07733, WO 99/07734, WO 00/09558, WO 00/09543, WO 00/59929 or WO 02/060926, the Boehringer Ingelheim clinical candidate identified as BILN 2061 and the Vertex pre-development candidate identified as VX-950. Particularly, compounds #2, 3, 5, 6, 8, 10, 11, 18, 19, 29, 30, 31, 32, 33, 37, 38, 55, 59, 71, 91, 103, 104, 105, 112, 113, 114, 115, 116, 120, 122, 123, 124, 125, 126 and 127 disclosed in the table of pages 224-226 in WO 02/060926, can be used in combination with the compounds of the present invention.

The term "other inhibitor of HCV polymerase" as used herein means an agent (compound or biological) that is effective to inhibit the function of HCV polymerase in a mammal, whereby this agent has a structure different from the compounds according to this invention and preferably binds to a site of the HCV polymerase different from the site targeted by the compounds according to this invention. Other inhibitors of HCV polymerase include non-nucleosides, for example, those compounds described in: WO 03/040112 (Rigel), WO 02/100846 A1 (Shire), WO 02/100851 A2 (Shire), WO 01/85172 A1 (GSK), WO 02/098424 A1 (GSK), WO 00/06529 (Merck), WO 02/06246 A1 (Merck), EP 1 256 628 A2 (Agouron). Furthermore other inhibitors of HCV polymerase also include nucleoside analogs, for example, those compounds described in: WO 01/90121 A2 (Idenix), WO 02/069903 A2 (Biocryst Pharmaceuticals Inc.), WO 02/057287 A2 (Merck/Isis) and WO 02/057425 A2 (Merck/Isis).

The term "inhibitor of another target in the HCV life cycle" as used herein means an agent (compound or biological) that is effective to inhibit the formation and/or replication of HCV in a mammal other than by inhibiting the RNA dependent RNA polymerase of HCV. This includes agents that interfere with either host or HCV viral mechanisms necessary for the formation and/or replication of HCV in a mammal. Inhibitors of another target in the HCV life cycle include, for example, agents that inhibit a target selected from a HCV helicase, HCV NS2/3 protease and HCV IRES.

Specific examples of inhibitors of another target in the HCV life cycle include ISIS-14803 (ISIS Pharmaceuticals).

The term "HIV inhibitor" as used herein means an agent (compound or biological) that is effective to inhibit the formation and/or replication of HIV in a mammal. This includes agents that interfere with either host or viral mechanisms necessary for the formation and/or replication of HIV in a mammal. HIV inhibitors include, for example, nucleosidic inhibitors, non-nucleosidic inhibitors, protease inhibitors, fusion inhibitors and integrase inhibitors.

The term "HAV inhibitor" as used herein means an agent (compound or biological) that is effective to inhibit the formation and/or replication of HAV in a mammal. This includes agents that interfere with either host or viral mechanisms necessary for the formation and/or replication of HAV in a mammal. HAV inhibitors include Hepatitis A vaccines, for example, Havrix® (GlaxoSmithKline), VAQTA® (Merck) and Avaxim® (Aventis Pasteur).

The term "HBV inhibitor" as used herein means an agent (compound or biological) that is effective to inhibit the formation and/or replication of HBV in a mammal. This includes agents that interfere with either host or viral mechanisms necessary for the formation and/or replication of HBV in a mammal. HBV inhibitors include, for example, agents that inhibit HBV viral DNA polymerase or HBV vaccines. Specific examples of HBV inhibitors include Lamivudine (Epivir-HBV®), Adefovir Dipivoxil, Entecavir, FTC (Coviracil®), DAPD (DXG), L-FMAU (Clevudine®), AM365 (Amrad), Ldt (Telbivudine), monoval-LdC (Valtorcitabine), ACH-126,443 (L-Fd4C) (Achillion), MCC478 (Eli Lilly), Racivir (RCV), Fluoro-L and D nucleosides, Robustaflavone, ICN 2001-3 (ICN), Bam 205 (Novelos), XTL-001 (XTL), Imino-Sugars (Nonyl-DNJ) (Synergy), HepBzyme; and immunomodulator products such as: interferon alpha 2b, HE2000 (Hollis-Eden), Theradigm (Epimmune), EHT899 (Enzo Biochem), Thymosin alpha-1 (Zadaxin®), HBV DNA vaccine (PowderJect), HBV DNA vaccine (Jefferon Center), HBV antigen (OraGen), BayHep B® (Bayer), Nabi-HB® (Nabi) and Anti-hepatitis B (Cangene); and HBV vaccine products such as the following: Engerix B, Recombivax HB, GenHevac B, Hepacare, Bio-Hep B, TwinRix, Comvax, Hexavac.

The term "class I interferon" as used herein means an interferon selected from a group of interferons that all bind to receptor type I. This includes both naturally and synthetically produced class I interferons. Examples of class I interferons include α-, β-, omega interferons, tau-interferons, consensus interferons, asialo-interferons.

The term "class II interferon" as used herein means an interferon selected from a group of interferons that all bind to receptor type II. Examples of class II interferons include γ-interferons.

Specific preferred examples of some of these agents are listed below:

antiviral agents: ribavirin and amantadine;

immunomodulatory agents: class I interferons, class II interferons and pegylated interferons;

HCV NS3 protease inhibitors;

other inhibitors of the HCV polymerase: nucleosidic and non-nucleosidic inhibitors;

inhibitor of another target in the HCV life cycle that inhibits a target selected from: HCV NS2/3 protease or internal ribosome entry site (IRES);

HIV inhibitors: nucleosidic inhibitors, non-nucleosidic inhibitors, protease inhibitors, fusion inhibitors and integrase inhibitors; or HBV inhibitors: agents that inhibit viral DNA polymerase or is an HBV vaccine.

As discussed above, combination therapy is contemplated wherein a compound of formula (I), or a pharmaceutically acceptable salt thereof, is co-administered with at least one additional agent selected from: an antiviral agent, an immunomodulatory agent, an inhibitor of HCV NS3 protease, another inhibitor of HCV polymerase, an inhibitor of another target in the HCV life cycle, an HIV inhibitor, an HAV inhibitor and an HBV inhibitor. Examples of such agents are provided in the Definitions section above. These additional agents may be combined with the compounds of this invention to create a single pharmaceutical dosage form. Alternatively these additional agents may be separately administered to the patient as part of a multiple dosage form, for example, using a kit. Such additional agents may be administered to the patient prior to, concurrently with, or following the administration of wherein a compound of formula (I), or a pharmaceutically acceptable salt thereof.

As used herein, the term "treatment" means the administration of a compound or composition according to the present invention to alleviate or eliminate symptoms of the hepatitis C disease and/or to reduce viral load in a patient.

As used herein, the term "prevention" means the administration of a compound or composition according to the present invention post-exposure of the individual to the virus but before the appearance of symptoms of the disease, and/or prior to the detection of the virus in the blood.

The following signs ---- and ∿∿∿ are used interchangeably in subformulas to indicate the bond, or in the case of a spiro-cyclic group the atom, which is bonded to the rest of the molecule as defined.

As used herein, the designation whereby a bond to a substituent R is drawn as emanating from the center of a ring, such as, for example,

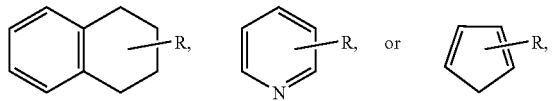

means that the substituent R may be attached to any free position on the ring that would otherwise be substituted by a hydrogen atom, unless specified otherwise.

Preferred Embodiments

As long as not stated otherwise, all groups, substituents and indices, like e.g. $R^1$, $R^{1q}$, $R^2$, $R^{2h}$, $R^{2q}$, $R^3$, $R^4$, $R^{4b}$, $R^5$, $R^{5a}$, $R^{5b}$, $R^{6a}$, $R^{6b}$, $R^{7a}$, $R^{8a}$, $R^{7b}$, $R^{8b}$, $R^{9a}$, $R^{9b}$, $R^{11}$, $R^{12}$, $R^{13}$, $R^{14}$, $R^{21}$, $R^{31}$, $R^{32}$, $R^{33}$, $R^{35}$, $R^{51}$, $R^{52}$, $R^{60}$, $R^{111}$, $R^{112}$, $R^{117}$, $R^{150}$, $R^{160}$, $R^{161}$, $R^{162}$, $R^{163}$, $R^{170}$, $R^O$, $R^C$, $R^L$, $R^{N1}$, $R^{N2}$, $R^{N3}$, $R^{N4}$, $R^Q$, A, B, L, $M^1$, $M^2$, $M^3$, $M^4$, $Q^1$, $Q^{1a}$, $Q^{1b}$, $Q^{1c}$, $Q^2$, $Q^{2a}$, $Q^{2b}$, $Q^{2c}$, $W^1$, $W^2$, $Y^0$, $Y^1$, $Y^2$, $Y^3$, X, Z, Sp, Het, HCy, Hetaryl, $k_1$, q, qa, and qb, have the meanings as defined hereinbefore and hereinafter. In the following the preferred embodiments, groups, substituents and indices according to this invention are described.

In a preferred embodiment of the first aspect of the invention, there is provided an isomer, enantiomer, diastereoisomer or tautomer of a compound, represented by formula I:

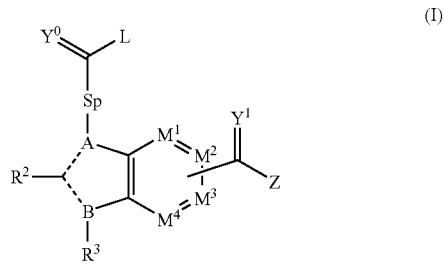

wherein:

either A or B is N and the other B or A is C, wherein ----- between two C-atoms represents a double bond and ----- between a C-atom and a N-atom represents a single bond, the group —C(=$Y^1$)—Z is covalently linked to either $M^2$ or $M^3$, $M^1$ is $CR^{4a}$, $M^2$ or $M^3$ is $CR^5$, $M^4$ is $CR^{4b}$, and in addition one or two of the groups selected from $M^1$, $M^2$, $M^3$ and $M^4$ may also be N, with the proviso that the group $M^2$ or $M^3$ to which —C(=$Y^1$)—Z is linked is an C-atom, Sp is a spacer group selected from —$(CR^{51}R^{52})_{k1}$—, wherein k1 is 1, 2 or 3;

$R^{51}$, $R^{52}$ are independently H, $(C_{1-6})$alkyl, $(C_{3-7})$cycloalkyl or $(C_{1-3})$alkyl-$(C_{3-7})$cycloalkyl, or $R^{51}$ and $R^{52}$ are covalently bonded together and to the carbon-atom to which they are attached to form a $(C_{3-6})$ cycloalkyl group, said alkyl, cycloalkyls or alkyl-cycloalkyl being optionally substituted by halogen, hydroxy, $(C_{1-6})$alkoxy, cyano, amino, —NH$(C_{1-4}$-alkyl) and/or —N$(C_{1-4}$-alkyl$)_2$;

$Y^0$ is O, S, NR$^{11}$ or CR$^{12}$R$^{13}$, wherein
  $R^{11}$, $R^{12}$, $R^{13}$ are each independently defined as $R^O$;
  $R^{13}$ may also be COOR$^O$ or SO$_2$R$^C$;
  wherein R$^C$ and each R$^O$ is optionally substituted with R$^{150}$;
  or both $R^{12}$ and $R^{13}$ are covalently bonded together and to the carbon-atom to which they are attached to form a 3, 4, 5, 6 or 7-membered saturated or 5, 6 or 7-membered unsaturated cyclic system whereby the 5, 6 or 7-membered saturated or unsaturated cyclic system may contain 1 to 3 heteroatoms selected from N, O or S;
  said cyclic systems being optionally substituted with R$^{150}$;

L is $C_{1-6}$alkyl, $(C_{3-6})$cycloalkyl, $C_{1-6}$alkyl-$(C_{3-6})$cycloalkyl, $(C_{2-6})$alkenyl, aryl, $(C_{1-6}$alkyl)aryl, Het, $(C_{1-6})$alkyl-Het, all of which being optionally substituted with R$^{60}$;

or if $Y^0$ is CR$^{12}$R$^{13}$, then L may also be H;

or if $Y^0$ is O, then L may also be OR$^C$,
  wherein R$^C$ is optionally substituted with R$^{60}$;

or if $Y^0$ is O, S or NR$^{11}$, then L may also be N(R$^{N2}$)R$^{N1}$, NR$^{N3}$—N(R$^{N2}$)R$^{N1}$, NR$^{N3}$—NR$^{N2}$—CO—R$^C$, NR$^{N4}$—NR$^{N3}$—CO—N(R$^{N2}$)R$^{N1}$, NR$^{N2}$—SO$_2$—R$^C$, NR$^{N2}$—CO—R$^C$, NR$^{N3}$—CO—N(R$^{N2}$)R$^{N1}$ or N(R$^{N1}$)OR$^O$;

said R$^{N1}$, including any heterocycle or heterobicycle formed by R$^{N1}$, R$^{N2}$ and/or R$^{N3}$, and R$^C$ and R$^O$ being optionally substituted with R$^{60}$;

or if $Y^0$ is O or S, then L may also be OR$^{6a}$ or N(R$^{5a}$)R$^{6a}$, wherein R$^{5a}$ is defined as R$^{N2}$,
  and wherein R$^{6a}$, is:

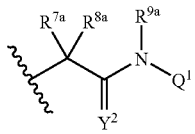

wherein R$^{7a}$ and R$^{8a}$ are each independently defined as R$^O$,
    wherein said R$^O$ is optionally substituted with R$^{60}$; or
  R$^{7a}$ and R$^{8a}$ are covalently bonded together to form a $(C_{3-7})$cycloalkyl or a 4, 5- or 6-membered heterocycle having from 1 to 3 heteroatom selected from O, N, and S;
  and when L is N(R$^{5a}$)R$^{6a}$, either of R$^{7a}$ or R$^{8a}$ may be covalently bonded to R$^{5a}$ to form a nitrogen-containing 5- or 6-membered heterocycle, wherein said cycloalkyl or heterocycle being optionally substituted by R$^{150}$; and
  $Y^2$ is O or S;
  R$^{9a}$ is defined as R$^O$, wherein said R$^O$ is optionally substituted with R$^{60}$; or
  R$^{9a}$ is covalently bonded to either of R$^{7a}$ or R$^{8a}$ to form a 5- or 6-membered heterocycle;
  Q$^1$ is aryl, Het, $(C_{1-6})$alkyl-aryl, $(C_{1-6})$alkyl-Het, $(C_{1-6})$alkyl-CONH-aryl or $(C_{1-6})$alkyl-CONH-Het, all of which being optionally substituted with R$^{60}$;

$Y^1$ is O, S or NR$^{14}$, wherein R$^{14}$ is H or $(C_{1-6})$alkyl;

Z is defined as
  a) OR$^O$;
  b) SO$_2$R$^C$;
  c) N(R$^{N2}$)R$^{N1}$;
  d) NR$^{N3}$—N(R$^{N2}$)R$^{N1}$;
  e) NR$^{N3}$—NR$^{N2}$—CO—R$^C$;
  f) NR$^{N4}$—NR$^{N3}$—CO—N(R$^{N2}$)R$^{N1}$;
  g) NR$^{N2}$—SO$_2$—R$^C$ or
  h) NR$^{N2}$—CO—R$^C$;
  i) COOR$^O$;
  j) N(R$^{N1}$)OR$^O$;
  wherein R$^O$ and R$^C$ are optionally substituted with R$^{60}$; and
  said R$^{N1}$, including any heterocycle or heterobicycle formed by R$^{N1}$, R$^{N2}$, and/or R$^{N3}$, being optionally substituted with R$^{60}$;

or Z is OR$^{6b}$ or N(R$^{5b}$)R$^{6b}$ wherein R$^{5b}$ is defined as R$^{N2}$ and R$^{6b}$ is:

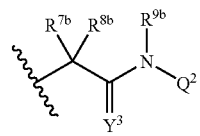

wherein R$^{7b}$, R$^{8b}$, Y$^3$, R$^{9b}$, Q$^2$, are defined as R$^{7a}$, R$^{8a}$, Y$^2$, R$^{9a}$, Q$^1$, respectively;

R$^2$ is selected from: halogen or R$^{21}$, wherein R$^{21}$ is aryl or Het, said R$^{21}$ is optionally substituted with R$^{150}$;

R$^3$ is selected from $(C_{1-6})$alkyl, $(C_{3-7})$cycloalkyl, $(C_{1-3})$alkyl-$(C_{3-7})$cycloalkyl, $(C_{5-7})$cycloalkenyl, $(C_{1-3})$alkyl-$(C_{5-7})$cycloalkenyl, $(C_{6-10})$bicycloalkyl, $(C_{1-3})$alkyl-$(C_{6-10})$bicycloalkyl, $(C_{6-10})$bicycloalkenyl, $(C_{1-3})$alkyl-$(C_{6-10})$bicycloalkenyl, HCy or $(C_{1-3})$alkyl-HCy, wherein HCy is a saturated or unsaturated 4 to 7-membered heterocyclic group with 1 to 3 heteroatoms selected from O, S and N;

said alkyl, cycloalkyl, cycloalkenyl, bicycloalkyl, bicycloalkenyl, HCy and alkyl-HCy being optionally substituted with from 1 to 4 substituents selected from:
  a) halogen;
  b) $(C_{1-6})$alkyl optionally substituted with:
    OR$^{31}$ or SR$^{31}$ wherein R$^{31}$ is H, $(C_{1-6}$alkyl), $(C_{3-7})$cycloalkyl or $(C_{1-3})$alkyl-$(C_{3-7})$cycloalkyl; or
    N(R$^{32}$)$_2$ wherein each R$^{32}$ is independently H, $(C_{1-6})$alkyl, $(C_{3-7})$cycloalkyl or $(C_{1-3})$alkyl-$(C_{3-7})$cycloalkyl; or both R$^{32}$ are covalently bonded together and to the nitrogen to which they are attached to form a 5, 6 or 7-membered saturated heterocycle;
  c) OR$^{33}$ or SR$^{33}$ wherein R$^{33}$ is H, $(C_{1-6})$alkyl, $(C_{3-7})$cycloalkyl or $(C_{1-3})$alkyl-$(C_{3-7})$cycloalkyl;
  d) N(R$^{35}$)$_2$ wherein each R$^{35}$ is independently H, $(C_{1-6})$alkyl, $(C_{3-7})$cycloalkyl or $(C_{1-3})$alkyl-$(C_{3-7})$cycloalkyl; or both R$^{35}$ are covalently bonded together and to the nitrogen to which they are attached to form a 5, 6 or 7-membered saturated heterocycle;

R$^{4a}$, R$^{4b}$, R$^5$ each are independently H or defined as R$^{150}$;

R$^{60}$ is each defined as 1 to 4 substituents independently selected from:
  1 to 3 substituents selected from halogen;
  one of each substituent selected from: OPO$_3$H, NO$_2$, cyano, azido, C(=NH)NH$_2$, C(=NH)NH$(C_{1-6})$alkyl or C(=NH)NHCO$(C_{1-6})$alkyl, SO$_3$H; and
  1 to 3 substituents selected from:
    a) $(C_{1-6})$ alkyl, $(C_{3-7})$cycloalkyl, $C_{3-7}$ spirocycloalkyl optionally containing 1 or 2 heteroatoms selected from N, O and S; $(C_{2-6})$alkenyl, $(C_{2-8})$alkynyl, $(C_{1-6})$alkyl-$(C_{3-7})$cycloalkyl, all of which optionally being substituted with R$^{150}$;
    b) OR$^O$;
    c) OC(O)R$^O$;
    d) SR$^O$, SO$_2$R$^C$, SO$_2$N(R$^{N2}$)R$^{N1}$, SO$_2$N(R$^{N2}$)C(O)R$^C$ or CONR$^{N2}$SO$_2$R$^C$;
    e) N(R$^{N2}$)R$^{N1}$, N(R$^{N2}$)COOR$^C$, or N(R$^{N2}$)SO$_2$R$^C$;
    f) N(R$^{N2}$)COR$^C$;

g) $N(R^{N3})CON(R^{N2})R^{N1}$;

h) $N(R^{N3})COCOR^C$, $N(R^{N3})COCOOR^O$ or $N(R^{N3})CO-CON(R^{N2})R^{N1}$;

i) $COR^O$;

j) $COOR^O$;

k) $CON(R^{N2})R^{N1}$;

l) aryl, Het, $(C_{1-4}$alkyl)aryl or $(C_{1-4}$alkyl)Het, all of which optionally being substituted with $R^{150}$;

wherein said $R^{N1}$, $R^C$ and $R^O$ are each independently optionally substituted with $R^{150}$ as defined, $R^{150}$ is each defined as 1 to 4 substituents independently selected from:

1 to 3 substituents selected from halogen;

one of each substituent selected from: $OPO_3H$, $NO_2$, cyano, azido, $C(=NH)NH_2$, $C(=NH)NH(C_{1-6})$alkyl or $C(=NH)NHCO(C_{1-6})$alkyl; and 1 to 3 substituents selected from:

a) $(C_{1-6})$ alkyl, $(C_{3-7})$cycloalkyl, $C_{3-7}$ spirocycloalkyl optionally containing 1 or 2 heteroatoms selected from N, O and S; $(C_{2-6})$alkenyl, $(C_{2-8})$alkynyl, $(C_{1-3})$alkyl-$(C_{3-7})$cycloalkyl, all of which optionally substituted with $R^{160}$;

b) $OR^O$;

c) $OC(O)R^O$;

d) $SR^O$, $SO_2R^C$, $SO_2N(R^{N2})R^{N1}$, $SO_2N(R^{N2})C(O)R^C$ or $CON(R^{N2})SO_2R^C$;

e) $N(R^{N2})R^{N1}$, $N(R^{N2})COOR^C$, or $N(R^{N2})SO_2R^C$;

f) $N(R^{N2})COR^C$;

g) $N(R^{N3})CON(R^{N2})R^{N1}$;

h) $N(R^{N3})COCOR^C$, $N(R^{N3})COCOOR^O$ or $N(R^{N3})CO-CON(R^{N2})R^{N1}$; wherein $R^{N1}$ is as defined or OH, O—$C_{1-4}$-alkyl;

i) $COR^O$;

j) $COOR^O$;

k) tetrazole or $CON(R^{N2})R^{N1}$;

wherein said $R^{N1}$, $R^C$ and/or $R^O$ are optionally substituted with $R^{160}$ as defined;

$R^{160}$ is each defined as 1, 2 or 3 substituents independently selected from:

1, 2 or 3 fluorine substituents; and one of each substituent selected from tetrazole, chlorine, bromine, iodine, CN, nitro, $C_{1-4}$alkyl, $CF_3$, $COOR^{161}$, $SO_3H$, $SR^{161}$, $SO_2R^{163}$, $OR^{161}$, $N(R^{162})_2$, $SO_2N(R^{162})_2$, $SO_2NR^{162}COR^{162}$, $NR^{162}SO_2R^{163}$, $NR^{162}COR^{162}$, or $CON(R^{162})_2$, wherein $R^{161}$, $R^{163}$ and each $R^{162}$ is independently $(C_{1-4})$alkyl, $(C_{3-7})$cycloalkyl or $(C_{1-3})$alkyl-$(C_{3-7})$cycloalkyl;

and $R^{161}$ and each $R^{162}$ may each independently also be H; or both $R^{162}$ are covalently bonded together and to the nitrogen to which they are attached to form a 5, 6 or 7-membered saturated heterocycle;

$R^O$, $R^C$ are independently defined as $(C_{1-6})$alkyl, $(C_{3-6})$cycloalkyl, $(C_{1-4})$alkyl-$(C_{3-6})$cycloalkyl, $(C_{2-6})$alkenyl, aryl, Het, $(C_{1-4})$alkyl-aryl and $(C_{1-4})$alkyl-Het; and $R^O$ may also be H;

$R^{N1}$ is independently selected from H, $(C_{1-6})$alkyl, $(C_{3-7})$ cycloalkyl, $(C_{1-4})$alkyl-$(C_{3-6})$cycloalkyl, $(C_{2-6})$alkenyl, aryl, Het, $(C_{1-4})$alkyl-aryl, $(C_{1-4})$alkyl-Het; or $R^{N2}$, $R^{N3}$, $R^{N4}$ are independently H, $CH_3$, $(C_{2-6}$alkyl), $(C_{3-6})$ cycloalkyl, $(C_{1-4})$alkyl$(C_{3-6})$cycloalkyl; wherein said alkyl, cycloalkyl or alkylcycloalkyl is optionally substituted with hydroxy, halogen, carboxy, $C_{1-6}$-alkoxycarbonyl, $C_{1-6}$-alkyl, $C_{1-6}$-alkoxy, amino, —$NH(C_{1-4}$-alkyl) and/or —$N(C_{1-4}$-alkyl)$_2$; and wherein said $CH_3$ is optionally substituted with halogen, carboxy or $C_{1-6}$-alkoxycarbonyl; and in the case a) of a group $N(R^{N2})R^{N1}$ the substituents $R^{N2}$ and $R^{N1}$; or b) of a group $NR^{N3}$—$N(R^{N2})R^{N1}$ the substituents $R^{N3}$ and $R^{N1}$, or $R^{N2}$ and $R^{N1}$;

may be covalently bonded together to form a 4-, 5-, 6- or 7-membered saturated or unsaturated N-containing heterocycle or a 8-, 9-, 10- or 11-membered N-containing heterobicycle each may have additionally from 1 to 3 heteroatoms selected from O N, and S;

wherein Het is defined as a 4-, 5-, 6- or 7-membered heterocycle having 1 to 4 heteroatoms selected from O, N and S, or a 8-, 9-, 10- or 11-membered heterobicycle having 1 to 5 heteroatoms selected from O, N and S;

or a salt thereof.

Core:

This invention comprises compounds of the formulas Ia and Ib

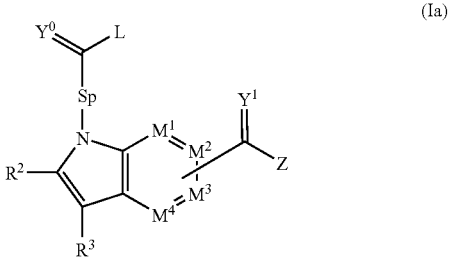

(Ia)

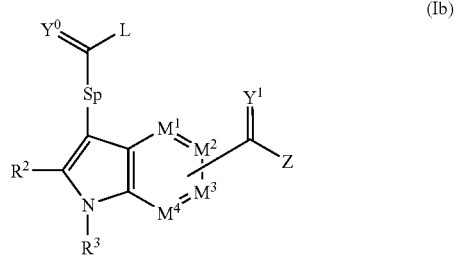

(Ib)

wherein the compounds of the formula Ia are preferred.

Furthermore this invention comprises compounds according to the formulas Ic and Id

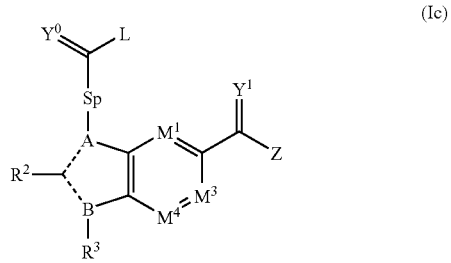

(Ic)

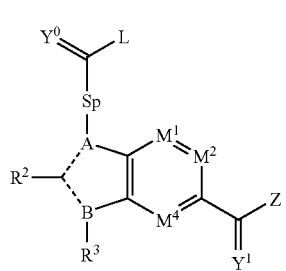
wherein the compounds of the formula Ic are preferred.
More explicitly, this invention comprises compounds of the following formulas
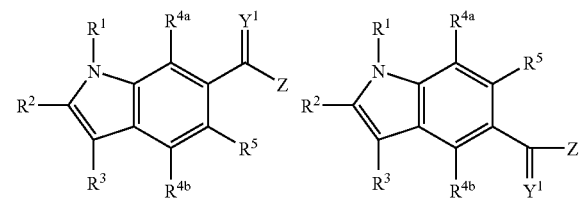
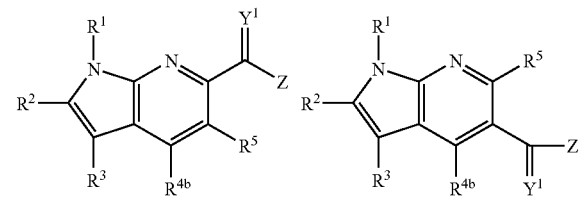
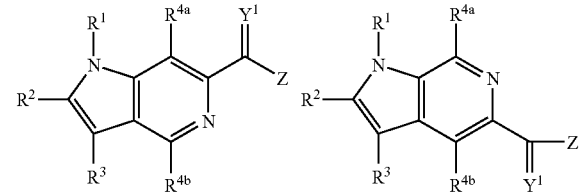
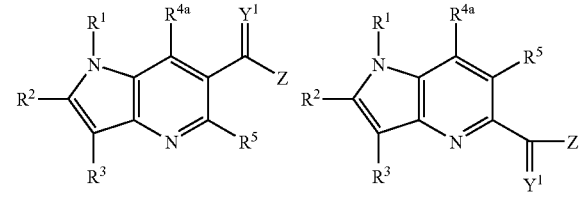
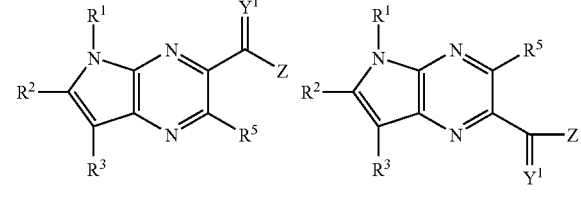
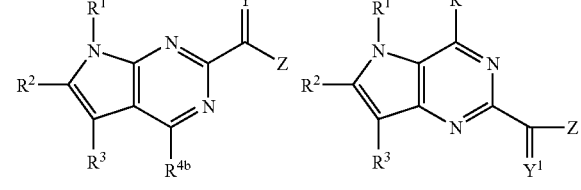
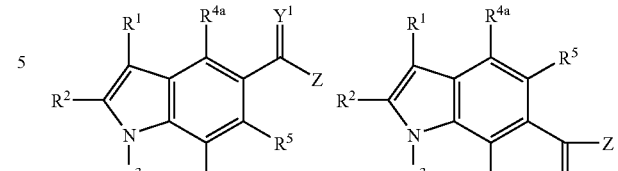
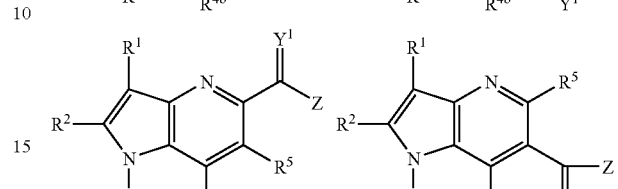
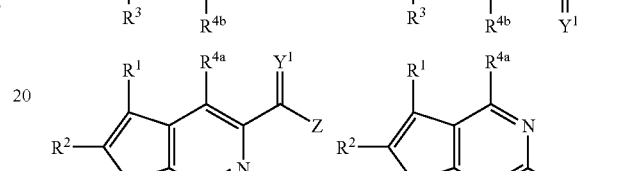
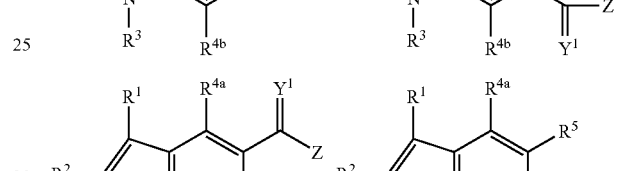
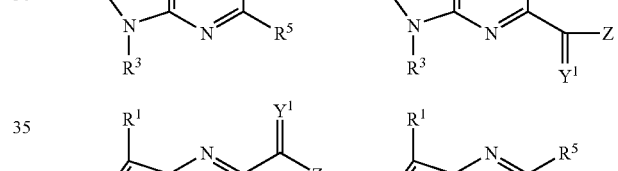
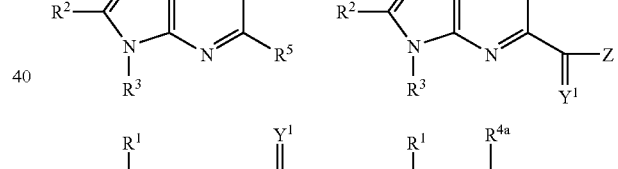
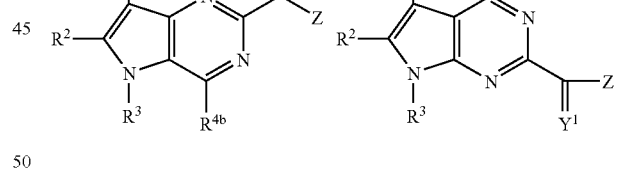
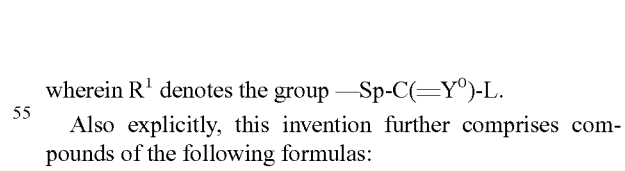
wherein $R^1$ denotes the group —Sp-C(=$Y^0$)-L.
Also explicitly, this invention further comprises compounds of the following formulas:
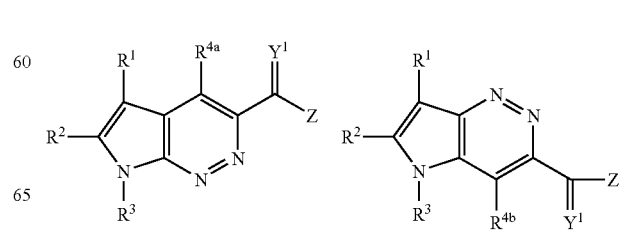

-continued

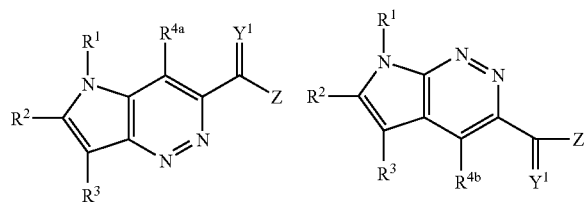

wherein R¹ denotes the group —Sp-C(=Y⁰)-L.

Preferably the groups M¹ and M⁴ are $CR^{4a}$ and $CR^{4b}$, respectively.

The group M² or M³ to which the group —C(=Y¹)—Z is covalently linked is C and the other group M³ or M² is preferably $CR^5$.

Therefore those compounds are preferred which are described by the following group of formulas I.1 to I.4

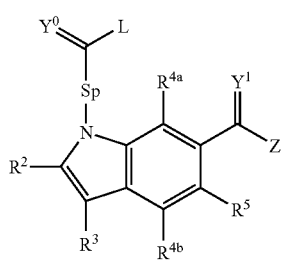

I.1

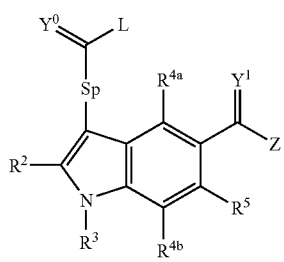

I.2

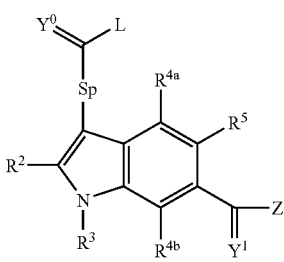

I.3

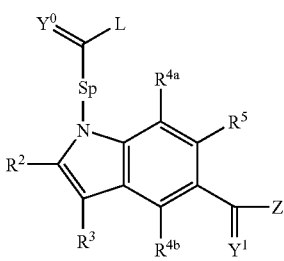

I.4

A group of most preferred compounds is described by the formula I.1

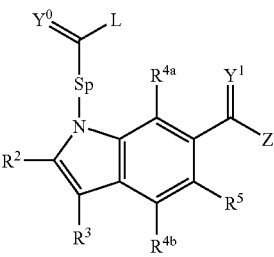

I.1

Another group of preferred compounds is described by the formula I.4 as given above.

Sp:

The preferred meaning of the spacer group Sp is a group selected from —$(CR^{51}R^{52})_{k1}$—, wherein k1 is 1, 2 or 3; and $R^{51}$, $R^{52}$ are independently H or $(C_{1-3})$alkyl, in particular H or methyl; and/or $R^{51}$, $R^{52}$ are covalently bonded together and to the carbon-atom to which they are attached to form a cyclopropyl, cyclobutyl or cyclopentyl group.

More preferably Sp is a spacer group selected from —CH₂—, —CH(CH₃)—, —C(CH₃)₂—, —CH₂—CH₂— and

Most preferably Sp is —CH₂—.

Y⁰:

According to a first preferred embodiment of this invention Y⁰ is O or S, most preferably O.

According to a second preferred embodiment of this invention Y⁰ and L are covalently bonded to form a 5, 6, 7 or 8-membered mono- or a 8, 9, 10 or 11-membered bicyclic group which may contain 1, 2 or 3 heteroatoms selected from N, O and S, wherein the mono- or bicyclic group is optionally substituted with $R^{60}$.

In this second embodiment those compounds are preferred, wherein Y⁰ and L are covalently bonded to form an unsaturated 5 or 6-membered monocyclic group which may contain 1 or 2 heteroatoms selected from N, O and S, wherein the monocyclic group is optionally substituted with $R^{60}$. Most preferably said monocyclic group is a monocyclic aromatic or heteroaromatic group. Preferred examples of such (hetero) aromatic groups are phenyl, pyridine and thiazole, being optionally substituted as described.

Therefore preferred groups of the subformula

-continued

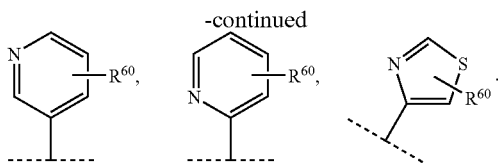

Beside said preferred first and second embodiment, $Y^0$ may also be $NR^{11}$ or $CR^{12}R^{13}$ wherein $R^{11}$, $R^{12}$, $R^{13}$ are defined as hereinbefore. Preferred meanings of $R^{11}$, $R^{12}$, $R^{13}$ are independently H or $C_{1-6}$alkyl; most preferably H or methyl.

L:

According to a first embodiment the group L has one of the following meanings:

a) $C_{1-6}$alkyl, $(C_{3-6})$cycloalkyl, $C_{1-6}$alkyl-$(C_{3-6})$cycloalkyl, $(C_{2-6})$alkenyl, all of which optionally substituted with $R^{60}$; or b) if $Y^0$ is $CR^{12}R^{13}$, then L may also be H; or c) if $Y^0$ is O then L may also be $OR^C$, wherein $R^C$ is optionally substituted with $R^{60}$, wherein $R^{12}$, $R^{13}$, $R^{60}$ and $R^C$ are as defined hereinbefore.

According to a preferred second embodiment, wherein $Y^0$ is O, S or $NR^{11}$, the group L has one of the following meanings:

a) L is $N(R^{N2})R^{N1}$, $NR^{N3}$—$N(R^{N2})R^{N1}$, $NR^{N3}$—$NR^{N2}$—CO—$R^C$, $NR^{N4}$—$NR^{N3}$—CO—$N(R^{N2})R^{N2}$, $NR^{N2}$—$SO_2$—$R^C$ or $N(R^{N2})OR^O$,
said $R^{N1}$, including any heterocycle or heterobicycle formed by $R^{N1}$, $R^{N2}$ and/or $R^{N3}$, and $R^C$ being optionally substituted with $R^{60}$; or b) L is $N(R^{5a})R^{6a}$ wherein $R^{5a}$ is defined as $R^{N2}$ and $R^{6a}$ is:

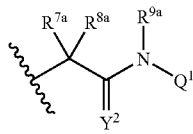

or $R^{6a}$ is:

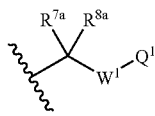

wherein $R^{7a}$ and $R^{8a}$ are each independently defined as $R^O$, wherein said $R^O$ is optionally substituted with $R^{60}$; or
$R^{7a}$ and $R^{8a}$ are covalently bonded together to form a second $(C_{3-7})$cycloalkyl or a 4, 5- or 6-membered heterocycle having from 1 to 3 heteroatom selected from O, N, and S; and either of $R^{7a}$ or $R^{8a}$ may be covalently bonded to $R^{5a}$ to form a nitrogen-containing 5- or 6-membered heterocycle, wherein said cycloalkyl or heterocycle being optionally substituted by $R^{150}$; and $W^1$ is selected from
a) a single bond;
b) —$CH_2$—;
c) —$CH_2$—$CH_2$—; and
d) —CH=CH—;

$Y^2$ is O or S;

$R^{9a}$ is defined as $R^O$, wherein said $R^O$ is optionally substituted with $R^{60}$; or
$R^{9a}$ is covalently bonded to either of $R^{7a}$ or $R^{8a}$ to form a 5- or 6-membered heterocycle;

$Q^1$ is aryl, Het, $(C_{1-6})$ alkyl-aryl, $(C_{1-6})$ alkyl-Het, $(C_{1-6})$ alkyl-CONH-aryl or $(C_{1-6})$ alkyl-CONH-Het, all of which being optionally substituted with $R^{60}$.

$Y^1$:

The group $Y^1$ is defined as O, S or $NR^{14}$, wherein $R^{14}$ is H or $(C_{1-6})$ alkyl; most preferably $Y^1$ is O.

Z:

Preferably the group Z is selected from the group of definitions:

a) $OR^O$;

c) $N(R^{N2})R^{N1}$;

g) $NR^{N2}$—$SO_2$—$R^C$;

h) $NR^{N3}$—$SO_2$—$N(R^{N2})R^{N1}$; or i) $NR^{N2}$—CO—$R^C$;

wherein $R^O$ and $R^C$ are optionally substituted with $R^{60}$; and said $R^{N1}$, including any heterocycle or heterobicycle formed by $R^{N1}$ and $R^{N2}$, being optionally substituted with $R^{60}$;

or Z is $OR^{6b}$ or $N(R^{5b})R^{6b}$ wherein $R^{5b}$ is defined as $R^{N2}$ and $R^{6b}$ is:

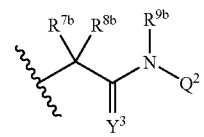

or $R^{6b}$ is:

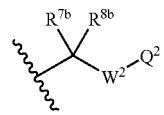

wherein $R^{7b}$, $R^{8b}$, $Y^3$, $R^{9b}$, $W^2$ are defined as $R^{7a}$, $R^{8a}$, $Y^2$, $R^{9a}$, $W^1$ respectively; and $Q^2$ is aryl, Het, $(C_{1-6})$ alkyl-aryl, $(C_{1-6})$ alkyl-Het, $(C_{1-6})$ alkyl-CONH-aryl or $(C_{1-6})$ alkyl-CONH-Het, all of which being optionally substituted with $R^{60}$ or $Q^2$ is $R^{160}$ or $Q^2$ is selected from the group consisting of O—$C_{1-4}$-alkyl, S—$C_{1-4}$-alkyl, $C_{1-4}$-alkyl, $C_{2-4}$-alkenyl and $C_{2-4}$-alkynyl, all of which being optionally substituted with $R^{160}$.

In the case Z being defined as $OR^O$, $SO_2R^C$, $COOR^O$ or $OR^{6b}$, wherein $R^{6b}$ is defined as above, then $Y^1$ is preferably O.

Sp, $Y^0$, L, $Y^1$ and Z:

Those compounds according to this invention are preferred, wherein:

Sp is a spacer group selected from —$CH_2$—, —$CH(CH_3)$—, —$C(CH_3)_2$—, —$CH_2$—$CH_2$—

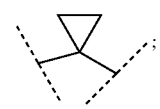

and most preferably Sp is —$CH_2$—; and
$Y^0$ is O or S; most preferably O;

L is $N(R^{N2})R^{N1}$, $NR^{N3}$—$N(R^{N2})R^{N1}$, $NR^{N3}$—$NR^{N2}$—CO—$R^C$, $NR^{N4}$—$NR^3$—CO—$N(R^{N2})R^{N1}$, $NR^2$—$SO_2$—$R^C$ or $N(R^{N1})OR^O$;

said $R^{N1}$, including any heterocycle or heterobicycle formed by $R^{N1}$, $R^{N2}$ and/or $R^{N3}$, and $R^C$ being optionally substituted with $R^{60}$; or L is $N(R^{5a})R^{6a}$ wherein $R^{5a}$ is defined as $R^{N2}$ and $R^{6a}$ is:

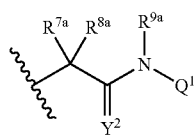

or $R^{6a}$ is:

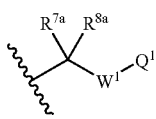

$Y^1$ is O or S; most preferably O;

Z is defined as
a) $OR^O$;
c) $N(R^{N2})R^{N1}$; or
g) $NR^{N2}$—$SO_2$—$R^C$;
wherein $R^O$ and $R^C$ are optionally substituted with $R^{60}$; and
said $R^{N1}$, including any heterocycle or heterobicycle formed by $R^{N1}$ and $R^{N2}$, being optionally substituted with $R^{60}$; or Z is $N(R^{5b})R^{6b}$ wherein $R^{5b}$ is defined as $R^{N2}$ and $R^{6b}$ is:

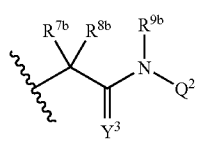

or $R^{6b}$ is:

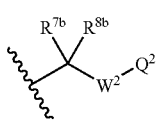

wherein $R^{7b}$, $R^{8b}$, $Y^3$, $R^{9b}$, $W^2$ are defined as $R^{7a}$, $R^{8a}$, $Y^2$, $R^{9a}$, $W^1$ respectively; and $Q^2$ is aryl, Het, $(C_{1-6})$ alkyl-aryl, $(C_{1-6})$ alkyl-Het, $(C_{1-6})$ alkyl-CONH-aryl or $(C_{1-6})$ alkyl-CONH-Het, all of which being optionally substituted with $R^{60}$
or $Q^2$ is $R^{160}$
or $Q^2$ is selected from the group consisting of O—$C_{1-4}$-alkyl, S—$C_{1-4}$-alkyl, $C_{1-4}$-alkyl, $C_{2-4}$-alkenyl and $C_{2-4}$-alkynyl, all of which being optionally substituted with $R^{160}$.

In the following, preferred groups of compounds according to this invention are described more specifically.

A first group of preferred compounds according to this invention is defined by formula I.1a

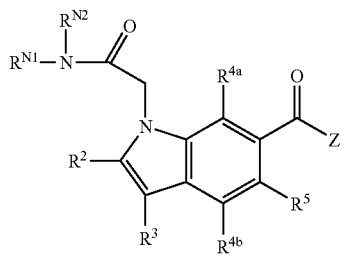

wherein $R^{N1}$, including any heterocycle formed by $R^{N1}$ and $R^{N2}$, is optionally substituted with $R^{60}$; and Z is defined as
a) $OR^O$;
c) $N(R^{N2})R^{N1}$; or
g) $NR^{N2}$—$SO_2$—$R^C$;
wherein $R^O$ and $R^C$ are optionally substituted with $R^{60}$; and
said $R^{N1}$, including any heterocycle or heterobicycle formed by $R^{N1}$ and $R^{N2}$, being optionally substituted with $R^{60}$; or Z is $N(R^{5b})R^{6b}$ wherein $R^{5b}$ is defined as $R^{N2}$ and $R^{6b}$ is:

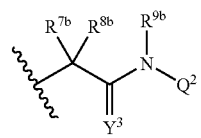

or $R^{6b}$ is:

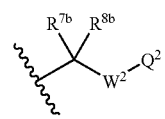

wherein $R^{7b}$, $R^{8b}$, $Y^3$, $R^{9b}$, $W^2$ are defined as $R^{7a}$, $R^{8a}$, $Y^2$, $R^{9a}$, $W^1$ respectively; and $Q^2$ is aryl, Het, $(C_{1-6})$ alkyl-aryl, $(C_{1-6})$ alkyl-Het, $(C_{1-6})$ alkyl-CONH-aryl or $(C_{1-6})$ alkyl-CONH-Het, all of which being optionally substituted with $R^{60}$
or $Q^2$ is $R^{160}$
or $Q^2$ is selected from the group consisting of O—$C_{1-4}$-alkyl, S—$C_{1-4}$-alkyl, $C_{1-4}$-alkyl, $C_{2-4}$-alkenyl and $C_{2-4}$-alkynyl, all of which being optionally substituted with $R^{160}$.

A second group of preferred compounds according to this invention is defined by formula I.1b

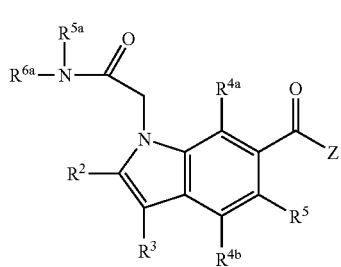

wherein
R$^{5a}$ is defined as R$^{N2}$;
R$^{6a}$ is defined as

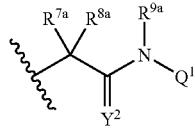

or R$^{6a}$ is:

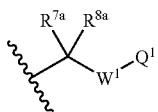

wherein R$^{7a}$, R$^{8a}$, Y$^2$, R$^{9a}$, Q$^1$, W$^1$ are defined as hereinbefore;

Z is defined as
a) OR$^O$;
c) N(R$^{N2}$)R$^{N1}$; or
g) NR$^2$—SO$_2$—R$^C$;
wherein R$^O$ and R$^C$ are optionally substituted with R$^{60}$; and
said R$^{N1}$, including any heterocycle or heterobicycle formed by R$^{N1}$ and R$^{N2}$, being optionally substituted with R$^{60}$; or
Z is N(R$^{5b}$)R$^{6b}$ wherein R$^{5b}$ is defined as R$^{N2}$ and R$^{6b}$ is:

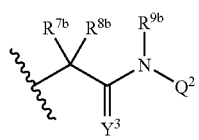

or R$^{6b}$ is:

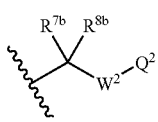

wherein R$^{7b}$, R$^{8b}$, Y$^3$, R$^{9b}$, W$^2$ are defined as R$^{7a}$, R$^{8a}$, Y$^2$, R$^{9a}$, W$^1$ respectively; and Q$^2$ is aryl, Het, (C$_{1-6}$) alkyl-aryl, (C$_{1-6}$) alkyl-Het, (C$_{1-6}$) alkyl-CONH-aryl or (C$_{1-6}$) alkyl-CONH-Het, all of which being optionally substituted with R$^{60}$
or Q$^2$ is R$^{160}$
or Q$^2$ is selected from the group consisting of O—C$_{1-4}$-alkyl, S—C$_{1-4}$-alkyl, C$_{1-4}$-alkyl, C$_{2-4}$-alkenyl and C$_{2-4}$-alkynyl, all of which being optionally substituted with R$^{160}$.

A third group of preferred compounds according to this invention is defined by formula I.1c

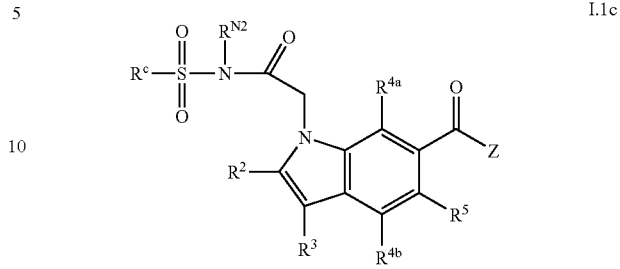

wherein R$^C$ is optionally substituted with R$^{60}$; and
Z is defined as
a) OR$^O$;
c) N(R$^{N2}$)R$^{N1}$; or
g) NR$^{N2}$—SO$_2$—R$^C$;
wherein R$^O$ and R$^C$ are optionally substituted with R$^{60}$; and said R$^{N1}$, including any heterocycle or heterobicycle formed by R$^{N1}$ and R$^{N2}$, being optionally substituted with R$^{60}$; or
Z is N(R$^{5b}$)R$^{6b}$ wherein R$^{5b}$ is defined as R$^{N2}$ and R$^{6b}$ is:

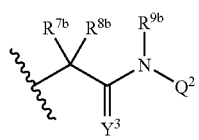

or R$^{6b}$ is:

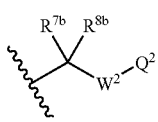

wherein R$^{7b}$, R$^{8b}$, Y$^3$, R$^{9b}$, W$^2$ are defined as R$^{7a}$, R$^{8a}$, Y$^2$, R$^{9a}$, W$^1$ respectively; and Q$^2$ is aryl, Het, (C$_{1-6}$) alkyl-aryl, (C$_{1-6}$) alkyl-Het, (C$_{1-6}$) alkyl-CONH-aryl or (C$_{1-6}$) alkyl-CONH-Het, all of which being optionally substituted with R$^{60}$
or Q$^2$ is R$^{160}$
or Q$^2$ is selected from the group consisting of O—C$_{1-4}$-alkyl, S—C$_{1-4}$-alkyl, C$_{1-4}$-alkyl, C$_{2-4}$-alkenyl and C$_{2-4}$-alkynyl, all of which being optionally substituted with R$^{160}$.

A fourth group of preferred compounds according to this invention is defined by formula I.1d wherein
L is selected from OR$^C$, NR$^{N3}$—N(R$^{N2}$)R$^{N1}$, NR$^{N3}$—NR$^{N2}$—CO—R$^C$, NR$^{N4}$, —NR$^{N3}$—CO—N(R$^{N2}$)R$^{N1}$ or N(R$^{N1}$)OR$^O$;
said R$^{N1}$, including any heterocycle or heterobicycle formed by R$^{N1}$, R$^{N2}$ and/or R$^{N3}$, and R$^C$ being optionally substituted with R$^{60}$;
Z is defined as
a) OR$^O$;
c) N(R$^{N2}$)R$^{N1}$; or
g) NR$^{N2}$—SO$_2$—R$^C$;
wherein R$^O$ and R$^C$ are optionally substituted with R$^{60}$; and
said R$^{N1}$, including any heterocycle or heterobicycle formed by R$^{N1}$ and R$^{N2}$, being optionally substituted with R$^{60}$; or
Z is N(R$^{5b}$)R$^{6b}$ wherein R$^{5b}$ is defined as R$^{N2}$ and R$^{6b}$ is:

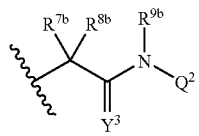

or R$^{6b}$ is:

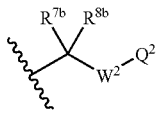

wherein R$^{7b}$, R$^{8b}$, Y$^3$, R$^{9b}$, W$^2$ are defined as R$^{7a}$, R$^{8a}$, Y$^2$, R$^{9a}$, W$^1$ respectively; and
Q$^2$ is aryl, Het, (C$_{1-6}$) alkyl-aryl, (C$_{1-6}$) alkyl-Het, (C$_{1-6}$) alkyl-CONH-aryl or (C$_{1-6}$)alkyl-CONH-Het, all of which being optionally substituted with R$^{60}$
or Q$^2$ is R$^{160}$
or Q$^2$ is selected from the group consisting of O—C$_{1-4}$-alkyl, S—C$_{1-4}$-alkyl, C$_{1-4}$-alkyl, C$_{2-4}$-alkenyl alkenyl and C$_{2-4}$-alkynyl, all of which being optionally substituted with R$^{160}$.

In the following, those preferred definitions of the groups L and Z which were described as preferred hereinbefore are formulated in more detail.

L:

In the case Y$^0$ is O, S or NR$^{11}$, L is more preferably
N(R$^{N2}$)R$^{N1}$, NR$^{N3}$—N(R$^{N2}$)R$^{N1}$, NR$^{N3}$—NR$^{N2}$—CO—R$^C$, NR$^{N4}$—NR$^{N3}$—CO—N(R$^{N2}$)R$^{N1}$, NR$^{N2}$—SO$_2$—R$^C$ or N(R$^{N1}$)OR$^O$; wherein R$^{N2}$, R$^{N3}$, R$^{N4}$ are each independently H, methyl, (C$_{2-4}$)alkyl, (C$_{3-6}$)cycloalkyl or (C$_{1-3}$)alkyl-(C$_{3-6}$)cycloalkyl, all of which being optionally substituted with C$_{1-3}$-alkyl, halogen, carboxy or (C$_{1-4}$)alkoxycarbonyl; and/or wherein said alkyl, cycloalkyl or alkyl-cycloalkyl, but preferably not the C-atom thereof directly bonded to the N-atom, is optionally substituted with hydroxy, amino, —NH(C$_{1-4}$-alkyl), —N(C$_{1-4}$-alkyl)$_2$ and/or —O—(C$_{1-4}$-alkyl);

R$^{N1}$ is H, methyl, (C$_{2-6}$)alkyl, (C$_{3-6}$)cycloalkyl, (C$_{1-3}$)alkyl-(C$_{3-6}$)cycloalkyl, benzyl, (C$_{2-4}$)alkyl-phenyl, phenyl, Het or (C$_{1-4}$)alkyl-Het;

wherein all of said methyl, alkyl, and cycloalkyl groups are optionally substituted with halogen, C$_{1-3}$-alkyl, carboxy or (C$_{1-4}$)alkoxycarbonyl, CONH$_2$, CONH(C$_{1-4}$-alkyl), CON(C$_{1-4}$-alkyl)$_2$; and/or wherein all of said alkyl, and cycloalkyl groups, but preferably not the C-atom thereof directly bonded to the N-atom, are optionally substituted with hydroxy, amino, —NH(C$_{1-4}$-alkyl), —N(C$_{1-4}$-alkyl)$_2$ and/or —O—(C$_{1-4}$-alkyl); and in the case a) of a group N(R$^{N2}$)R$^{N1}$ the substituents R$^{N1}$ and R$^{N2}$ or b) of a group NR$^{N3}$—N(R$^{N2}$)R$^{N1}$ the substituents R$^{N1}$ and R$^{N3}$ or R$^{N1}$ and R$^{N2}$ may be covalently bonded together to form a 5-, 6- or 7-membered saturated or unsaturated heterocycle which may have additionally 1 or 2 heteroatoms or a 8-, 9-, 10- or 11-membered saturated or unsaturated heterobicycle which may have additionally from 1, 2 or 3 heteroatoms, whereby the heteroatoms are selected from O, N, and S; and wherein Het is a 4-, 5-, 6- or 7-membered, preferably 5- or 6-membered, monocyclic group which contains 1 or 2 heteroatoms selected from N, O and S, wherein a benzene ring may be fused to the monocyclic group; and wherein said phenyl group, heterocycle, heterobicycle or Het is optionally substituted by 1 to 4 substituents independently selected from:
1 to 3 substituents selected from halogen;
one of each substituent selected from: NO$_2$, cyano, azido; and
1 to 3 substituents selected from: (C$_{1-4}$)alkyl, hydroxy, O—(C$_{1-4}$)alkyl, amino, —COOH, —COO(C$_{1-4}$)alkyl, CONH$_2$, CONH(C$_{1-4}$-alkyl), CON(C$_{1-4}$-alkyl)$_2$, —NH(C$_{1-4}$-alkyl N-pyrrolidinyl, N-piperidinyl, N-morpholinyl, N-thiomorpholinyl, N-piperazinyl, —(C$_{1-4}$)alkyl-OH, —(C$_{1-4}$)alkyl-O—(C$_{1-4}$)alkyl, —(C$_{1-4}$)alkyl-COOH, —(C$_{1-4}$)alkyl-COO(C$_{1-4}$)alkyl, —(C$_{1-4}$—CONH$_2$, —(C$_{1-4}$)alkyl-CONH(C$_{1-4}$-alkyl), —(C$_{1-4}$)alkyl-CON(C$_{1-4}$-alkyl)$_2$, —(C$_{1-4}$)alkyl-amino, —(C$_{1-4}$)alkyl-NH(C$_{1-4}$-alkyl), —(C$_{1-4}$)alkyl-N(C$_{1-4}$-alkyl)$_2$, wherein the alkyl-groups may be substituted with halogen; and wherein the N-piperazinyl-group may be N-substituted with C$_{1-4}$-alkyl, (C$_{3-6}$)cycloalkyl or (C$_{1-3}$)alkyl-(C$_{3-6}$)cycloalkyl.

In the above described preferred case, wherein Y$^0$ is O, S or NR$^{11}$ and L is N(R$^{N2}$)R$^{N1}$ the substituents have most preferably the following meanings:

R$^{N2}$ is H, methyl, (C$_{2-4}$)alkyl, (C$_{3-6}$)cycloalkyl or (C$_{1-3}$)alkyl-(C$_{3-6}$)cycloalkyl, all of being optionally substituted with C$_{1-3}$-alkyl, halogen, carboxy or (C$_{1-4}$)alkoxycarbonyl; and/or wherein said alkyl, cycloalkyl or alkyl-cycloalkyl, but preferably not the C-atom thereof directly bonded to the N-atom, is optionally substituted with hydroxy, amino, —NH(C$_{1-4}$-alkyl), —N(C$_{1-4}$-alkyl)$_2$ and/or —O—(C$_{1-4}$-alkyl);

R$^{N1}$ is methyl, (C$_{2-6}$)alkyl, (C$_{3-7}$)cycloalkyl, (C$_{1-3}$)alkyl-(C$_{3-7}$)cycloalkyl, benzyl, (C$_{2-4}$)alkyl-phenyl, Het and (C$_{1-4}$)alkyl-Het; wherein the methyl and alkyl groups are optionally substituted with C$_{1-3}$-alkyl, halogen, carboxy or (C$_{1-4}$)alkoxycarbonyl, CONH$_2$, CONH(C$_{1-4}$-alkyl), CON(C$_{1-4}$-alkyl)$_2$; and/or wherein said alkyl, but preferably not the C-atom thereof directly bonded to the N-atom, is optionally substituted with hydroxy, amino, —NH(C$_{1-4}$-alkyl), —N(C$_{1-4}$-alkyl)$_2$ and/or —O—(C$_{1-4}$-alkyl); and wherein Het is a saturated or unsaturated 4-, 5-, 6- or 7-membered, preferably 5- or 6-membered, monocyclic group which contains 1 or 2 heteroatoms selected from N, O and S, wherein a benzene ring may be fused to the monocyclic group; and wherein said phenyl group, heterocycle, heterobicycle or Het is optionally substituted by 1 to 4 substituents independently selected from:
1 to 3 substituents selected from halogen;
one of each substituent selected from: $NO_2$, cyano, azido; and
1 to 3 substituents selected from: $(C_{1-4})$alkyl, hydroxy, O—$(C_{1-4})$alkyl, amino, —COOH, —COO$(C_{1-4})$alkyl, $CONH_2$, CONH$(C_{1-4}$-alkyl), CON$(C_{1-4}$-alkyl)$_2$, —NH$(C_{1-4}$-alkyl), —N$(C_{1-4}$-alkyl)$_2$, N-pyrrolidinyl, N-piperidinyl, N-morpholinyl, N-thiomorpholinyl, N-piperazinyl, —$(C_{1-4})$alkyl-OH, —$(C_{1-4})$alkyl-O—$(C_{1-4})$alkyl, —$(C_{1-4})$alkyl-COOH, —$(C_{1-4})$alkyl-COO$(C_{1-4})$alkyl, —$(C_{1-4})$alkyl-$CONH_2$, —$(C_{1-4})$alkyl-CONH$(C_{1-4}$-alkyl) —$(C_{1-4})$alkyl-CON$(C_{1-4}$-alkyl)$_2$, —$(C_{1-4})$alkyl-amino, —$(C_{1-4})$alkyl-NH$(C_{1-4}$-alkyl), —$(C_{1-4})$alkyl-N$(C_{1-4}$-alkyl)$_2$,
wherein the alkyl-groups may be substituted with halogen; and
wherein the N-piperazinyl-group may be N-substituted with $C_{1-4}$-alkyl, $(C_{3-6})$cycloalkyl or $(C_{1-3})$alkyl-$(C_{3-6})$cycloalkyl.

Both $R^{N2}$ and $R^{N1}$ may also be H, so that L is —$NH_2$.

According to the latter embodiment very preferred meanings for $R^{N2}$ are selected from H, methyl, ethyl, n-propyl, i-propyl, cyclopropyl and cyclopropylmethyl; in particular H and methyl; and $R^{N1}$ is selected from methyl, ethyl, n-propyl, i-propyl, 1-methylpropyl, 2-methylpropyl, $(C_{4-7})$cycloalkyl, $(C_{4-7})$cycloalkylmethyl-, $(C_{4-7})$cycloalkylethyl-, $(C_{4-7})$cycloalkenyl, $(C_{4-7})$cycloalkenylmethyl-, $(C_{4-7})$cycloalkenylethyl-, HCy-, HCy-methyl-, HCy-ethyl-, benzyl-, phenylethyl-, Hetaryl-methyl- and Hetaryl-ethyl-, wherein Hetaryl is an aromatic 5 or 6-membered monocyclic group which contains 1 or 2 heteroatoms selected from N, O and S; to which a benzene ring may be fused; and HCy is a 4-, 5-, 6- or 7-membered saturated or mono-unsaturated heterocyclic group which contains 1 or 2 heteroatoms selected from N, O, S; and wherein all $(C_{4-7})$cycloalkyl, $(C_{4-7})$cycloalkenyl, phenyl groups, Hetaryl and HCy are optionally substituted by 1 to 3 substituents independently selected from:
1 to 3 substituents selected from fluorine;
one of each substituent selected from: chlorine, bromine, $NO_2$, cyano; and
1 to 3 substituents selected from: methyl, ethyl, n-propyl, i-propyl, cyclopropyl, cyclobutyl, cyclopentyl, hydroxy, $C_{1-3}$-alkoxy, —COOH, —COO$(C_{1-3})$alkyl, $CONH_2$, CONH$(C_{1-3}$-alkyl), CON$(C_{1-3}$-alkyl)$_2$, amino, —NH$(C_{1-3}$-alkyl), —N$(C_{1-3}$-alkyl)$_2$; and the C-atom in α-position to the N-atom (of the group N$(R^{N2})R^{N1}$) is optionally substituted with methyl, $CH_2OH$, $CH_2NH_2$, $CH_2NH(C_{1-3}$-alkyl), $CH_2N(C_{1-3}$-alkyl)$_2$, carboxy, $(C_{1-3})$alkoxycarbonyl, $CONH_2$, CONH$(C_{1-3}$-alkyl), CON$(C_{1-3}$-alkyl)$_2$; and/or, preferably or, any C-atom in β-position to the N-atom (of the group N$(R^{N2})R^{N1}$) is optionally substituted with hydroxy, $C_{1-3}$-alkoxy, amino, —NH$(C_{1-3}$-alkyl) or —N$(C_{1-3}$-alkyl)$_2$.

According to this preferred embodiment preferred examples of the group L are:

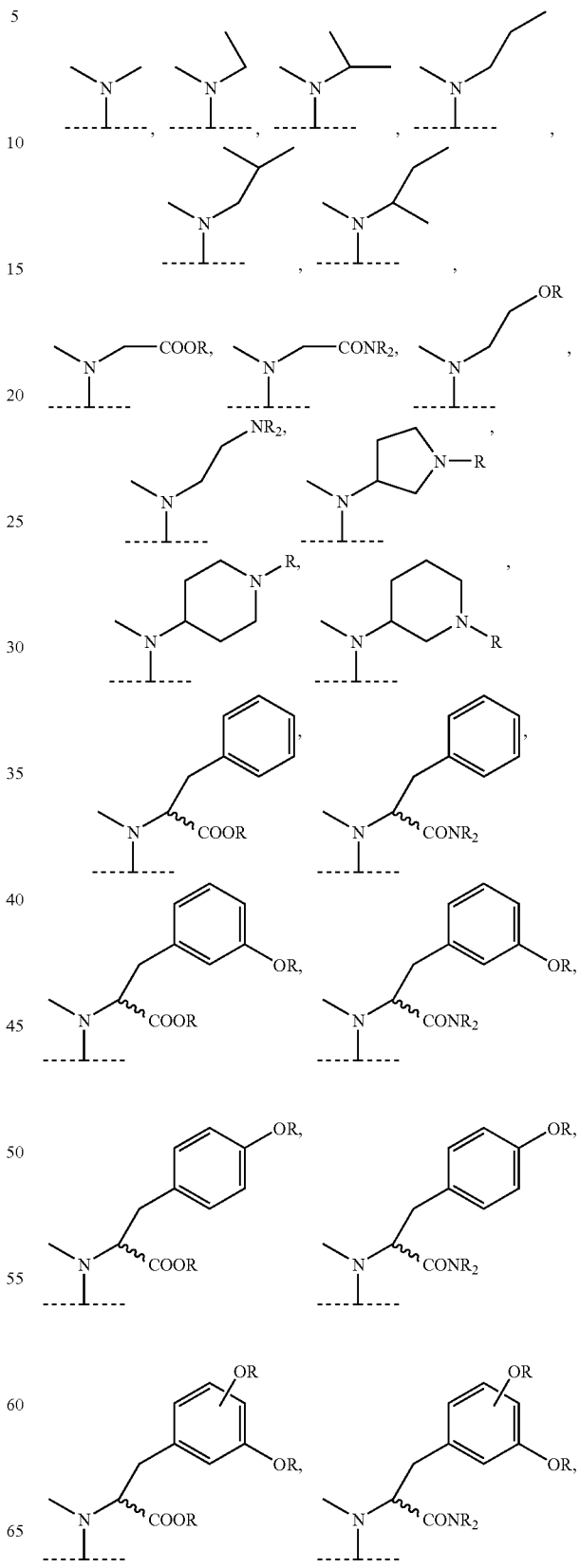

-continued

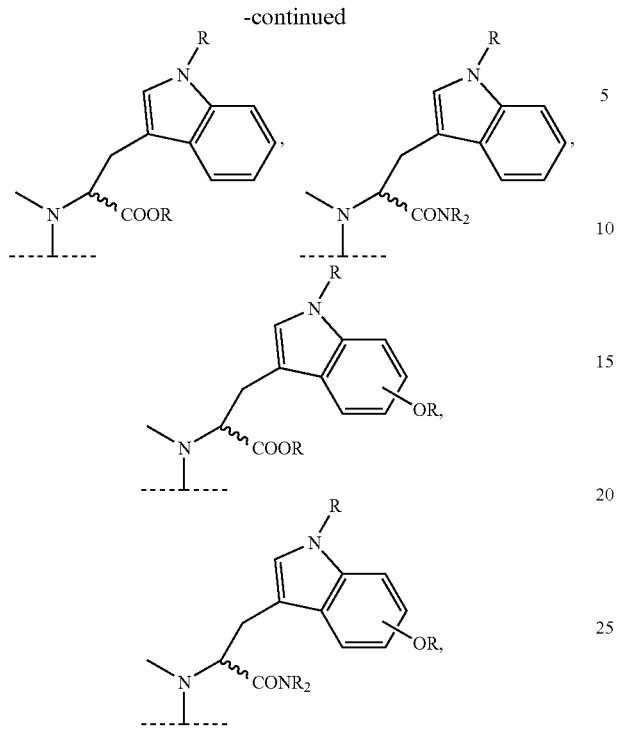

wherein each R is independently H, methyl, ethyl, n-propyl, i-propyl or cyclopropyl; most preferably H or methyl.

In the above described preferred case, wherein $Y^0$ is O, S or $NR^{11}$ and L is $N(R^{N2})R^{N1}$ wherein $R^{N2}$ and $R^{N1}$ are covalently bonded together to form a heterocycle, the following meanings are most preferred:

$R^{N2}$ and $R^{N1}$ are covalently bonded together to form a heterocycle selected from azetidine, pyrrolidine, piperidine, piperazine, morpholine, thiomorpholine, homopiperidine and homopiperazine;
  wherein said piperazine and homopiperazine may be N-substituted with $C_{1-4}$alkyl, $(C_{3-6})$cycloalkyl or $C_{1-4}$alkyl-$(C_{3-6})$cycloalkyl; and
  wherein said heterocycles are optionally monosubstituted by $(C_{3-6})$cycloalkyl, $(C_{1-3})$alkyl-$(C_{3-6})$cycloalkyl, HCy or $C_{1-3}$alkyl-HCy, wherein HCy is selected from azetidine, pyrrolidine, piperidine, piperazine, morpholine, thiomorpholine, homopiperidine and homopiperazine; and
  wherein said heterocycles, including an optional alkyl-, cycloalkyl- or alkylcycloalkyl-group and/or HCy or $C_{1-3}$alkyl-HCy group, are optionally substituted by 1 to 4 substituents independently selected from:
    1 to 3 substituents selected from halogen and $(C_{1-4})$alkyl;
    one of each substituent selected from: $NO_2$, cyano, azido; and
    1 or 2 substituents selected from: hydroxy, O—$(C_{1-4})$alkyl, amino, —COOH, —COO$(C_{1-4})$alkyl, $CONH_2$, $CONH(C_{1-4}$-alkyl), $CON(C_{1-4}$-alkyl$)_2$, —NH$(C_{1-6}$-alkyl), —N$(C_{1-6}$-alkyl$)_2$, —$(C_{1-4})$alkyl-OH, —$(C_{1-4})$alkyl-O—$(C_{1-4})$alkyl, —$(C_{1-4})$alkyl-COOH, —$(C_{1-4})$alkyl-COO$(C_{1-4})$alkyl, —$(C_{1-4})$alkyl-$CONH_2$, —$(C_{1-4})$alkyl-CONH$(C_{1-4}$-alkyl), —$(C_{1-4})$alkyl-CON$(C_{1-4}$-alkyl$)_2$, —$(C_{1-4})$alkyl-amino, —$(C_{1-4})$alkyl-NH$(C_{1-4}$-alkyl), —$(C_{1-4})$alkyl-N$(C_{1-4}$-alkyl$)_2$;

wherein said alkyl-groups may be substituted with halogen.

According to this preferred embodiment preferred examples of the group L are:

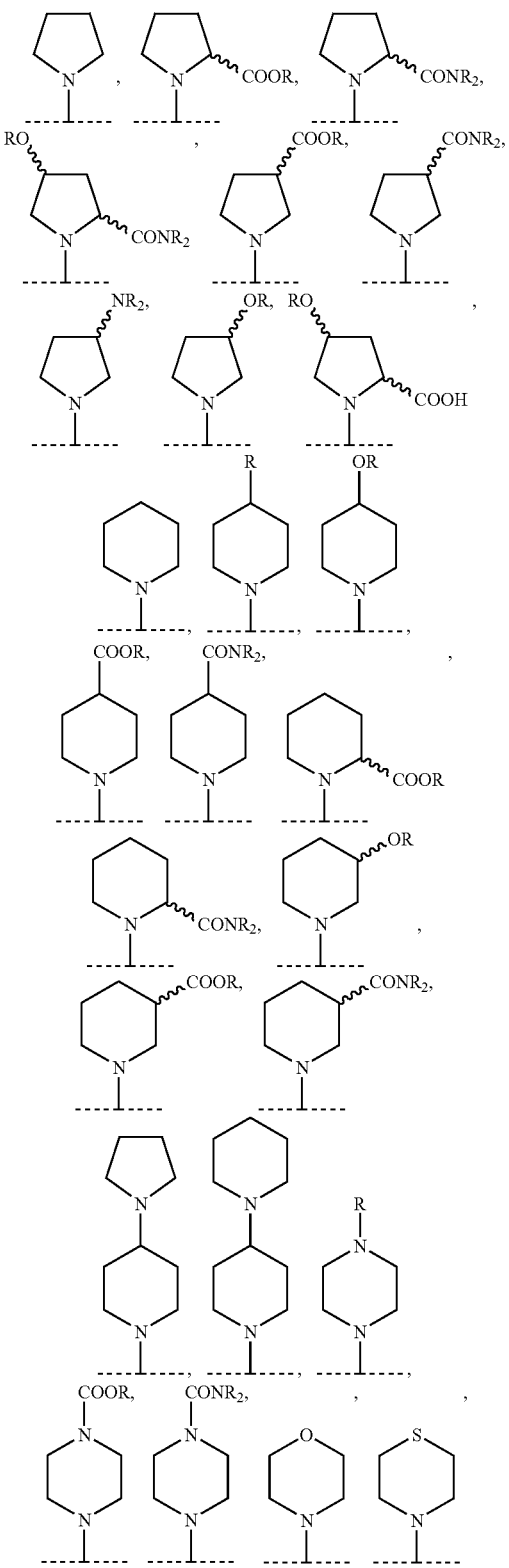

wherein each R is independently H, methyl, ethyl, n-propyl, i-propyl or cyclopropyl; most preferably H or methyl.

According to another preferred embodiment wherein $Y^O$ is O and L is $OR^{6a}$, or wherein $Y^O$ is O or S and L is $N(R^{5a})R^{6a}$, wherein $R^{5a}$ is defined as $R^{N2}$, and
$R^{6a}$ is defined according to the following subformula:

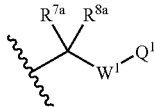

wherein
$R^{7a}$ is defined as H, COOH, $CONH_2$, $(C_{1-6})$alkyl, $(C_{3-6})$cycloalkyl, $(C_{1-4})$alkyl-$(C_{3-6})$cycloalkyl, $(C_{2-6})$alkenyl, aryl, Het, $(C_{1-4})$alkyl-aryl, $(C_{1-4})$alkyl-Het; all of which are optionally substituted with $R^{60}$; and
$R^{8a}$ is H or $(C_{1-4})$alkyl; or
$R^{7a}$ and $R^{8a}$ are covalently bonded together to form a $(C_{3-7})$ cycloalkyl or a 4, 5- or 6-membered heterocycle having from 1 to 3 heteroatom selected from O, N, and S; and
when L is $N(R^{5a})R^{6a}$, either of $R^{7a}$ or $R^{8a}$ may be covalently bonded to $R^{5a}$ to form a nitrogen-containing 5- or 6-membered heterocycle, wherein said cycloalkyl or heterocycle being optionally substituted by $R^{150}$; and
$W^1$ is selected from
a) a single bond;
b) —$CH_2$—;
c) —$CH_2$—$CH_2$—; and
d) —CH=CH—;
wherein the alkylene and alkenylene groups according to b), c) and d) may be substituted with $(C_{1-3})$ alkyl;
$Q^1$ is a group of the subformula IIIa

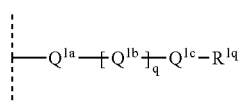

wherein
$Q^{1a}$ is aryl, Hetaryl, $(C_{1-3})$ alkyl-aryl or $(C_{1-3})$alkyl-Hetaryl;
$Q^{1b}$ is phenyl or Hetaryl;
$Q^{1c}$ is a bond, O—$C_{1-4}$-alkyl, S—$C_{1-4}$-alkyl, $C_{1-4}$-alkyl, $C_{2-4}$-alkenyl or $C_{2-4}$-alkynyl; and
$R^{1q}$ is selected from H, CN, $COOR^{161}$, $CON(R^{162})_2$, $SO_2N(R^{162})_2$, —$N(R^{162})_2$, $OR^{161}$, $SR^{161}$, —$NHCOR^{162}$, —NH—CO—$COOR^{161}$, —NH—CO—$CON(R^{162})_2$, $NHSO_2R^C$, $CONHSO_2R^C$, $SO_2NHCOR^C$, tetrazole, triazole and $CONHSO_2N(R^{162})_2$;
q is 0 or 1;
wherein each aryl, phenyl, Hetaryl, alkyl, alkenyl and/or alkynyl-groups is optionally substituted with $R^{160}$; and
wherein Hetaryl is an aromatic 5- or 6-membered heterocycle having 1 or 2 heteroatoms selected from O, N, and S, or a 8-, 9- or 10-membered aromatic heterobicycle having 1 to 4 heteroatoms selected from O, N, and S.

In another above described preferred case, wherein $Y^O$ is O and L is $OR^{6a}$, or wherein $Y^O$ is O or S and L is $N(R^{5a})R^{6a}$ wherein $R^{5a}$ is defined as $R^{N2}$, and $R^{6a}$ is defined as:

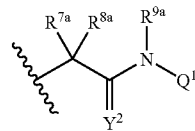

the substituents have most preferably one of the following meanings:
$R^{7a}$ and $R^{8a}$ are each independently defined as $R^O$, wherein said $R^O$ is optionally substituted with $R^{60}$; or
$R^{7a}$ and $R^{8a}$ are covalently bonded together to form a second $(C_{3-7})$cycloalkyl or a 4, 5- or 6-membered heterocycle having from 1 to 3 heteroatom selected from O, N, and S; and when L is $N(R^{5a})R^{6a}$, either of $R^{7a}$ or $R^{8a}$ may be covalently bonded to $R^{5a}$ to form a nitrogen-containing 5- or 6-membered heterocycle, wherein said cycloalkyl or heterocycle being optionally substituted by $R^{150}$; and
$Y^2$ is O or S;
$R^{9a}$ is defined as $R^O$, wherein said $R^O$ is optionally substituted with $R^{60}$; or
$R^{9a}$ is covalently bonded to either of $R^{7a}$ or $R^{8a}$ to form a 5- or 6-membered heterocycle;
$Q^1$ is a group of the subformula IIIa

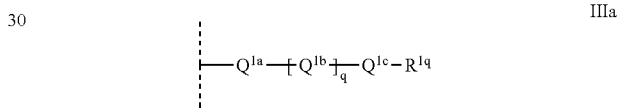

wherein
$Q^{1a}$ is aryl, Hetaryl, $(C_{1-3})$ alkyl-aryl or $(C_{1-3})$alkyl-Hetaryl;
$Q^{1b}$ is phenyl or Hetaryl;
$Q^{1c}$ is a bond, O—$C_{1-4}$-alkyl, S—$C_{1-4}$-alkyl, $C_{1-4}$-alkyl, $C_{2-4}$-alkenyl or $C_{2-4}$-alkynyl; and
$R^{1q}$ is selected from H, CN, $COOR^{161}$, $CON(R^{162})_2$, $SO_2N(R^{162})_2$, —$N(R^{162})_2$, $OR^{161}$, $SR^{161}$, —$NHCOR^{162}$, —NH—CO—$COOR^{161}$, —NH—CO—$CON(R^{162})_2$, $NHSO_2R^C$, $CONHSO_2R^C$, $SO_2NHCOR^C$, tetrazole, triazole and $CONHSO_2N(R^{162})_2$;
q is 0 or 1;

wherein each aryl, phenyl, Hetaryl, alkyl, alkenyl and/or alkynyl-groups is optionally substituted with $R^{160}$; and wherein Hetaryl is an aromatic 5- or 6-membered heterocycle having 1 or 2 heteroatoms selected from O, N, and S, or a 8-, 9- or 10-membered aromatic heterobicycle having 1 to 4 heteroatoms selected from O, N, and S.

Z:

According to one preferred embodiment Z is defined as $OR^O$, wherein $R^O$ is optionally substituted with $R^{60}$.

In this embodiment wherein Z is $OR^O$ the preferred meaning of
$R^O$ is H, $C_{1-4}$alkyl, $(C_{3-6})$cycloalkyl, $C_{1-3}$alkyl-$(C_{3-6})$cycloalkyl, $(C_{2-6})$alkenyl, $(C_{1-3}$alkyl)phenyl, $(C_{1-3})$alkyl-pyridinyl, wherein said alkyl, alkyl-cycloalkyl, cycloalkyl, alkenyl, alkyl-phenyl or alkyl-pyridinyl is optionally substituted with 1 to 3 substituents independently selected from:
1, 2 or 3 fluorine substituents; and
one of each substituent selected from chlorine, bromine, iodine, CN, nitro, $C_{1-4}$alkyl, $CF_3$, $COOR^{161}$, $SO_2R^{161}$, $OR^{161}$, $N(R^{162})_2$, $SO_2N(R^{162})_2$, $NR^{162}COR^{162}$ or $CON(R^{162})_2$, wherein $R^{161}$ and each $R^{162}$ is independently H, $(C_{1-4})$alkyl, $(C_{3-7})$cycloalkyl or $(C_{1-3})$alkyl-$(C_{3-7})$cycloalkyl; or both $R^{162}$ are covalently bonded together and to the nitrogen to which they are attached to form a 5, 6 or 7-membered saturated heterocycle.

A most preferred meaning of Z according to this embodiment is OH.

According to another preferred embodiment Z is defined as $N(R^{N2})R^{N1}$ wherein $R^{N1}$, including any heterocycle or heterobicycle formed by $R^{N1}$ and $R^{N2}$, is optionally substituted with $R^{60}$.

Preferred meanings of $R^{N1}$ and $R^{N2}$ in this embodiment are:

$R^{N2}$ is H, methyl, $(C_{2-4})$alkyl, $(C_{3-6})$cycloalkyl or $(C_{1-3})$alkyl-$(C_{3-6})$cycloalkyl, all of which being optionally substituted with $C_{1-3}$-alkyl, halogen, carboxy or $(C_{1-4})$alkoxycarbonyl; and/or wherein said alkyl, cycloalkyl or alkyl-cycloalkyl, but preferably not the C-atom thereof directly bonded to the N-atom, is optionally substituted with hydroxy, amino, —NH($C_{1-4}$-alkyl), —N($C_{1-4}$-alkyl)$_2$ and/or —O—($C_{1-4}$-alkyl); whereby $R^{N2}$ is most preferably H; and $R^{N1}$ is methyl, $(C_{2-6})$alkyl, $(C_{1-4})$alkyl-phenyl or $(C_{1-4})$alkyl-Het; wherein all of the methyl and alkyl groups are optionally substituted with $C_{1-3}$-alkyl, halogen, carboxy or $(C_{1-4})$alkoxycarbonyl, $CONH_2$, $CONH(C_{1-4}$-alkyl), $CON(C_{1-4}$-alkyl)$_2$; and/or wherein said alkyl, but preferably not the C-atom thereof directly bonded to the N-atom, is optionally substituted with hydroxy, amino, —NH($C_{1-4}$-alkyl), —N($C_{1-4}$-alkyl)$_2$ and/or —O—($C_{1-4}$-alkyl); and wherein Het is a 4-, 5-, 6- or 7-membered, preferably 5- or 6-membered, monocyclic group which contains 1 or 2 heteroatoms selected from N, O and S, wherein a benzene ring may be fused to the monocyclic group; and wherein said phenyl group, heterocycle, heterobicycle or Het is optionally substituted by 1 to 4 substituents independently selected from:

1 to 3 substituents selected from halogen;

one of each substituent selected from: $NO_2$, cyano, azido; and 1 to 3 substituents selected from: $(C_{1-4})$alkyl, hydroxy, O—$(C_{1-4})$alkyl, amino, —COOH, —COO($C_{1-4}$)alkyl, $CONH_2$, $CONH(C_{1-4}$-alkyl), $CON(C_{1-4}$-alkyl)$_2$, —NH($C_{1-4}$-alkyl), —N($C_{1-4}$-alkyl)$_2$, N-pyrrolidinyl, N-piperidinyl, N-morpholinyl, N-thiomorpholinyl, N-piperazinyl, —$(C_{1-4})$alkyl-OH, —$(C_{1-4})$alkyl-O—$(C_{1-4})$alkyl, —$(C_{1-4})$alkyl-COOH, —$(C_{1-4})$alkyl-COO($C_{1-4}$)alkyl, —$(C_{1-4})$alkyl-$CONH_2$, —$(C_{1-4})$alkyl-CONH($C_{1-4}$-alkyl), —$(C_{1-4})$alkyl-CON($C_{1-4}$-alkyl)$_2$, —$(C_{1-4})$alkyl-amino, —$(C_{1-4})$alkyl-NH($C_{1-4}$-alkyl), —$(C_{1-4})$alkyl-N($C_{1-4}$-alkyl)$_2$, wherein the alkyl-groups may be substituted with halogen; and wherein the N-piperazinyl-group may be N-substituted with $C_{1-4}$-alkyl, $C_{3-6}$-cycloalkyl or $C_{1-3}$-alkyl-$C_{3-6}$-cycloalkyl.

Most preferred meanings of $R^{N1}$ and $R^{N2}$ in this embodiment wherein Z is defined as $N(R^{N2})R^{N1}$ are:

$R^{N2}$ is H, methyl, ethyl, n-propyl, i-propyl, all of which being optionally substituted with methyl, fluorine, chlorine, carboxyl or methoxycarbonyl; and/or wherein said ethyl, n-propyl or i-propyl, but preferably not the C-atom thereof directly bonded to the N-atom, is optionally substituted with hydroxy, amino, —NH($CH_3$), —N($CH_3$)$_2$ and/or —O—($CH_3$);

$R^{N1}$ is methyl, ethyl, n-propyl, i-propyl, benzyl, phenylethyl, pyridinylmethyl or pyridinylethyl; wherein said methyl, ethyl, n-propyl, and i-propyl, groups are optionally substituted with fluorine, chlorine, methyl, ethyl, n-propyl, i-propyl, carboxy, methoxycarbonyl, $CONH_2$, $CONH(CH_3)$, $CON(CH_3)_2$; and/or wherein said ethyl, n-propyl or i-propyl, but preferably not the C-atom thereof directly bonded to the N-atom, is optionally substituted with hydroxy, amino, —NH($CH_3$), —N($CH_3$)$_2$ and/or —O—$CH_3$; and wherein said phenyl and pyridinyl group is optionally substituted by 1, 2 or 3 substituents independently selected from:

1, 2 or 3 substituents selected from halogen;

one of each substituent selected from: $NO_2$, cyano, azido; and 1, 2 or 3 substituents selected from: methyl, trifluoromethyl, ethyl, n-propyl, i-propyl, hydroxy, methoxy, ethoxy, —COOH, —$COOCH_3$, $CONH_2$, $CONH(CH_3)$, $CON(CH_3)_2$, amino, —NH($CH_3$), —N($CH_3$)$_2$, —$CH_2$—OH, —$CH_2$—O—$CH_3$, —$CH_2$—$NH_2$, —$CH_2$—N($CH_3$)$_2$ and —$(CH_2)_2$—OH.

In the latter embodiment $R^{N2}$ is preferably H, methyl or ethyl, most preferably H, and $R^{N1}$ is preferably benzyl or phenylethyl, both of which are optionally substituted with methyl, ethyl, n-propyl, i-propyl, fluorine, chlorine, carboxy, methoxycarbonyl, $CONH_2$, $CONH(CH_3)$, $CON(CH_3)_2$; and which at the phenyl group is optionally substituted with 1, 2 or 3 substituents independently selected from:

1, 2 or 3 substituents selected from halogen;

one of each substituent selected from: $NO_2$, cyano, azido; and 1, 2 or 3 substituents selected from: methyl, trifluoromethyl, ethyl, n-propyl, i-propyl, hydroxy, methoxy, ethoxy, —COOH, —$COOCH_3$, $CONH_2$, $CONH(CH_3)$, $CON(CH_3)_2$, amino, —NH($CH_3$), —N($CH_3$)$_2$, —$CH_2$—OH, —$CH_2$—O—$CH_3$, —$CH_2$—$NH_2$, —$CH_2$—N($CH_3$)$_2$ and —$(CH_2)_2$—OH.

Therefore most preferred meanings of Z according to this embodiment are:

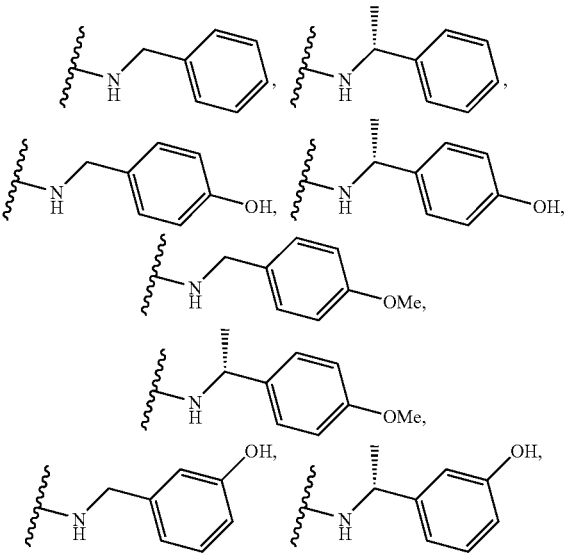

-continued

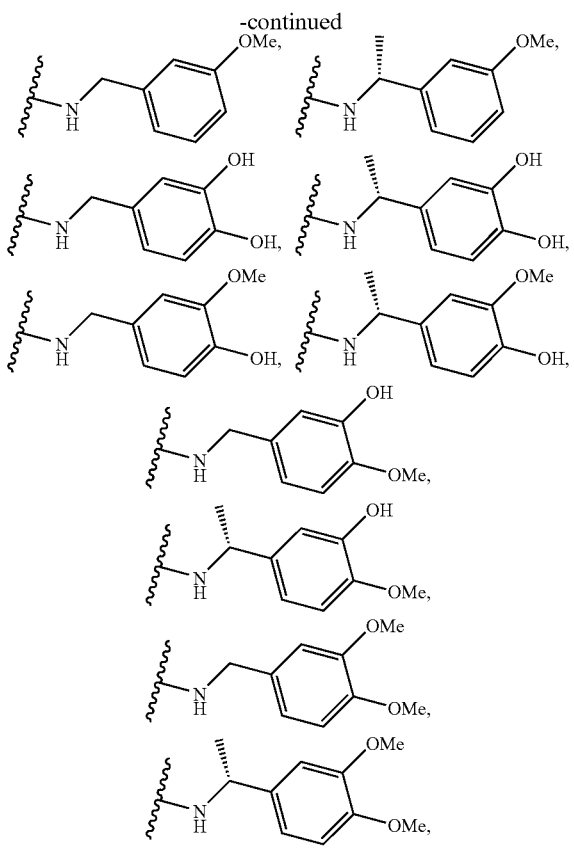

wherein those groups wherein the phenyl is substituted twice with OMe and/or OH are the very most preferred ones.

According to another preferred embodiment Z is defined as $NR^{N2}$—$SO_2$—$R^C$ or $NR^{N2}$—CO—$R^C$ wherein $R^{N2}$ and $R^C$ are preferably defined as follows:

$R^{N2}$ is H, $(C_{1-4})$alkyl, $(C_{3-6})$cycloalkyl or $(C_{1-3})$alkyl-$(C_{3-6})$cycloalkyl; in particular H; and $R^C$ is $(C_{1-6})$alkyl, $(C_{3-6})$cycloalkyl, $(C_{1-3})$alkyl-$(C_{3-6})$cycloalkyl, $(C_{2-6})$alkenyl, phenyl, naphthyl, Het, $(C_{1-3})$alkyl-phenyl, $(C_{1-3})$alkyl-naphthyl, $(C_{1-3})$alkyl-Het, wherein said alkyl, cycloalkyl, alkyl-cycloalkyl, alkenyl, phenyl, naphthyl, Het, alkyl-phenyl, alkyl-naphthyl, or alkyl-Het, are all optionally substituted with 1 to 4 substituents selected from $R^{60}$.

In this embodiment the preferred meaning of $R^C$ is methyl, ethyl, n-propyl, i-propyl, cyclopropyl, cyclobutyl, cyclopentyl, cyclopropylmethyl, cyclobutylmethyl, cyclopentylmethyl, pyrrolidine, piperidine, morpholine, thiomorpholine, piperazine, phenyl, naphthyl, benzyl, thiophene, furan, pyrrole, imidazole, pyrazole, oxazole, isoxazole, thiazole, pyridazine, pyrimidine, pyrazine, diazepine, azepine, quinoline, isoquinoline, benzofuran, benzothiophene, benzothiazole, purine, pteridine,

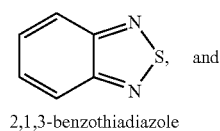
2,1,3-benzothiadiazole

-continued

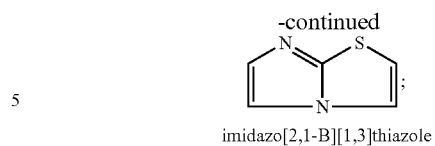
imidazo[2,1-B][1,3]thiazole all of which are optionally substituted with 1 to 3 substituents selected from $R^{60}$, particularly OH, CN, halogen, nitro, $(C_{1-3})$alkyl, $O(C_{1-3})$alkyl, carboxyl, $COO(C_{1-3})$alkyl, amino, $NH(C_{1-3})$alkyl, $N((C_{1-3})$alkyl$)_2$, $NHCO(C_{1-3})$alkyl, wherein the alkyl groups may be substituted by halogen.

According to another preferred embodiment wherein Z is $OR^{6b}$ or $N(R^{5b})R^{6b}$ wherein $R^{5b}$ is defined as $R^{N2}$ and $R^{6b}$ is:

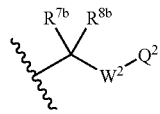

wherein $R^{7b}$ is defined as H, COOH, $CONH_2$, $(C_{1-6})$alkyl, $(C_{3-6})$cycloalkyl, $(C_{1-4})$alkyl-$(C_{3-6})$cycloalkyl, $(C_{2-6})$alkenyl, aryl, Het, $(C_{1-4})$alkyl-aryl, $(C_{1-4})$alkyl-Het; all of which are optionally substituted with $R^{60}$; and $R^{8b}$ is H or $(C_{1-4})$alkyl; or $R^{7b}$ and $R^{8b}$ are covalently bonded together to form a second $(C_{3-7})$cycloalkyl or a 4, 5- or 6-membered heterocycle having from 1 to 3 heteroatom selected from O, N and S; and when Z is $N(R^{5b})R^{6b}$, either of $R^{7b}$ or $R^{8b}$ may be covalently bonded to $R^{5b}$ to form a nitrogen-containing 5- or 6-membered heterocycle, wherein said cycloalkyl or heterocycle being optionally substituted by $R^{150}$; and $W^2$ is selected from
a) a single bond;
b) —$CH_2$—;
c) —$CH_2$—$CH_2$—; and
d) —CH=CH—;
wherein the alkylene and alkenylene groups according to b), c) and d) may be substituted with $(C_{1-3})$ alkyl;

$Q^2$ is a group of the subformula IIIb

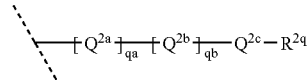

wherein $Q^{2a}$ is aryl, Hetaryl, $(C_{1-3})$ alkyl-aryl or $(C_{1-3})$alkyl-Hetaryl;

$Q^{2b}$ is phenyl or Hetaryl;

$Q^{2c}$ is a bond, O—$C_{1-4}$-alkyl, S—$C_{1-4}$-alkyl, $C_{1-4}$-alkyl, $C_{2-4}$-alkenyl or $C_{2-4}$-alkynyl, wherein said O—$C_{1-4}$-alkyl, S—$C_{1-4}$-alkyl, $C_{1-4}$-alkyl, $C_{2-4}$-alkenyl or $C_{2-4}$-alkynyl are optionally substituted with $R^{170}$;

wherein $R^{170}$ is defined as H or as 1, 2 or 3 substituents independently selected from:
1, 2, or 3 substituents selected from halogen;
one or two of each substituent selected from $(C_{1-4})$ alkyl, $(C_{1-4})$ alkoxy, $(C_{3-5})$ cycloalkyl, or cyano; wherein $(C_{1-4})$ alkyl may optionally be substituted with 1 to 3 halogen atoms;

and $R^{2q}$ is selected from H, CN, COOR$^{161}$, CON(R$^{162}$)$_2$, SO$_2$N(R$^{162}$)$_2$, —N(R$^{162}$)$_2$, OR$^{161}$, SR$^{161}$, —NHCOR$^{162}$, —NH—CO—COOR$^{161}$, —NH—CO—CON(R$^{162}$)$_2$, NHSO$_2$R$^C$, CONHSO$_2$R$^C$, SO$_2$NHCOR$^C$, tetrazole, triazole and CONHSO$_2$N(R$^{162}$)$_2$;

qa is 0 or 1;

qb is 0 or 1;

wherein each aryl, phenyl, Hetaryl, alkyl, alkenyl and/or alkynyl-groups is optionally substituted with R$^{160}$; and wherein Hetaryl is an aromatic 5- or 6-membered heterocycle having 1 or 2 heteroatoms selected from O, N, and S, or a 9- or 10-membered aromatic heterobicycle having 1 to 4 heteroatoms selected from O, N, and S.

Most preferably the index qa is 1.

In another above described preferred case, wherein Z is OR$^{6b}$ or N(R$^{5b}$)R$^{6b}$ wherein R$^{5b}$ is defined as R$^{N2}$ and R$^{6b}$ is:

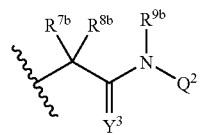

the substituents have most preferably one of the following meanings:

$R^{7b}$ and $R^{8b}$ are each independently defined as $R^O$, wherein said $R^O$ is optionally substituted with R$^{60}$; or $R^{7b}$ and $R^{8b}$ are covalently bonded together to form a ($C_{3-7}$) cycloalkyl or a 4, 5- or 6-membered heterocycle having from 1 to 3 heteroatom selected from O, N and S; or when Z is N(R$^{5b}$)R$^{6b}$, either of R$^{7b}$ or R$^{8b}$ may be covalently bonded to R$^{5b}$ to form a nitrogen-containing 5- or 6-membered heterocycle, wherein said cycloalkyl or heterocycle being optionally substituted by R$^{150}$; and $Y^3$ is O or S;

$R^{9b}$ is defined as $R^O$, wherein said $R^O$ is optionally substituted with R$^{60}$; or $R^{9b}$ is covalently bonded to either of R$^{7b}$ or R$^{8b}$ to form a 5- or 6-membered heterocycle;

$Q^2$ is a group of the subformula IIIb

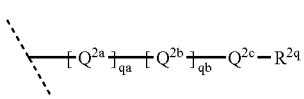

wherein $Q^{2a}$ is aryl, Hetaryl, ($C_{1-3}$) alkyl-aryl or ($C_{1-3}$)alkyl-Hetaryl;

$Q^{2b}$ is a phenyl or Hetaryl;

$Q^{2c}$ is a bond, O—$C_{1-4}$-alkyl, S—$C_{1-4}$-alkyl, $C_{1-4}$-alkyl, $C_{2-4}$-alkenyl or $C_{2-4}$-alkynyl, wherein said O—$C_{1-4}$-alkyl, S—$C_{1-4}$-alkyl, $C_{1-4}$-alkyl, $C_{2-4}$-alkenyl or $C_{2-4}$-alkynyl are optionally substituted with R$^{170}$ wherein R$^{170}$ is defined as H or as 1, 2 or 3 substituents independently selected from:
1, 2, or 3 substituents selected from halogen;
one or two of each substituent selected from ($C_{1-4}$) alkyl, ($C_{1-4}$) alkoxy, ($C_{3-5}$) cycloalkyl, or cyano; wherein ($C_{1-4}$) alkyl may optionally be substituted with 1 to 3 halogen atoms;

and $R^{2q}$ is selected from H, CN, COOR$^{161}$, CON(R$^{162}$)$_2$, SO$_2$N(R$^{162}$)$_2$, —N(R$^{162}$)$_2$, OR$^{161}$, SR$^{161}$, —NHCOR$^{162}$, —NH—CO—COOR$^{161}$, —NH—CO—CON(R$^{162}$)$_2$, NHSO$_2$R$^C$, CONHSO$_2$R$^C$, SO$_2$NHCOR$^C$, tetrazole, triazole and CONHSO$_2$N(R$^{162}$)$_2$;

qa is 0 or 1;

qb is 0 or 1;

wherein each aryl, phenyl, Hetaryl, alkyl, alkenyl and/or alkynyl-groups is optionally substituted with R$^{160}$; and wherein Hetaryl is an aromatic 5- or 6-membered heterocycle having 1 or 2 heteroatoms selected from O, N, and S, or a 9- or 10-membered aromatic heterobicycle having 1 to 4 heteroatoms selected from O, N, and S.

Most preferably the index qa is 1.

Hereinafter, preferred groups and substituents are described for those cases wherein either L or Z, or both L and Z are defined as follows:

L is OR$^{6a}$ or N(R$^{N2}$)R$^{6a}$ wherein R$^6$ is:

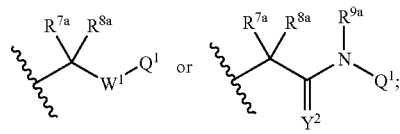

Z is OR$^{6b}$ or N(R$^{N2}$)R$^{6b}$ wherein R$^{6b}$ wherein R$^{6b}$ is:

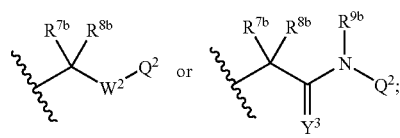

wherein $Q^1$ is defined as

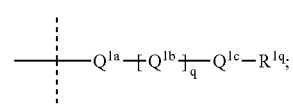

IIIa wherein $Q^2$ is defined as

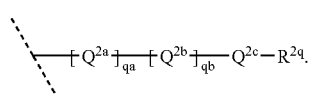

IIIb

Most preferably one of W$^1$ and W$^2$ or both W$^1$ and W$^2$ represent a single bond.

Preferred meanings of one of R$^{7a}$ and R$^{7b}$ or both R$^{7a}$ and R$^{7b}$ are H, COOH, CONH$_2$, CF$_3$, ($C_{1-4}$)alkyl, ($C_{3-7}$)cycloalkyl, ($C_{1-3}$)alkyl-($C_{3-7}$)cycloalkyl, Hetaryl or ($C_{1-3}$) alkyl-Hetaryl, wherein the alkyl, cycloalkyl groups and Hetaryl groups are optionally substituted with R$^{160}$.

Preferred meanings of one of R$^{8a}$ and R$^{8b}$ or both R$^{8a}$ and R$^{8b}$ are H and CH$_3$.

Furthermore, it is preferred that R$^{7a}$ and R$^{8a}$ and/or R$^{7b}$ and R$^{8b}$ are covalently bonded together to form a second ($C_{3-7}$) cycloalkyl or a 4, 5- or 6-membered heterocycle having from 1 to 2 heteroatom selected from O, N and S, wherein said cycloalkyl or heterocycle being optionally substituted with $R^{160}$, preferably with 1 to 3 substituents selected from hydroxy, $(C_{1-3})$alkyl, $CO(C_{1-3})$alkyl and $SO_2(C_{1-3})$alkyl.

According to the hereinbefore described embodiment $R^{7a}$ and $R^{7b}$ is each independently preferably selected from COOH, CONH$_2$, methyl, ethyl, n-propyl, i-propyl, 2-methylpropyl, hydroxy-methyl, 1-hydroxy-ethyl, amino-methyl, 1-amino-ethyl, 2-hydroxy-ethyl, 2-methylthio-ethyl, 2-amino-ethyl, 2-(dimethylamino)-ethyl and thiazolyl, wherein the thiazolyl group is optionally substituted with $R^{160}$; or $R^{7b}$ and $R^{8b}$ are covalently bonded together to form a cyclic group preferably selected from:

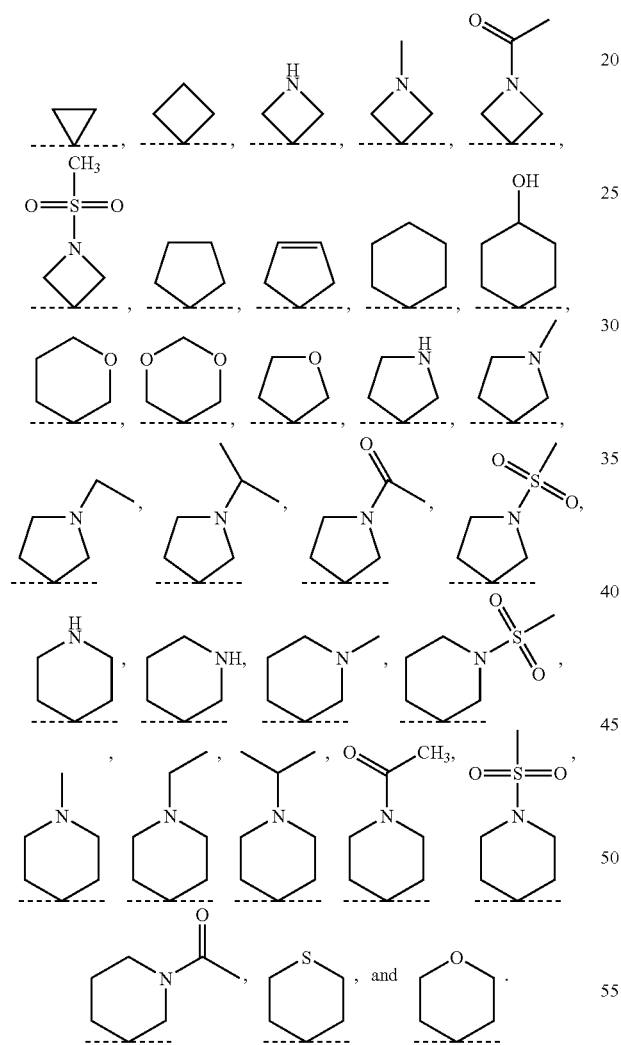

Most preferably, the groups $CR^{7a}R^{8a}$ and $CR^{7b}R^{8b}$ are independently selected from:

-continued

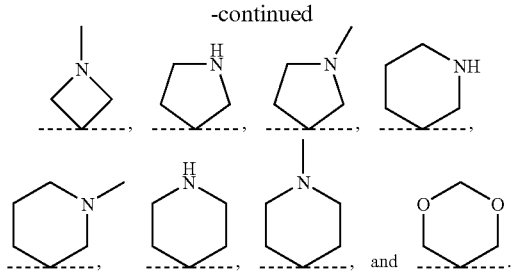

$R^{9a}$ and/or $R^{9b}$ is preferably H, $(C_{1-3}$alkyl), $(C_{3-6})$cycloalkyl or $(C_{1-3})$alkyl-$(C_{3-6})$cycloalkyl, all of which optionally substituted with 1 to 3 substituents selected from halogen, hydroxy and methyl; most preferably $R^{9a}$ and/or $R^{9b}$ is H or methyl.

Preferably $Q^{1a}$ and $Q^{2a}$ are independently selected from

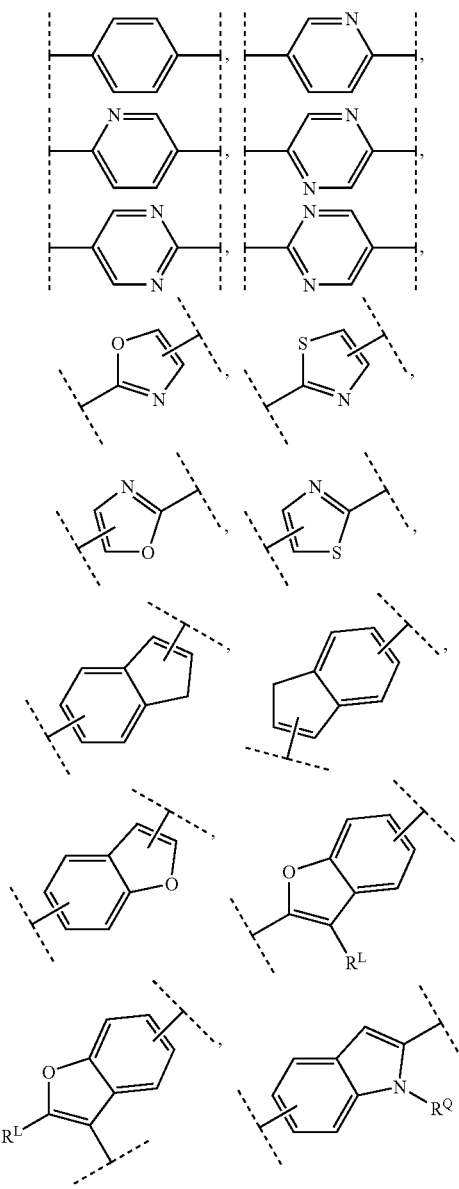

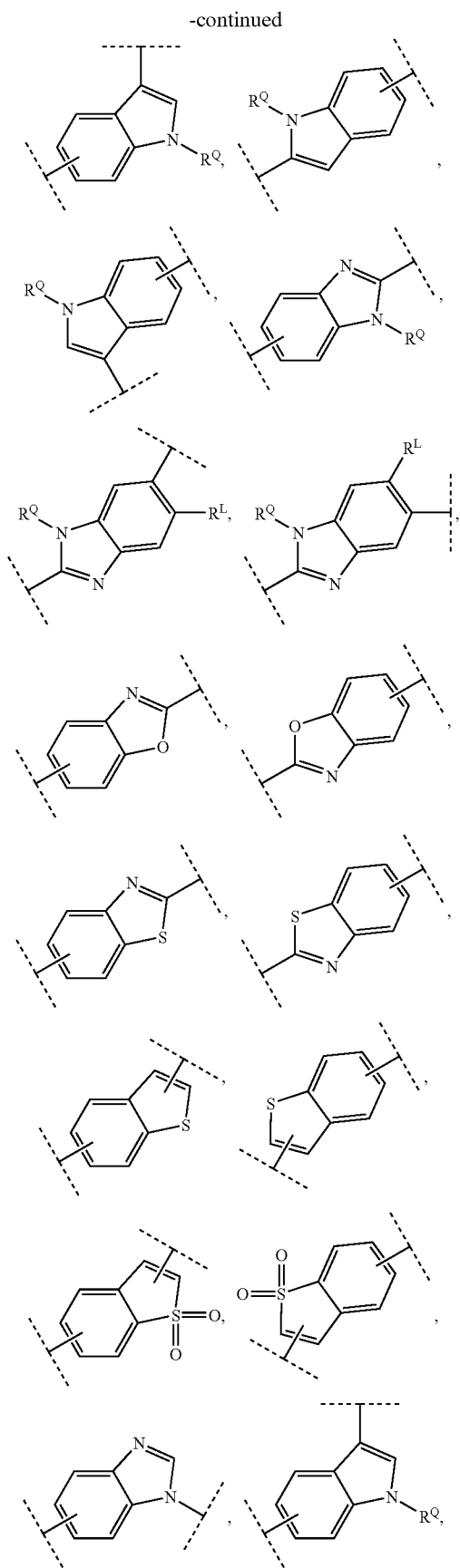

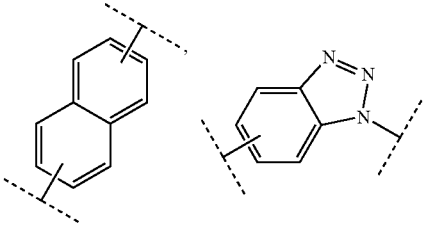

wherein 1 or 2 C-atoms of each cyclic group as listed above may be substituted with $R^{160}$;

$R^L$ is H, $(C_{1-4}$alkyl) or $(C_{1-4})$alkoxy, and $R^Q$ is H or $CH_3$, $(C_{2-6}$alkyl), —$CH_2$—$(C_{2-6}$alkenyl), —$CH_2$—$(C_{2-6}$alkynyl), $(C_{3-6})$cycloalkyl, $(C_{1-4})$alkyl-$(C_{3-6})$cycloalkyl; all of which being optionally substituted with $C_{1-6}$-alkyl, halogen, carboxy or $C_{1-6}$-alkoxycarbonyl; and/or wherein said alkyl, cycloalkyl or alkylcycloalkyl, but preferably not the C-atom thereof directly bonded to the N-atom, is optionally substituted with hydroxy, $C_{1-6}$-alkoxy, amino, —$NH(C_{1-4}$-alkyl) and/or —$N(C_{1-4}$-alkyl$)_2$;

Preferably $Q^{1b}$ and/or $Q^{2b}$ are selected from the group consisting of phenyl, furan, thiophene, oxazole, thiazole, pyridine, pyrimidine, pyrrazole, imidazole and pyrazine.

Most preferably $Q^{1b}$ and $Q^{2b}$ are independently selected from the group consisting of

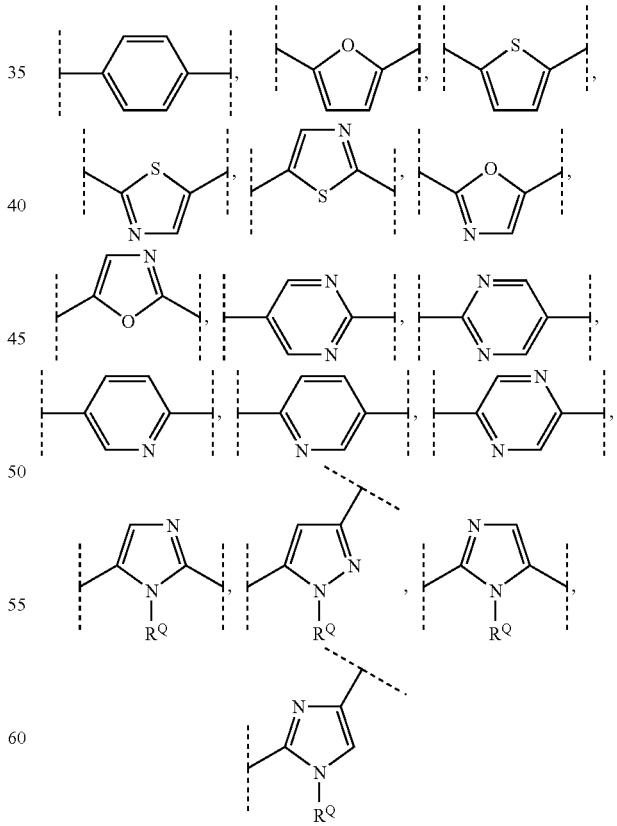

wherein all shown cyclic groups are optionally substituted with $R^{160}$.

$Q^{1c}$ and $Q^{2c}$ are preferably selected from a bond, —O—CH$_2$—, —CH$_2$—CH$_2$—, —C(R$^{170}$)=CH— and —CH=C(R$^{170}$)—;

most preferably selected from a bond and —CH=C(R$^{170}$)—, wherein R$^{170}$ is preferably selected from H, F, —CH$_3$, —CH$_2$CH$_3$, —CF$_3$ and cyclopropyl; most preferably selected from H, F, —CH$_3$ and —CH$_2$CH$_3$.

$R^{1q}$ and $R^{2q}$ are preferably selected from H, CN, COOR$^{161}$, CON(R$^{162}$)$_2$, SO$_2$N(R$^{162}$)$_2$, —N(R$^{162}$)$_2$, OR$^{161}$, —NH—COR$^{162}$, —NH—CO—COOR$^{161}$, —NH—CO—CON(R$^{162}$)$_2$, NHSO$_2$R$^C$, CONHSO$_2$R$^C$, SO$_2$NHCOR$^C$, tetrazole, triazole and CONHSO$_2$N(R$^{162}$)$_2$; most preferably selected from COOR$^{161}$, CON(R$^{162}$)$_2$ and SO$_2$N(R$^{162}$)$_2$; wherein R$^{161}$ and R$^{162}$ are as defined, but most preferably H and/or methyl.

In the case of L comprising the group Q$^1$ as defined hereinbefore, especially preferred compounds obey one of the following conditions a) Q$^{1a}$ is phenyl, q is 1 and Q$^{1c}$ is a bond;

b) Q$^{1a}$ is phenyl, q is 0 and Q$^{1c}$ is vinyl; or c) Q$^{1a}$ is a 9- or 10-membered aromatic heterobicycle having 1 or 2 heteroatoms selected from O, N and S, said heterobicycle optionally being substituted with R$^{160}$; q is 0 and Q$^{1c}$ is a bond, —CH$_2$—CH$_2$— or —CH=CH—.

Furthermore, those compounds of the above described embodiment are especially preferred wherein the group Q$^{1c}$-R$^{1q}$ is —CH=CH—COOH.

In the case of Z comprising the group Q$^2$ as defined hereinbefore, especially preferred compounds obey one of the following conditions:

a) qa is 1, Q$^{2a}$ is phenyl, qb is 1 and Q$^{2c}$ is a bond;

b) qa is 1, Q$^{2a}$ is phenyl, qb is 0 and Q$^{2c}$ is —CH=C(R$^{170}$)—, wherein R$^{170}$ is selected from H, F, —CH$_3$ or —CH$_2$CH$_3$; or c) qa is 1, Q$^{2a}$ is a 9- or 10-membered aromatic heterobicycle having 1 or 2 heteroatoms selected from O, N and S, said heterobicycle optionally being substituted with R$^{160}$; qb is 0 and Q$^{2c}$ is a bond, —CH$_2$—CH$_2$— or —CH=C(R$^{170}$)—, wherein R$^{170}$ is selected from H, F, —CH$_3$ or —CH$_2$CH$_3$.

Furthermore, those compounds of the above described embodiment are especially preferred wherein the group Q$^{2c}$-R$^{2q}$ is —CH=C(R$^{170}$)—COOH, wherein R$^{170}$ is selected from H, F, —CH$_3$ or —CH$_2$CH$_3$.

Preferably Q$^1$ and Q$^2$ are independently selected from:

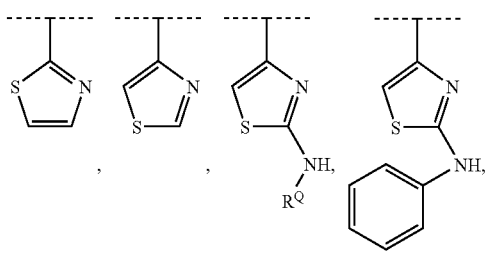

-continued

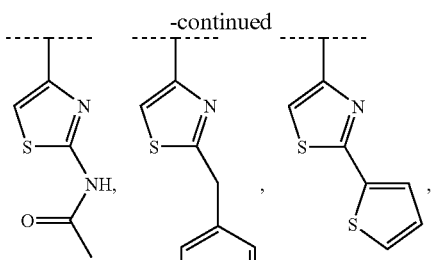

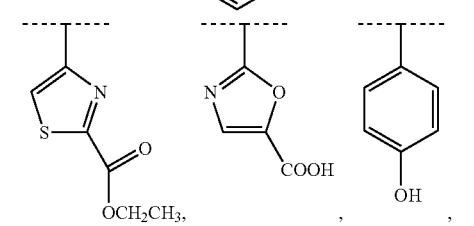

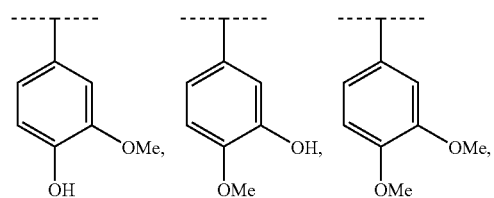

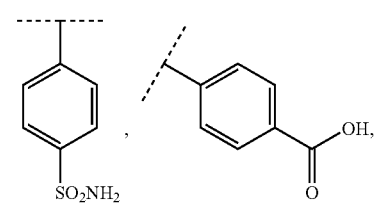

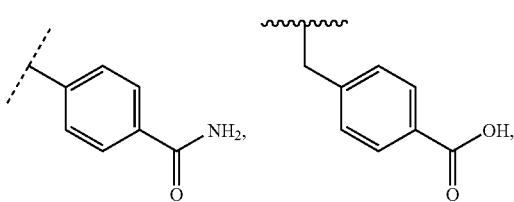

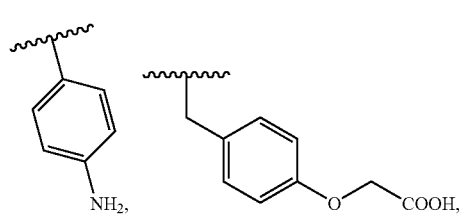

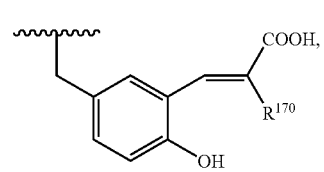

-continued
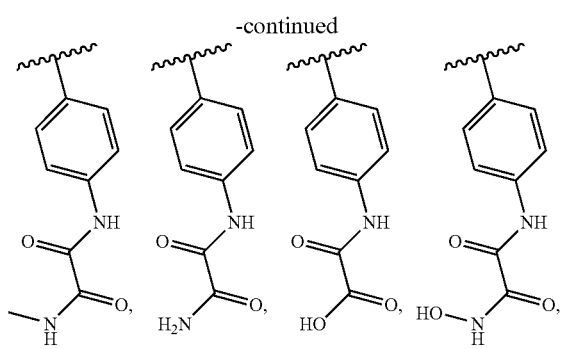
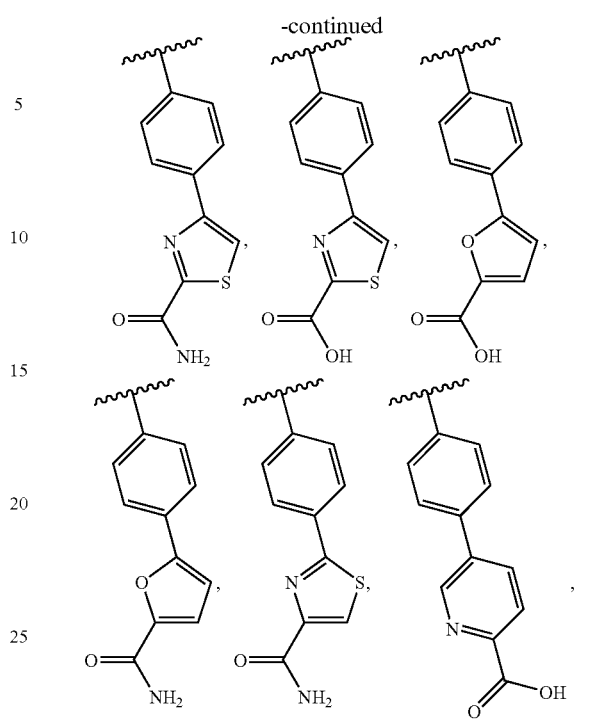
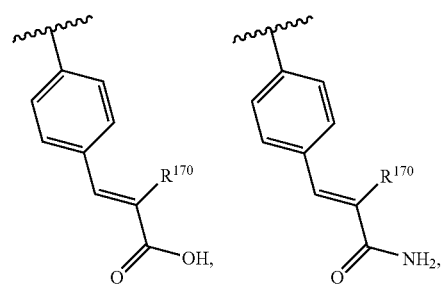
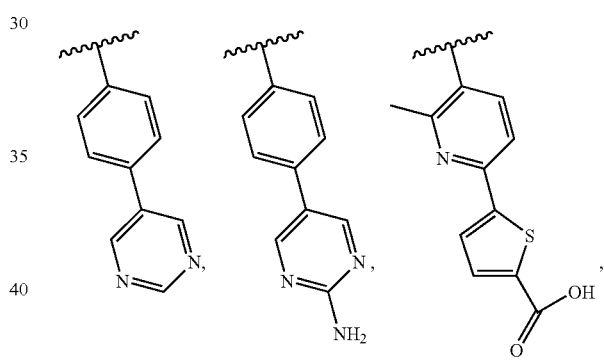
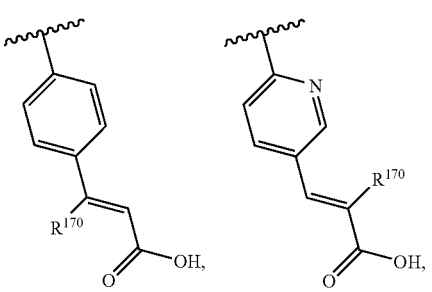
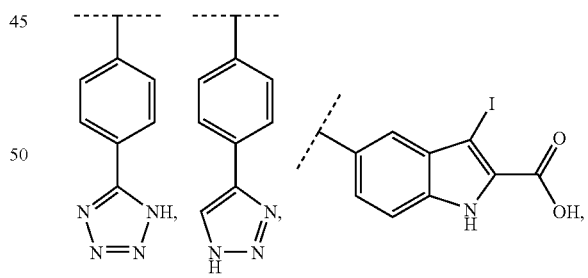
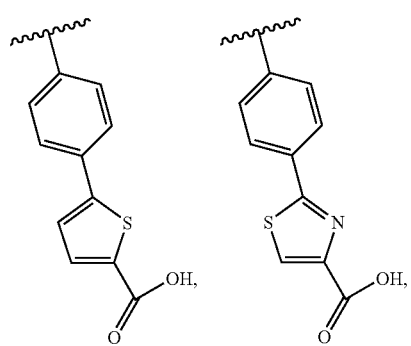
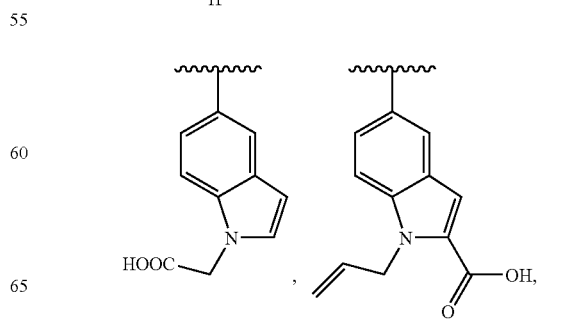

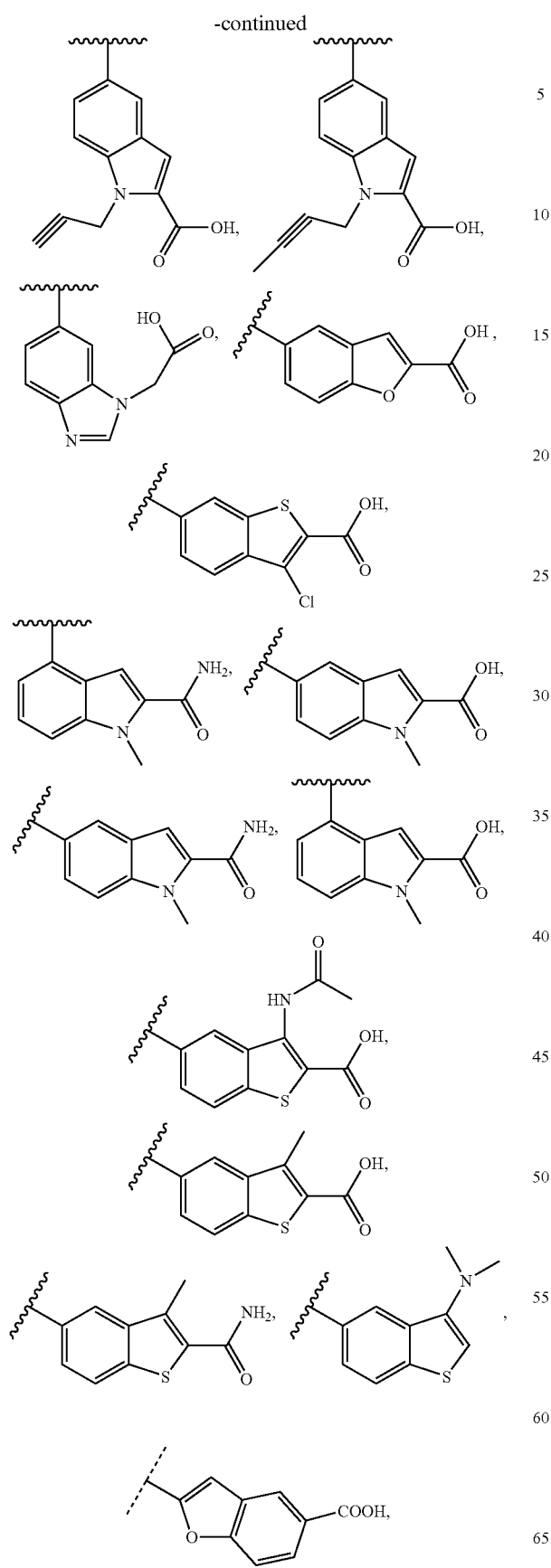
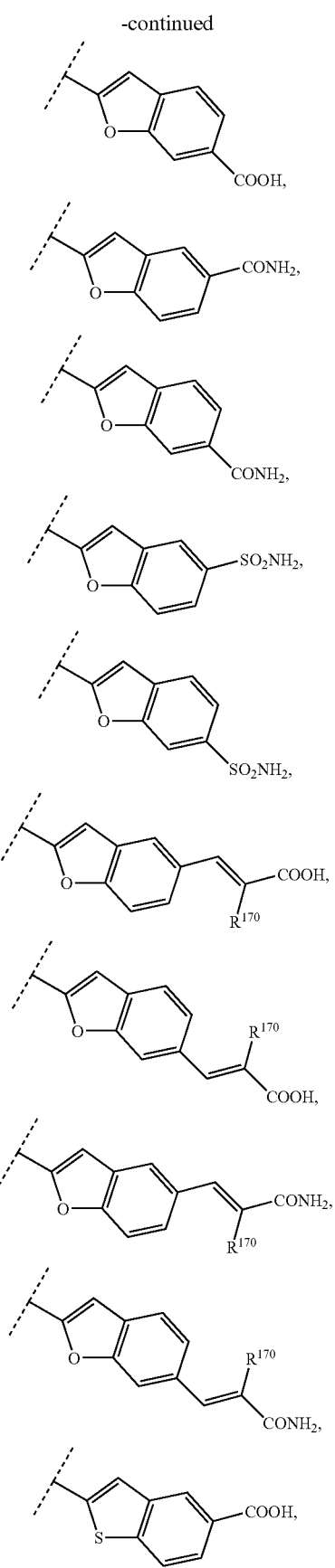

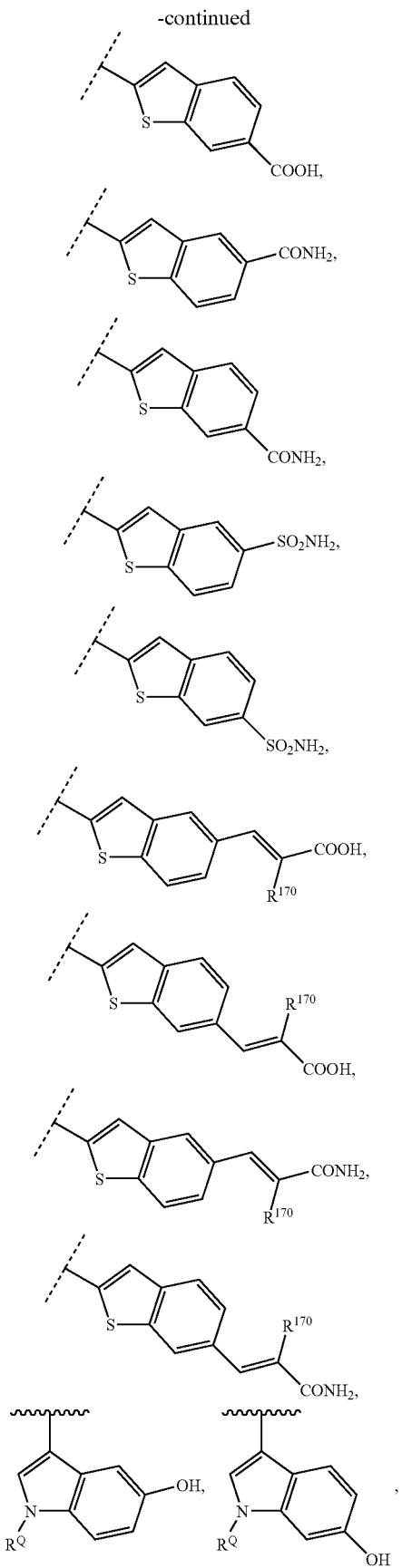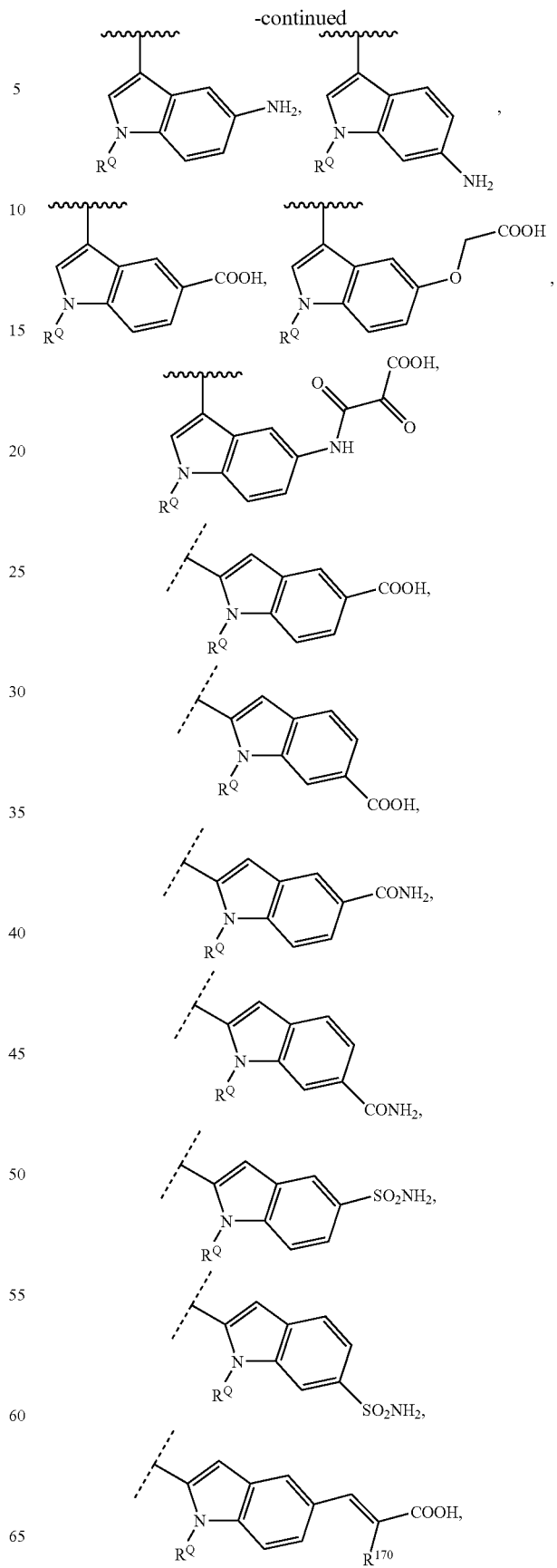

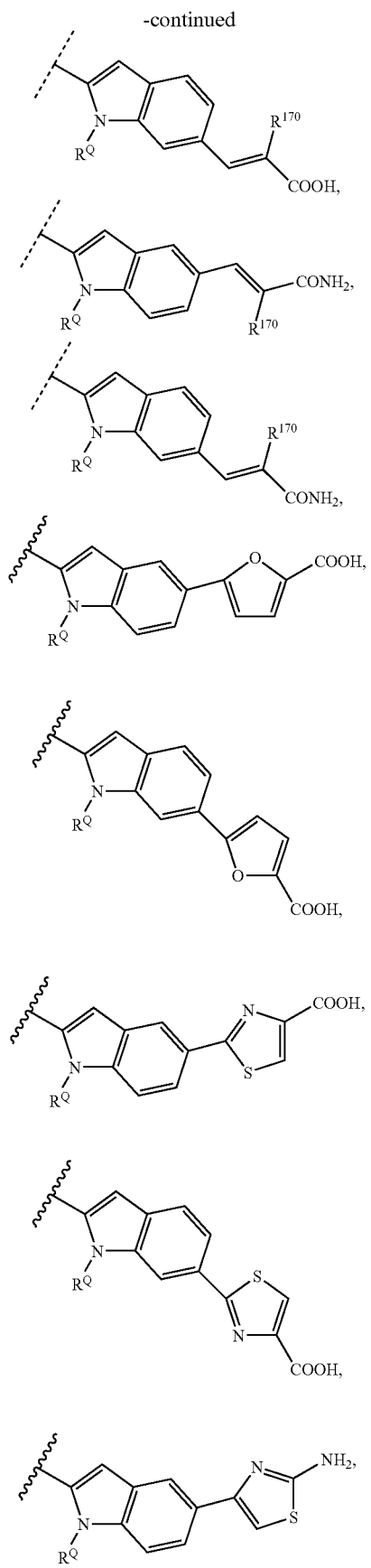
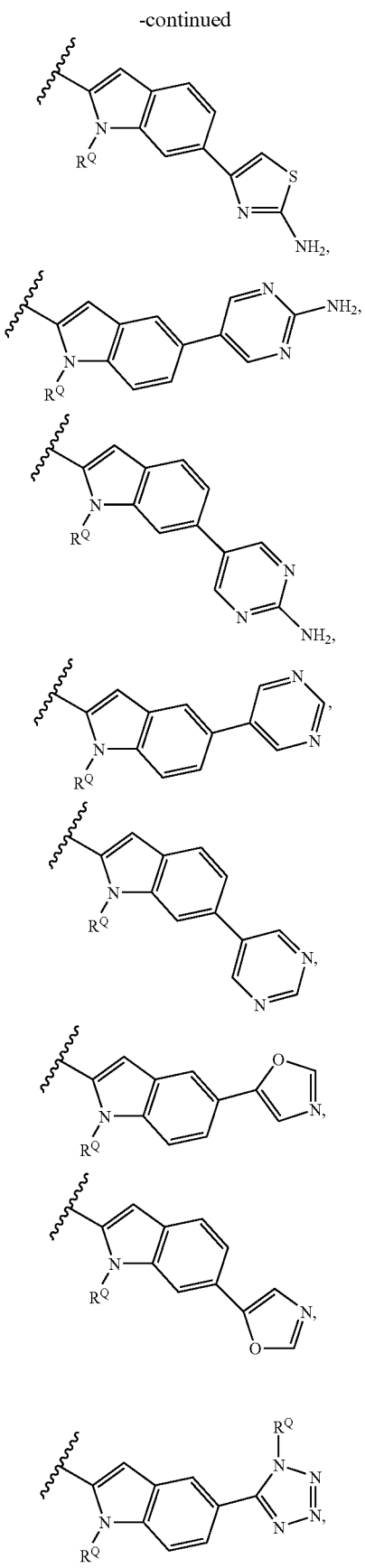

-continued
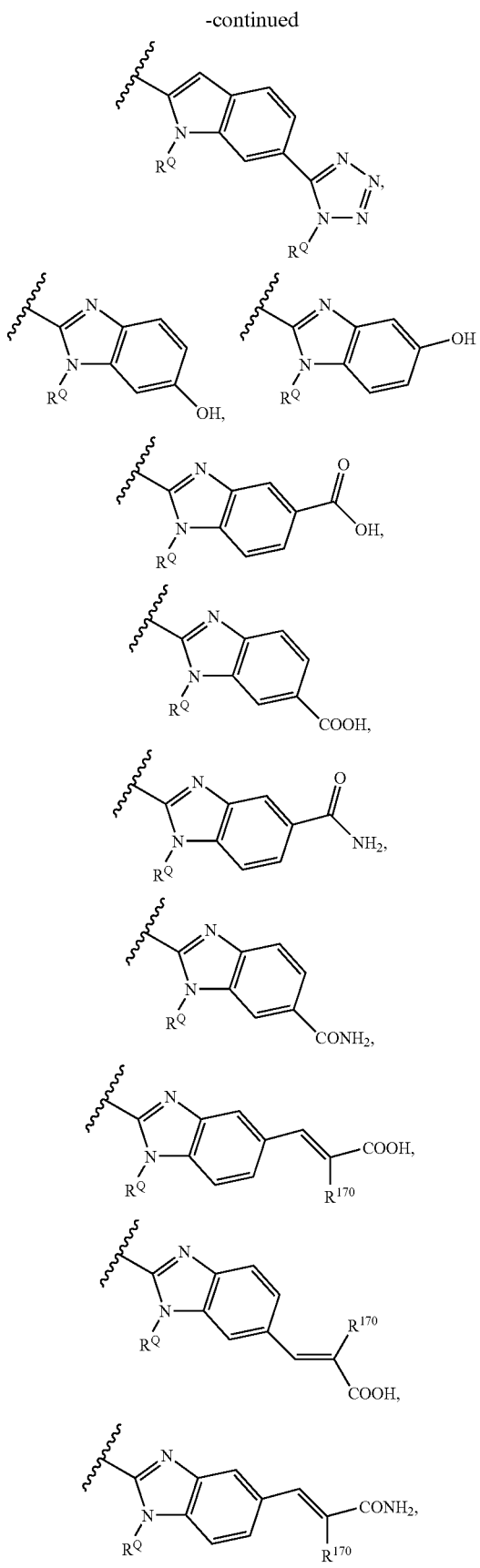
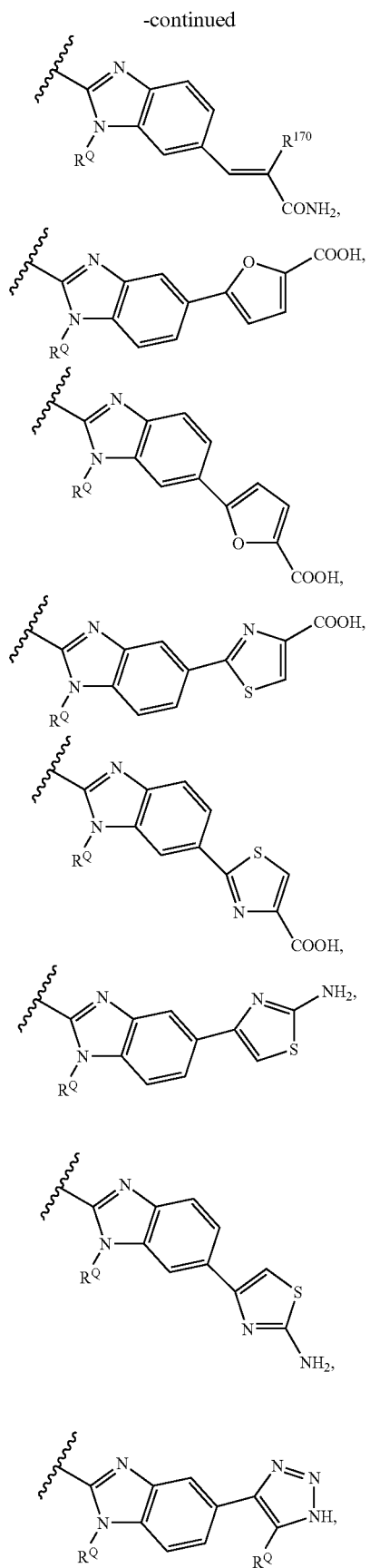

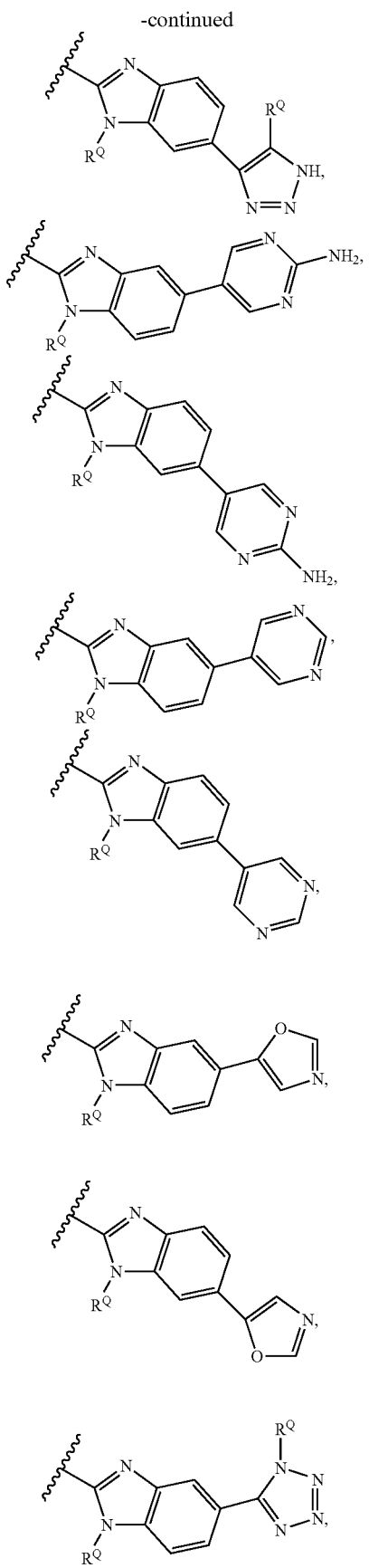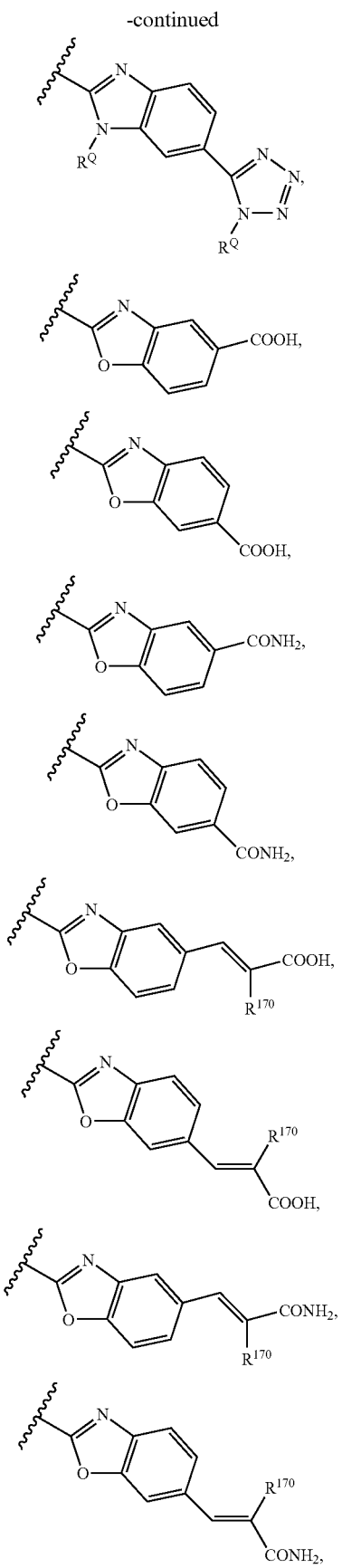

-continued

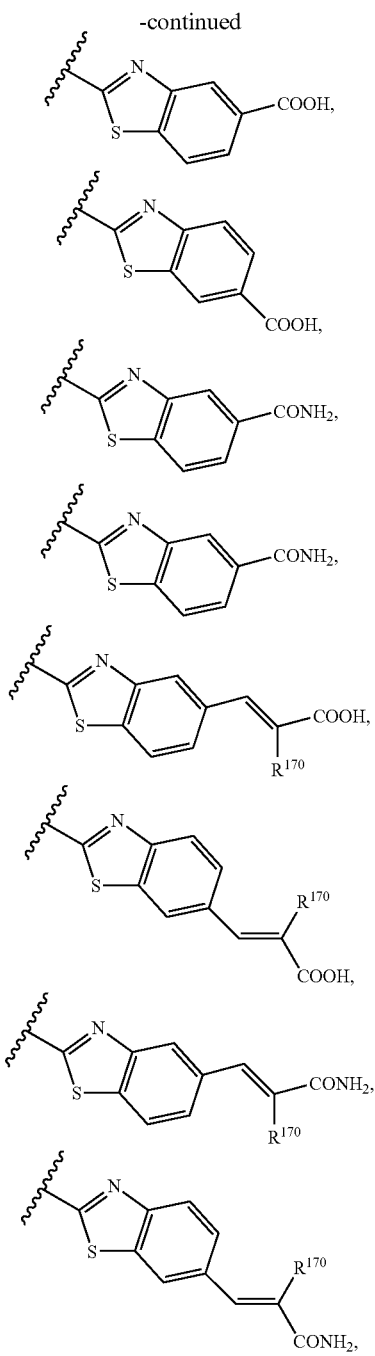

wherein all shown cyclic groups are optionally substituted with $R^{160}$; most preferably 1 or 2 substituents selected from fluorine, chlorine, bromine, OH, methoxy, ethoxy, amino, $NH(CH_3)$, methyl, ethyl, i-propyl and n-propyl;

wherein $R^{170}$ is each independently defined as hereinbefore; preferably $R^{170}$ is defined as H, F, —$CH_3$, —$CH_2CH_3$, —$CF_3$, or cyclopropyl; most preferably H, F, —$CH_3$, or —$CH_2CH_3$; and wherein $R^Q$ is each independently defined as hereinbefore; preferably $R^Q$ is defined as H, $(C_{1-6}$alkyl), $(C_{3-6})$cycloalkyl or $(C_{1-4})$alkyl-$(C_{3-6})$cycloalkyl; most preferably H or methyl.

Most preferably, $Q^1$ and $Q^2$ are independently selected from:

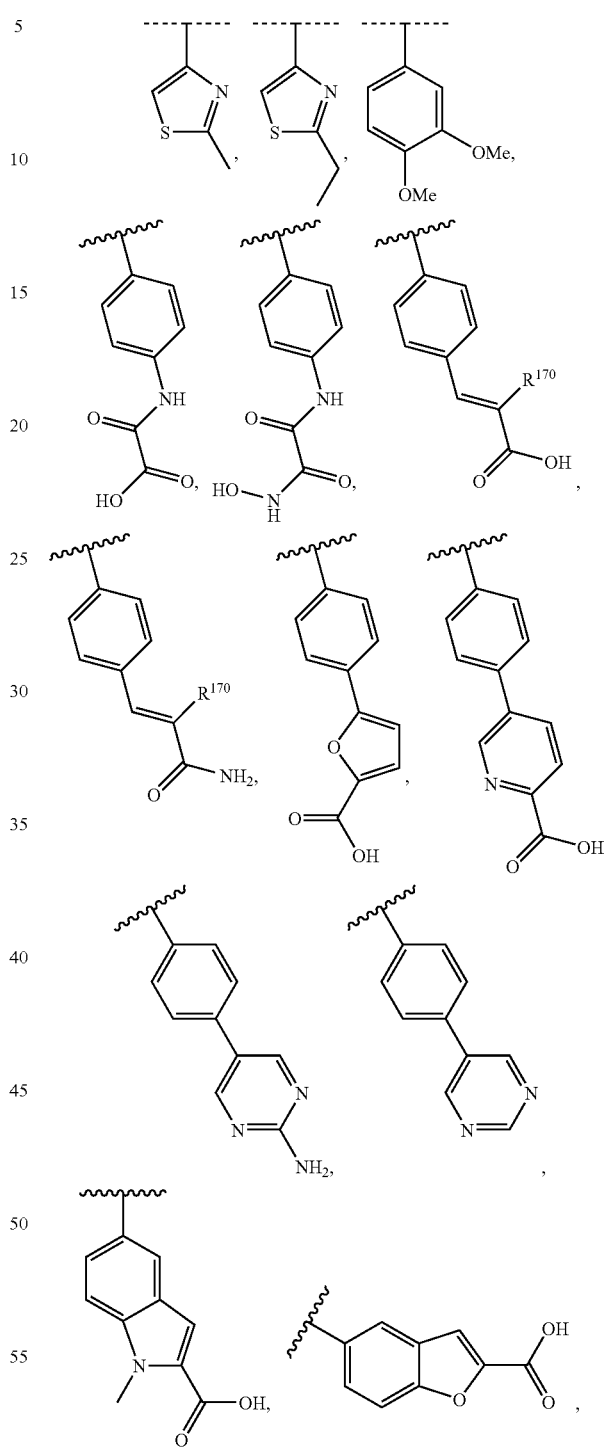

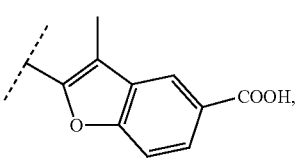

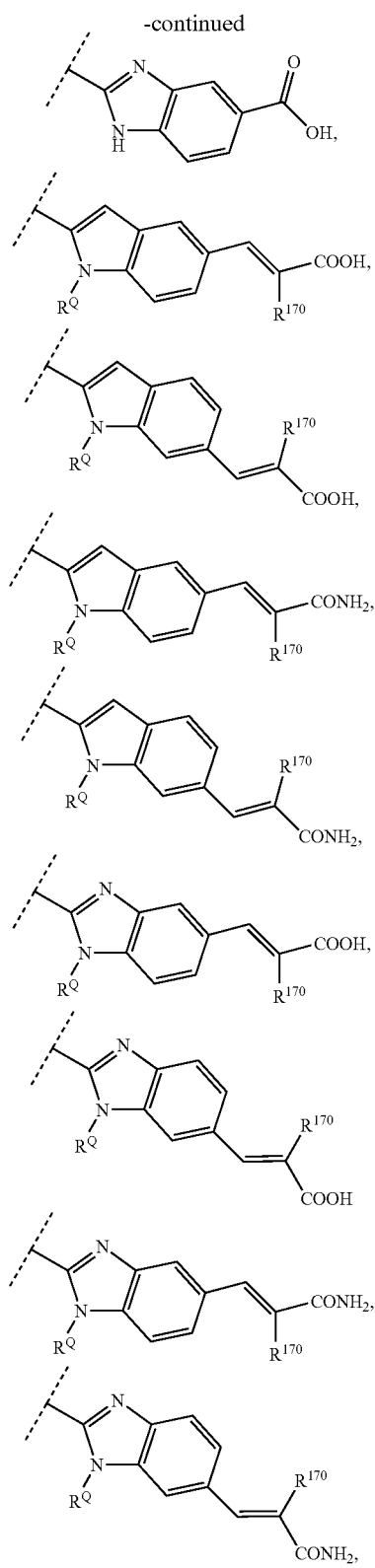

wherein all shown cyclic groups are optionally substituted with $R^{160}$; most preferably 1 or 2 substituents selected from fluorine, chlorine, bromine, OH, methoxy, ethoxy, amino, NH(CH$_3$), methyl, ethyl, i-propyl and n-propyl;

wherein $R^{170}$ is each independently defined as hereinbefore; preferably $R^{170}$ is defined as H, F, —CH$_3$, —CH$_2$CH$_3$, —CF$_3$, or cyclopropyl; most preferably H, F, —CH$_3$, or —CH$_2$CH$_3$; and wherein $R^Q$ is each independently defined as hereinbefore; preferably $R^Q$ is defined as H, (C$_{1-6}$alkyl), (C$_{3-6}$)cycloalkyl or (C$_{1-4}$)alkyl-(C$_{3-6}$)cycloalkyl; most preferably H or methyl.

In case $Q^{1a}$ or $Q^{2a}$ is a phenylene or Hetaryl group, preferred substituents of this group are selected from (C$_{1-3}$)alkyl and (C$_{1-3}$)alkoxy, especially from methyl, ethyl, methoxy, ethoxy. In the case where $Q^{1a}$ or $Q^{2a}$ is phenylene, the substituent is preferably in meta-position to $Q^{1b}$, in case q=1, or to $Q^{2b}$, in case qb=1; or to $Q^{1c}$, in case q=0, or to $Q^{2c}$, in case qb=0, respectively. Thus, most preferred groups $Q^1$ and $Q^2$ which are substituted are for example:

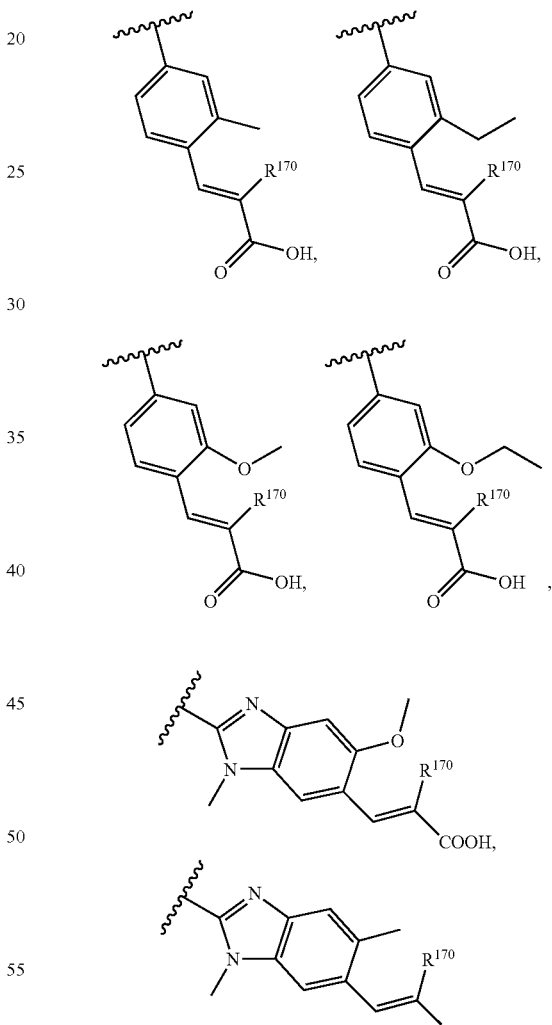

wherein $R^{170}$ is each independently defined as hereinbefore; preferably $R^{170}$ is defined as H, F, —CH$_3$, —CH$_2$CH$_3$, —CF$_3$, or cyclopropyl; most preferably H, F, —CH$_3$, or —CH$_2$CH$_3$.

Hereinafter preferred groups N(R$^{5a}$)R$^{6a}$ and N(R$^{5b}$)R$^{6b}$ are described for those cases wherein either L or Z, or both L and Z are defined as follows:

L is N($R^{5a}$)$R^{6a}$ wherein $R^{6a}$ is:
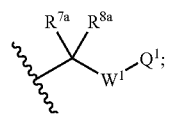
Z is N($R^{5b}$)$R^{6b}$ wherein $R^{6b}$ is:
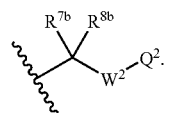
Therefore, according to this embodiment examples of very preferred groups L and Z, in case qa is 1, are independently selected from the group consisting of:
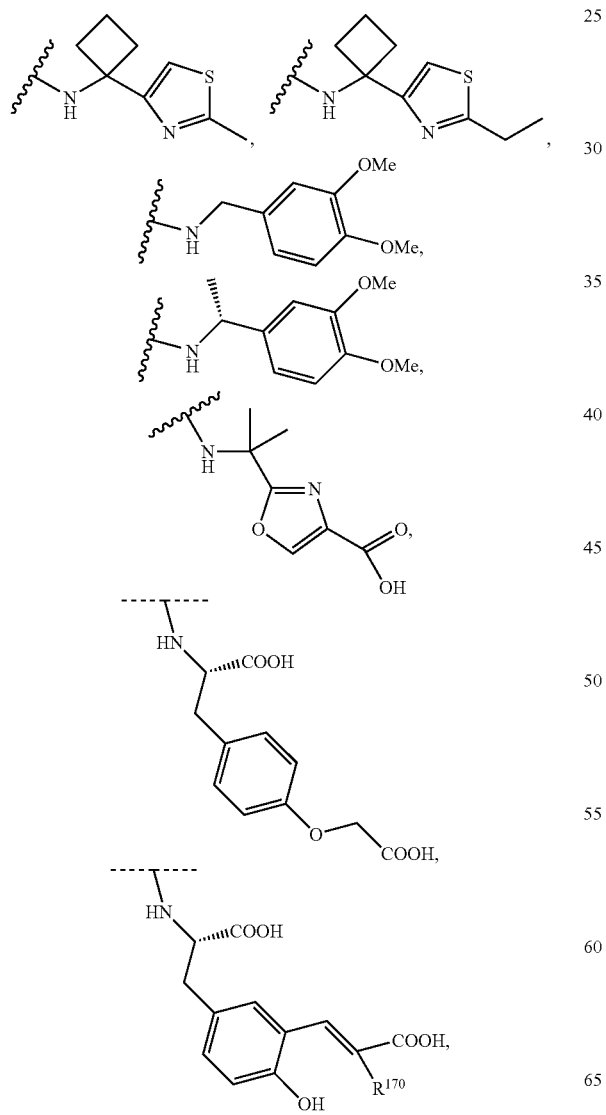
-continued
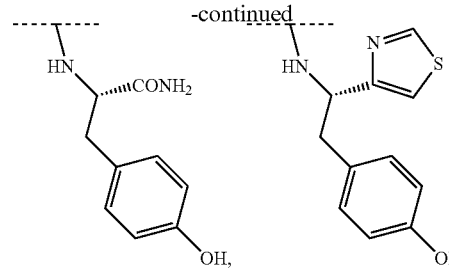
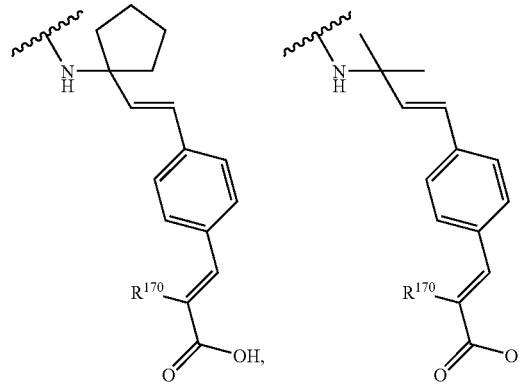
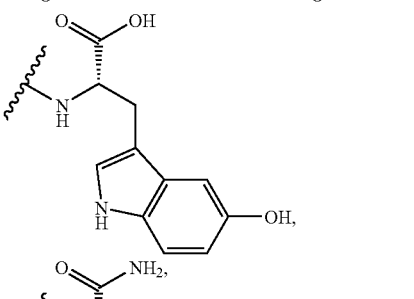
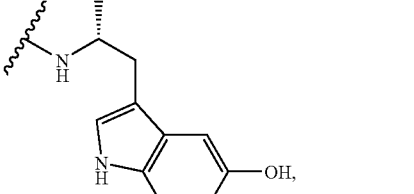
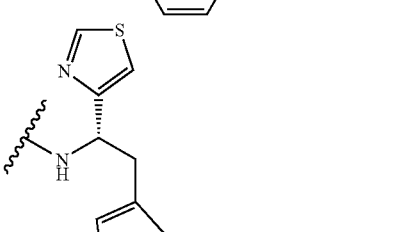
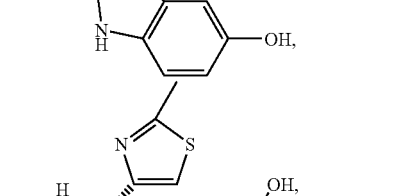
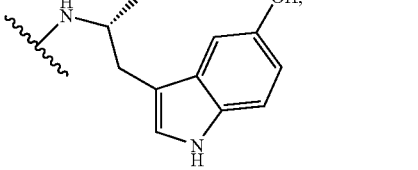

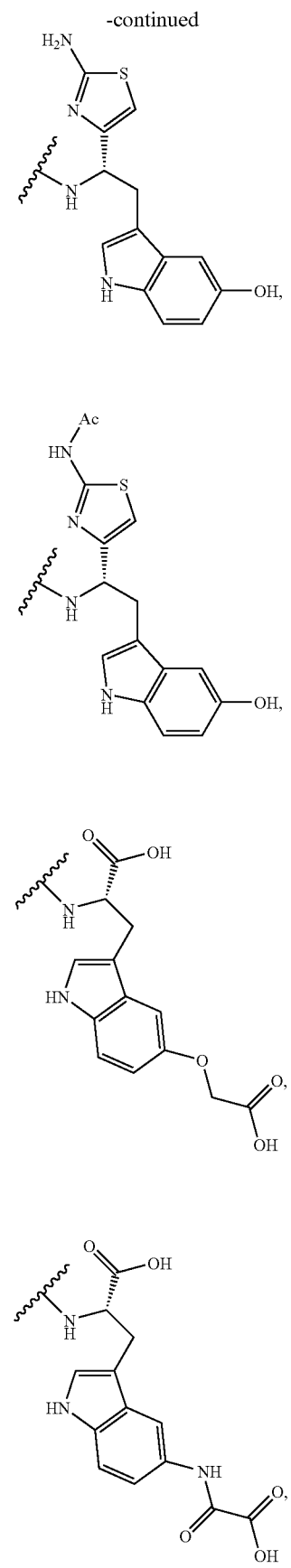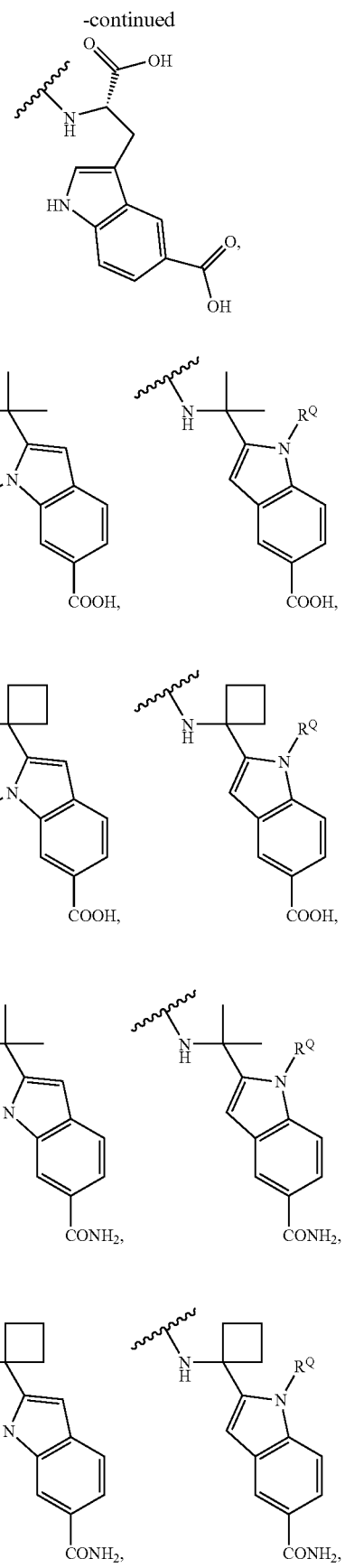

-continued
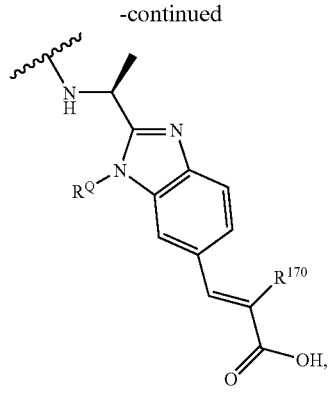
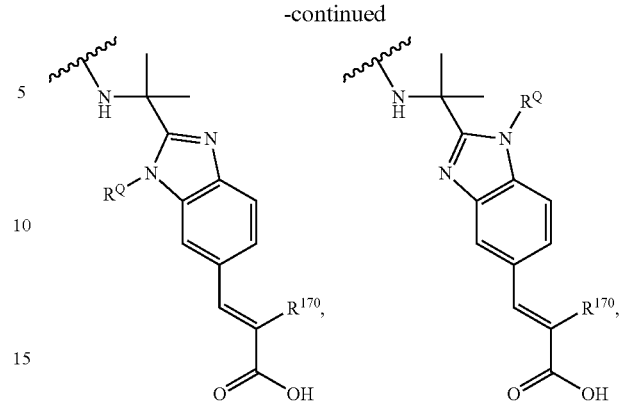
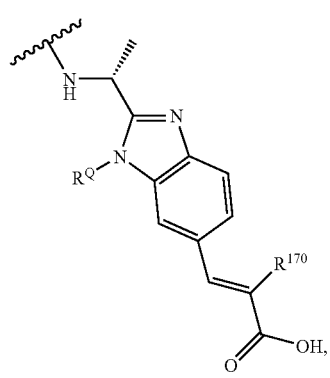
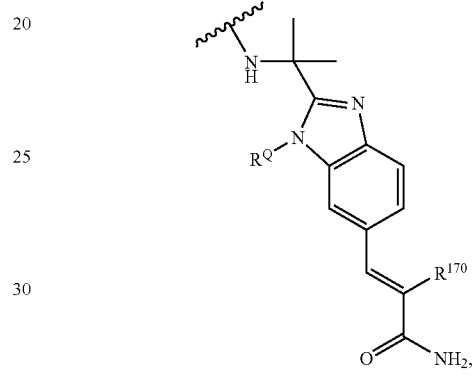
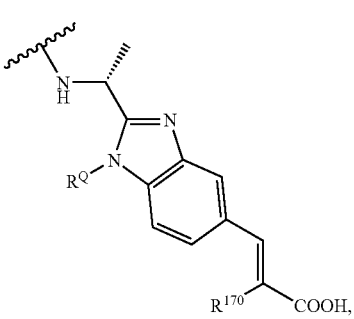
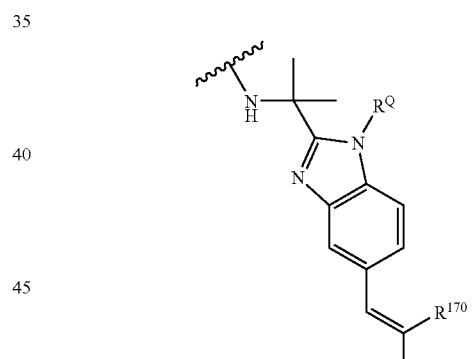
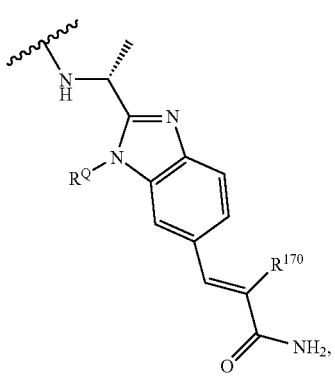
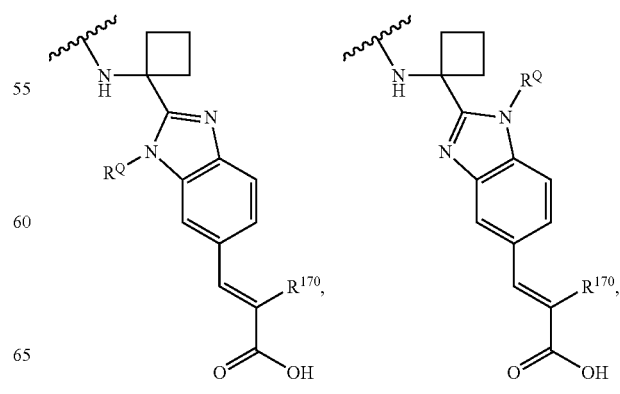

-continued
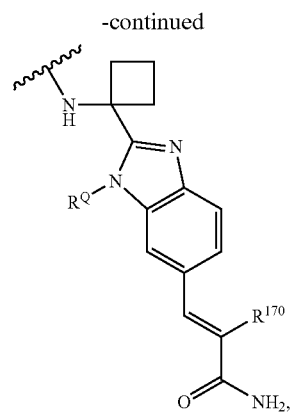
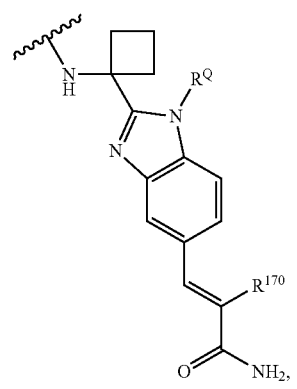
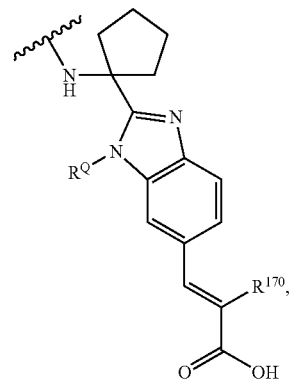
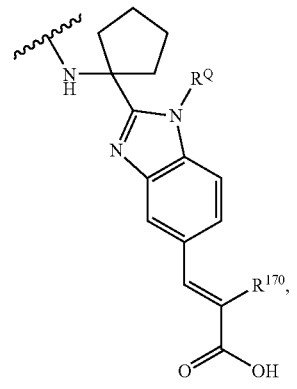
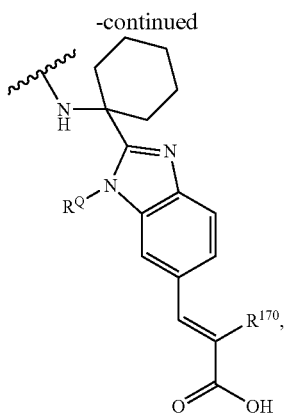
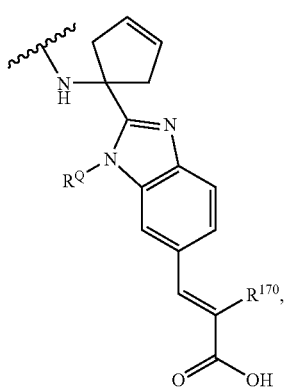
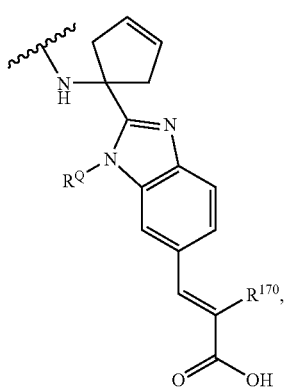
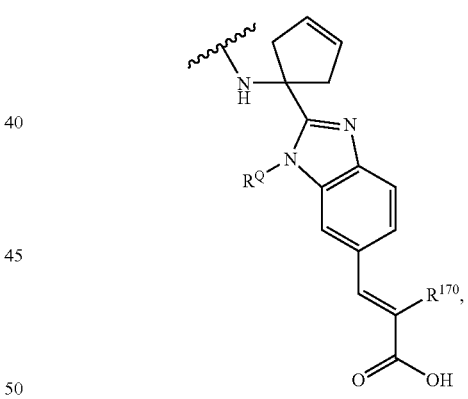

-continued
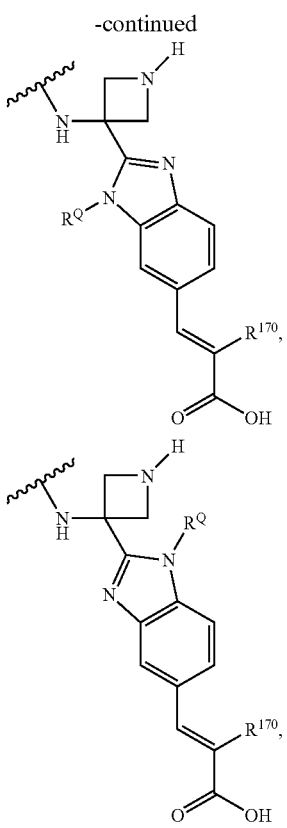
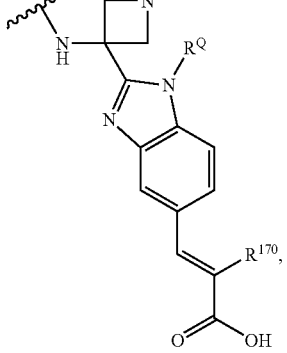
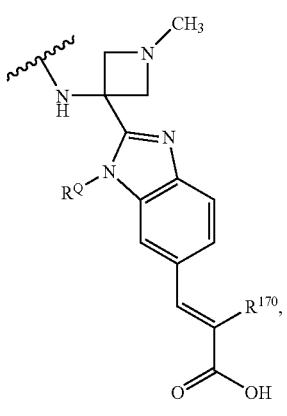
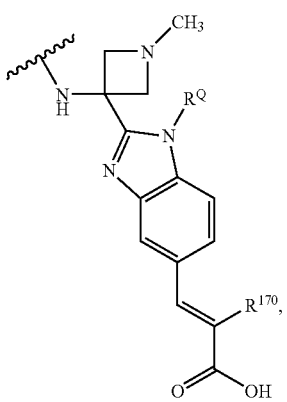
-continued
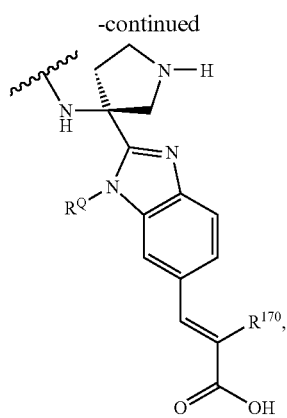
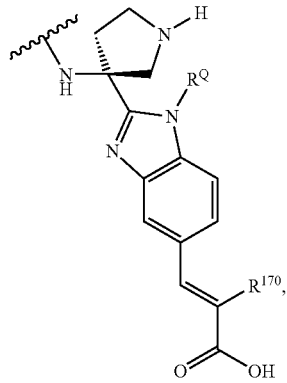
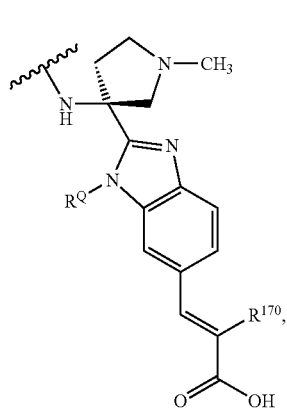
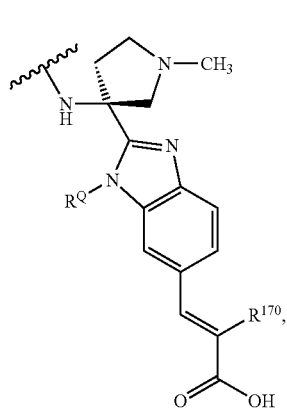

-continued
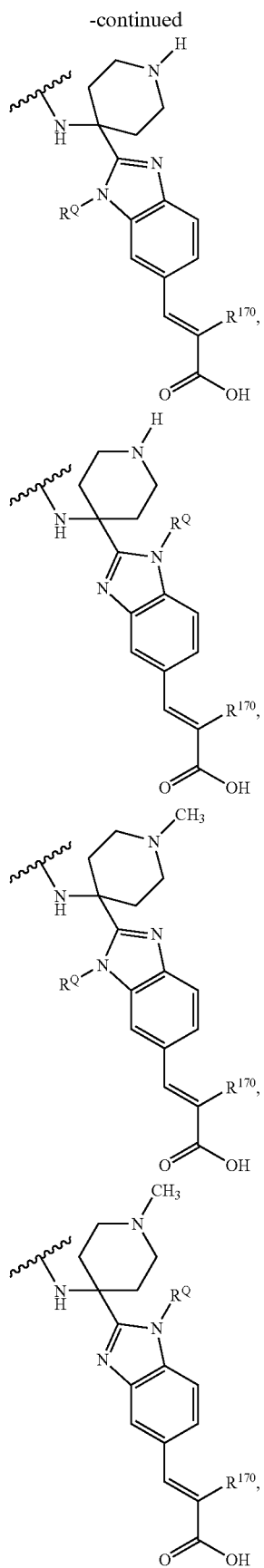
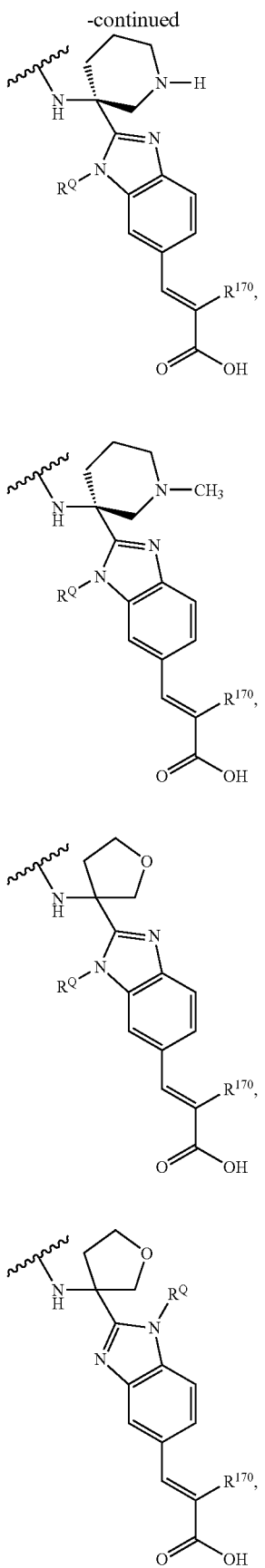

-continued
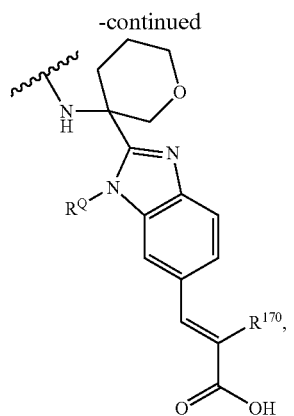
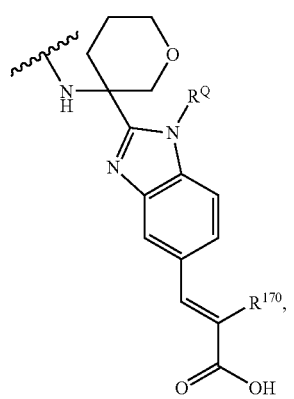
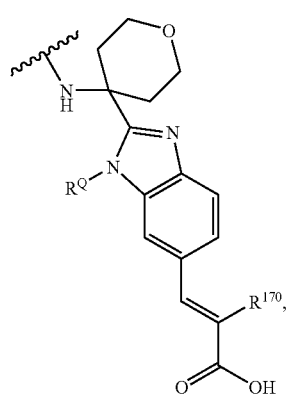
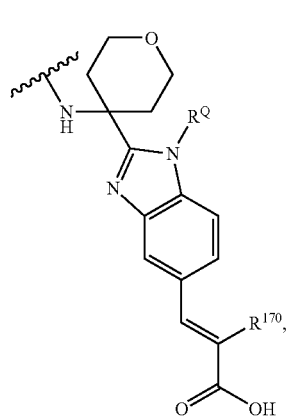
-continued
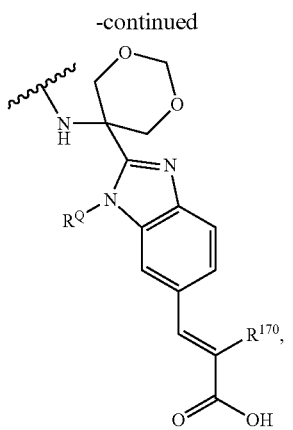
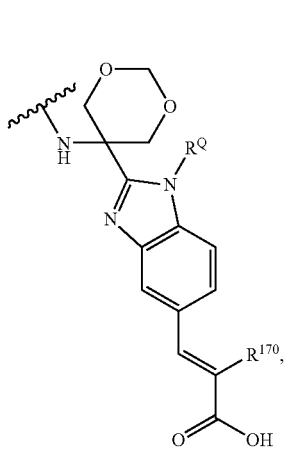
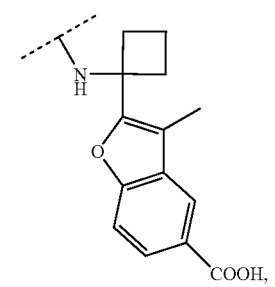
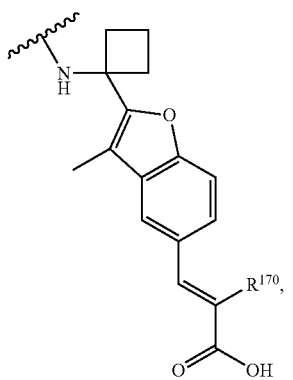

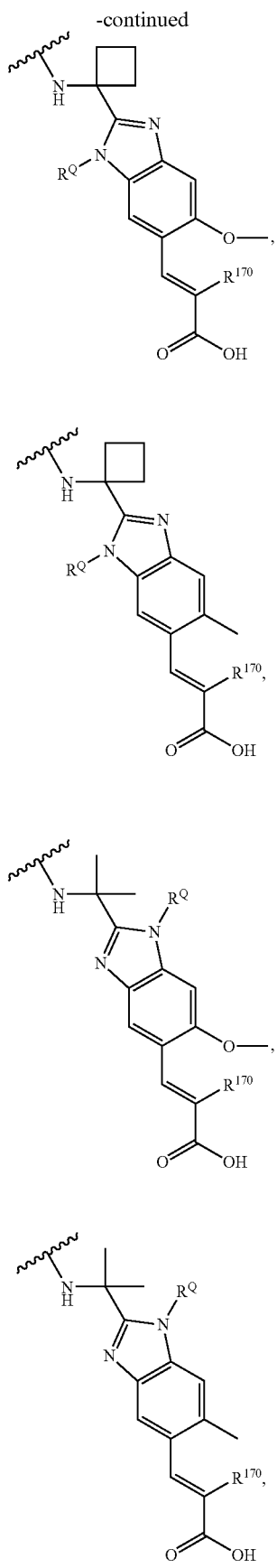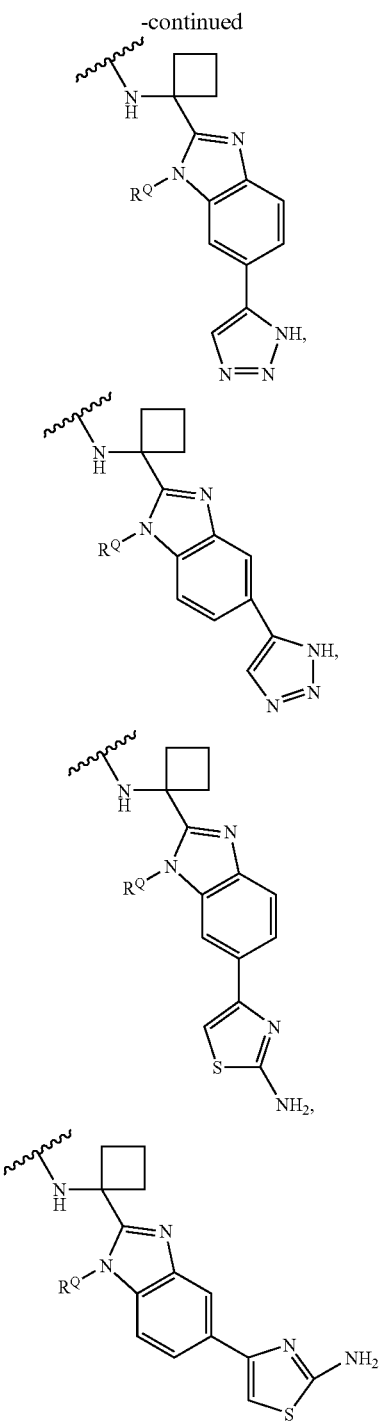

wherein all shown cyclic groups are optionally substituted with $R^{160}$; most preferably 1 or 2 substituents selected from fluorine, chlorine, bromine, OH, methoxy, ethoxy, amino, $NH(CH_3)$, methyl, ethyl, i-propyl and n-propyl;

wherein $R^{170}$ is each independently defined as hereinbefore; preferably $R^{170}$ is defined as H, F, —$CH_3$, —$CH_2CH_3$, —$CF_3$, or cyclopropyl; most preferably H, F, —$CH_3$, or —$CH_2CH_3$; and wherein $R^Q$ is each independently defined as hereinbefore; preferably $R^Q$ is defined as H, $(C_{1-6}$alkyl), $(C_{3-6})$cycloalkyl or $(C_{1-4})$alkyl-$(C_{3-6})$cycloalkyl; most preferably H or methyl.

Examples of preferred groups Z, in case qa is 0, are independently selected from the group consisting of:

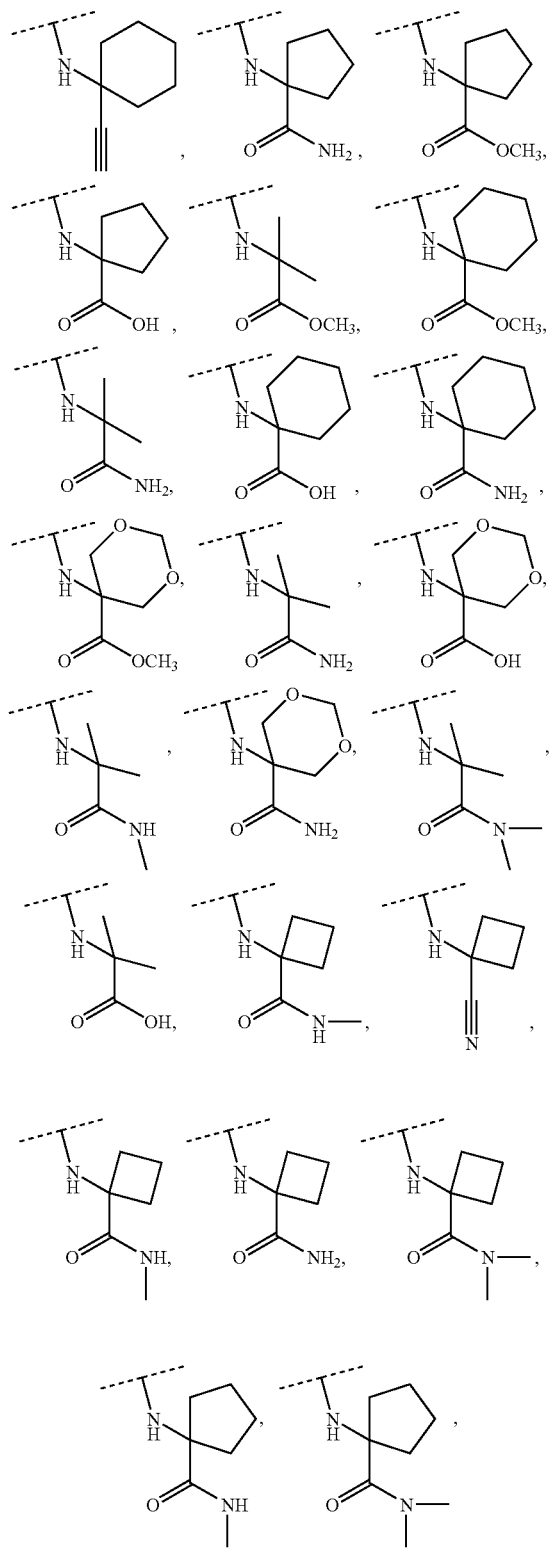

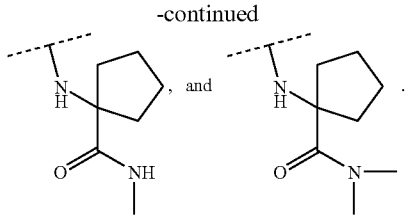

Hereinafter, preferred groups $N(R^{5a})R^{6a}$ and $N(R^{5b})R^{6b}$ are described for those cases wherein either L or Z, or both L and Z are defined as follows:

L is $N(R^{5a})R^{6a}$ wherein $R^{6a}$ is:

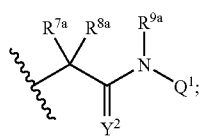

Z is $N(R^{5b})R^{6b}$ wherein $R^{6b}$ is:

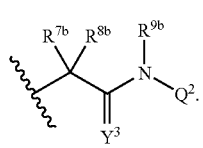

Therefore, according to this embodiment L and Z are more preferably independently selected from the group consisting of:

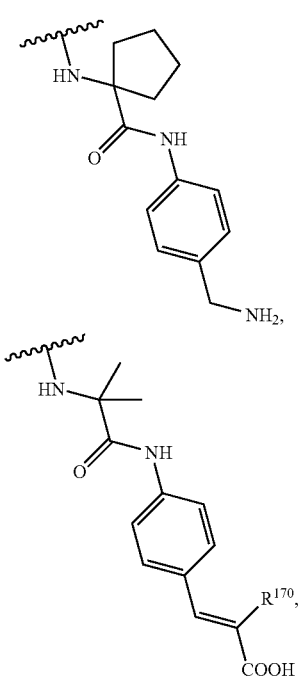

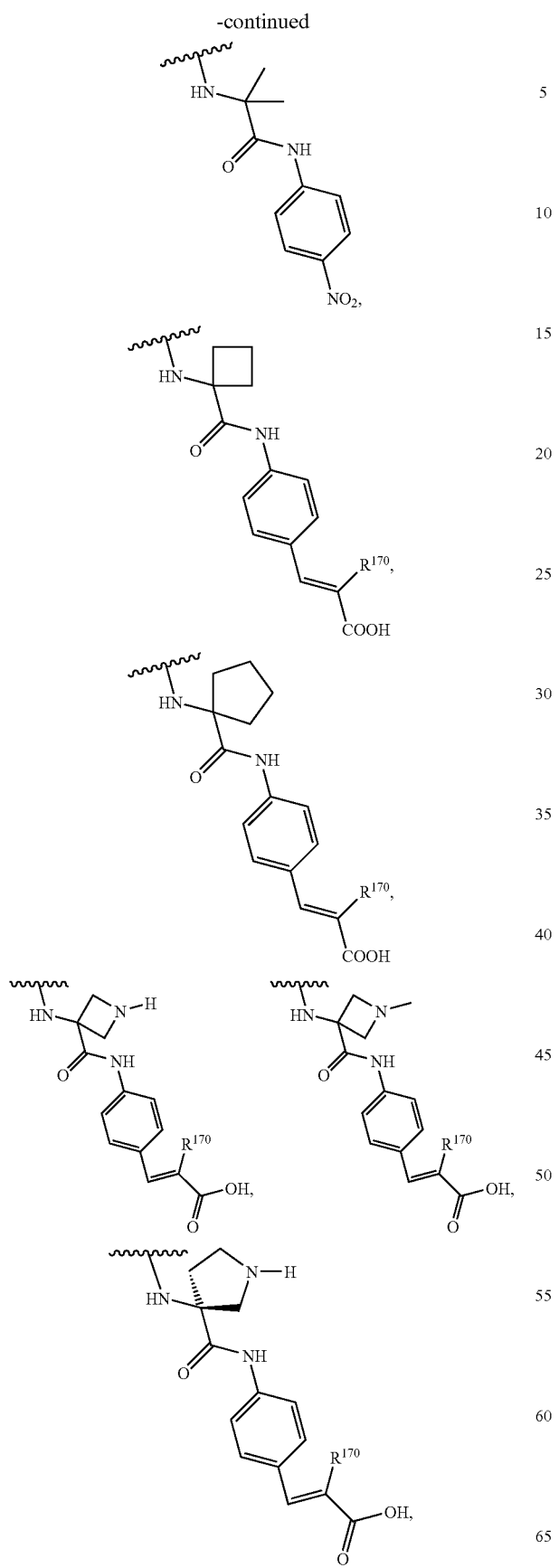
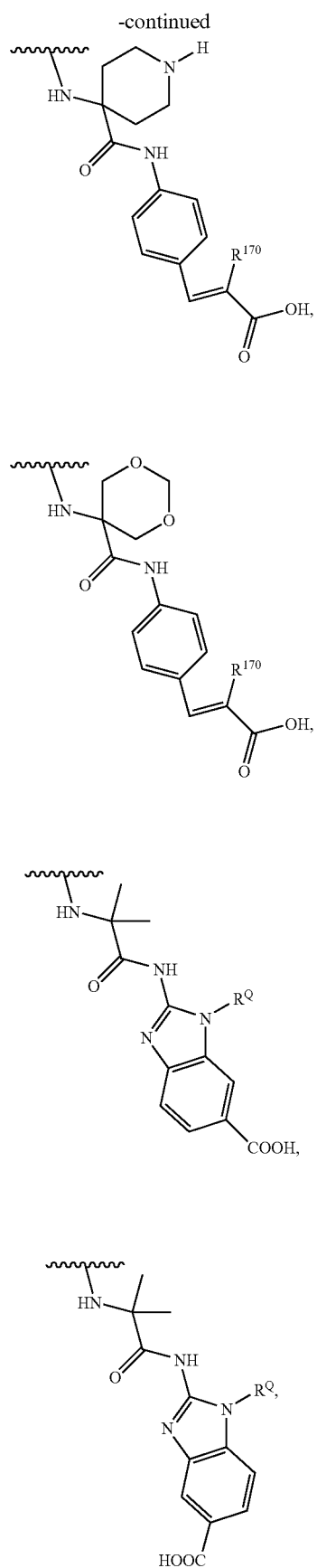

-continued
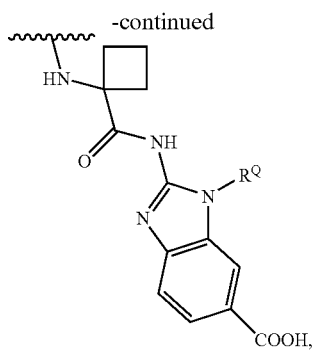
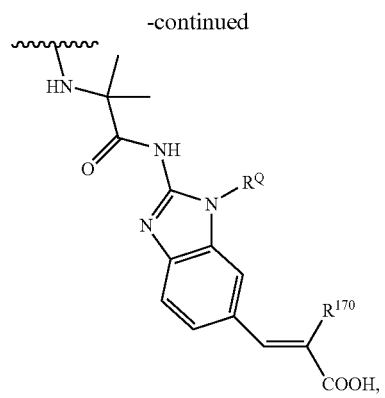
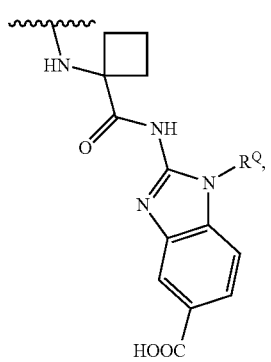
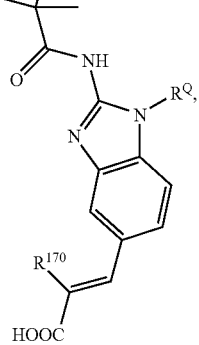
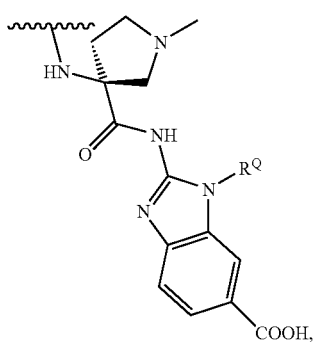
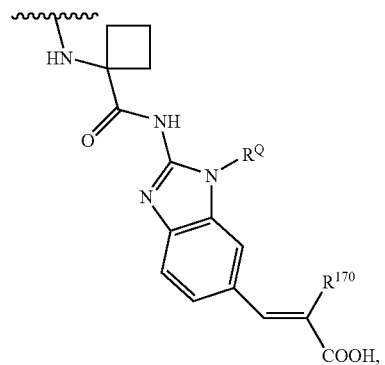
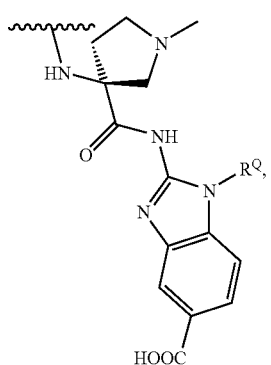
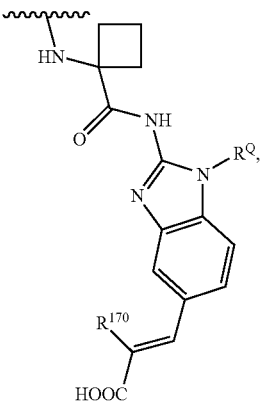

91
-continued
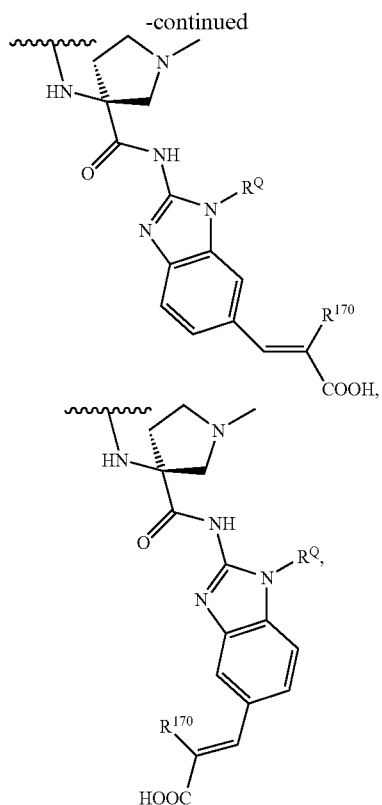
92
-continued
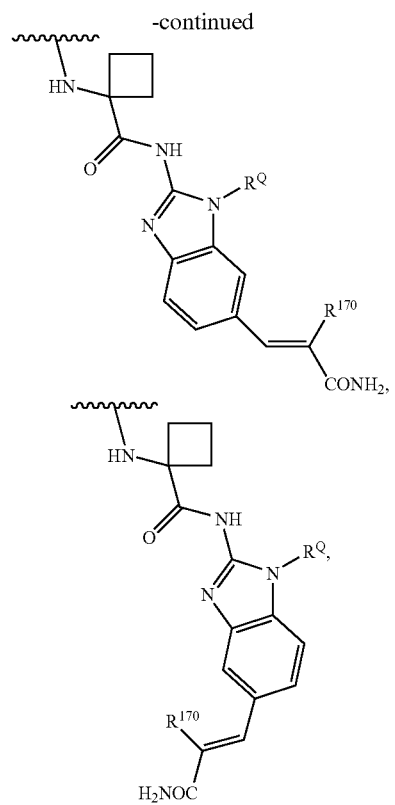
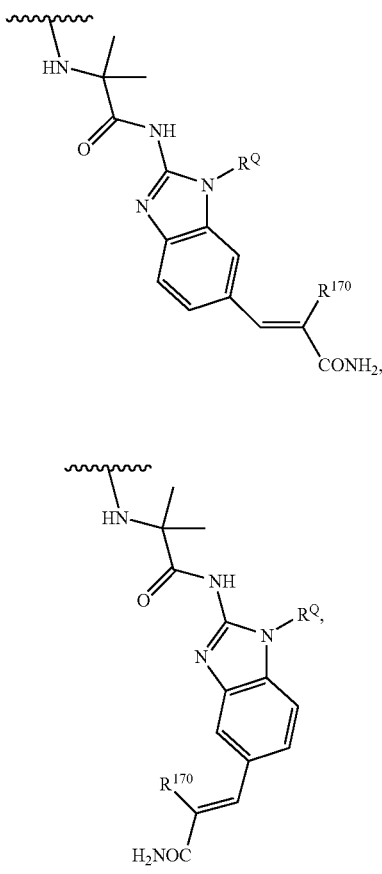
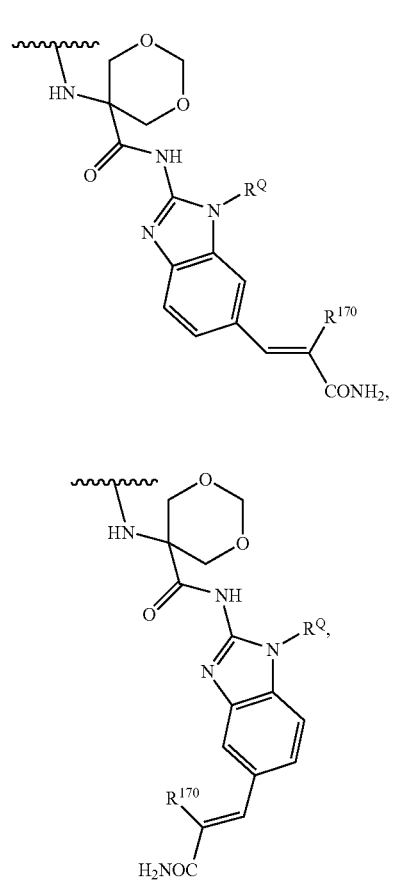

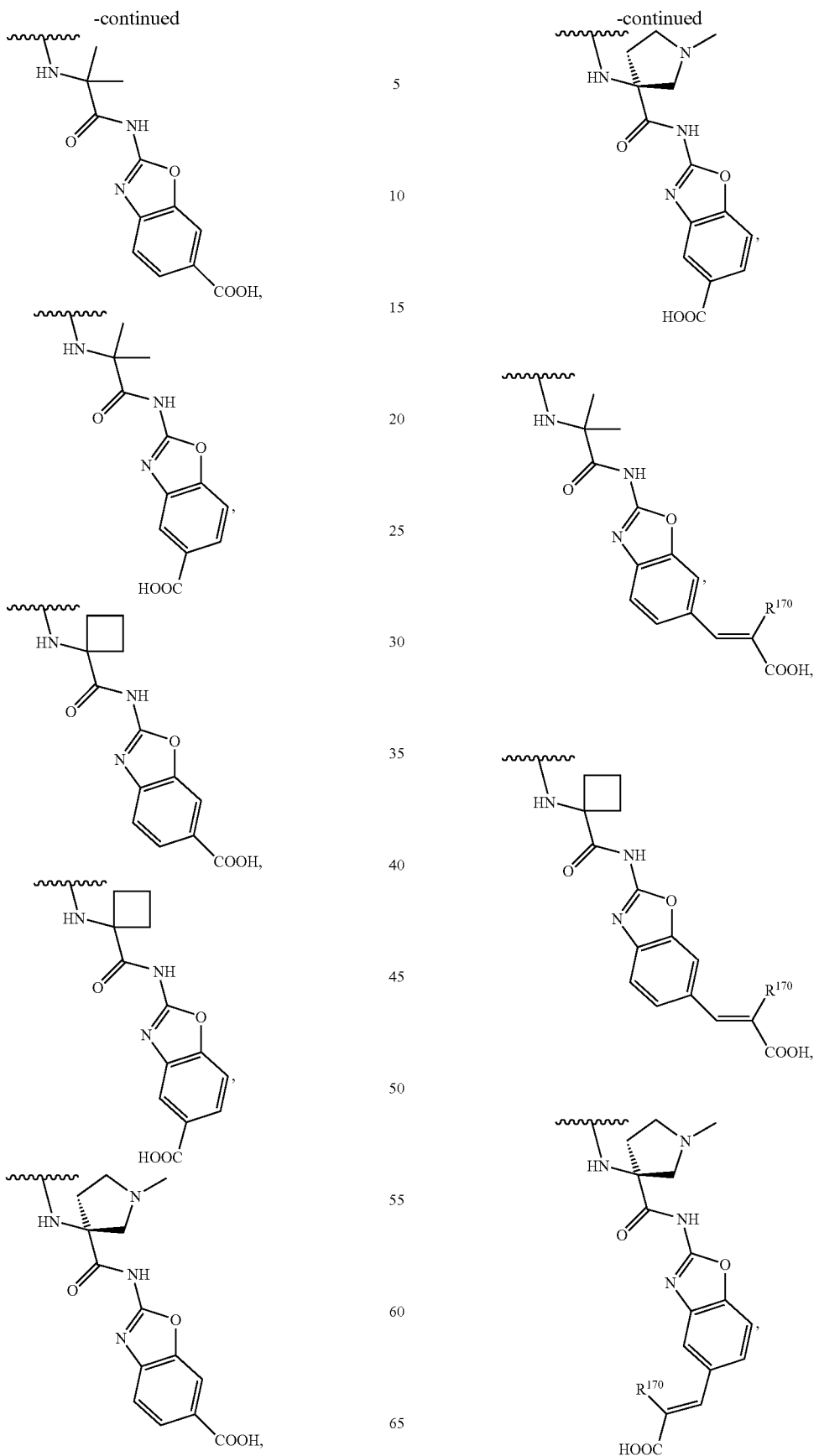

-continued
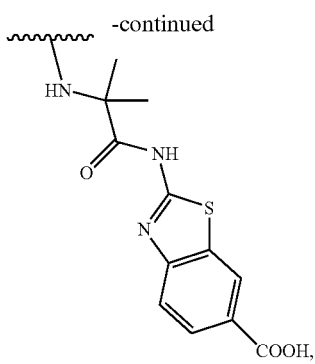
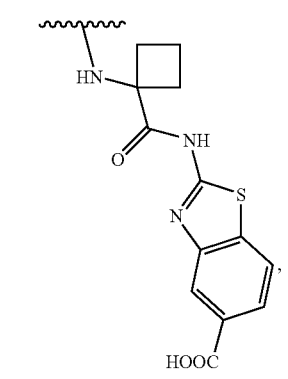
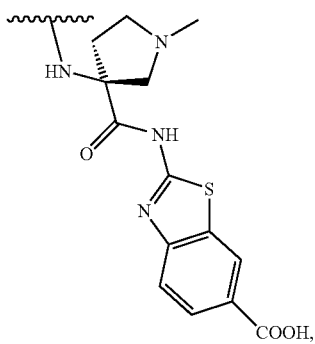
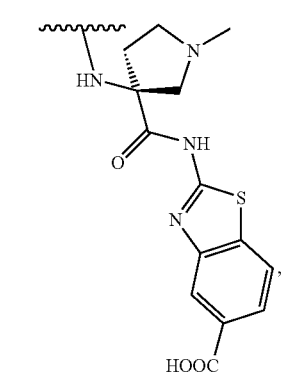
-continued
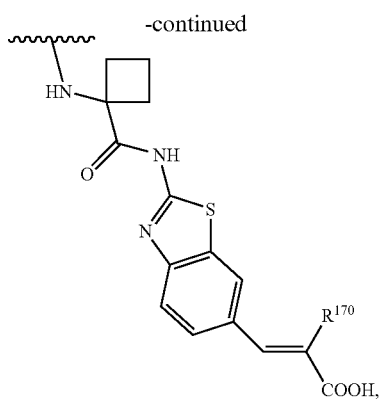
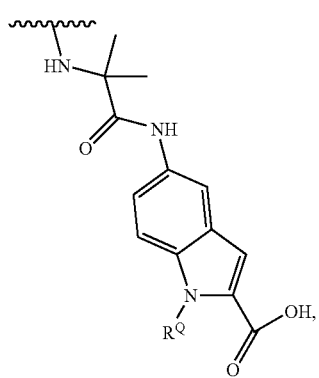
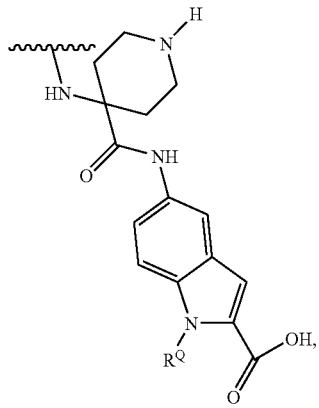
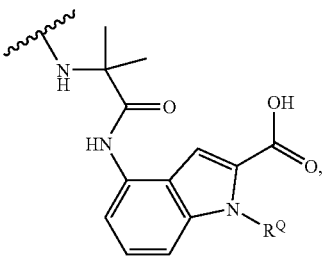

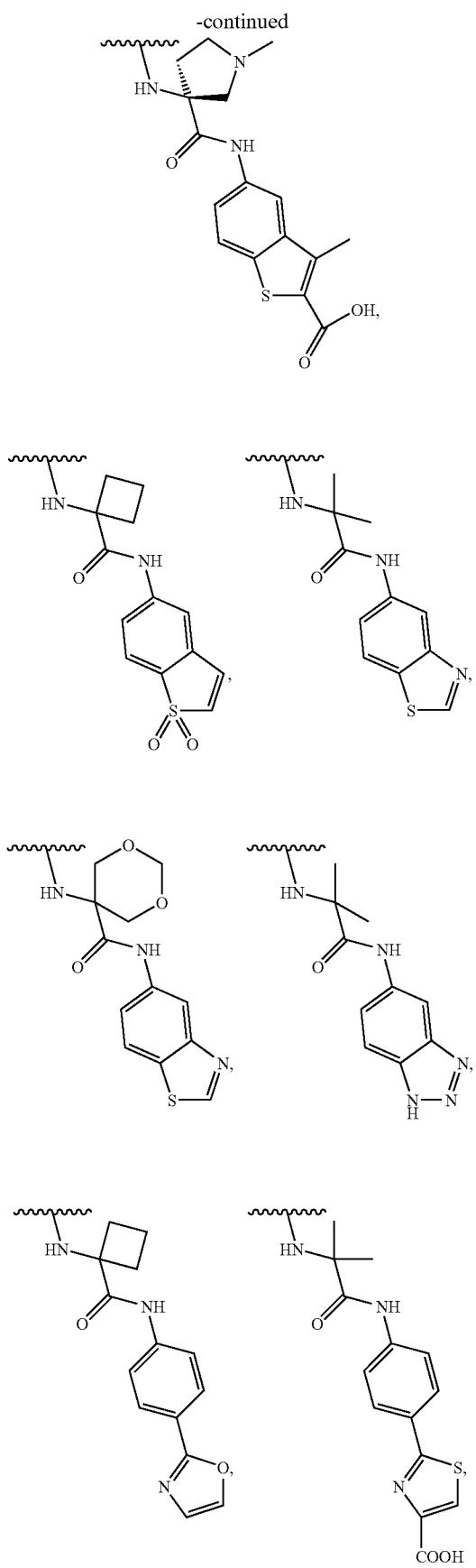
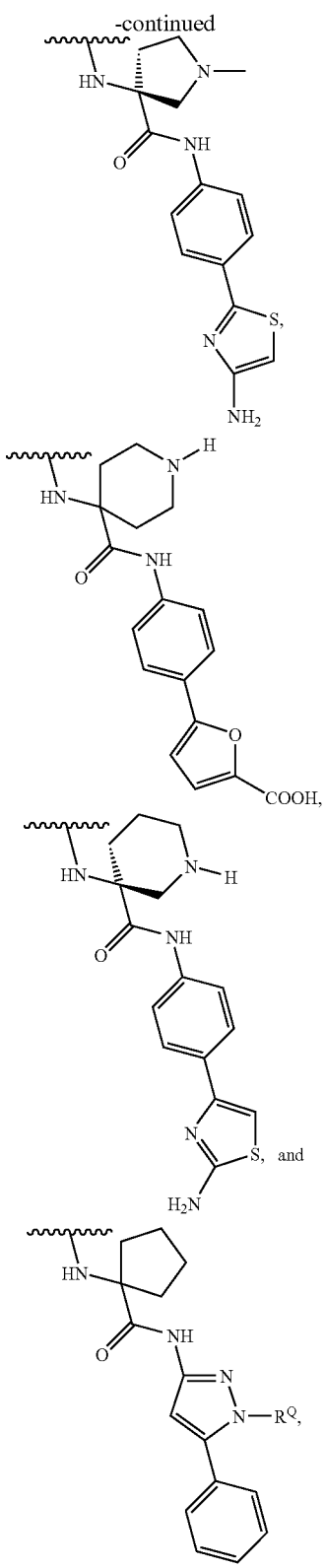
wherein all shown cyclic groups are optionally substituted with $R^{160}$; most preferably 1 or 2 substituents selected from fluorine, chlorine, bromine, OH, methoxy, ethoxy, amino, $NH(CH_3)$, methyl, ethyl, i-propyl and n-propyl;

wherein $R^{170}$ is each independently defined as hereinbefore; preferably $R^{170}$ is defined as H, F, —$CH_3$, —$CH_2CH_3$, —$CF_3$, or cyclopropyl; most preferably H, F, —$CH_3$, or —$CH_2CH_3$; and wherein $R^Q$ is each independently defined as hereinbefore; preferably $R^Q$ is defined as H, ($C_{1-6}$alkyl), ($C_{3-6}$)cycloalkyl or ($C_{1-4}$)alkyl-($C_{3-6}$)cycloalkyl; most preferably H or methyl.

$R^2$:

Preferably $R^2$ is $R^{21}$, wherein $R^{21}$ is a phenyl or Het selected from the group of formulas

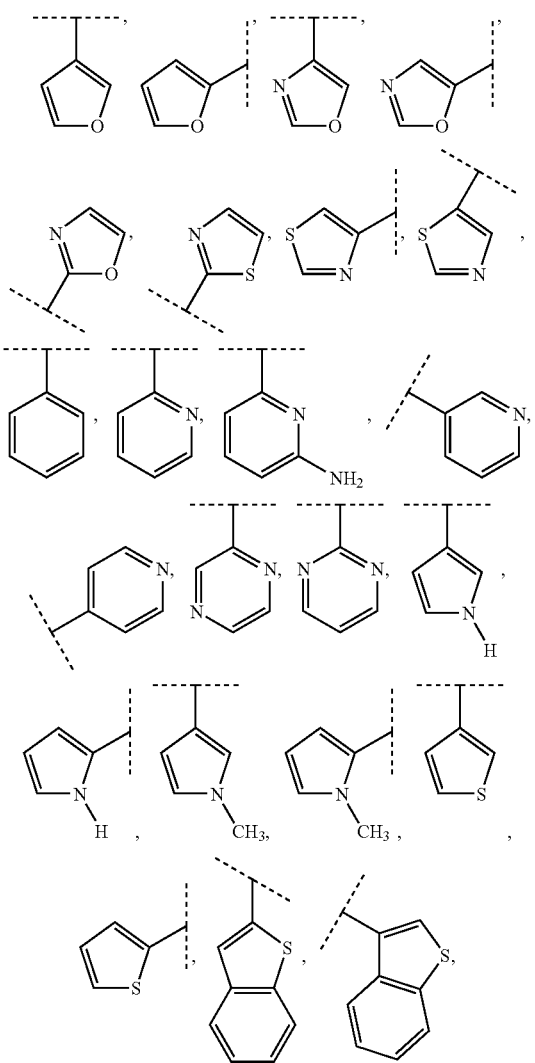

and wherein said $R^{21}$ is optionally substituted with $R^{150}$.

A very most preferred definition of $R^2$ is

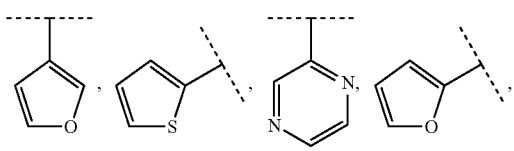

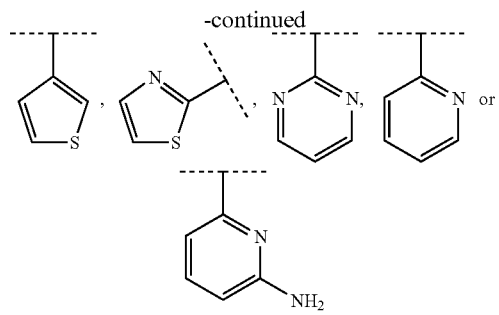

all of which may be unsubstituted or substituted as defined.

In the case $R^2$ as defined above is substituted, it is preferably substituted with 1, 2 or 3 substituents selected from:

1 to 3 substituents selected from halogen;

one of each substituent selected from: $NO_2$, cyano, azido; and 1 to 2 substituents selected from:

a) ($C_{1-4}$)alkyl or ($C_{1-4}$)alkoxy, both optionally substituted with OH, O($C_{1-4}$)alkyl, $SO_2$($C_{1-4}$alkyl); 1 to 3 halogen atoms, amino, NH($CH_3$) or N($CH_3$)$_2$);

b) $NR^{111}R^{112}$ wherein both $R^{111}$ and $R^{112}$ are independently H, ($C_{1-4}$)alkyl, or $R^{112}$ is ($C_{3-7}$)cycloalkyl, ($C_{1-3}$)alkyl ($C_{3-7}$)cycloalkyl, phenyl, benzyl; or both $R^{111}$ and $R^{112}$ are covalently bonded together and to the nitrogen to which they are attached to form a nitrogen-containing heterocycle, each of said alkyl, cycloalkyl, alkylcycloalkyl, phenyl and benzyl, being optionally substituted with halogen or:

—$OR^{2h}$ or $N(R^{2h})_2$, wherein each $R^{2h}$ is independently H, ($C_{1-4}$)alkyl, or both $R^{2h}$ are covalently bonded together and to the nitrogen to which they are attached to form a nitrogen-containing heterocycle;

c) $NHCOR^{117}$ wherein $R^{117}$ is ($C_{1-4}$)alkyl, O($C_{1-4}$)alkyl or O($C_{3-7}$)cycloalkyl; and e) $CONH_2$, $CONH(C_{1-4}$alkyl), $CON(C_{1-4}$alkyl)$_2$.

Most preferred substituents of $R^2$ are selected from:

1 to 2 substituents selected from fluorine;

one of each substituent selected from: chlorine, bromine, $NO_2$, cyano; and 1 to 2 substituents selected from:

a) methyl, trifluoromethyl, ethyl, n-propyl, i-propyl, methoxy, trifluoromethoxy, ethoxy, n-propoxy or i-propoxy, wherein said methyl, ethyl, n-propyl, i-propyl, ethoxy, n-propoxy and i-propoxy are optionally substituted with OH, methoxy, amino, NH($CH_3$) or N($CH_3$)$_2$;

b) $NR^{111}R^{112}$ wherein both $R^{111}$ and $R^{112}$ are independently H or methyl, or $R^{112}$ is phenyl or benzyl;

c) $NHCOR^{117}$ wherein $R^{117}$ is methyl or methoxy; and e) $CONH_2$, $CONH(CH_3)$, $CON(CH_3)_2$.

$R^3$:

$R^3$ is preferably selected from ($C_{3-7}$)cycloalkyl, ($C_{5-7}$)cycloalkenyl, ($C_{6-10}$)bicycloalkyl, ($C_{6-10}$)bicycloalkenyl, or HCy wherein said groups are unsubstituted or mono- or disubstituted by halogen, hydroxy, $C_{1-4}$alkyl and/or O—$C_{1-4}$alkyl, wherein the alkyl groups may be fluorinated.

Most preferably $R^3$ is cyclopropyl, cyclobutyl, cyclopentyl, cyclohexyl or cycloheptyl, or a group selected from:

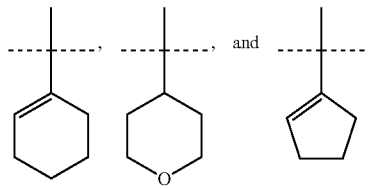

wherein all said cyclic groups are unsubstituted or substituted by fluorine, $C_{1-3}$alkyl or $CF_3$.

The very most preferred meaning of $R^3$ is cyclopentyl, or cyclohexyl.

$R^{4a}$, $R^{4b}$, $R^5$:

Preferably $R^{4a}$, $R^{4b}$, $R^5$ each are independently H, hydroxy, halogen, cyano, nitro, carboxyl, $(C_{1-4})$alkyl, $CF_3$, $(C_{1-4})$alkoxy, —O—$(C_{3-7})$cycloalkyl, —O—$(C_{1-3})$alkyl-$(C_{3-7})$cycloalkyl, —O-aryl, —O—$(C_{1-3})$alkyl-aryl, —O—Het, —O—$(C_{1-3})$alkyl-Het, $NR^{N1}R^{N2}$, or $COR^O$, $NR^{N2}COR^C$, $CONR^{N2}R^{N1}$, $NR^{N3}CONR^{N1}R^{N2}$, in particular $NHCO(C_{1-4})$alkyl or $CONHR^{N1}$, $NHCONHR^{N1}$;

wherein $R^O$, $R^{N1}$, $R^{N2}$, $R^{N3}$ are as defined; preferably $R^O$, $R^{N1}$ are independently of each other H, $(C_{1-4})$alkyl, aryl, $(C_{1-3})$alkyl-aryl, wherein aryl is preferably optionally substituted phenyl; and preferably $R^{N2}$, $R^{N3}$ are H or methyl; wherein all said alkyl groups, including alkoxy, may be mono-, di- or trisubstituted by fluorine or mono-substituted by chlorine or bromine.

Most preferred substituents $R^{4a}$, $R^{4b}$, $R^5$ each are independently H, hydroxy, halogen, cyano, nitro, methyl, $CF_3$, methoxy, carboxy, amino, —$NMe_2$, —$CONH_2$, —$NHCONH_2$, —CO—NHMe, —NHCONHMe, —CO—$NMe_2$ or —NH—$CONMe_2$; in particular H, methyl or methoxy. Preferably $R^{4a}$ is H or methyl. Very most preferably at least two of the substituents selected from $R^{4a}$, $R^{4b}$, $R^5$ are H.

$R^{60}$:

The substituents $R^{60}$ are preferably each defined as 1 to 4 substituents independently selected from:
  1 to 3 substituents selected from halogen;
  one of each substituent selected from: $NO_2$, cyano, azido; and
  1 to 3 substituents selected from:

a) $(C_{1-4})$ alkyl, $(C_{3-7})$cycloalkyl, $(C_{2-4})$alkenyl, $(C_{2-4})$alkynyl, $(C_{1-3})$alkyl-$(C_{3-7})$cycloalkyl, all of which optionally being substituted with $R^{150}$;

b) $OR^O$;

e) $N(R^{N2})R^{N1}$;

f) $N(R^{N2})COR^C$;

j) $COOR^O$;

k) $CON(R^{N2})R^{N1}$;

l) phenyl, Het, $(C_{1-3}$alkyl)phenyl or $(C_{1-3}$alkyl)Het; wherein Het is selected from furan, tetrahydrofuran, thiophene, tetrahydrothiophene, tetrahydropyran, pyridinyl, azetidine, pyrrolidine, piperidine, piperazine, morpholine, thiomorpholine, homopiperidine and homopiperazine;

wherein said $R^{N1}$, $R^C$ and/or $R^O$ are optionally substituted with $R^{150}$ as defined.

$R^{150}$:

$R^{150}$ is preferably defined as 1 to 4 substituents independently selected from:
  1 to 3 fluorine-substituents;
  one of each substituent selected from: chlorine, bromine, iodine, $NO_2$, cyano, azido; and
  1 to 3 substituents selected from:

a) $(C_{1-3})$ alkyl, $CF_3$, $(C_{3-6})$cycloalkyl, $(C_{1-3})$ alkyl-$(C_{3-6})$cycloalkyl, all of which optionally substituted with $R^{160}$;

b) $OR^O$;

e) $N(R^{N2})R^{N1}$;

f) $N(R^{N2})COR^C$;

j) $COOR^O$;

k) $CON(R^{N2})R^{N1}$;

wherein said $R^{N1}$, $R^C$ and/or $R^O$ are optionally substituted with $R^{160}$ as defined.

$R^{160}$:

$R^{160}$ is preferably defined as 1, 2 or 3 substituents independently selected from:
  1, 2 or 3 fluorine substituents; and
  one of each substituent selected from chlorine, bromine, iodine, CN, nitro, methyl, trifluoromethyl, ethyl, n-propyl, i-propyl, COOH, $COOCH_3$, OH, $OCH_3$, $OCF_3$, $NH_2$, $NHCH_3$, $N(CH_3)_2$, $SO_2NH_2$, $NHCOCH_3$, $SO_2NHCOCH_3$, $CONH_2$, $CONHCH_3$ and $CON(CH_3)_2$.

$R^O$, $R^C$:

Preferably $R^O$, $R^C$ are independently selected from $(C_{1-4})$alkyl, $(C_{3-6})$cycloalkyl, $(C_{1-3})$alkyl-$(C_{3-6})$cycloalkyl, phenyl, benzyl, Het, $(C_{1-3})$alkyl-Het; all of which are optionally substituted as defined; and $R^O$ may also be H.

$R^{N1}$, $R^{N2}$, $R^{N3}$, $R^{N4}$:

$R^{N1}$ is preferably selected from H, $(C_{1-4})$alkyl, $(C_{3-6})$cycloalkyl, $(C_{1-3})$alkyl-$(C_{3-6})$cycloalkyl, phenyl, benzyl, phenylethyl, Het, $(C_{1-3})$alkyl-Het; wherein said alkyl, cycloalkyl, alkyl-cycloalkyl, phenyl, benzyl, phenylethyl, Het and alkyl-Het are optionally substituted as defined; and $R^{N2}$, $R^{N3}$, $R^{N4}$ are independently selected from H, methyl, ethyl, n-propyl, i-propyl, cyclopropyl, cyclopropylmethyl; all of which being optionally substituted with methyl, fluorine, carboxy or methoxycarbonyl; and/or wherein said ethyl, n-propyl or i-propyl, but preferably not the C-atom thereof directly bonded to the N-atom, is optionally substituted with hydroxy, methoxy, amino, —$NH(CH_3)$ and/or —$N(CH_3)_2$; and in the case a) of a group $N(R^{N2})R^{N1}$, $R^{N2}$ and $R^{N1}$ or b) of a group $NR^{N3}$—$N(R^{N2})R^{N1}$, $R^{N3}$ and $R^{N1}$, or $R^{N2}$ and $R^{N1}$ may be covalently bonded together to form a 5-, 6- or 7-membered saturated heterocycle which may have additionally one heteroatom selected from O, N and S, wherein said heterocycle is optionally substituted as defined.

Included within the scope of this invention are all compounds of formula I as presented in Tables 1 to 8.

Preferred compounds according to this invention are listed in the tables. Particularly compounds of these tables are preferred which show an $IC_{50}$ value of below 200 nM, as for example those compounds included in the claims 40 and 41.

Polymerase Activity

The ability of the compounds of formula (I) to inhibit RNA synthesis by the RNA dependent RNA polymerase of HCV can be demonstrated by any assay capable of measuring RNA dependent RNA polymerase activity. A suitable assay is described in the examples.

Specificity for RNA Dependent RNA Polymerase Activity

To demonstrate that the compounds of the invention act by specific inhibition of HCV polymerase, the compounds may be tested for inhibitory activity in a DNA dependent RNA polymerase assay.

When a compound of formula (I), or one of its therapeutically acceptable salts, is employed as an antiviral agent, it is administered orally, topically or systemically to mammals, e.g. humans, cattle, pigs, dogs, cats, rabbits or mice, in a vehicle comprising one or more pharmaceutically acceptable carriers, the proportion of which is determined by the solubility and chemical nature of the compound, chosen route of administration and standard biological practice.

For oral administration, the compound or a therapeutically acceptable salt thereof can be formulated in unit dosage forms such as capsules or tablets each containing a predetermined amount of the active ingredient, ranging from about 25 to 500 mg, in a pharmaceutically acceptable carrier.

For topical administration, the compound can be formulated in pharmaceutically accepted vehicles containing 0.1 to 5 percent, preferably 0.5 to 5 percent, of the active agent. Such formulations can be in the form of a solution, cream or lotion.

For parenteral administration, the compound of formula (I) is administered by either intravenous, subcutaneous or intramuscular injection, in compositions with pharmaceutically acceptable vehicles or carriers. For administration by injection, it is preferred to use the compounds in solution in a sterile aqueous vehicle which may also contain other solutes such as buffers or preservatives as well as sufficient quantities of pharmaceutically acceptable salts or of glucose to make the solution isotonic.

Suitable vehicles or carriers for the above noted formulations are described in pharmaceutical texts, e.g. in "Remington's The Science and Practice of Pharmacy", 19th ed., Mack Publishing Company, Easton, Pa., 1995, or in "Pharmaceutical Dosage Forms And Drugs Delivery Systems", 6th ed., H. C. Ansel et al., Eds., Williams & Wilkins, Baltimore, Md., 1995.

The dosage of the compound will vary with the form of administration and the particular active agent chosen. Furthermore, it will vary with the particular host under treatment. Generally, treatment is initiated with small increments until the optimum effect under the circumstance is reached. In general, the compound of formula I is most desirably administered at a concentration level that will generally afford antivirally effective results without causing any harmful or deleterious side effects.

For oral administration, the compound or a therapeutically acceptable salt is administered in the range of 10 to 200 mg per kilogram of body weight per day, with a preferred range of 25 to 150 mg per kilogram.

For systemic administration, the compound of formula (I) is administered at a dosage of 10 mg to 150 mg per kilogram of body weight per day, although the aforementioned variations will occur. A dosage level that is in the range of from about 10 mg to 100 mg per kilogram of body weight per day is most desirably employed in order to achieve effective results.

When the compositions of this invention comprise a combination of a compound of formula I and one or more additional therapeutic or prophylactic agent, both the compound and the additional agent should be present at dosage levels of between about 10 to 100%, and more preferably between about 10 and 80% of the dosage normally administered in a monotherapy regimen.

When these compounds or their pharmaceutically acceptable salts are formulated together with a pharmaceutically acceptable carrier, the resulting composition may be administered in vivo to mammals, such as man, to inhibit HCV polymerase or to treat or prevent HCV virus infection. Such treatment may also be achieved using the compounds of this invention in combination with agents which include, but are not limited to: immunomodulatory agents, such as α-, β-, or γ-interferons; other antiviral agents such as ribavirin, amantadine; other inhibitors of HCV NS5B polymerase; inhibitors of other targets in the HCV life cycle, which include but are not limited to, helicase, NS2/3 protease, NS3 protease, or internal ribosome entry site (IRES); or combinations thereof. The additional agents may be combined with the compounds of this invention to create a single dosage form. Alternatively these additional agents may be separately administered to a mammal as part of a multiple dosage form.

Methodology and Synthesis

Indole derivatives or analogs according to the present invention can be prepared from known monocyclic aromatic compounds by adapting known literature sequences such as those described by J. W. Ellingboe et al. (*Tet. Lett.* 1997, 38, 7963) and S. Cacchi et al. (*Tet. Lett.* 1992, 33, 3915). Scheme 1, shown below wherein $R^1$, $R^2$, Sp, Y and L are as described herein, illustrate how these procedures can be adapted to the synthesis of compounds of formula I of this invention.

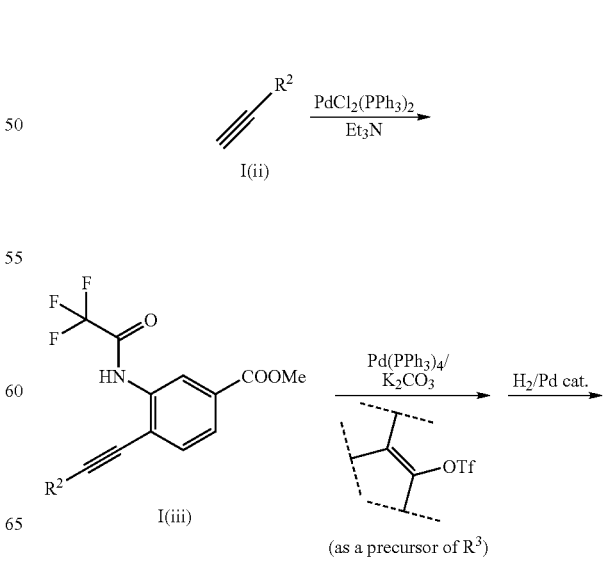

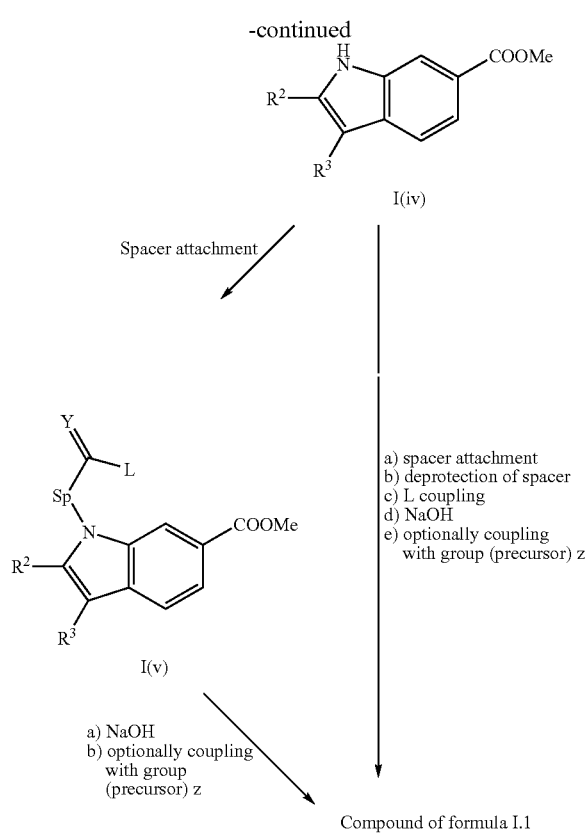

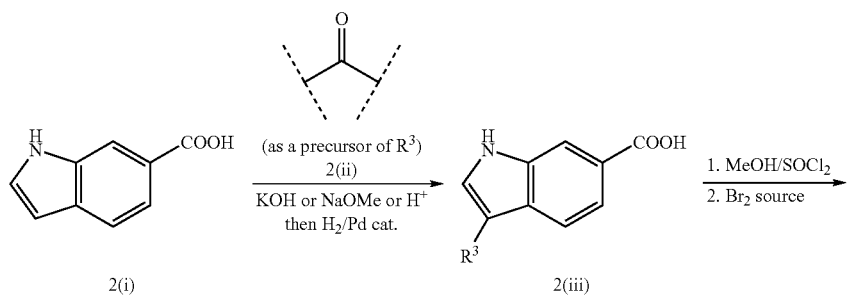

solvents for this reaction include DMF, dioxane, THF, DME, toluene, MeCN, DMA and the like at temperatures ranging from 20° C. to 170° C., or alternatively without solvent by heating the components together. Alternatively, the cross-coupling reaction can be carried out on a suitably protected form of 3-amino-4-iodobenzoate and the amino group can be trifluoroacetylated in the subsequent step as described by J. W. Ellingboe et al. (*Tet. Lett.* 1997, 38, 7963).

Reaction of the above diarylalkynes I(iii) with an enol triflate or equivalent under cross-coupling conditions similar to those described above gives after hydrogenation of the double bond, indole derivatives I(iv). Enol triflates are known and can be prepared from the corresponding ketones by following known literature methods (for example, cyclohexene triflate can be prepared from cyclohexanone, triflic anhydride and a hindered organic base such as 2,6-di-tert-butyl-4-methylpyridine). The hydrogenation of the double bond originally present in $R^3$ can be carried out with hydrogen gas or a hydrogen donor (ammonium formate, formic acid and the like) in the presence of a metal catalyst (preferably Pd) in a suitable solvent (lower alkyl alcohols, THF etc.).

The indole derivative I(iv) is then alkylated on nitrogen with an appropriate spacer (Sp) and further elaborated if necessary to give N-alkylated indole carboxylates where Y, Sp and L are as defined herein.

Finally, following hydrolysis of the indole ester protecting group, the resulting carboxyindole derivative is converted to compounds of formula 1 by coupling with the appropriate Z group. Condensation of the 6-indolecarboxylic acid with amines or alcohols can be accomplished using standard amide bond forming reagents such as TBTU, HATU, BOP, BroP, EDAC, DCC, isobutyl chloroformate and the like, or by activation of the carboxyl group by conversion to the corresponding acid chloride prior to condensation with an amine. Any remaining protecting group is removed following this step to give compounds of formula I.1.

Alternatively, compounds of formula I..1 can be prepared by elaboration from a pre-existing indole core by following adaptations of literature procedures as described, for example, by P. Gharagozloo et al. (*Tetrahedron* 1996, 52, 10185) or K. Freter (*J. Org. Chem.* 1975, 40, 2525). Such a methodology is illustrated in Scheme 2:

In carrying out the route illustrated in Scheme 1, a suitably protected form of 3-trifluoroacetamido-4-iodobenzoic acid I(i) is reacted with an alkyne I(ii) in the presence of a metal catalyst (e.g. a palladium metal complex such as $PdCl_2(PPh_3)_2$, $Pd_2dba_3$, $Pd(PPh_3)_4$ and the like), a base ($Et_3N$, DIEA and the like or an inorganic basic salt including metal carbonates, fluorides and phosphates), and optionally in the presence of an additional phosphine ligand (triaryl or heteroarylphosphine, dppe, dppf, dppp and the like). Suitable -continued

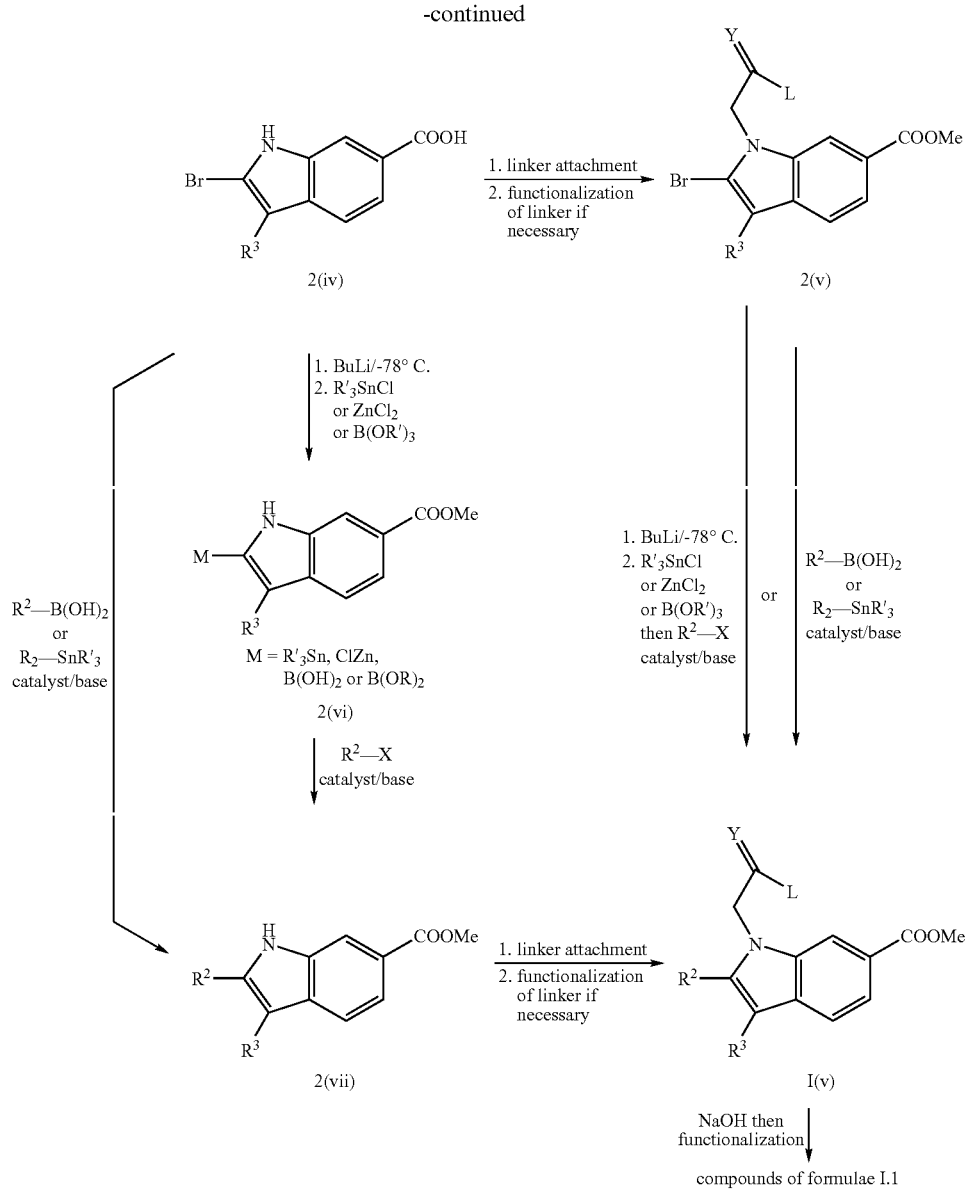

In carrying out the route illustrated in Scheme 2, commercially available 6-indolecarboxylic acid 2(i), which can also be prepared according to the method of S. Kamiya et al. (*Chem. Pharm. Bull.* 1995, 43, 1692) is used as the starting material. The indole 2(i) is reacted with a ketone 2(ii) under basic or acidic aldol-type conditions. Suitable conditions to affect this condensation include strong bases such as alkali metal hydroxides, alkoxides and hydrides in solvents such as lower alkyl alcohols (MeOH, EtOH, tertBuOH etc.), THF, dioxane, DMF, DMSO, DMA and the like at reaction temperature ranging from −20° C. to 120° C.

Alternatively, the condensation can be carried out under acid conditions using organic or mineral acids or both. Appropriate conditions include mixtures of AcOH and aqueous phosphoric acid at temperatures ranging from 15° C. to 120° C.

The carboxylic acid group is then protected in the form of an ester (usually lower alkyl) using known methods. Halogenation (usually bromination, but also iodination) of the 2-position of the indole 2(iii) gives 2(iv). Suitable halogenating agents include, for example, elemental bromine, N-bromosuccinimide, pyridine tribromide, dibromohydantoin and the corresponding iodo derivatives. Suitable solvents for this reaction are inert to reactive halogenating agents and include for example hydrocarbons, chlorinated hydrocarbons (DCM, $CCl_4$, $CHCl_3$), ethers (THF, DME, dioxane), acetic acid, ethyl acetate, IPA, and mixtures of these solvents. Reaction temperature ranges from −40° C. to 100° C. A method of choice to carry out the bromination of indoles as shown in Scheme 2 was described by L. Chu (*Tet. Lett.* 1997, 38, 3871).

The 2-bromoindole derivatives 2(iv) can be converted to fully substituted key intermediates I(v) by different sequences: (1) Trans-metallation of the 2-bromoindole to tin, boron, zinc species and the like, followed by cross-coupling reaction with aryl or heteroaryl halides under transition metal catalysis as described in scheme 1 gives indole derivative 2(vii) which can then be elaborated on nitrogen as described in scheme 1 to give key intermediate 1(v). In this approach, the indoleic NH is optionally protected with known protecting groups such as BOC, MOM, SEM, SO$_2$Ph and the like. The protecting group is removed at a later stage of the sequence, prior to linker attachment. The conversion of 2-bromoindole derivatives 2(iv) to the corresponding organotin species 2(vi) is carried out via initial low-temperature (usually −78° to −30° C.) halogen-metal exchange using an alkyllithium reagent (e.g. nBuLi or tert-BuLi) or using lithium metal. The transient 2-lithioindole species is then trapped with a trialkyltin halide (e.g. nBu$_3$SnCl or Me$_3$SnCl) or a borate ester (e.g. trimethyl or triisopropyl borates). Alternatively, the lithioindole intermediate can be trapped with zinc chloride to form the corresponding organozincate which can also undergo transition metal-catalyzed cross-coupling with aromatic and heteroaromatic halides or triflates as described, for example, by M. Rowley (*J. Med. Chem.* 2001, 44, 1603). Alternatively, species such as 2(vi) where the indoleic NH is masked with a protecting group, can be generated directly from 2(iii) by ester formation followed by indole NH protection and abstraction of the 2-H proton with strong base (e.g. alkyllithiums, alkalimetal amides) followed by trans-metallation. Alternatively, 2-bromoindole 2(iv) can be cross-coupled directly to aryl and heteroaryl stannanes or boronic acid derivatives to give 2(vii) directly. Boron or tin organometallic species are from commercial sources or can be prepared by standard literature procedures. (2) In a second approach, 2-bromoindole 2(iv) is first elaborated on nitrogen to give 2(v) which is then cross-coupled to R$^2$ to give the same intermediate 1(v) as described above.

Cross-coupling with organoboron reagents can be carried out by any variations of the Suzuki cross-coupling reaction reported in the literature. This usually involves the use of a transition metal catalyst (usually Pd°), triaryl or triheteroarylphosphine ligands, an additive such as an inorganic chloride (e.g. LiCl), and a base (usually an aqueous inorganic base such as sodium or potassium carbonate or phosphate). The reaction is usually carried out in an alcoholic solvent (EtOH), DME, toluene, THF and the like at temperatures ranging from 25° C. to 140° C.

Cross-coupling with tin reagents can be carried out by any variations of the Stille cross-coupling reaction reported in the literature. This usually involves the use of a transition metal catalyst (usually Pd°), triaryl or triheteroaryl phosphine ligands, and an additive such as an inorganic chloride (e.g. LiCl) or iodide (e.g. CuI). Suitable solvents for this reaction include toluene, DMF, THF, DME and the like at temperatures ranging from 25° C. to 140° C. Intermediate I(v) is then converted to compounds of formula I.1 as described for Scheme 1. Reaction conditions to alkylate the nitrogen of an indole derivative are well known to those skilled in the art and include the use of strong bases such as alkali metal hydrides, hydroxides, carbonates, amides, alkoxides and alkylmetals, in the appropriate solvent (such as THF, dioxane, DME, DMF, MeCN, DMSO, alcohols and the like) at temperatures ranging from −78° C. to 140° C. An electrophilic form of Sp is used for the alkylation of the indole anion. Such electrophilic species include iodides, bromides, chlorides and sulfonate esters (mesylate, tosylate, brosylate or triflate).

EXAMPLES

The present invention is illustrated in further detail by the following non-limiting examples. All reactions were performed in a nitrogen or argon atmosphere. Temperatures are given in degrees Celsius. Flash chromatography was performed on silica gel. Solution percentages or ratios express a volume to volume relationship, unless stated otherwise. Mass spectral analyses were recorded using electrospray mass spectrometry. Hereinbefore and hereinafter the following abbreviations or symbols are used:

AcOH: acetic acid

BOC or Boc: tert-butyloxycarbonyl

BOP: benzotriazole-1-yloxy-tris(dimethylamino)phosphonium hexafluorophosphate

BroP: Bromo tris(dimethylamino)phosphonium hexafluorophosphate

Bu: butyl

Cbz: carbobenzyloxy carbonyl;

DBA: dibenzylideneacetone;

DBU: 1,8-diazabicyclo[5.4.0]undec-7-ene

DCC: 1,3-Dicyclohexyl carbodiimide

DCM: dichloromethane

DEPC: diethyl pyrocarbonate;

DIEA: diisopropylethylamine;

DMAP: 4-(dimethylamino)pyridine;

DME: dimethoxyethane;

DMF: N,N-dimethylformamide;

DMSO: dimethylsulfoxide;

dppe: 1,2-bis(diphenylphosphino)ethane dppf: 1,1'-bis(diphenylphosphino)ferrocene dppp: 1,2-bis(diphenylphosphino)propane DTT: dithiothreitol EDAC: see EDC EDC: 1-(3-dimethylaminopropyl)-3-ethyl carbodiimide hydrochloride EDTA: ethylenediaminetetraacetate ES$^-$: electro spray (negative ionization)

ES$^+$: electro spray (positive ionization)

Et: ethyl;

Et$_2$O: diethyl ether;

EtOAc: ethyl acetate;

EtOH: ethanol

Fmoc: 9-Fluorenylmethyloxycarbonyl

HATU: O-(7-azabenzotriazol-1-yl)-N,N,N',N'-tetramethyluronium hexafluorophosphate HBTU: O-Benzotriazol-1-yl-N,N,N',N'-tetramethyluronium hexafluorophosphate HOAT: 1-hydroxy-7-azabenzotriazole HOBt: 1-Hydroxybenzotriazole HPLC: high performance liquid chromatography;

IPA: isopropyl acetate $^i$Pr: isopropyl $^i$PrOH: isopropanol

Me: methyl;

MeCN: acetonitrile;

MeOH: Methanol;

MOM: methoxymethyl;

MS (ES): electrospray mass spectrometry;

NMP: N-methylpyrrolidone

PFU: plaque forming units;

Ph: phenyl;

RNAsin: A ribonuclease inhibitor marketed by Promega Corporation

RT: room temperature (approximately 25° C.)

SEM: trimethylsilylethoxymethyl;

TBE: tris-borate-EDTA;

TBME: tert-butylmethyl ether

TBTU: 2-(1H-benzotriazol-1-yl)-N,N,N',N'-tetramethyluronium tetrafluoroborate;

tBu: tert.-butyl;

TFA: trifluoroacetic acid;

TFAA: trifluoroacetic anhydride;

THF: tetrahydrofuran;

TLC: thin layer chromatography

Tris: 2-amino-2-hydroxymethyl-1,3-propanediol

UMP: uridine 5'-monophosphate

UTP: uridine 5'-triphosphate

Examples 1-33 illustrate methods of synthesis of representative compounds of this invention.

Example 1

3-Cyclohexyl-2-phenylindole-6-carboxylic acid

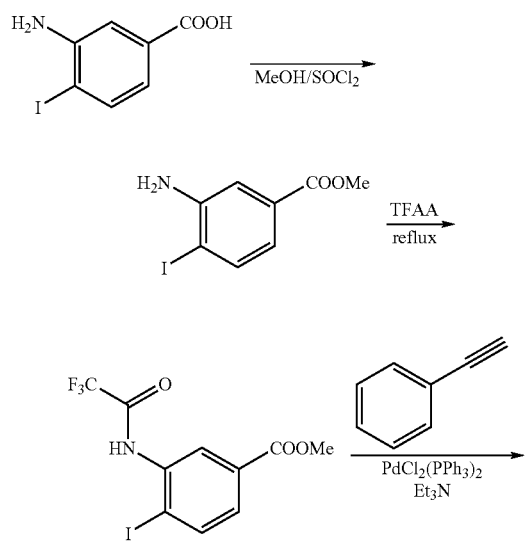

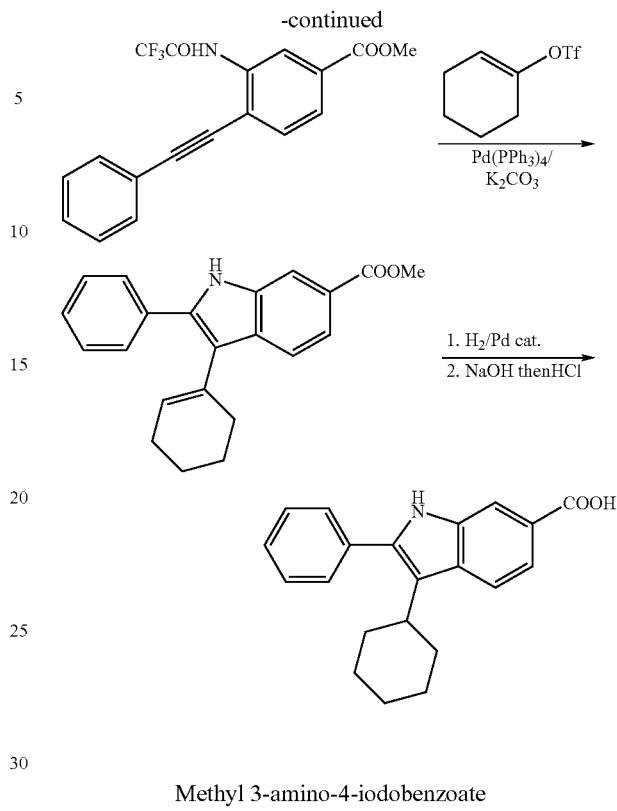

Methyl 3-amino-4-iodobenzoate

3-Amino-4-iodobenzoic acid (13.35 g, 50.8 mmol) was added to MeOH (150 mL) and SOCl$_2$ (4.8 mL, 65.8 mmol, 1.3 equivalent) was added. The mixture was refluxed for 3 h and then volatiles were removed under reduced pressure. The residue was co-evaporated 3× with MeOH and dried in vacuo (15.23 g).

Methyl 3-trifluoroacetamido-4-iodobenzoate

The aniline derivative from above (14.53 g, 52 mmol) was dissolved in DCM (200 mL) and TFAA (15 mL, 104 mmol) was added. The dark purple solution was refluxed overnight. Volatiles were removed under reduced pressure and the residue was passed through a short pad of silica gel using DCM as eluent. The desired product was obtained as a pink solid (13.81 g): MS (ES$^-$) m/z 371.9 (M–H).

4-Phenylethynyl-3-(2,2,2-trifluoro-ethanoylamino)-benzoic acid methyl ester

The iodide from above (0.742 g, 2 mmol), phenylacetylene (0.37 mL, 3.9 mmol, 1.7 equivalent) and Et$_3$N (6 mL) were charged in a dry flask under argon. PdCl$_2$(PPh$_3$)$_2$ (0.241 g, 0.3 mmol) was added and the mixture was stirred at room temperature until judged complete by HPLC analysis (~5 h). The reaction mixture was concentrated to ½ volume under reduced pressure and diluted with water (80 mL). The mixture was extracted with EtOAc (3×100 mL) and the organic extract washed with 5% HCl (100 mL), after (100 mL) and brine (40 mL). After drying over MgSO$_4$, the residue was purified by flash chromatography using 20% EtOAc-hexane

Methyl 3-(cyclohexenyl)-2-phenylindole 6-carboxylate

A flame-dried flask was charged with finely powdered anhydrous K$_2$CO$_3$ (0.153 g, 1.1 mmol) and the alkyne derivative from above (0.390 g, 1.1 mmol). Dry DMF (4 mL) was added and the suspension degassed with a stream of argon. The enol triflate derived from cyclohexanone, prepared following the procedure described by A. G. Martinez, M. Hanack et al. (*J. Heterocyclic Chem.* 1988, 25, 1237) or equivalent methods described in the literature (0.802 g, 3.3 mmol, 3 equivalents) was added followed by Pd(PPh$_3$)$_4$ (0.086 g, 0.07 mmol) and the mixture was stirred for 8 h at room temperature. DMF was removed under vacuum and the residue purified by flash chromatography using DCM as eluent (0.260 g): MS (ES$^+$) m/z 332.2 (MH$^+$).

Methyl 3-cyclohexyl-2-phenylindole-6-carboxylate

The material from above was hydrogenated (1 atm H$_2$ gas) over 20% Pd(OH)$_2$ in the usual manner, using MeOH as solvent. The desired cyclohexane indole was isolated after filtration of the catalyst: MS (ES$^+$) m/z 334.1 (MH$^+$).

3-Cyclohexyl-2-phenylindole-6-carboxylic acid

The methyl ester from above (0.154 g, 0.15 mmol) was refluxed overnight in a mixture of MeOH (10 mL) and 2N NaOH (6 mL) until complete hydrolysis had occurred as shown by HPLC analysis. After cooling to room temperature, 2N HCl (5 mL) was added followed by AcOH to pH 7. MeOH was removed under reduced pressure, water (50 mL) was added and the product extracted with EtOAc. The extract was washed with water and brine, and dried (MgSO$_4$). Removal of volatiles under reduced pressure gave the title indole carboxylic acid of example 1 as a light-orange solid (0.149 g): MS (ES$^-$) m/z 319 (M−H).

Following the same procedure but using 2-ethynylpyridine instead of phenylacetylene, 3-cyclohexane-2-(2-pyridyl)indole-6-carboxylic acid was obtained.

Example 2

Methyl 2-bromo-3-cyclohexyl-6-indole carboxylate

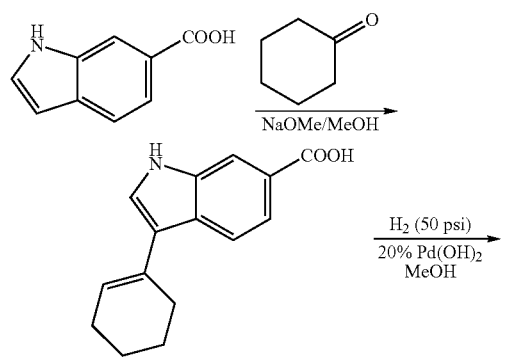

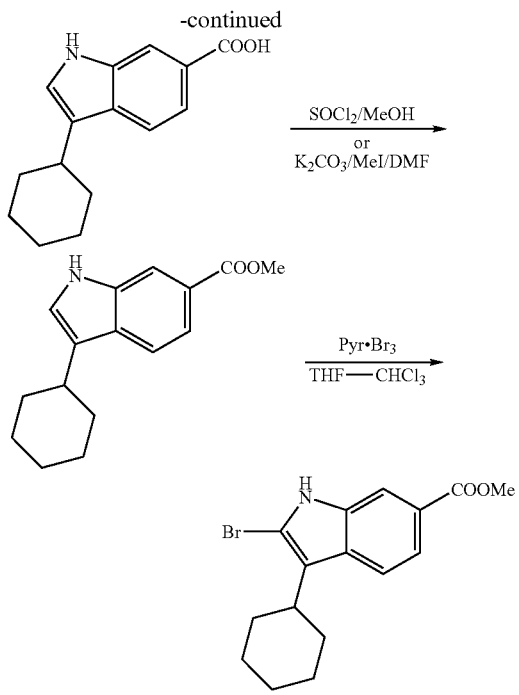

3-Cyclohexenyl-6-indole carboxylic acid

A 12 L round-bottomed flask was equipped with a reflux condenser and a mechanical stirrer, and the system was purged with nitrogen gas. 6-indole carboxylic acid (300.00 g, 1.86 mole, 3 equivalents) was charged into the flask, followed by MeOH (5.5 L). After stirring for 10 min at room temperature, cyclohexanone (579 mL, 5.58 mole) was added. Methanolic sodium methoxide (25% w/w, 2.6 L, 11.37 mole, 6.1 equivalents) was added in portions over 10 min. The mixture was then refluxed for 48 h. After cooling to room temperature, water (4 L) was added and methanol removed under reduced pressure. The residual aqueous phase was acidified to pH 1 with concentrated HCl (~1.2 L). The resulting yellowish precipitate was collected by filtration, washed with water and dried under vacuum at 50° C. The desired cyclohexene derivative was obtained as a beige solid (451.0 g, 100% yield).

3-Cyclohexyl-6-indole carboxylic acid

The unsaturated derivative from above was hydrogenated for 20 h under 55 psi hydrogen gas pressure over 20% Pd(OH)$_2$/C (10.25 g) using 1:1 THF-MeOH (2.5 L) as solvent. After filtration of the catalyst, volatiles were removed under reduced pressure and the residue was triturated with hexane. The beige solid was collected by filtration, washed with hexane and dried under vacuum (356.4 g, 78% yield).

Methyl 3-cyclohexyl-6-indole carboxylate (thionyl chloride procedure)

A 5 L three-necked flask was equipped with a reflux condenser and a mechanical stirrer, and the system was purged with nitrogen gas. The indole carboxylic acid from above (300.00 g, 1.233 mole) was charged into the flask and suspended in MeOH (2 L). Thionyl chloride (5 mL, 0.0685 mole, 0.05 equivalent) was added dropwise and the mixture was refluxed for 48 h. Volatiles were removed under reduced pressure and the residue was triturated with hexane to give a beige solid that was washed with hexane and dried under vacuum (279.6 g, 88% yield).

Methyl 3-cyclohexyl-6-indole carboxylate (carbonate/iodomethane procedure)

A 2 L flask equipped with a dropping funnel and mechanical stirrer was charged with crude 3-cyclohexyl-6-indole carboxylic acid (99.4 g, 0.409 mole) and anhydrous DMF (665 mL) was added followed by anhydrous potassium carbonate (78.13 g, 0.565 mole). Iodomethane (63.72 g, 0.449 mole) was added dropwise over 35 min with stirring to the slurry which was then stirred overnight at room temperature until complete disappearance of starting material (TLC). The resulting suspension was then poured into water (1350 mL) and acidified to pH 4 with 4N HCl (200 mL). The product was extracted into ether (3×1700 mL), washed with water and brine and dried ($Na_2SO_4$). Volatiles were removed under reduced pressure and the residue was triturated with hexane (700 mL). The beige solid was filtered and dried under vacuum (94.3 g, 90% yield).

Methyl 2-bromo-3-cyclohexyl-6-indole carboxylate

Adapting the procedure of L. Chu (*Tet. Lett.* 1997, 38, 3871) methyl 3-cyclohexyl-6-indole carboxylate (4.65 g, 18.07 mmol) was dissolved in a mixture of THF (80 mL) and $CHCl_3$ (80 mL). The solution was cooled in an ice bath and pyridinium bromide perbromide (pyridine tribromide, 7.22 g, 22.6 mmol, 1.25 equivalent) was added. After stirring for 1.5 h at 0° C., the reaction was judged complete by TLC. It was diluted with $CHCl_3$ (200 mL), washed with 1M $NaHSO_3$ (2×50 mL), saturated aqueous $NaHCO_3$ (2×50 mL) and brine (50 mL). After drying over $Na_2SO_4$, the solvent was removed under reduced pressure and the residue crystallized from TBME-hexane. The desired 2-bromoindole derivative was collected by filtration, washed with hexane and dried (3.45 g). Evaporation of mother liquors gave a red solid that was purified by flash chromatography using 15% EtOAc in hexane yielding an additional 3.62 g of pure material. Total yield was 5.17 g (85% yield).

Example 3

Methyl 2-bromo-3-cyclopentyl-6-indole carboxylate

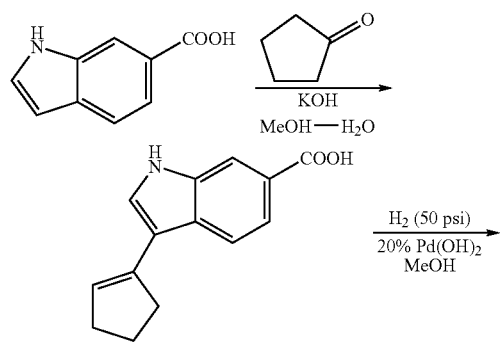

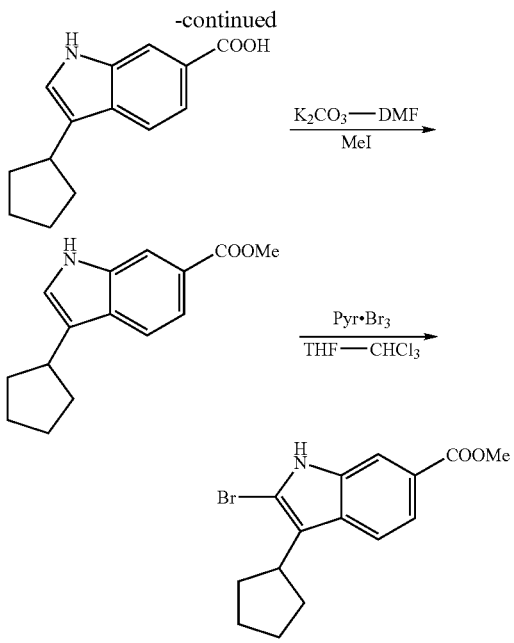

3-Cyclopentenyl-6-indole carboxylic acid

A 3 L three-necked flask equipped with a mechanical stirrer was charged with indole 6-carboxylic acid (220 g, 1.365 mole) and KOH pellets (764.45 g, 13.65 mole, 10 equivalents). Water (660 mL) and MeOH (660 mL) were added and the mixture heated to 75° C. Cyclopentanone (603.7 mL, 6.825 mole, 5 equivalents) was added dropwise over 18 h using a pump. The reaction mixture was heated for an additional 3 h (after which the reaction was judged complete by HPLC) and cooled to 0° C. for 1 h. The precipitated potassium salt is collected by filtration, and washed with TBME (2×500 mL) to remove cyclopentanone self-condensation products. The brown solid was re-dissolved in water (2.5 L) and the solution washed with TBME (2×1 L). Following acidification to pH 3 with conc. HCl (425 mL), the beige precipitate was collected by filtration, washed with water (2×1 L) and dried under vacuum at 70° C. The crude product weighed 275.9 g (88.9% mass recovery) and had an homogeneity of 85% (HPLC).

3-Cyclopentyl-6-indole carboxylic acid

The crude product from above (159.56 g, 0.70 mole) was dissolved in MeOH (750 mL) and 20% $Pd(OH)_2$ on charcoal (8.00 g) was added. The mixture was hydrogenated in a Parr apparatus under 50 psi hydrogen gas for 18 h. After completion, the catalyst was removed by filtration through celite and the solvent removed under reduced pressure. The resulting brown solid was dried at 70° C. under vacuum for 12 h. The crude product (153.2 g) was obtained as a brown solid and was 77% homogeneous by HPLC.

Methyl 3-cyclopentyl-6-indole carboxylate

The indole carboxylic acid from above was converted to the corresponding methyl ester using the carbonate/iodomethane procedure described in example 2.

Methyl 2-bromo-3-cyclopentyl-6-indole carboxylate

The indole carboxylate from above was brominated using pyridinium bromide perbromide following the procedure described in example 2.

Example 4

General Procedure for the Suzuki Cross-Coupling of Aryl and Heteroarylboronic Acids with 2-Bromoindole Derivatives Cross-coupling of aromatic/heteroaromatic boronic acid or ester derivatives with 2-bromoindoles such as the ones described in examples 2 and 3 can be performed using any variations of the standard metal-catalyzed Suzuki cross-coupling reaction as described in the literature and well known to those skilled in the art. The following example serves to illustrate such a process and is non-limiting.

3-Cyclohexyl-2-furan-3-yl-1H-indole-6-carboxylic acid methyl ester

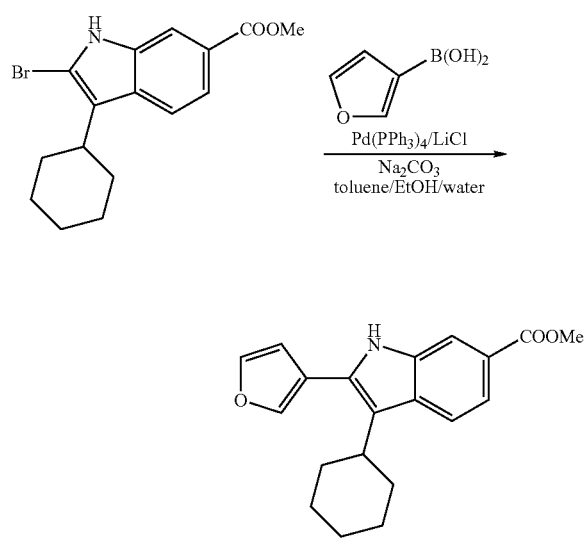

The 2-bromoindole of example 2 (8.92 g, 26.5 mmol), 3-furanboronic acid (B. P. Roques et al. *J. Heterocycl. Chem.* 1975, 12, 195; 4.45 g, 39.79 mmol, 1.5 equivalent) and LiCl (2.25 g, 53 mmol, 2 equivalents) were dissolved in a mixture of EtOH (100 mL) and toluene (100 mL). A 1M aqueous $Na_2CO_3$ solution (66 mL, 66 mmol) was added and the mixture was degassed with argon for 45 min. $Pd(PPh_3)_4$ (3.06 g, 2.65 mmol, 0.1 equivalent) was added and the mixture stirred overnight at 75-85° C. under argon. Volatiles were removed under reduced pressure and the residue re-dissolved in EtOAc (500 mL). The solution was washed with water, saturated $NaHCO_3$ (100 mL) and brine (100 mL). After drying over a mixture of $MgSO_4$ and decolorizing charcoal, the mixture was filtered and concentrated under reduced pressure. The residual oil was triturated with a mixture of TBME (20 mL) and hexane (40 mL), cooled in ice and the precipitated solid collected by filtration, washed with cold 25% TBME in hexane, and dried (3.09 g). The filtrate and washings from the above trituration were combined, concentrated and purified by flash chromatography using 10-25% EtOAc in hexane to give an additional 4.36 g of product. The total yield of the 2-(3-furyl)indole of example 4 was 8.25 g.

Example 5

General Procedure for the Stille Cross-Coupling of Aryl and Heteroarylstannanes with 2-Bromoindole Derivatives Cross-coupling of aromatic/heteroaromatic stannane derivatives with 2-bromoindoles such as the ones described in examples 2 and 3 can be performed using any variations of the standard metal-catalyzed Stille cross-coupling reaction as described in the literature and well known to those skilled in the art. The following example serves to illustrate such a process and is non-limiting.

3-Cyclohexyl-2-thiophen-2-yl-1H-indole-6-carboxylic acid methyl ester

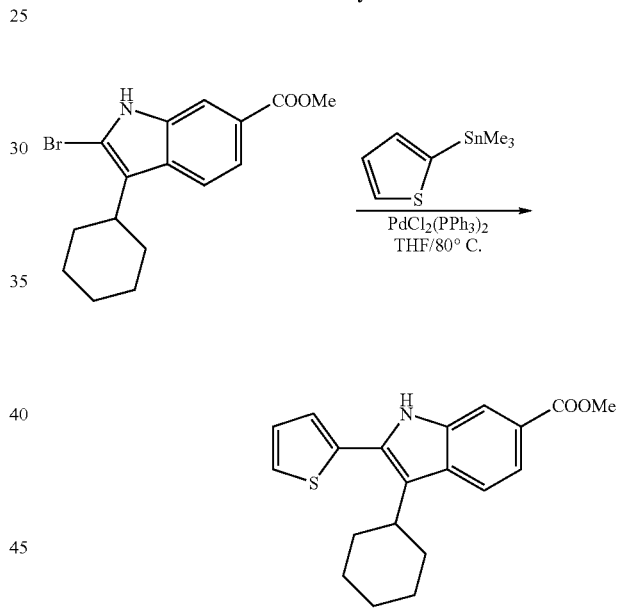

A 1 L flask equipped with a reflux condenser was charged with 2-trimethylstannylthiophene (11.16 g, 45 mmol), the 2-bromoindole of example 2 (7.00 g, 21 mmol) and anhydrous THF (300 mL). The solution was degassed by bubbling argon through the solution for 1 h. The catalyst, dichloro-bis(triphenylphosphine)palladium (1.76 g, 2.5 mmol) was added and the mixture was stirred at 80° C. under an argon atmosphere for 24 h. The reaction mixture was cooled to room temperature, filtered to remove solids and concentrated under reduced pressure. The residue was purified by flash chromatography using 9:1 hexane-EtOAc as eluent, to give the desired 2-(2-thiophene)indole product of example 5 (7.10 g, 99% yield).

Example 6

General Procedure for N-Alkylation of Indole Derivatives to Give N-(Methylcarboxy)Indoles The following example serves to illustrate such a process and is non-limiting.

Methyl 1-carboxymethyl-3-cyclohexyl-2-furan-3-yl-1H-indole-6-carboxylate

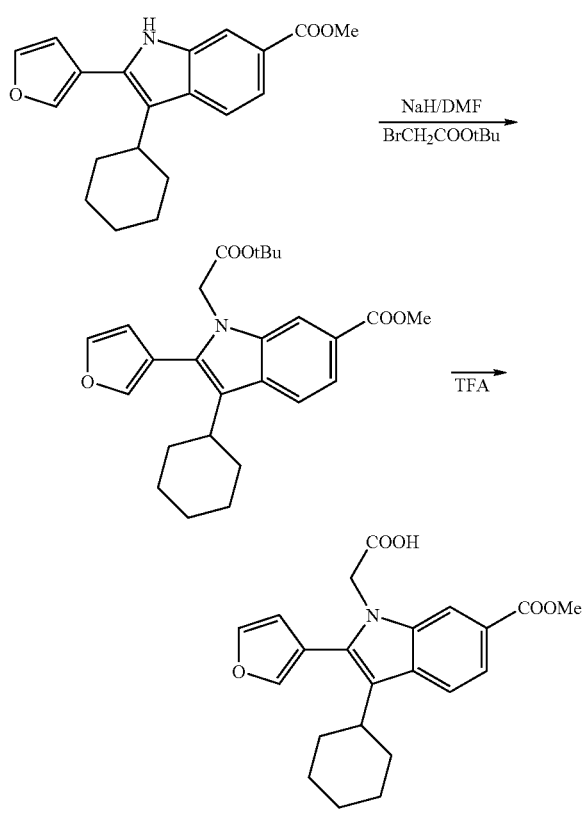

Methyl 1-tert-butoxycarbonylmethyl-3-cyclohexyl-2-furan-3-yl-1H-indole-6-carboxylate The indole derivative from example 4 (18.50 g, 57.4 mmol) was dissolved in anhydrous DMF (120 mL) and the solution was cooled in an ice bath under an argon atmosphere. NaH (60% oil dispersion, 2.88 g, 72 mmol) was added in 3 portions and the mixture stirred 1 h at 0° C. tert-Butylbromoacetate (13.88 g, 71 mmol, 1.24 equiv.) was added dropwise over 10 min and then the ice bath was removed. The reaction mixture was stirred overnight at room temperature. It was then diluted with TBME (1500 mL) and washed with 10% HCl (2×250 mL), water (3×500 mL) and brine (1×400 mL). After drying (Na$_2$SO$_4$), the solvent was removed under reduced pressure to give a white solid. The solid was triturated with hexane (300 mL), filtered and triturated a second time with hexane (500 mL). Filtration followed by drying under vacuum gave the desired tert-butyl ester as a white solid (21.6 g, 86% yield).

Methyl 1-carboxymethyl-3-cyclohexyl-2-furan-3-yl-1H-indole-6-carboxylate

The tert-butyl ester from above (21.5 g, 49 mmol) was dissolved in dichloromethane (90 mL) and TFA (65.6 mL) was added dropwise to the solution which was stirred for 5 h at room temperature. Volatiles were removed under reduced pressure, the residue was co-evaporated 3× with DCM and then dried under vacuum. The crude product was triturated with a mixture of hexane (200 mL) and DCM (20 mL), filtered and dried under vacuum to give the title compound of example 6 as a white solid (18.62 g, 99% yield).

Example 7

Methyl 1-carboxymethyl-3-cyclopentyl-2-furan-3-yl-1H-indole-6-carboxylate

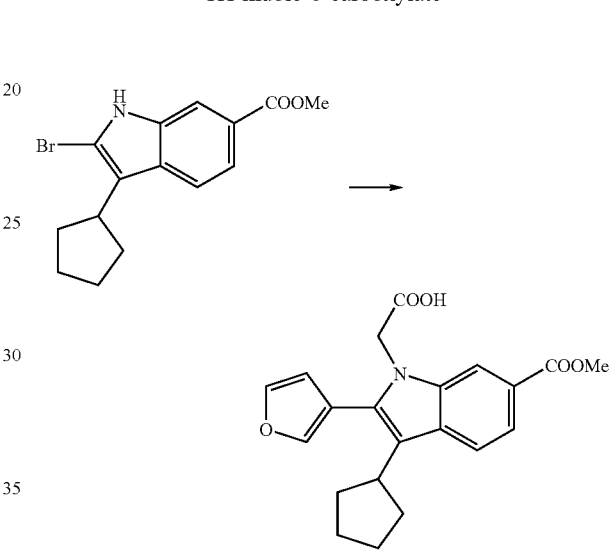

The procedures for examples 4 and 6 were followed, using the 2-bromoindole of example 3 as starting material.

Example 8

Methyl 2-bromo-1-carboxymethyl-3-cyclohexyl-1H-indole-6-carboxylate

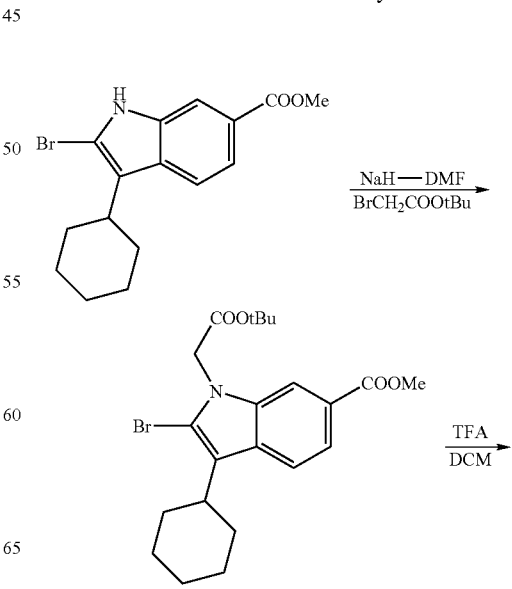

-continued

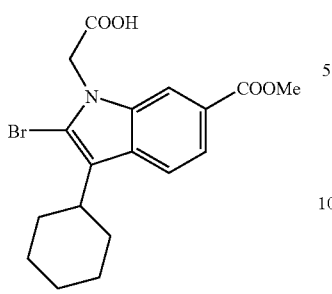

The 2-bromoindole from example 2 was N-alkylated with tert-butylbromoacetate using NaH in DMF and the tert-butyl ester cleaved with TFA as described in example 6 to give the title compound of example 8 as a white solid.

Example 9

General Procedure for Amidation of N-(Methylcarboxy)Indoles with Amines and Saponification to Give Inhibitors of General Formula I.1

The following example serves to illustrate such a process and is non-limiting.

3-Cyclohexyl-2-furan-3-yl-1-(2-morpholin-4-yl-2-oxo-ethyl)-1H-indole-6-carboxylic acid

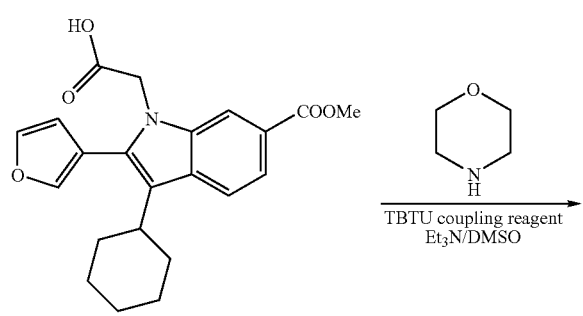

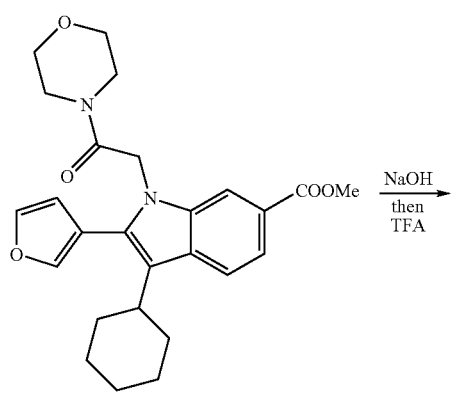

Methyl 3-cyclohexyl-2-furan-3-yl-1-(2-morpholin-4-yl-2-oxo-ethyl)-1H-indole-6-carboxylate The N-(methylcarboxy)indole derivative of example 6 (0.500 g, 1.31 mmol, 1 equiv.), morpholine (141 μL, 1.6 mmol, 1.22 equiv.) and triethylamine (432 μL, 3.1 mmol, 2.36 equiv.) were dissolved in a mixture of THF (13 mL0 and DMF (3 m). TBTU (0.514 g, 1.6 mmol, 1.22 equiv.) was added and the mixture stirred at room temperature for 3 h (complete by TLC). The reaction mixture was diluted with EtOAc and washed successively with 10% aqueous HCl, water and brine. The extract was dried (MgSO$_4$), concentrated and the residue purified by flash chromatography on silica gel using 70% EtOAc in hexane as eluent. The methyl ester of example 9 was obtained as a yellow solid (0.498 g, 84% yield).

3-Cyclohexyl-2-furan-3-yl-1-(2-morpholin-4-yl-2-oxo-ethyl)-1H-indole-6-carboxylic acid The methyl ester from above (0.480 g, 0.995 mmol) was dissolved in a mixture of THF (8 mL) and MeOH (4 mL) and the solution heated to 50° C. 4N NaOH (2.5 mL) was added dropwise to the mixture that was then stirred for an additional 3.5 h at 50° C., at which it was judged complete by TLC. The reaction mixture was evaporated to dryness under reduced pressure and the residue partitioned between 10% aqueous HCl and DCM. The organic phase was separated, dried (MgSO$_4$) and concentrated to give a residue that was purified by flash chromatography with 60% EtOAc in hexane+3% AcOH. The title compound of example 9 was obtained as a yellow solid (0.320 g, 74% yield).

Example 10

Methyl 2-(2-bromo-ethanoyl)-3-cyclohexyl-1-dimethylcarbamoylmethyl-1H-indole-6-carboxylate

-continued

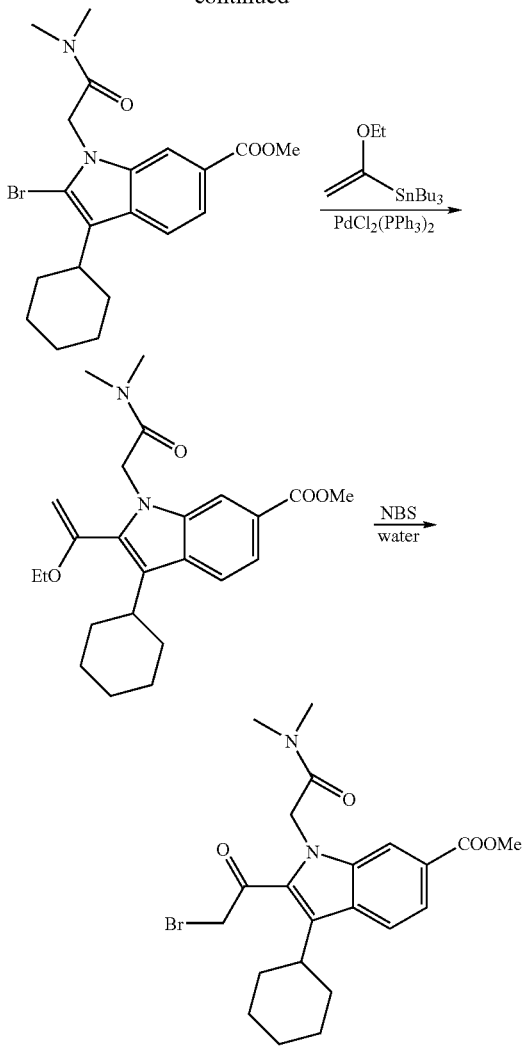

Methyl 2-bromo-3-cyclohexyl-1-dimethylcarbam-oylmethyl-1H-indole-6-carboxylate

The 2-bromoindole derivative of example 8 (7.00 g, 17.75 mmol) was dissolved in THF (150 mL) and triethylamine (8.7 mL, 62.14 mmol, 3 equiv.) was added followed by TBTU (7.13 g, 22.44 mmol, 1.25 equiv.). The white suspension was stirred for 20 min and dimethylamine hydrochloride (1.81 g, 22.2 mmol, 1.25 equiv.) was added followed by DMF (75 mL). After stirring overnight at room temperature, the reaction was judged complete by TLC (additional TBTU, Et₃N and dimethylamine hydrochloride can be added if required to complete the reaction). The reaction mixture was diluted with EtOAc (200 mL), washed with 10% HCl (100 mL), water (12×320 mL) and brine. After drying over Na₂SO₄, the solvent was removed under reduced pressure and the residue purified by flash chromatography to give the desired dimethyl amide as a white solid (6.10 g, 81% yield).

Methyl 3-cyclohexyl-1-dimethylcarbamoylmethyl-2-(1-ethoxy-vinyl)-1H-indole-6-carboxylate The 2-bromoindole derivative from above (6.10 g, 13.54 mmol) was charged in a 100 mL flask equipped with a stirrer and reflux condenser. Anhydrous dioxane (50 mL) was added and tributyl(1-ethoxyvinyl)tin (6.27 g, 17.37 mmol, 1.2 equiv.) was added. The reaction mixture was degassed by bubbling argon through the suspension for 40 min. Dichloro-bis(triphenylphosphine)palladium (0.51 g, 0.72 mmol) was added and the reaction mixture was stirred overnight at 100° C. under an argon atmosphere. The reaction mixture was then cooled to room temperature and volatiles removed under reduced pressure. EtOAc (120 mL) was added and insoluble solids removed by filtration through celite. Removal of solvent under reduced pressure and trituration of the residue with THF gave the desired product as a beige solid. Purification of the mother liquors by flash chromatography gave additional material. The total yield was 5.36 g (89%).

Methyl 2-(2-bromo-ethanoyl)-3-cyclohexyl-1-dimethylcarbamoylmethyl-1H-indole-6-carboxylate The vinyl ether from above (5.30 g, 12.85 mmol) was dissolved in THF (300 mL) and the solution cooled in an ice-water bath. Water (30 mL) was added followed by N-bromosuccinimide (2.29 g, 12.85 mmol, 1 equiv.) in five equal portions over 10 min. After stirring for 1 h, addition N-bromosuccinimide (0.5 g) was added and after stirring for an additional 30 min at 0° C., a final portion (0.5 g) was added to complete the reaction. The reaction mixture was diluted with ether (200 mL) and water (100 mL) was added. The organic phase was separated and the aqueous phase extracted with ether (2×100 mL). The extract was washed with water (3×100 mL) and brine and then dried over Na₂SO₄. Removal of volatiles under reduced pressure gave a yellow oil that was purified by flash chromatography on silica gel using 20-50% EtOAc in hexane as eluent to give the desired bromoketone of example 10 as a yellow solid (3.74 g, 62% yield).

Example 11

Methyl 2-(2-bromo-ethanoyl)-3-cyclohexyl-1-(2-morpholin-4-yl-2-oxo-ethyl)-1H-indole-6-carboxylate

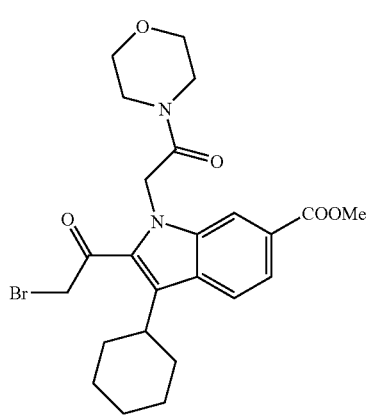

The same procedures described in example 10 were used but dimethylamine hydrochloride was replaced with morpholine in step 1.

Example 12

General Procedure for the Conversion of Bromomethylketones (Such as Those of Examples 10 and 11) to Thiazolyl-Substituted Indoles and Hydrolysis to Give Inhibitors of General Formula I.1 where $R^2$ is a (2-Substituted 5-Thiazolyl) Heterocycle

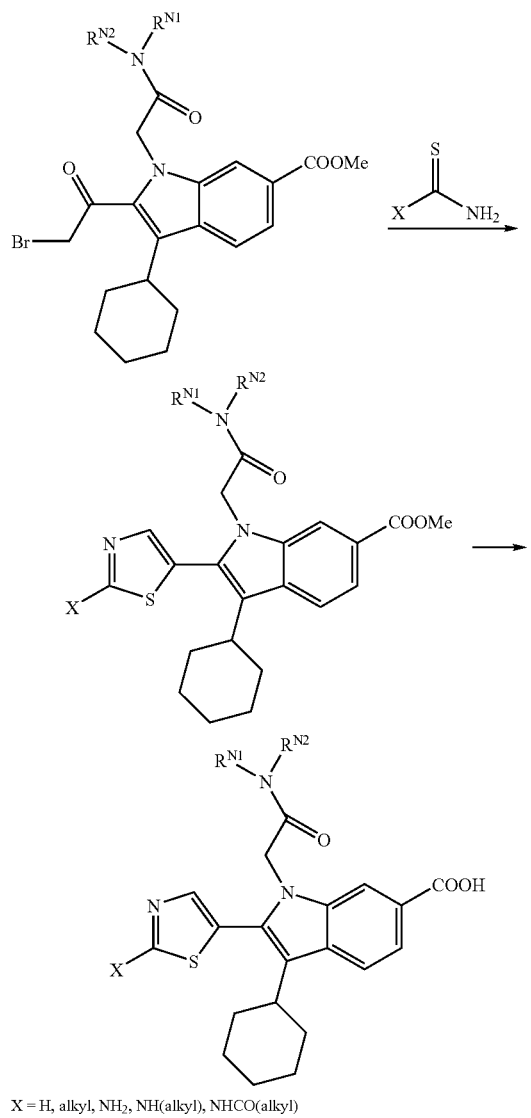

X = H, alkyl, $NH_2$, NH(alkyl), NHCO(alkyl)

Bromomethylketones such as those described in examples 10 and 11 were reacted with thioamides and thioureas and then saponified to give the carboxylic acids of example 12. The following example serves to illustrate such a process and is non-limiting.

2-(2-tert-Butylamino-thiazol-4-yl)-3-cyclohexyl-1-(2-morpholin-4-yl-2-oxo-ethyl)-1H-indole-6-carboxylic acid

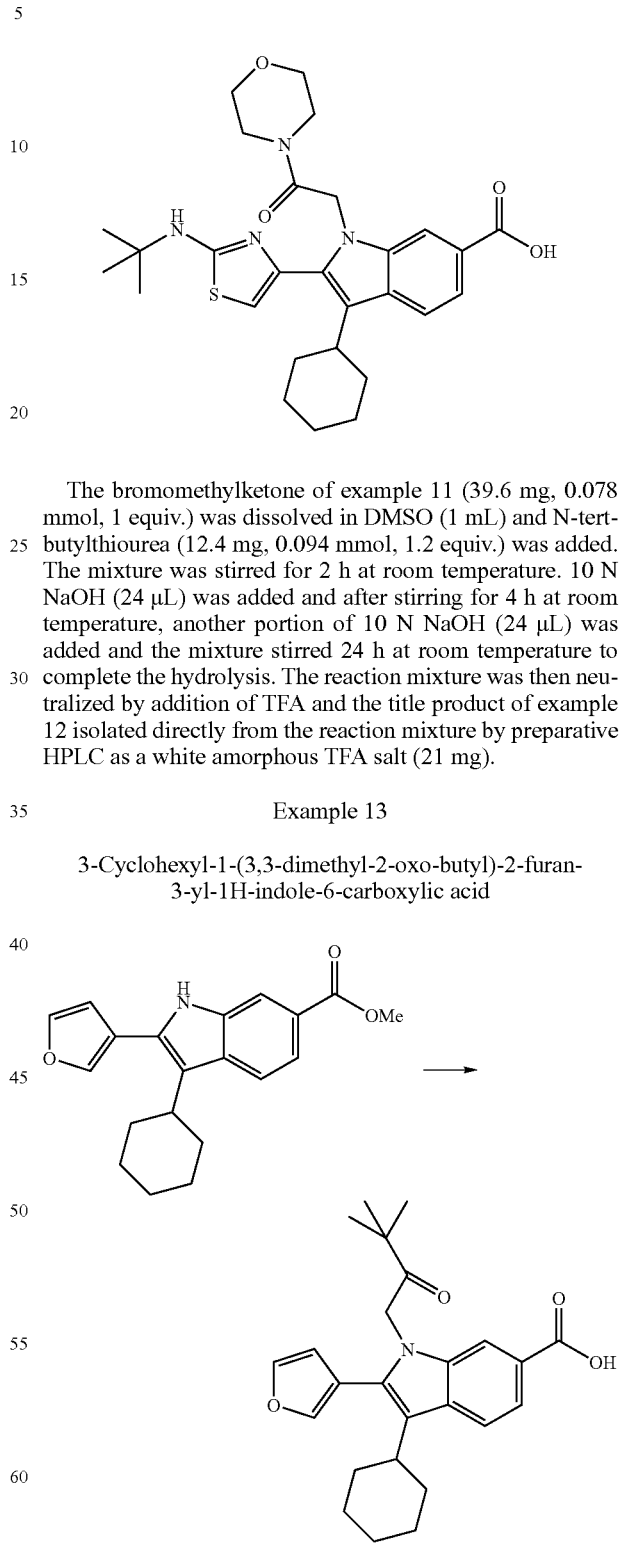

The bromomethylketone of example 11 (39.6 mg, 0.078 mmol, 1 equiv.) was dissolved in DMSO (1 mL) and N-tert-butylthiourea (12.4 mg, 0.094 mmol, 1.2 equiv.) was added. The mixture was stirred for 2 h at room temperature. 10 N NaOH (24 µL) was added and after stirring for 4 h at room temperature, another portion of 10 N NaOH (24 µL) was added and the mixture stirred 24 h at room temperature to complete the hydrolysis. The reaction mixture was then neutralized by addition of TFA and the title product of example 12 isolated directly from the reaction mixture by preparative HPLC as a white amorphous TFA salt (21 mg).

Example 13

3-Cyclohexyl-1-(3,3-dimethyl-2-oxo-butyl)-2-furan-3-yl-1H-indole-6-carboxylic acid The indole ester of example 4 (0.080 g, 0.247 mmol, 1 equiv.) was dissolved in DMF (2 mL) and NaH (60% oil dispersion; 0.016 mg, 0.3 mmol, 1.6 equiv.) was added. After stirring for 30 min, 1-bromopinacolone (45 µL, 0.3 mmol, 22 equiv.) was added and the mixture stirred for 2.5 h at room temperature. The reaction was quenched by addition of 10% aqueous HCl and extracted with TBME. The extract was washed with water, dried (MgSO$_4$) and concentrated to give a residue that was purified by flash chromatography on silica gel using 15-20% EtOAc in hexane as eluent. The methyl ester of example 13 was obtained as a light-yellow solid.

The methyl ester from above (0.040 g, 0.095 mmol) was dissolved in a mixture of THF (3 mL) and MeOH (2 mL) and 2.5 N NaOH (400 µL) was added. The mixture was stirred at 50° C. for 5 h after which the reaction was judged complete by TLC. Volatiles were removed under reduced pressure and the residue was partitioned between 10% aqueous HCl and DCM. The organic phase was washed with water, dried (Na$_2$SO$_4$) and concentrated. The residue was purified by preparative HPLC to give the title compound of example 13 as a white amorphous solid (22 mg).

Example 14

3-Cyclohexyl-2-furan-3-yl-1-(2-morpholin-4-yl-2-thioxo-ethyl)-1H-indole-6-carboxylic acid

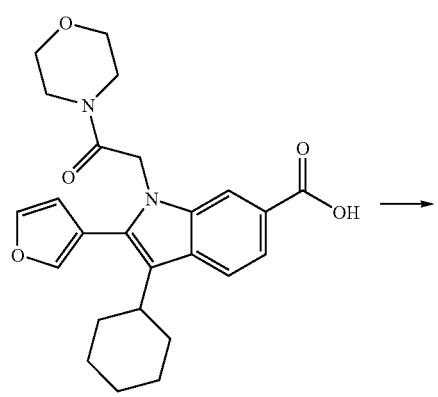

-continued

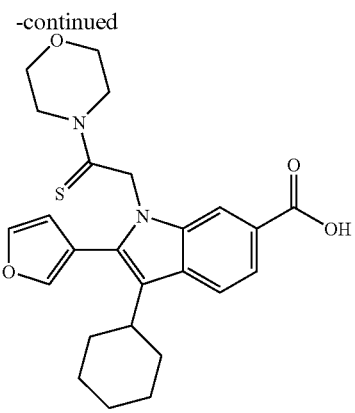

The amide of example 9 (0.060 g, 0.137 mmol, 1 equiv.) was dissolved in THF (2 mL) and P$_2$S$_5$ (0.031 g, 0.07 mmol, 0.51 equiv.) was added. The mixture was stirred at 50° C. for 15 h after which another portion of P$_2$S$_5$ (0.020 g) was added. After stirring for an additional 2 h at 50° C., the reaction mixture was concentrated under reduced pressure and the residue passed through a plug of silica gel using 60% EtOAc in hexane+3% AcOH as eluent. The fractions containing the product were combined and after removal of solvents under reduced pressure, the residue was purified by preparative HPLC to give the title compound of example 14 as a white amorphous solid (11 mg).

Example 15

Procedures for the Preparation of Benzimidazole-Derivatives (Group Q$^1$ or Q$^2$)

Example 15a (E)-3-[2-(1-Amino-cyclobutyl)-1-methyl-1H-benzoimidazol-5-yl]-acrylic acid methyl ester

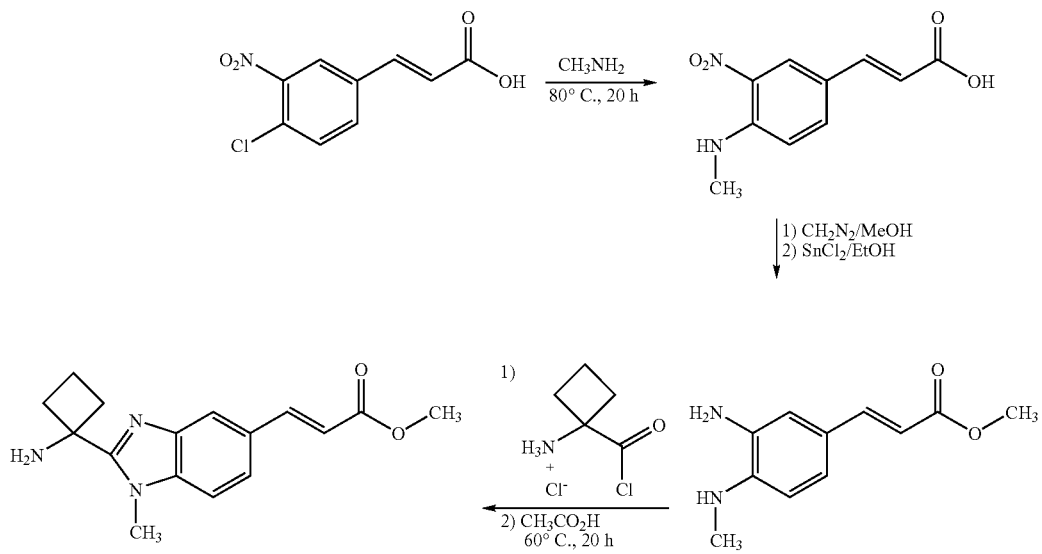

A mixture of 4-chloro-3-nitrocinnamic acid (500 mg, 2.2 mmol) and methylamine (8 mL of 2M in THF, 16 mmol) were heated in a sealed tube at 80° C. for 20 hours. The mixture was then cooled to room temperature and concentrated to an orange solid that was used in the following step without further purification.

The crude 4-methylamino-3-nitrocinnamic acid intermediate (488 mg, 2.2 mmol) was dissolved in methanol (20 mL) and an ether solution of diazomethane was added until HPLC analysis indicated complete conversion of the acid to the methyl ester. The solution was concentrated to dryness to obtain 540 mg of the methyl ester as an orange solid which was used further without purification.

The crude methyl ester (540 mg, ~2.2 mmol) and $SnCl_2$ dihydrate (2.25 g, 10 mmol) were dissolved in ethanol (20 mL) and the mixture was stirred at 80° C. for 4 hours. After that period, the mixture was cooled to room temperature and was slowly added to aqueous solution of saturated $NaHCO_3$. The reaction mixture was extracted with ethyl acetate (100 mL), the organic layer was dried over anhydrous $MgSO_4$ and the solvent was removed under reduced pressure. The residue was purified by flash column chromatography, using a gradient of hexane in ethyl acetate (from 50% to 30%) to give the pure diamino cinnamate ester intermediate as a yellow solid (245 mg). ES+ MS m/z: 207.1 (M+H)+, ES− MS m/z: 205.0 (M−H)−

A sample of the above diamino intermediate (40 mg, 0.194 mmol) was suspended in $CH_2Cl_2$ (3 mL) and the aminocyclobutyl acid chloride prepared from 1-aminocyclobutanecarboxylic acid, following a similar procedure to that described in example 20, (31 mg, 0.18 mmol) was added. The reaction mixture was stirred at room temperature for 2 hours and then concentrated to obtain a white solid. The solid was then dissolved in acetic acid (5 mL) and heated to 60° C. for 20 hours. The reaction crude was diluted with aqueous saturated $NaHCO_3$, extracted with $CH_2Cl_2$ (2×50 mL) and brine, the organic layer was dried over anhydrous $MgSO_4$ and the solvent was removed under reduced pressure to give the title compound of example 15a as a light brown foam (53 mg): ES+ MS m/z: 286.0 (M+H)+

Example 15b (E)-3-[2-(1-Amino-cyclobutyl)-3-methyl-3H-benzoimidazol-5-yl]-acrylic acid methyl ester A mixture of 3-hydroxy-4-nitrobenzaldehyde (1.24 g, 7.4 mmol) and (carbethoxy-methylene)triphenylphosphorane (2.6 g, 7.4 mmol) were dissolved in THF (60 mL) and stirred at 60° C. for 2 hours. The mixture was then concentrated and purified by flash column chromatography, using hexane in ethyl acetate (70%) as the eluent, to obtain a the trans-cinnamate ester derivative as a pure yellow solid (1.73 g).

The above cinnamate ester was dissolved in DMF (15 mL), methyl iodide (1.35 mL, 21.7 mmol) and $K_2CO_3$ (3.0 g, 21.7 mmol) and the mixture was stirred at room temperature for 20 hours. After that period, water was added and the precipitate formed was filtered and washed with water (2×). The solid was dissolved in ethyl acetate, dried over anhydrous $MgSO_4$, filtered and concentrated to dryness to give the crude methoxy analogue as a white solid (~1.7 g).

The crude 3-methoxy-4-nitrocinnamate ester (570 mg, 2.27 mmol) and methylamine (30 mL of 2M in THF, 60 mmol) were heated in sealed tube at 85° C. for 40 hours. After that period the mixture was cooled to room temperature, concentrated and purified by flash column chromatography, using ethyl acetate in hexane (10%) as the eluent, to obtain the desired 3-methylamino-4-nitrocinnamate ester (~160 mg). ES+ MS m/z: 251.0 (M+H)+Intermediate 3-methylamino-4-nitrocinnamate ester (~150 mg) and $SnCl_2$ dihydrate (950 mg, 4.2 mmol) were dissolved in ethanol (10 mL) and the mixture was stirred at 80° C. for 20 hours. The mixture was cooled to room temperature and concentrated to dryness. The residue was dissolved in ethyl acetate (100 mL) and was slowly added to an aqueous solution of saturated $NaHCO_3$ and stirred for 30 min. The organic layer was then extracted with ice cold brine, dried over anhydrous $MgSO_4$ and the solvent was removed under reduced pressure. The residue was purified by flash column chromatography (using a gradient from 70% to 60% of hexane in ethyl acetate) to give the pure diamino cinnamate ester as a yellow solid (100 mg). ES+ MS m/z: 221.0 (M+H)+

The above diamino intermediate (100 mg, 0.45 mmol) was suspended in $CH_2Cl_2$ (5 mL) and the aminocyclobutyl acid chloride prepared from 1-aminocyclobutanecarboxylic acid, following a similar procedure to that described in example 20 (77 mg, 0.45 mmol) was added. The reaction mixture was stirred at room temperature for 2 hours and then concentrated

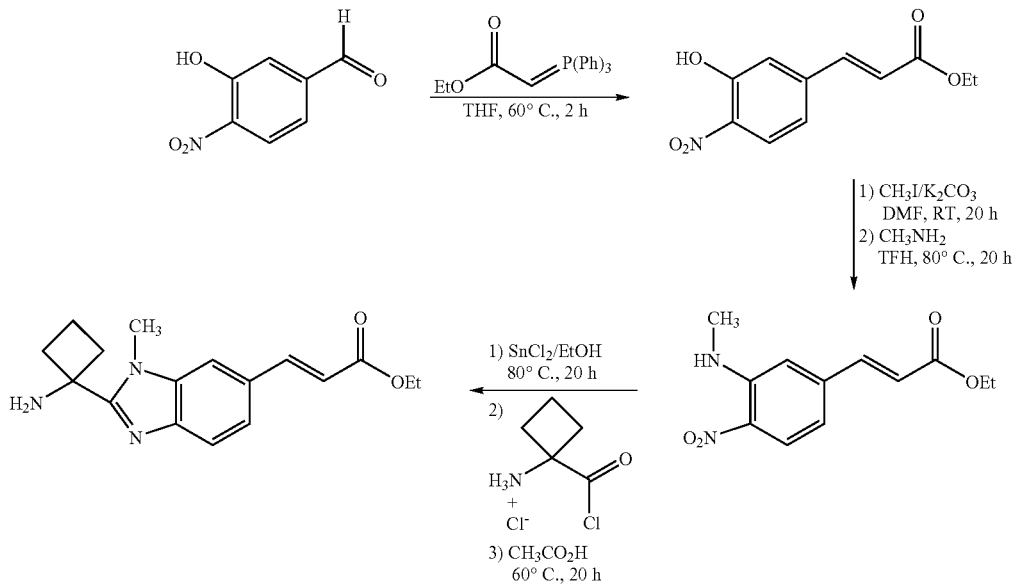

to obtain a white solid. The solid was then dissolved in acetic acid (5 mL) and heated to 60° C. for 16 hours. The reaction mixture was cooled and the precipitate formed was filtered and washed with cold acetic acid, and then dissolved in ethyl acetate (100 mL) and washed with aqueous saturated NaHCO$_3$ (2×) and ice cold brine. The organic layer was dried over anhydrous MgSO$_4$ and the solvent was removed under reduced pressure to give the title compound of example 15b (E)-3-[2-(1-amino-cyclobutyl)-3-methyl-3H-benzoimidazol-5-yl]-acrylic acid methyl ester as a white solid (58 mg).

Note: it will be apparent to the person skilled in the art that the (carbethoxymethylene)triphenylphosphorane used in this procedure can be replaced by appropriately substituted derivatives to prepare analogues bearing various substituents on the cinnamate double bond. In addition, cinnamate methyl esters can also be prepared in an analogous fashion using the appropriate reagent.

Example 15c 2-(1-Amino-cyclobutyl)-1H-benzoimidazole-5-carboxylic acid methyl ester

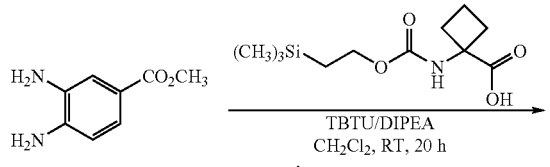

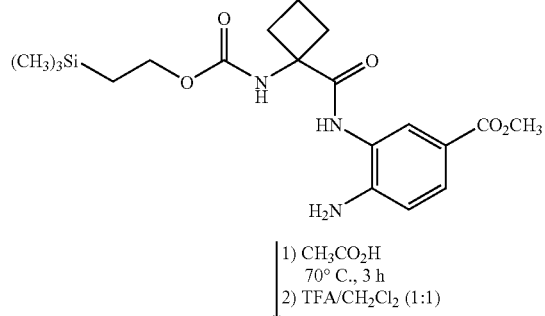

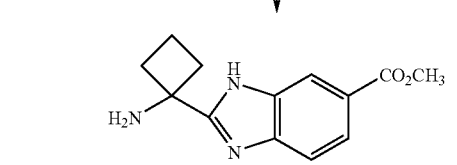

Methyl 3,4-diaminobenzoate (320 mg, 1.9 mmol), the SEM-protected cyclobutylamino acid (500 mg, 1.9 mmol) of example 21 and TBTU (836 mg, 2.2 mmol) were dissolved in CH$_2$Cl$_2$ (10 mL) and DIPEA (1.1 mL, 6 mmol) was added. The reaction mixture was stirred at room temperature for 20 hours, then diluted with ethyl acetate (100 mL) and extracted with aqueous saturated NaHCO$_3$ (2×) and brine. The organic layer was dried over anhydrous MgSO$_4$ and filtered, and the solvent was evaporated under vacuum to isolate the crude amide intermediate as a yellow oil (407 mg). The amide was dissolved in acetic acid (10 mL) and stirred at 70° C. for 3 hours to induce dehydration and cyclization to the benzymidazole. The reaction mixture was concentrated to dryness, diluted with ethyl acetate (100 mL) and washed with 10% aqueous citric acid (2×), aqueous saturated NaHCO$_3$ and brine. The organic layer was dried over MgSO$_4$, filtered and concentrated to dryness. The residue was purified by flash column chromatography, using a solvent gradient of hexane in ethyl acetate (from 80% to 50%), to give the SEM-protected benzymidazole intermediate as a pink solid (574 mg). ES$^+$ MS m/z: 390.2 (M+H)$^+$ The protecting group was then removed by dissolving this solid in TFA/CH$_2$Cl$_2$ (2 mL, 1:1 ratio) and stirring the solution at room temperature for 2 hours. The solution was evaporated to dryness under vacuum to give the products, 2-(1-amino-cyclobutyl)-1H-benzoimidazole-5-carboxylic acid methyl ester, which was used for the synthesis of inhibitors without further purification.

Example 16

General Procedure for N-Allylation of Indole Derivative of Example 6

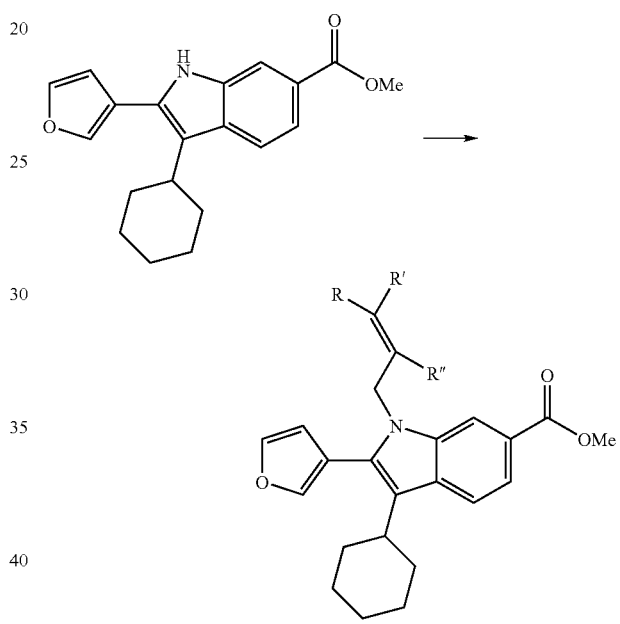

wherein R, R', R" are H or alkyl. The following example serves to illustrate such as process and is non-limiting:

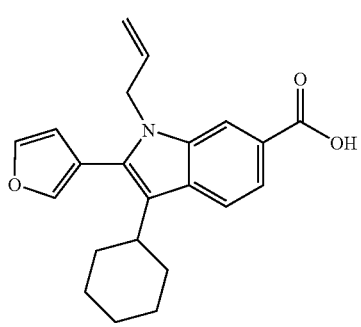

1-Allyl-3-cyclohexyl-2-furan-3-yl-1H-indole-6-carboxylic acid

The indole derivative of example 4 (0.050 g, 0.156 mmol, 1 equiv.) was dissolved in DMF (1 mL) and the solution was cooled in ice-water. NaH (60% oil dispersion, 7 mg, 0.175 mmol, 1.13 equiv.) was added and the ice-bath removed. Allyl bromide (15 μL, 0.17 mmol, 1.11 equiv.) was added and the reaction stirred overnight at room temperature (complete by TLC). The reaction mixture was diluted with DMSO (1 mL) and 5N NaOH (200 μL) was added. The mixture was stirred at 60° C. for 3 h (complete by HPLC), neutralized by addition of TFA and the product isolated directly from the reaction mixture by preparative HPLC. The title product of example 16 was isolated as a white amorphous solid (33 mg).

Example 17

3-Cyclohexyl-2-furan-3-yl-1-(3-morpholin-4-yl-3-oxo-propyl)-1H-indole-6-carboxylic acid

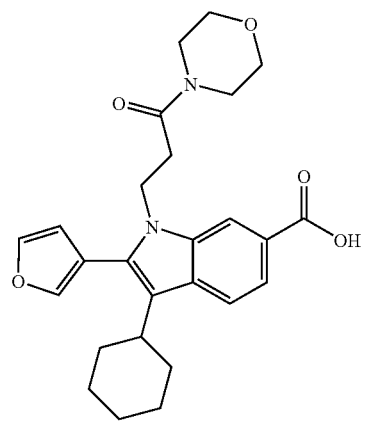

Methyl 1-(2-tert-butoxycarbonyl-ethyl)-3-cyclohexyl-2-furan-3-yl-1H-indole-6-carboxylate The indole ester of example 4 (0.100 g, 0.31 mmol, 1 equiv.) was dissolved in DMF (2 mL) and NaH (60% oil dispersion, 0.020 g, 0.50 mmol, 1.6 equiv.) was added. After stirring for 1 h at room temperature, tert-butyl 3-bromopropionate (0.102 g, 0.49 mmol, 1.6 equiv.) was added and the mixture stirred overnight at room temperature. The solvent was the removed under vacuum and the residue purified by flash chromatography on silica gel to give the N-alkylated indole (41 mg).

Methyl 1-(2-carboxy-ethyl)-3-cyclohexyl-2-furan-3-yl-1H-indole-6-carboxylate

The tert-butyl ester from above (40 mg) was dissolved in DCM (1 mL) and TFA (2 mL) was added. The mixture was stirred for 1 h at room temperature after which volatiles were removed under reduced pressure. The residue was co-evaporated twice with DCM and used as such in the next step.

3-Cyclohexyl-2-furan-3-yl-1-(3-morpholin-4-yl-3-oxo-propyl)-1H-indole-6-carboxylic acid The acid from above (18 mg, 0.046 mmol, 1 equiv.) was dissolved in DMSO (0.5 mL) and HATU (26 mg, 0.069 mmol, 1.5 equiv.), DIEA (16 μL, 0.092 mmol, 2 equiv.) and morpholine (8 μL, 0.092 mmol, 2 equiv.) were added. The mixture was stirred for 3.5 h at room temperature (complete by HPLC). 5N NaOH (184 μL) was added and the mixture stirred overnight at room temperature. The reaction was then quenched by addition of AcOH (100 μL) and the product isolated directly by preparative HPLC. The title compound of example 17 was isolated as a brownish amorphous solid (1.2 mg).

Example 18

1-(2-Benzenesulfonylamino-2-oxo-ethyl)-3-cyclohexyl-2-furan-3-yl-1H-indole-6-carboxylic acid

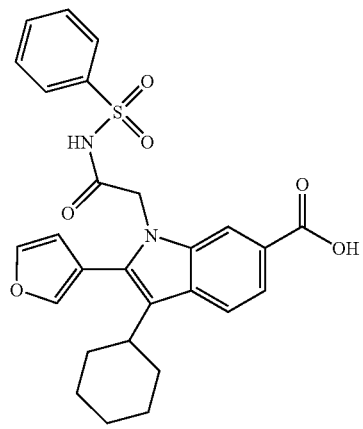

The acid derivative of example 6 (0.050 g, 0.13 mmol, 1 equiv.) was dissolved in DCM (5 mL) and EDCI (25 mg, 0.13 mmol, 1 equiv.), DMAP (16 mg, 0.13 mmol, 1 equiv.) and benzene sulfonamide (23.6 mg, 0.15 mmol, 1.14 equiv.) were added. The greenish reaction mixture was stirred for 24 h at room temperature (>80% conversion by HPLC). The reaction mixture was diluted with DCM, washed with 10% aqueous HCl and dried (Na$_2$SO$_4$). Evaporation of the solvent gave a residue that was dissolved in DMSO (2 mL) and 2.5N NaOH (0.5 mL) was added. The mixture was stirred for 2.5 h at room temperature (complete by HPLC), neutralized with AcOH and the product isolated directly by preparative HPLC. The title compound of example 18 was obtained as a beige amorphous solid (15 mg).

Example 19

(E)-3-(4-{[1-(5-Amino-1,3-dioxinan-5-yl)-methanoyl]-amino}-phenyl)-acrylic acid ethyl ester (Building Block for Group L and/or Z According to Formula I)

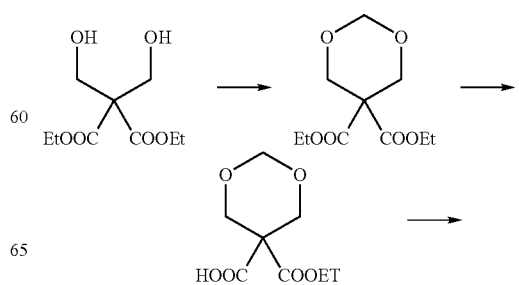

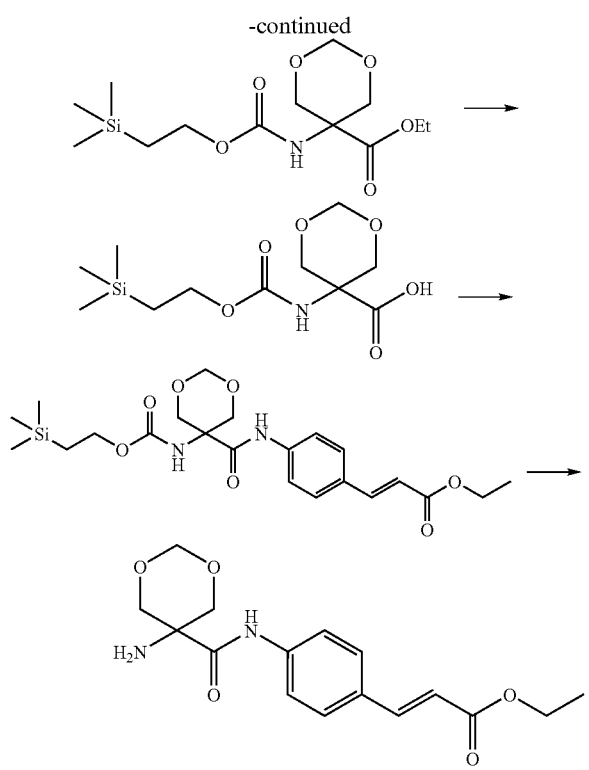

1,3-Dioxinane-5,5-dicarboxylic acid diethyl ester

A 500 mL round-bottomed flask equipped with a reflux condenser was charged with diethyl bis(hydroxymethyl)malonate (5.00 g, 22.7 mmol, 1.00 equiv.), 1,3,5-trioxane (4.09 g, 45.41 mmol, 2.00 equiv.), (1R)-(−)-10-camphorsulfonic acid (CSA) (10.55 g, 45.41 mmol, 2.00 equiv.), and 4 Å molecular sieves (2.00 g). Chloroform (200 mL) was then added and the mixture was refluxed for 72 h (complete by TLC). The reaction mixture was filtered on celite and the filtrate was washed with aqueous 0.5 N sodium hydroxide (100 mL). The layers were separated and the aqueous phase was back-extracted with chloroform (50 mL). Organic layers were then combined, dried (MgSO$_4$), filtered and concentrated in vacuo. The resulting crude mixture was finally purified by flash chromatography (eluting hexane/EtOAc 4:1) to give the desired dioxane malonate as a colorless oil (3.41 g, 65%).

1,3-Dioxinane-5,5-dicarboxylic acid ethyl ester

A 50 mL round-bottomed flask was charged with the intermediate from above (1.00 g, 4.31 mmol, 1.00 equiv.). EtOH and aqueous 1.0 N sodium hydroxide (4.50 mL, 4.50 mmol, 1.05 equiv.) was added and the resulting mixture was stirred at RT for 16 hrs (TLC monitoring). Then the pH of the reaction mixture was brought to 12 using aqueous 1.0 N sodium hydroxide and EtOH was removed in vacuo. The resulting aqueous solution was diluted with water (50 mL) and extracted with EtOAc (2×50 mL). Then the pH of the aqueous solution was brought to 2 using aqueous conc. HCl. The aqueous solution was extracted with EtOAc (2×50 mL). Organic phases were combined, dried (MgSO$_4$), filtered and concentrated in vacuo. To give the desired monoester contaminated with ~10 mole % of the corresponding diacid as a colorless oil (0.91 g). The material was used in the next step without further purification.

5-(2-Trimethylsilanyl-ethoxycarbonylamino)-1,3-dioxinane-5-carboxylic acid ethyl ester In a 100 mL round-bottomed flask equipped with a reflux condenser was mixed the above monoester (0.91 g, 4.31 mmol of monoacid, 1.00 equiv.) contaminated with approximately 10% of diacid, anhydrous toluene (20 mL) and triethylamine (TEA) (750 µL, 5.39 mmol, 1.25 equiv.) under nitrogen. The resulting mixture was heated to 80° C. and then diphenylphosphoryl azide (1.07 mL, 4.96 mmol, 1.15 equiv.) was slowly added in one minute. The mixture was then stirred at 80° C. for 1 h. 2-(Trimethylsilyl)ethanol (680 µL, 4.74 mmol, 1.10 equiv.) was added drop wise and the reaction mixture was stirred at 110° C. After 24 h, the reaction was judged to be complete. The reaction mixture was then diluted with EtOAc (50 mL) and washed successively with water (25 mL), aqueous 1.0 N HCl and sat. aqueous sodium carbonate. The organic layer was then dried (MgSO$_4$), filtered and concentrated in vacuo. The crude material was finally purified by flash chromatography (eluting Hexane/EtOAc 9:1) to give the desired SEM-carbamate-protected amino ester as a colorless oil (0.61 g, 45%).

5-(2-Trimethylsilanyl-ethoxycarbonylamino)-1,3-dioxinane-5-carboxylic acid

The ester from above (612 mg, 1.91 mmol, 1.00 equiv.) was dissolved in 15 mL of a 4:1 THF/MeOH mixture in a 50 mL round-bottomed flask. Aqueous 10 N Sodium hydroxide (0.96 mL, 9.56 mmol, 5.00 equiv.) was then added, and the mixture was stirred at RT for 4 h (TLC monitoring). The solvent was removed in vacuo and the residue was dissolved in dichloromethane (20 mL). The organic phase was washed with 20 mL of 1.0 N aqueous HCl, layers were separated and the organic phase was back-extracted with dichloromethane (2×20 mL). Organic layers were combined, dried (MgSO$_4$), filtered and concentrated in vacuo to give the desired acid as a white foam (466 mg, 84%).

(E)-3-[4-({1-[5-(2-Trimethylsilanyl-ethoxycarbonylamino)-1,3-dioxinan-5-yl]-methanoyl}-amino)-phenyl]-acrylic acid ethyl ester 5-(2-trimethylsilanyl-ethoxycarbonylamino)-1,3-dioxane-5-carboxylic acid from above (0.050 g, 0.17 mmol), ethyl-4-aminocinnamate (0.036 g, 0.19 mmol), HATU (0.098 g, 0.26 mmol), HOAt (0.035 g, 0.26 mmol) and 2,4,6-collidine (0.062 mL, 0.51 mmol) were combined in anhydrous DMSO (1 mL). The solution was warmed to 60° C. and stirred for 6 h before another 1.5 equivalents of HATU was added and stirring was continued for another 2 hours to ensure complete consumption of the acid. The reaction mixture was diluted with dichloromethane and washed with 1N HCl (×2). The organic phase was dried with MgSO$_4$, filtered and concentrated. The residue was subjected to flash chromatography to afford 0.043 g (54%) of the protected amide derivative as a yellow oil.

(E)-3-(4-{[1-(5-Amino-1,3-dioxinan-5-yl)-methanoyl]-amino}-phenyl)-acrylic acid ethyl ester Deprotection of the SEM carbamate from above was carried out with TFA-DCM in the usual manner.

Example 20

General Procedure for Coupling α,α-Disubstituted Amino Acids to Aromatic Amines

Ethyl (E)-3-[4-(2-amino-2-methyl-propanoylamino)-phenyl]-acrylate

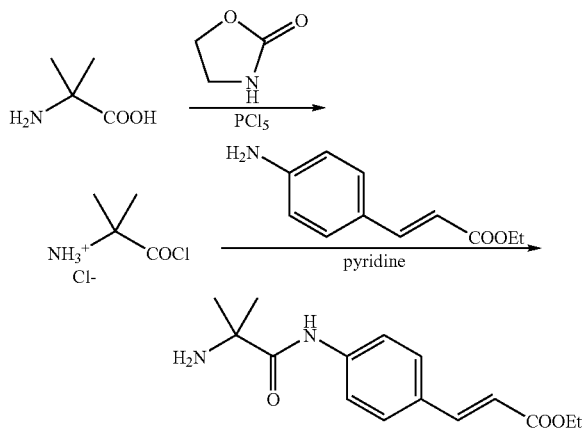

Adapting the procedure described by E. S. Uffelman et al. (*Org. Lett.* 1999, 1, 1157), 2-aminoisobutyric acid was converted to the corresponding amino acid chloride hydrochloride: 2-oxazolidinone (12.30 g, 0.141 mole) was dissolved in MeCN (150 mL) and phosphorous pentachloride (49.02 g, 0.235 mole, 1.7 equivalent) was added in one portion. The homogeneous mixture was stirred for 24 h at room temperature. 2-Aminoisobutyric acid (14.55 g, 0.141 mole) was added and the suspension was stirred for 48 h at room temperature. The desired acid chloride hydrochloride was collected by filtration, washed with MeCN and dried under vacuum. Other α,α-disubstituted amino acid chloride hydrochlorides can be prepared in an analogous fashion starting from the corresponding amino acid (e.g. 1-aminocyclobutanecarboxylic acid, 1-aminocyclopentanecarboxylic acid, 1-aminocyclohexanecarboxylic acid and the like).

The acid chloride (12.778 g, 80 mmol, 1.4 equivalent) was suspended in DCM (200 mL) and ethyl 4-aminocinnamate (11.045 g, 57.7 mmol, 1 equivalent) was added. Pyridine (7.01 mL, 86.6 mmol, 1.5 equivalent) was added drop wise and the mixture was stirred for 3.5 h at room temperature. The reaction was then poured into a mixture of 1N NaOH (25 mL) and saturated aqueous NaHCO₃ (100 mL) and extracted with EtOAc. The organic phase was washed with aqueous NaHCO₃, water and brine, and dried over MgSO₄. Removal of solvent under reduced pressure gave the title compound as a white solid (15.96 g, 101% yield).

Example 21

Ethyl (E)-3-(4-{[1-(1-amino-cyclobutyl)-methanoyl]-amino}-phenyl)-acrylate

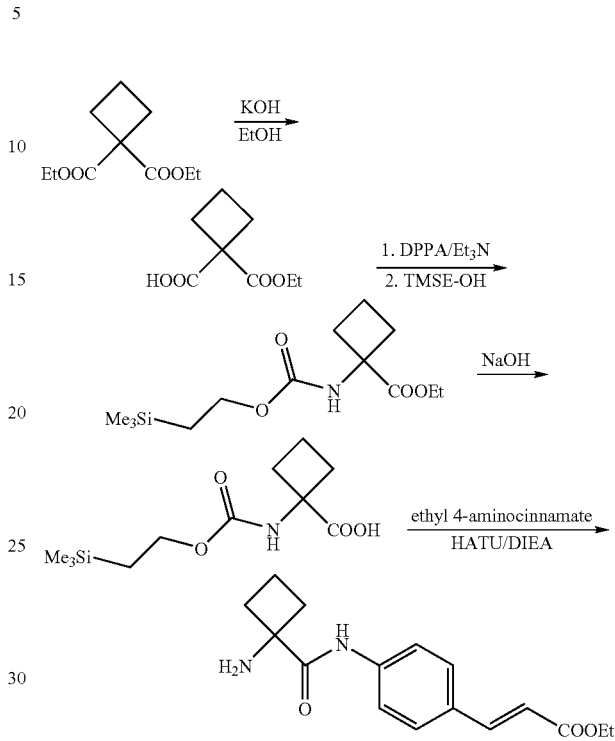

Diethyl 1,1-cyclobutanedicarboxylate (20.00 g, 100 mmol) and KOH (6.60 g, 100 mmol) were refluxed in EtOH (100 mL) for 2 h. After cooling to room temperature, volatiles were removed under reduced pressure and the residue partitioned between Et₂O and 4N HCl. The organic extract was washed with water and brine, and dried over MgSO₄. Removal of the solvent under reduced pressure gave the monoester as a clear oil (14.45 g, 84% yield). The monoester from above (14.45 g, 84 mmol), Et₃N (14.1 mL, 100 mmol) and diphenylphosphoryl azide (DPPA) (24.05 g, 87.4 mmol) were dissolved in dry toluene (114 mL) and the mixture heated at 80° C. for 1 h and 110° C. for an additional hour. Trimethylsilylethanol (9.94 g, 100 mmol) was added in one portion and the mixture refluxed for 48 h. Toluene was then removed under reduced pressure and the residue dissolved in DCM. The solution was washed with water and brine and dried over MgSO₄. Concentration under reduced pressure gave a dark oil which was purified by passage through a pad of silica gel using 30% EtOAc in hexane as eluent. The desired carbamate was obtained as a clear yellow liquid (21.0 g).

The carbamate from above (1.50 g, 5.22 mmol) was dissolved in THF (5 mL) and 2N NaOH (5 mL) was added. The mixture was stirred at 70° C. for 1 h. Following dilution with water, the aqueous phase was washed with Et₂O to remove unreacted starting material. The aqueous phase was then acidified with KHSO₄ and the product extracted with EtOAc. The desired free carboxylic acid was obtained as an oil (1.25 g).

The acid from above (0.519 g, 2.0 mmol) was dissolved in DCM (10 mL). DIEA (1.39 mL, 8.0 mmol, 4 equivalents) was added, followed by ethyl 4-aminocinnamate (0.573 g, 3.0 mmol, 1.5 equivalent) and HATU (1.143 g, 3.0 mmol, 1.5 equivalents). The mixture was stirred at room temperature for 3 days. The reaction was poured into TBME (100 mL) and the solution washed successively with 10% aqueous citric acid (2×25 mL) and saturated aqueous NaHCO₃ (25 mL), and dried over MgSO₄. The solvent was removed under reduced pressure and the residue stirred with TFA (10 mL) for 30 min. Volatiles were then removed under reduced pressure and the residue was co-evaporated twice with hexane. The crude product was dissolved in TBME (60 mL) and the solution washed with 1N NaOH (2×25 mL). After drying (Na₂SO₄), volatiles were removed in vacuum to give the title compound as a beige solid (0.500 g).

Example 22

Methyl (Z)-3-[2-(1-amino-cyclopentyl)-1H-benzoimidazol-5-yl]-acrylate

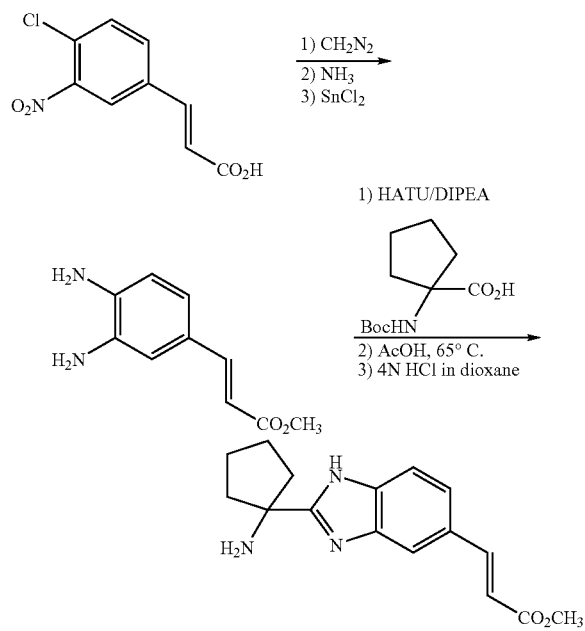

Diazomethane was slowly added to a solution of 4-chloro-3-nitrocinnamic acid in CH₃OH/CH₂Cl₂ until the yellow color persisted, indicating the presence of excess diazomethane. The solution was evaporated to dryness under reduced pressure and the residue was dissolved in DMSO. The solution was heated to 140° C. and ammonia gas was bubbled through for a period of 4 hours. The mixture was cooled to room temperature and degassed with N₂, and poured onto ice. The precipitate formed was filtered, washed with cold water and dried under vacuum for 16 hours to give the crude 4-amino-3-nitrocinnamic ester as a yellow solid (2.05 g). The solid was dissolved in ethanol (40 mL), SnCl₂.dihydrate (9.91 g, 43.9 mmol) was added and the reaction mixture was heated to reflux for 4 hours. The solution was concentrated to remove most of the ethanol, diluted with EtOAc and saturated aqueous NaHCO₃ was added slowly. The mixture was stirred for 20 min, the organic layer was extracted with brine, dried over anhydrous Na₂SO₄ and evaporated to dryness under reduced pressure. The residue was purified by flash column chromatography (using 50% to 70% EtOAc in hexane) to give the diamino intermediate as a yellow solid (1.03 g).

A portion of the 3,4-diaminocinnamate ester (186 mg, 0.970 mmol) and N-Boc-1-aminocyclopentane-1-carboxylic acid (222 mg, 0.970 mmol) were coupled in the presence of HATU/DIEA (in the usual way) and the amide product formed was dehydrated by heating at 65° C. in a solution of acetic acid (4 mL). The reaction residue was purified by reversed HPLC to give the N-Boc protected (Z)-3-[2-(1-amino-cyclopentyl)-1H-benzoimidazol-5-yl]-acrylic acid ethyl ester.

The Boc protecting group was removed with 4N HCl in dioxane in the usual way to give (Z)-3-[2-(1-amino-cyclopentyl)-1H-benzoimidazol-5-yl]-acrylic acid ethyl ester as yellow foam (200 mg).

Example 23 tert-Butyl (S)-3-amino-3-[4-((E)-2-ethoxycarbonyl-vinyl)-phenylcarbamoyl]-pyrrolidine-1-carboxylate

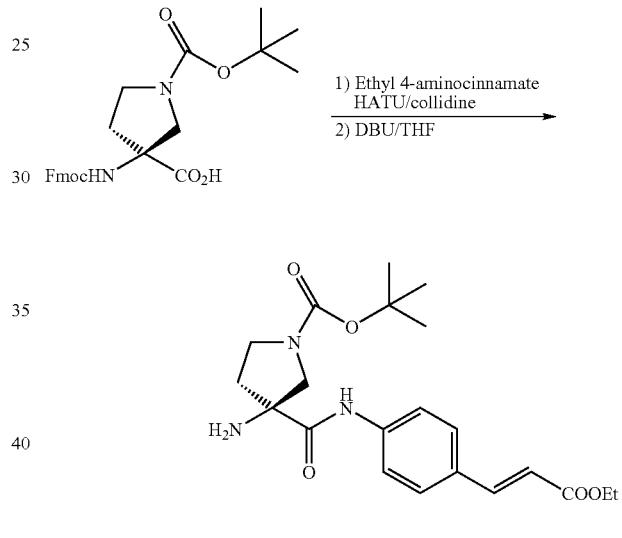

N-Fmoc-(3-N-Boc)-(S)-cucurbitine (0.495 g, 1.09 mmol), ethyl 4-aminocinnamate (0.300 g, 1.57 mmol), HOAt (0.224, 1.65 mmol) and HATU (0.626 g, 1.65 mmol) were dissolved in DMF (7 mL). To this mixture, 2,4,6-collidine (0.435 mL, 3.30 mmol) was added and the solution was stirred at room temperature for 2 days. The reaction mixture was poured into EtOAc (100 mL) and the solution washed successively with 10% aqueous citric acid (2×25 mL), saturated aqueous NaHCO₃ (25 mL) and brine (25 mL), and dried over anhydrous MgSO₄. The solvent was removed under reduced pressure and the residue was dissolved in CH₂Cl₂, DBU (0.658 mL, 4.4 mmol) was added and the reaction mixture was stirred at room temperature for 15 hours.

The reaction mixture was poured into EtOAc (100 mL) and the solution washed successively with saturated aqueous NaHCO₃ (2×25 mL) and brine (25 mL), and dried over anhydrous MgSO₄. The solvent was removed under reduced pressure and the residue was purified by flash column chromatography (40% to 70% EtOAc in hexane) to give the product shown above as a white solid (0.234 mg).

Example 24

Ethyl (E)-3-(4-{[1-(3-amino-piperidin-3-yl)-methanoyl]-amino}-phenyl)-acrylate

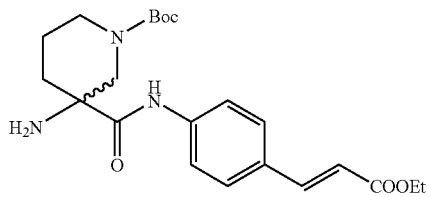

Commercially available N-Fmoc-amino-(3-N-Boc-piperidinyl)carboxylic acid was coupled to the ethyl ester of 4-aminocinnamic acid using HATU/HOAT/collidine in DMF and the Fmoc protecting group was removed with piperidine to give the title compound of example 24 in racemic form.

Racemic N-Fmoc-amino-(3-N-Boc-piperidinyl)carboxylic acid, could also be resolved into its two enantiomers by preparative HPLC on a chiral support (Chiralcel OD, 10 micron, 2.00 cm I.D.×25 cm), using 35% $H_2O$ in MeCN as the eluent. Enantiomeric amines could then be coupled to indole carboxylic acids to prepare enantiomerically pure inhibitors.

Example 25

Ethyl 4-(4-amino-phenyl)-thiazole-2-carboxylate

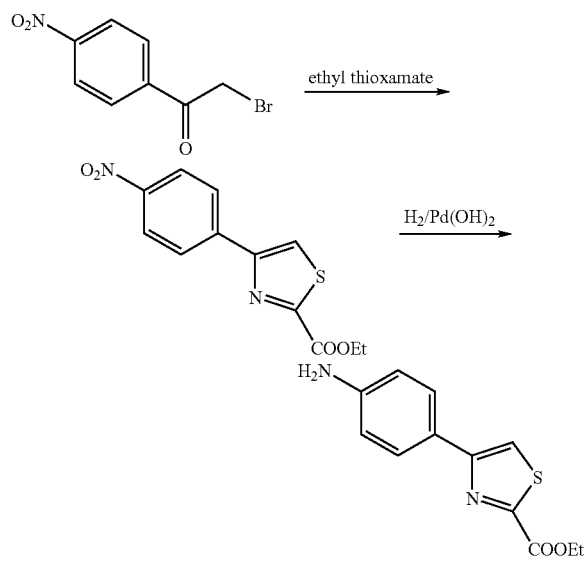

2-bromoacetophenone (6.100 g, 25 mmol) and ethyl thioxamate (3.460 g, 26 mmol) were dissolved in MeOH (20 mL) and the solution was refluxed for 1 h. After cooling to room temperature, the precipitated solid was collected by filtration, washed with cold MeOH and dried under vacuum (5.15 g, 75% yield).

A suspension of the nitroester from above (2.50 g, 8.98 mmol) and 20% $Pd(OH)_2$ on carbon (200 mg) in 2:1 EtOH-THF (60 mL) was stirred for 3 h under 1 atm of hydrogen gas. The suspension was filtered to remove the catalyst and volatiles removed under reduced pressure to give the title compound of example 25 as a reddish foam (2.05 g, 92% yield).

Example 26

4-(4-Ethoxycarbonyl-thiazol-2-yl)-phenyl-ammonium chloride

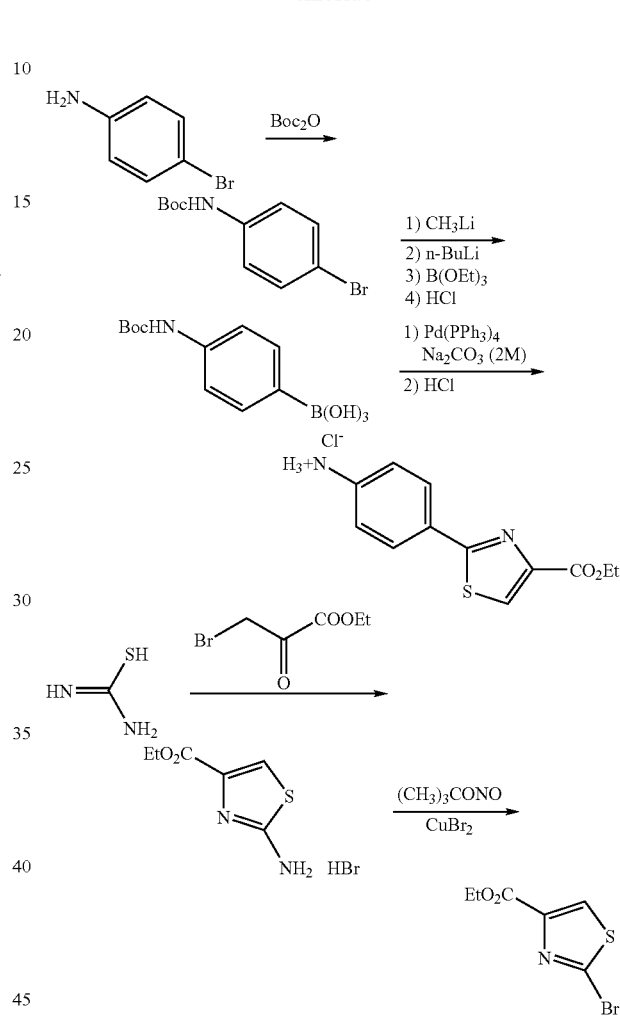

para-Bromoaniline (13.0 g, 76 mmol) and $Boc_2O$ (19.8 g, 91 mmol) were dissolved in toluene (380 mL) and stirred at 70° C. for 15 h. The reaction mixture was cooled to RT, evaporated to dryness, re-dissolved in EtOAc and washed with 0.1M HCl and brine. The organic solution was dried over anhydrous $MgSO_4$, evaporated to dryness and purified by flash column chromatography, using 5% to 10% EtOAc in hexane as the eluent, to obtain the Boc-protected aniline (23 g). The Boc-protected bromoaniline (10.7 g, 39.2 mmol) was dissolved in anhydrous THF (75 mL) in a flask equipped with an overhead stirrer. The solution was cooled to 0° C. and MeLi (1.2 M in $Et_2O$, 33 mL, 39.2 mmol) was added drop wise while maintaining the internal temperature below 7° C. The reaction mixture was stirred at 0° C. for 15 min and then cooled to −78° C. before n-BuLi (2.4 M in hexane, 17 mL, 39.2 mmol) was added drop wise, maintaining the internal temperature below −70° C.). The reaction mixture was stirred at −78° C. for 1 h, $B(OEt)_3$ (17 mL, 98 mmol) was added drop wise (internal temperature <−65° C.) and stirring was continued for 45 min at −78° C. and at 0° C. for 1 h. The reaction mixture was then treated with 5% aqueous HCl (~100 mL, to pH ~1) for 15 min and NaCl(s) was added to saturate the aqueous layer. The aqueous layer was extracted with 0.5 M NaOH (4×100 mL) and the combined aqueous layers were acidified with 5% HCl (150 mL, to pH ~1) and extracted with Et₂O (3×200 mL). The combined organic layers were dried over anhydrous MgSO₄, filtered and concentrated to give the N-Boc carbamate of 4-aminophenylboronic acid as a solid (7.5 g).

Thiourea (7.60 g, 100 mmol) and ethyl bromopyruvate (12.6 mL, 100 mmol) were mixed and heated to 100° C. for 45 min. After cooling of the reaction mixture, the solid obtained was triturated with acetone, filtered and recrystallized from EtOH to obtain the desired aminothiazole product (10.6 g, 40 mmol). The aminothiazole was then added slowly (over a period of 20 min) to a solution of t-butylnitrite (6.2 g, 60 mmol) and CuBr₂ (10.7 g, 48 mmol) in MeCN (160 mL) at 0° C. The reaction mixture was allowed to warm-up to RT and to stirred for 2.5 h. The mixture was then added to an aqueous HCl solution (20%) and extracted with Et₂O (2×400 mL). The organic layer was washed with aqueous HCl (10%), dried over anhydrous MgSO₄ and evaporated to dryness. The desired bromothiazole product was isolated in ~85% yield (4.3 g) after flash column chromatography using 15% EtOAc in hexane as the eluent.

To a de-gassed solution of the bromothiazole product (230 mg, 0.97 mmol), the boronic acid derivative from above (230 mg, 0.97 mmol) and aqueous Na₂CO₃ (2M, 3 mL) in DME (3 mL), a catalytic amount of Pd(PPh₃)₄ (56 mg, 0.049 mmol) was added and the reaction mixture was stirred at 80° C. under argon for 20 h. The reaction mixture was then cooled to RT, diluted with EtOAc and extracted with brine, aqueous NaHCO₃ (2×) and brine. The organic layer was dried over anhydrous MgSO₄ and concentrated to dryness. The carbamate-ester product was isolated after flash column chromatography using 20% to 30% EtOAc in hexane: 180 mg. The aniline hydrochloride of example 26 was isolated after removal of the Boc protecting group with 4N HCl in dioxane for 30 min.

Example 27

Ethyl 5-amino-1-methyl-1H-indole-2-carboxylate

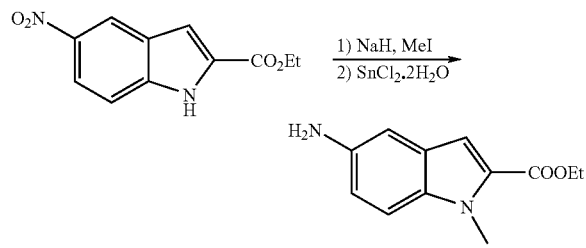

The ethyl ester of 5-nitroindole-2-carboxylic acid (0.300 g, 1.28 mmol) was dissolved in anhydrous DMF (6 mL) and NaH (0.078 g, 60%, 1.92 mmol) was added. The reaction was stirred at RT for 20 min, then MeI (160 µL, 2.56 mmol) was added and stirring was continued for 3 h. The reaction was quenched with the addition of aqueous NaHCO₃ (~1%) while stirring vigorously. The brown solid formed (0.096 g) was filtered and dried in air overnight. The N-methyl nitro derivative (196 mg, 0.79 mmol) was then dissolved in DMF (4 mL), H₂O (400 µL) and SnCl₂.2H₂O (888 mg, 3.95 mmol) were added, and the mixture was stirred at 60° C. for 3 h. The mixture was then partitioned between 10% aqueous NaHCO₃ and EtOAc and stirred vigorously. The aqueous layer was re-extracted with EtOAc and the combined EtOAc layers were washed with brine, dried over anhydrous MgSO₄ and concentrated to dryness. The residue was purified by flash column chromatography, using 1:1 ration EtOAc/hexane as the eluent, to obtain the pure 5-aminoindole derivative (118 mg) of example 27.

Example 28

Ethyl 5-{[1-(4-amino-1-ethyl-piperidin-4-yl)-methanoyl]-amino}-1-methyl-1H-indole-2-carboxylate

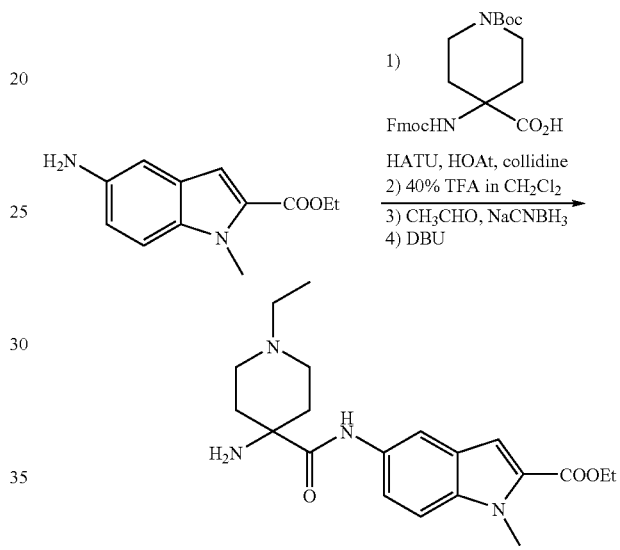

The 5-aminoindole derivative of example 27 was coupled to N-Fmoc-amino-(4-N-Boc-piperidinyl)carboxylic acid. The Boc protecting group was removed with 25% TFA in CH₂Cl₂ in the usual way, and the product was then dissolved in EtOH (6 mL). AcOH (133 mg), acetaldehyde (33 mg, 0.74 mmol) and NaCNBH₃ (23 mg, 0.37 mmol) were added and the reaction mixture was stirred at room temperature for 2 h. The reaction mixture was concentrated to remove most of the solvent, the residue was re-dissolved in EtOAc and washed with saturated NaHCO₃ and brine. The organic layer was dried over anhydrous MgSO₄ and concentrated to give the N-ethyl derivative as an orange solid.

This solid was dissolved in THF (2.5 mL), DBU (113 mg, 0.74 mmol) was added and the mixture was stirred at room temperature for 30 min. The solvent was evaporated, the remaining residue was dissolved in EtOAc and the organic layer was washed with saturated NaHCO₃ and brine. The organic layer was further extracted with 1N HCl and H₂O (2×), and the pH of the combined aqueous layers was adjusted to pH ~10 with 1N NaOH. The aqueous layer was then extracted with EtOAc (3×), the combined organic layers were washed with brine, dried over anhydrous MgSO₄ and concentrated to dryness to give the title amine derivative of example 28 (44 mg): MS (ES⁺) m/z 373.1 (MH⁺).

A similar reductive amination procedure was used to prepare other N-alkylated pyrrolidine (e.g. cucurbitine) and piperidine derivatives. Alternatively, the reductive amination can be performed as the last step on a fully assembled inhibitor.

Example 29

General Procedure for Coupling Amines to 6-Indole Carboxylic Acids to Give Amide Derivatives of General Formulae I Indole carboxylic acids were coupled to various amines (for example according to the examples 15a, 15b, 15c, 19, 20, 21, 22, 23, 24, 25, 28, 34, 35, 36, 42, 43, or 45) using standard amide bond forming procedures familiar to those skilled in the art. Amide bond forming reagents include but are not limited to carbodiimides (DCC, EDC), TBTU, HBTU, HATU and BOP-CI in the presence or absence of additives such as HOBt or HOAT. Indole carboxylic acids can also be activated for coupling by conversion to the corresponding acid chloride, symmetrical anhydride or unsymmetrical anhydrides using standard protocols familiar to those skilled in the art of organic chemistry. The coupling of indole carboxylic acids with amines is generally carried out in solvents such as THF, DCM, DMF, DMSO or MeCN, in the presence of a tertiary organic base including, but not limited to triethylamine, N-methylmorpholine, collidine and diisopropylethylamine. Following coupling of the indole carboxylic acid with the amine, any remaining protecting group that remains in the molecule can then be removed using the appropriate procedure. The following example serves to illustrate such a process and is non-limiting.

(E)-3-[4-({1-[1-({1-[3-Cyclohexyl-2-furan-3-yl-1-(2-morpholin-4-yl-2-oxo-ethyl)-1H-indole-6-yl]-methanoyl}-amino)-cyclobutyl]-methanoyl}-amino)-phenyl]-acrylic acid The indole carboxylic acid of example 9 (0.030 g, 0.069 mmol, 1 equiv.), the amine of example 21 (0.044 g, 0.153 mmol, 2.2 equiv.) and TBTU (0.076 g, 0.24 mmol, 3.4 equiv.) were dissolved in DMSO (2 mL) and triethylamine (84 μL, 0.6 mmol, 8.7 equiv.) was added. The mixture was stirred overnight at room temperature (complete by HPLC). 3N NaOH (0.7 mL) was added and the mixture stirred at 50° C. for 40 min (complete hydrolysis by HPLC). Acetic acid was added to neutralize the reaction mixture and the product was isolated directly by preparative HPLC as a beige amorphous solid (19 mg).

Example 30

General Procedure for the Preparation of Indole 6-Acylsulfonamide Derivatives Indole carboxylic acids were converted to the corresponding acid chloride and coupled to various sulfonamides in the presence of DMAP and an organic base such as triethylamine, DIEA, N-methylmorpholine and the like. Alternatively, the carboxylic acid was activated using amide bond forming agents such as carbodiimides (DCC, EDC), TBTU, HATU and the like and treated with sulfonamides in the presence of DMAP. Sulfonamides were either from commercial sources or prepared from the corresponding sulfonyl chlorides and a solution of ammonia in dioxane.

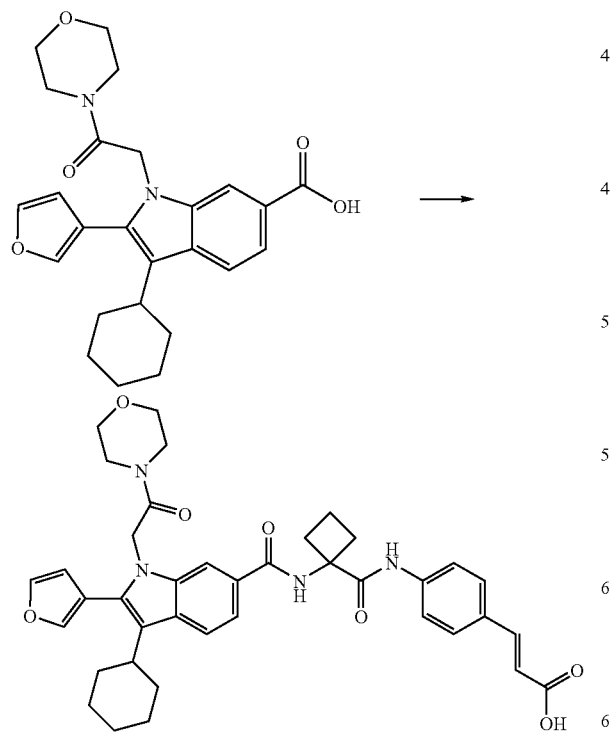

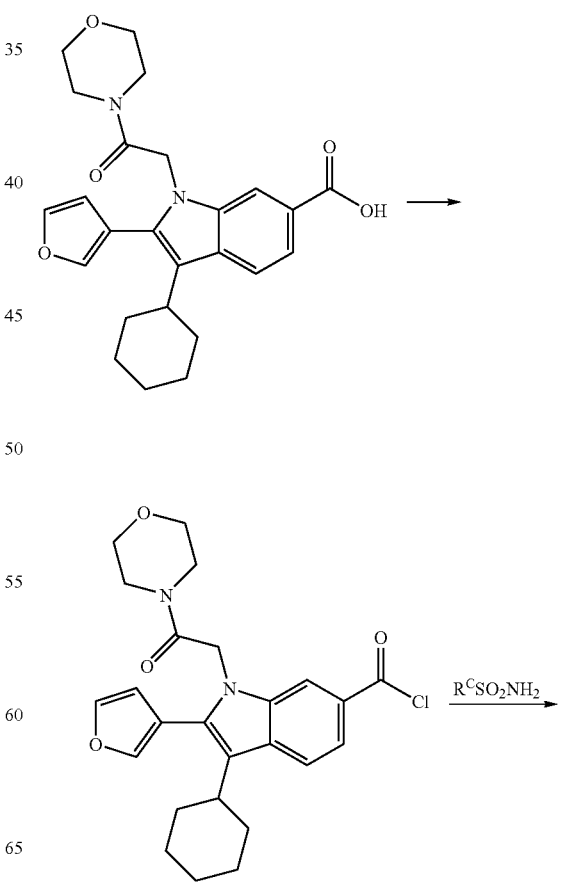

-continued

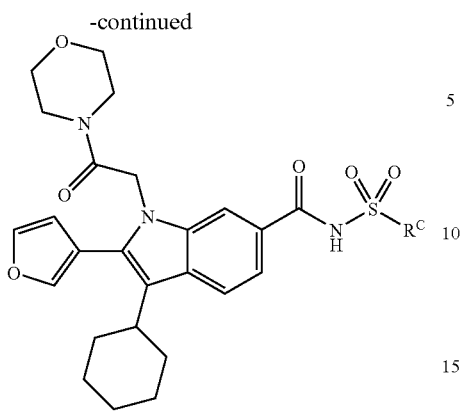

The following example serves to illustrate such as process and is non-limiting.

4-Bromo-N-{1-[3-cyclohexyl-2-furan-3-yl-1-(2-morpholin-4-yl-2-oxo-ethyl)-1H-indole-6-yl]-methanoyl}-benzenesulfonamide

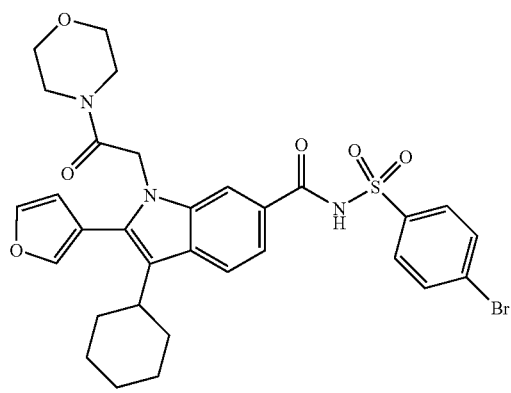

3-Cyclohexyl-2-furan-3-yl-1-(2-morpholin-4-yl-2-oxo-ethyl)-1H-indole-6-carbonyl chloride The carboxylic acid of example 9 (0.800 g, 1.833 mmol, 1 equiv.) was suspended in DCM (15 mL) and DMF (20 μL) was added followed by oxalyl chloride (323 μL, 3.7 mmol, 2 equiv.). After stirring for 2 h at room temperature, volatiles were removed under reduced pressure and the residue co-evaporated twice with DCM. After drying under vacuum for 1.5 h, the acid chloride was obtained as a brown solid that was used directly in the next step.

4-Bromo-N-{1-[3-cyclohexyl-2-furan-3-yl-1-(2-morpholin-4-yl-2-oxo-ethyl)-1H-indole-1-yl]-methanoyl}-benzenesulfonamide The acid chloride from above (0.032 g, 0.07 mmol, 1 equiv.) was dissolved in DCM (2 mL) and 4-bromobenzenesulfonylamide (0.0205 g, 0.085 mmol, 1.2 equiv.) was added. Triethylamine (21 μL, 0.15 mmol, 2.16 equiv.) and DMAP (0.018 g, 0.147 mmol, 2.1 equiv.) were added and the mixture was stirred overnight at room temperature (complete by HPLC). DCM was then evaporated in air and the residue re-dissolved in DMSO (2 mL). The title compound of example 30 was isolated directly by preparative HPLC as a light yellow powder (27 mg).

Example 31

N-{1-[3-Cyclohexyl-2-furan-3-yl-1-(2-morpholin-4-yl-2-oxo-ethyl)-1H-indole-6-yl]-methanoyl}-N-methyl-benzenesulfonamide

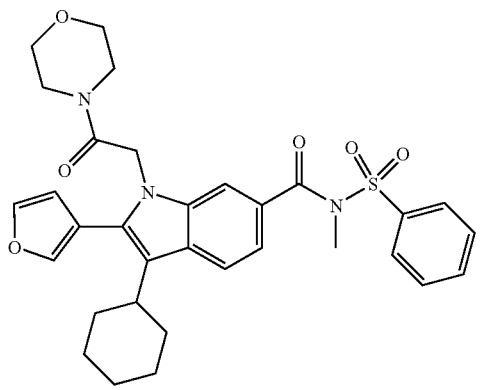

The N-methylacylsulfonamide of example 31 was prepared from the acid chloride described in example 30 and N-methylbenzenesulfonamide using the procedure of example 30.

Example 32

3-Cyclohexyl-2-furan-3-yl-1-(2-morpholin-4-yl-2-oxo-ethyl)-1H-indole-6-carboxylic acid acetyl-amide

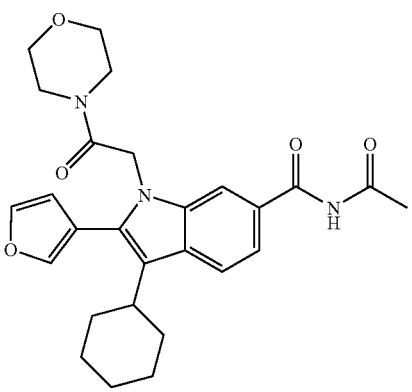

Acetamide (9 mg, 0.152 mmol, 1.38 equiv.) was dissolved in THF (2 mL) and NaH (60% oil dispersion, 8 mg, 0.2 mmol, 1.81 equiv.) was added. The mixture was stirred for 30 min and the acid chloride of example 30 (0.050 g, 0.11 mmol, 1 equiv.) in THF (1 mL) was added. The reaction mixture was then stirred for 2 h at room temperature (complete by TLC). The reaction was diluted with EtOAc and the solution washed with 10% aqueous HCl and dried ($Na_2SO_4$). After evaporation of the solvent under reduced pressure, the residue was purified by flash chromatography on silica gel using EtOAc as eluent. The title compound of example 32 was obtained as a white solid (24 mg).

Example 33

Methyl 2-bromo-3-cyclohexyl-1H-indole-5-carboxylate

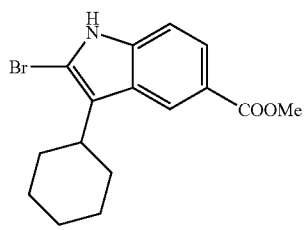

Using the same series of reactions described in example 2 but starting from indole 5-carboxylic acid, the title compound of example 33 was obtained. This compound is a starting material for the synthesis of compounds according to the general formula I.4, whereby the methods as described hereinbefore, e.g. 4 to 8 and/or in combination with 9 to 32, can be employed in an analogous manner.

Example 34

2-(1-Amino-cyclobutyl)-3-methyl-benzofuran-5-carboxylic acid methyl

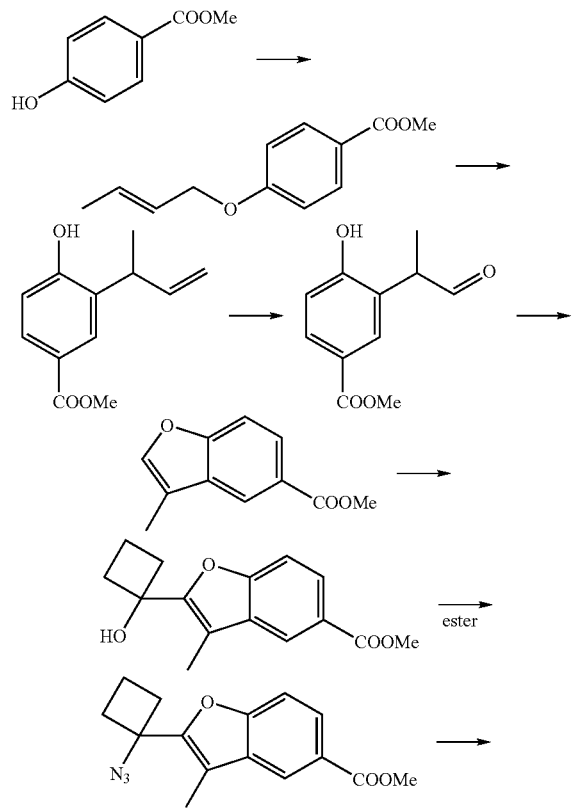

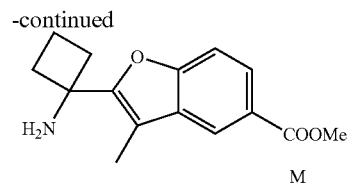

M ethyl 4-hydroxybenzoate (20.00 g, 131 mmol) was dissolved in DMF (350 mL) and $K_2CO_3$ (24.19 g, 175 mmol) was added. The mixture was stirred for 30 min and crotyl bromide (85%, 16.47 mL, 160 mmol) was added dropwise over 4 min. The resulting amber suspension was stirred for 4 h at room temperature. It was then poured into DCM and the solution washed with water and brine. The extract was dried ($MgSO_4$) and evaporated to a pale yellow oil consisting of a mixture of two isomeric allyl ether (4:1 ratio). Upon standing at room temperature, the oil partially crystallized. The supernatant was decanted and the crystals washed with hexane to provide 12.5 g of the desired ether as white crystals. The above material (10.30 g, 50 mmol) was added to a flask heated to 230° C. in a sand bath and the melted oil was stirred for 25 min at that temperature. The material was then brought back to room temperature and the resulting waxy solid used without purification in the next step.

The rearranged phenol from above (10.00 g, 48.5 mmol) was dissolved in MeOH and the solution cooled to −78° C. in a dry ice-acetone bath. Ozone was bubbled through the solution until complete disappearance of starting material (TLC). Dimethyl sulfide (7 mL) was then added dropwise at −78° C. and the mixture stirred for 10 min at −78° C. and at room temperature for 30 min. Volatiles were removed under reduced pressure, the residue was dissolved in ether and the solution washed with water (2×) and brine. After drying ($MgSO_4$) and removal of volatiles, the crude product which consists of a mixture of aldehyde and lactol was obtained as a milky oil (9.9 g).

The crude product from above (9.9 g, 48 mmol) was suspended in 85% phosphoric acid (40 mL) and heated to 50° C. for 50 min after which a white solid precipitated. Water (50 mL) was added and the solid collected by filtration. The material was then dissolved in EtOAc and washed with saturated aqueous $NaHCO_3$ and water. The solution was dried ($MgSO_4$) and concentrated to yield a residue that was purified by flash chromatography on silica gel using 10% EtOAc-hexanes as eluent. The desired benzofuran derivative was obtained (2.39 g).

The benzofuran derivative from above (2.20 g, 11.6 mmol) was dissolved in THF (65 mL) and the solution cooled to −78° C. A solution of lithium diisopropylamide (LDA, 2M in heptane/THF/ethylbenzene, 6.9 mL) was added dropwise over 10 min. After stirring for 35 min, cyclobutanone (1.793 mL, 24 mmol) was added dropwise and stirring continued at −78° C. for 15 min. The reaction mixture was then warmed to room temperature and quenched with 1N HCl. The product was extracted with EtOAc, washed with water and brine and dried ($Na_2SO_4$). Purification by flash chromatography on silica gel using 25% EtOAc in hexanes gave the desired cyclobutyl carbinol (1.39 g) as a clear gum.

The alcohol from above (1.38 g, 5.3 mmol) and sodium azide (1.105 g, 17 mmol) were suspended in $CHCl_3$ (30 mL) and the mixture cooled in ice. TFA (1.695 mL, 22 mmol) was added dropwise over 10 min, the cooling bath was removed and the mixture stirred at room temperature for 20 min. The reaction mixture was diluted with $CHCl_3$, washed with saturated aqueous NaHCO₃ and dried (MgSO₄). Removal of solvents under reduced pressure gave a amber oil that was purified by flash chromatography on silica gel using 5% EtOAc in hexane as eluent. The desired azide was obtained as a clear oil (882 mg).

The azide from above (880 mg) was hydrogenated (1 atm H₂) in MeOH over 5% Lindlar catalyst (374 mg). After 15 min, the reduction was judged complete by TLC. Removal of the catalyst by filtration and solvent under reduced pressure gave the desired amine derivative of example 34 (785 mg) as a colorless oil: ES-MS: m/z 243 (M-NH₂).

Example 35

3-[2-(1-Amino-cyclobutyl)-1-(toluene-4-sulfonyl)-1H-indol-6-yl]-acrylic acid ethyl

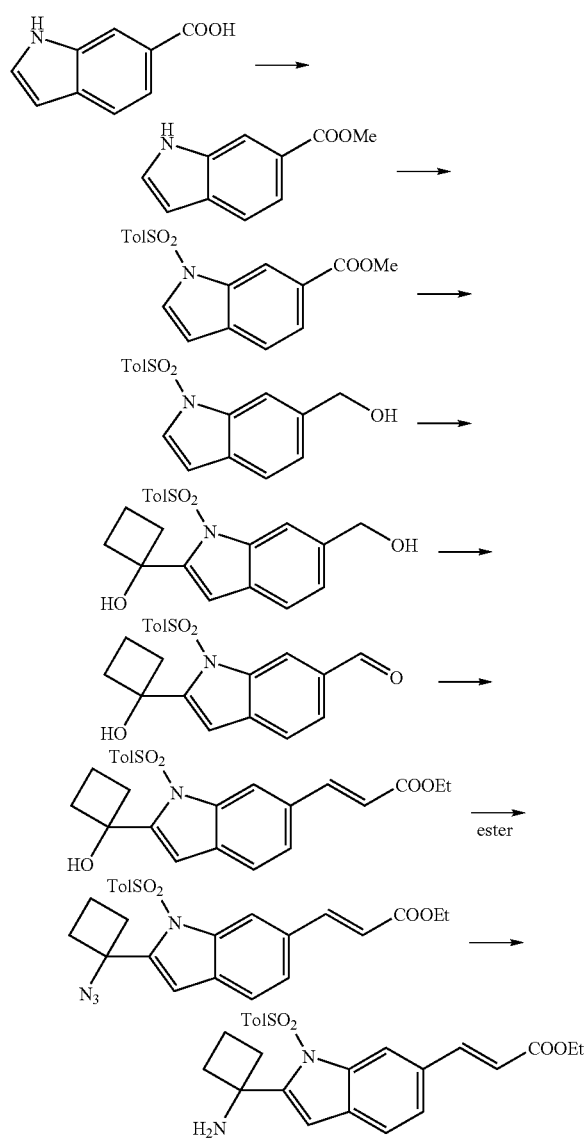

Indole 6-carboxylic acid (10.00 g, 62 mmol) was esterified by refluxing overnight in a mixture of MeOH (200 mL) and conc. H₂SO₄ (1 mL). After cooling, the reaction mixture was poured into sat. aqueous NaHCO₃ and extracted with EtOAc. The extract was washed with aqueous NaHCO₃ twice and water. Drying (MgSO₄) and removal of volatiles gave the desired methyl ester as a brown oil (10.4 g).

The ester from above (10.40 g, 62 mmol) was dissolved in DMF (80 mL) and the solution cooled in ice. Sodium Hydride (60% oil dispersion, 2.852 g, 71.3 mmol) was added in small portions and the mixture was stirred at room temperature for 40 min. The reaction mixture was brought back to 0° C. and para-toluenesulfonyl chloride (14.49 g, 76 mmol) was added. The mixture was stirred for 2 h at room temperature. The reaction mixture was then diluted with EtOAc, washed consecutively with 10% citric acid (2×), NaHCO₃ (2×) and brine. After drying (MgSO₄), removal of solvent gave a beige residue that was triturated twice with ether-hexanes (7.7 g). Concentration of mother liquors and trituration of the residue with MeOH gave an additional 5.8 g of the desired tosylated indole.

The material from above (1.750 g, 5.31 mmol) was dissolved in DCM (40 mL) and the solution cooled to −78° C. Diisobutylaluminum hydride (1M in DCM, 12.72 mL, 12.72 mmol) was added dropwise and the mixture stirred for 30 min at −78° C. The reaction mixture was then warmed to room temperature, quenched with aqueous potassium sodium tartrate and stirred overnight at room temperature. The organic phase was decanted, washed with brine and dried (MgSO₄). Removal of volatiles and purification by flash chromatography on silica gel gave the desired alcohol as a colorless oil (1.35 g).

The alcohol from above (1.250 g, 4.15 mmol) was dissolved in THF (150 mL) and the solution was cooled to −78° C. Lithium diisopropylamide (2M in THF/heptane/ethyl benzene, 10.37 mL) was added dropwise over 5 min. After stirring for an additional 30 min at −78° C., cyclobutanone (1.55 mL, 20.7 mmol) was added and the reaction mixture allowed to warm up to 0° C. The reaction was quenched with 10% citric acid and THF removed under reduced pressure. Water was added and the product was extracted with EtOAc, washed with aqueous NaHCO₃ and brine, and dried (MgSO₄). The material was purified by flash chromatography on silica gel using 30-50% EtOAc in hexanes as eluent. The desired cyclobutyl carbinol was obtained as an oil (0.94 g).

The alcohol from above (0.870 g, 2.34 mmol) was dissolved in DCM (20 mL) and 1,1,1-tris(acetyloxy-1,1-dihydro-1,2-benzodioxol-3-(1H)-one (Dess-Martin periodinane) (1.060 g, 2.50 mmol) was added. The mixture was stirred at room temperature for 3 h, quenched with aqueous NaHCO₃ an d extracted with EtOAc. The extract was washed with brine, dried (MgSO₄) and concentrated to give the desired aldehyde as an oil that was used directly in the next step.

The crude aldehyde (assume 2.34 mmol) from above was dissolved in DCM (20 mL) and (carbethoxymethylene)triphenylphosphorane (0.871 g, 2.5 mmol) was added. The mixture was refluxed for 4 h, concentrated and the product isolated by flash chromatography on silica gel using 20-30% EtOAc in hexanes as eluent. The desired cinnamate was obtained as a foam (0.400 g).

The cinnamate derivative from above (0.400 g, 0.9 mmol) was dissolved in CHCl₃ (15 mL) and sodium azide (138 mg, 2.1 mmol) was added. TFA (0.39 mL, 5.1 mmol) was added dropwise over 5 min and the mixture was then stirred at 60° C. for 4 h. The reaction mixture was diluted with CHCl₃, washed with aqueous NaHCO₃ and dried (MgSO₄). The product was purified by flash chromatography on silica gel using 20% EtOAc in hexane as eluent, to give the desired azide as a yellow foam (0.207 g).

The azide from above (0.183 g) was dissolved in THF (5 mL) containing 1% water and triphenylphosphine (180 mg) was added. The mixture was stirred at 60° C. for 20 h and the final product of example 35 isolated by preparative reversed-phase HPLC (42 mg).

This amine was coupled in the usual manner to indole carboxylic acid derivative to give final inhibitors after cleavage of the N-tosyl and ester protecting groups with NaOH.

Final products obtained as above were also methylated on the indole nitrogen by treating the fully deprotected molecules with NaH and iodomethane, followed by saponification of the methyl ester which was formed concomitantly.

Example 36

3-(4-Amino-2-ethoxy-phenyl)-acrylic acid methyl-ester

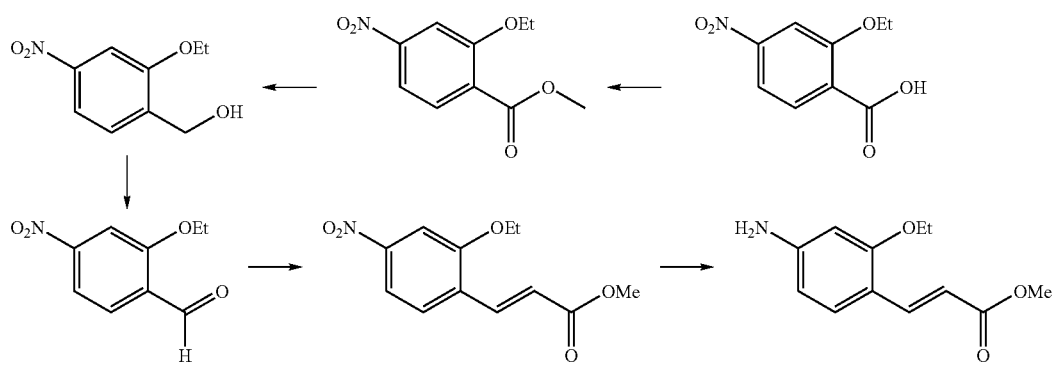

2-Ethoxy-4-nitrobenzoic acid (1.56 g; 7.38 mmol) was dissolved in methanol (15 mL) and the resulting solution stirred at 0° C. A solution of diazomethane in ethyl ether was slowly added until the yellow color persisted and was stirred for a further 20 min. The solvents were evaporated to afford the methyl ester as a pale yellow solid (1.66 g, quant.) which was used without further purification.

The ester from above (1.60 g; 7.10 mmol) was dissolved in dry toluene and the solution cooled to −78° C. under a nitrogen atmosphere. A solution of diisobutylaluminum hydride in tetrahydrofuran (1M; 8 mL; 8 mmol) was added and the reaction allowed to warm to ambient temperature. Two additional portions of DIBAL-H were added in this way (7 and 10 mL) after 1 h and a further 1.5 h. 0.5 h after the last addition, the reaction was cooled to 0° C. and 1N HCl (25 mL) was slowly added and the mixture stirred vigorously for 0.5 h. The organic solvents were then evaporated and the aqueous residue was extracted with ethyl acetate (2×50 mL) and washed with water (50 mL) and brine (50 mL). The combined extracts were then dried over MgSO$_4$ and evaporated to afford the alcohol as a pale yellow, fibrous solid (1.40 g; quant.) which was used as such.

A turbid solution of 1,1,1-tris(acetyloxy-1,1-dihydro-1,2-benzodioxol-3-(1H)-one (Dess-Martin periodinane) (2.32 g; 5.47 mmol) in dichloromethane (40 mL+5 mL rinse) was added to a stirred solution of the above alcohol (0.98 g; 4.97 mmol) in DCM (40 mL) and the reaction stirred at ambient temperature under a nitrogen atmosphere. After 4 h, saturated NaHCO$_3$/10% Na$_2$S$_2$O$_3$ (1:1, 160 mL) was added and the mixture stirred vigorously until the phases were clear (ca. 0.5 h). The organic phase was separated and the aqueous phase was extracted with dichloromethane (50 mL) and washed with saturated NaHCO$_3$ (2×150 mL). The combined organic phases were then dried over MgSO$_4$ and evaporated to yield the aldehyde as a pale yellow solid (960 mg; 99%) which was used as such.

Sodium hydride (95% dry powder; 158 mg; 6.25 mmol) was suspended in anhydrous THF (10 mL) and trimethyl phosphonoacetate (0.945 mL; 5.84 mmol) added dropwise at 0° C. under a nitrogen atmosphere resulting in a solid white mass which could not be stirred. A solution of the aldehyde from above (950 mg; 4.87 mmol) in THF (7 mL+3 mL rinse) was then added dropwise resulting in a yellow colour and slow dissolution of the white solid mass. After the addition, the reaction was allowed to warm to ambient temperature. After 15 h, the cloudy reaction mixture was evaporated to a pale yellow solid which was extracted with ethyl acetate (2×50 mL) and washed with saturated NaHCO$_3$ (3×75 mL). The combined extracts were dried over MgSO$_4$ and evaporated to afford the cinnamate ester as pale yellow solid (1.212 g; 99%) which was used without further purification.

The nitro cinnamate from above (0,300 g, 1.2 mmol) was suspended in EtOH (12 mL) and water (7.5 mL) and K$_2$CO$_3$ (0.990 g, 7.16 mmol) and 85% sodium hydrosulfite (1.247 g. 7.16 mmol) were added successively. The mixture was stirred vigorously at room temperature for 1.5 h. It was then diluted with water (10 mL) and the ethanol removed under reduced pressure. The reaction mixture was extracted with EtOAc (2×), washed with water and brine and dried (MgSO$_4$). Removal of the solvent under reduced pressure gave the desired aniline as a yellow solid.

Note: the analogous methoxy derivative was prepared in the same manner using commercially available 2-methoxy-4-nitrobenzoic acid as starting material.

Example 37

3-(4,5-Diamino-2-alkoxy-phenyl)-acrylic acid methyl esters

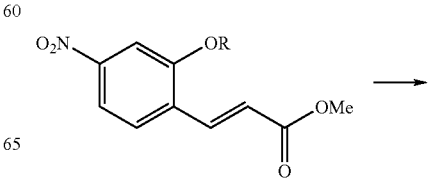

-continued

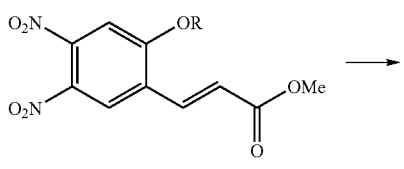

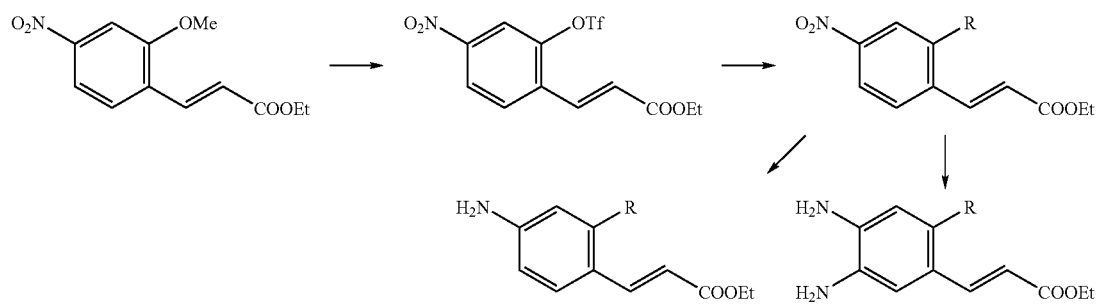

R = (C$_{1-6}$)alkyl, (C$_{2-6}$)alkenyl, (C$_{3-6}$)cycloalkyl, (C$_{2-6}$)alkynyl -continued

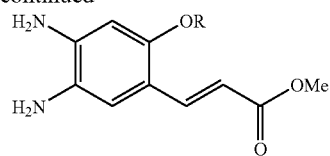

The procedures will be illustrated for R=Et but similar protocols can be used to prepare derivatives with other alkoxy substituents.

The ortho-ethoxy-para-nitro cinnamate derivative prepared as described in example 36 (600 mg; 2.39 mmol) was dissolved in concentrated sulphuric acid (5.5 mL) at 0° C. and potassium nitrate (253 mg; 2.50 mmol) added in portions over 3 min. After 5 min, the resulting yellow-brown solution was allowed to warm to ambient temperature and was stirred under a nitrogen atmosphere. After 3 h, the reaction was added to ice (75 g) resulting in a pale yellow precipitate. Once the ice had melted, the suspension was sonicated, filtered and washed several times with distilled water. Air drying overnight afforded the dinitrocinnamate as a pale yellow, chalky solid (661 mg; 93%) which was used without further purification. The dinitrocinnamate (657 mg; 2.22 mmol) was dissolved/suspended in ethanol/water (1:1; 40 mL) resulting in a yellow suspension which was stirred vigorously at ambient temperature. Potassium carbonate (3.06 g; 22.2 mmol) and sodium hydrosulfite (3.86 g; 22.2 mmol) were successively added resulting immediately in a dark violet/green colour which quickly began to lighten to a pale orange. After 3 h, the reaction was diluted with water (20 mL) and the ethanol evaporated. The aqueous residue was extracted with ethyl acetate (2×50 mL) and washed with saturated NaHCO$_3$ (2×60 mL) and brine (30 mL). The combined extracts were dried over Na$_2$SO$_4$ and evaporated to afford the dianiline as a dark orange syrup which solidified under high vacuum (377 mg; 72%).

Such dianiline derivatives as described in this example could be converted to benzimidazole derivatives by coupling to amino acid derivatives as described in example 22 to prepare inhibitors.

Example 38

3-(4-Amino-2-alkyl-phenyl)-acrylic acid methyl esters and 3-(4,5-diamino-2-alkyl-phenyl)-acrylic acid methyl esters As one skilled in the art would recognize, analogs of derivatives presented in examples 36 and 37 where the alkoxy group has been replaced by an alkyl, alkenyl or alkynyl substitutent (e.g. R=Me, Et, Pr, vinyl, allyl) can be prepared by converting such an alkoxy derivative (e.g. methoxy) to the corresponding phenol by cleaving the ether linkage with reagents such as BBr$_3$ and then converting the phenol substituent to the corresponding triflate. Such triflates can then be used as substrates in a variety of transition metal catalyzed cross-coupling reactions with organometallic reagents that would allow replacement of the triflate functionality by an alkyl substituent. Such reagents might include tetraalkyltin, tetraalkenyltin, alkylboronic acid and alkenylboronic acid derivatives that would undergo cross-coupling under Pd° catalysis. In some cases (e.g. allyl or vinyl), the substituent can be further elaborated (e.g. the double bond can be converted to a cyclopropane ring using a cyclopropanating reagent known to people skilled in the art)

Once the alkyl group has been introduced, the intermediates can then be elaborated to inhibitors following synthetic sequences described in previous examples.

Example 39

1-Carboxymethyl-3-cyclohexyl-2-furan-3-yl-7-methyl-1H-indole-6-carboxylic acid methyl ester

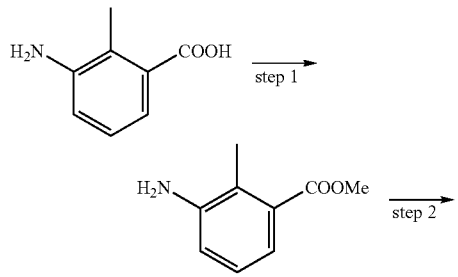

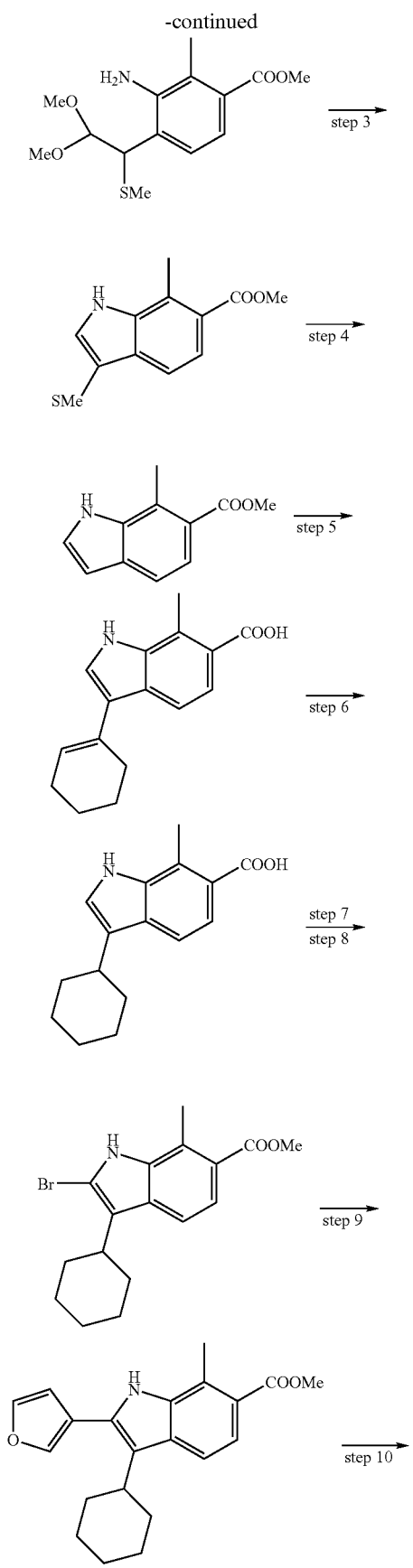
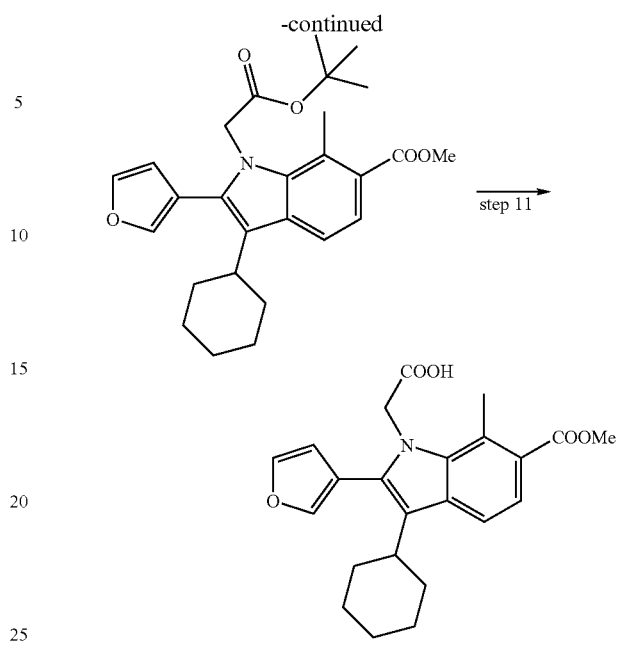

Step 1: 3-amino-4-methylbenzoic acid (15.00 g, 0.099 mol) was suspended in MeOH (150 mL) and thionyl chloride (25.33 mL, 0.347 mol. 3.5 equiv.) was added dropwise. The mixture was heated overnight at 70° C. After cooling to RT, volatiles were removed under reduced pressure and the residue triturated with ether (150 mL). The solid was filtered off and dried (18.36 g). The solid was suspended in DCM (600 mL) and saturated aqueous $NaHCO_3$ (250 mL) was added. After stirring for 15 minutes, the organic layer was separated and washed successively with $NaHCO_3$ solution (2×250 mL), water (250 mL) and brine (250 mL). The solution was dried ($Na_2SO_4$), filtered and evaporated to dryness to give the desired aniline (14.8 g, 90% yield).

Steps 2 and 3: the ester from above (12.50 g, 75.6 mmol) was dissolved in DCM (190 mL) and methylthioaldehyde dimethyl acetal (10.1 mL, 75.6 mmol) was added. The solution was cooled to −30° C. N-chlorosuccinimide (10.10 g, 75.6 mmol) was added in 6 portions over 30 minutes. Triethylamine (10.6 mL, 75.6 mmol) was then added dropwise over 10 min and after stirring for an additional 15 min, the cooling bath was removed and the temperature brought to reflux. After 5 h, the reaction mixture was cooled to RT and evaporated to dryness. The residue was dissolved in ether (750 mL) and 2M HCl (303 mL) was added. After stirring at RT for 1.5 h, the ether layer was separated and washed with $NaHCO_3$ solution (2×150 mL) and brine (250 mL). The original acidic aqueous phase was extracted with DCM (2×100 mL) and the extracts washed as above and then combined with the first ether phase. The combined organic phases were dried ($Na_2SO_4$) and evaporated to dryness and the material purified by flash chromatography on silica gel using 30-0% hexane in DCM as eluent to give the desired 3-thiomethylindole derivative (9.37 g).

Step 4: the thiomethyl indole from above (8.37 g, 35.4 mmol) was dissolved in absolute EtOH (220 mL) and Raney-nickel (Ra—Ni) (25 g) was added. After stirring at RT for 3 h, another portion of Ra—Ni (15 g) was added and stirring resumed for an additional 45 min. The mixture was filtered and the filtrate evaporated to dryness to give the desired indole (6.26 g, 93%).

Steps 5: the indole ester from above (4.00 g, 21 mmol) was dissolved in a mixture of MeOH (18 mL) and water (18 mL). KOH (11.86 g, 210 mmol) was added and the mixture stirred at 75° C. for 2 h. Cyclohexanone (7.26 g, 74 mmol, 3 equiv.) was added dropwise over 15 min and stirring at 75° C. was continued overnight. MeOH was removed under reduced pressure and water (500 mL) was added to the residue. Insoluble material was removed by filtration and the aqueous phase was then washed with TBME (200 mL). The aqueous phase was acidified to pH 4 with formic acid to produce a white precipitate that was collected by filtration, washed with water and dried. The desired cyclohexenylindole was obtained (4.77 g, 89%).

Steps 6-8: as described in example 2.

Steps 9-11: as described in examples 4 and 6.

Example 40

1-Carboxymethyl-3-cyclohexyl-2-furan-3-yl-5-methoxy-1H-indole-6-carboxylic acid methyl ester

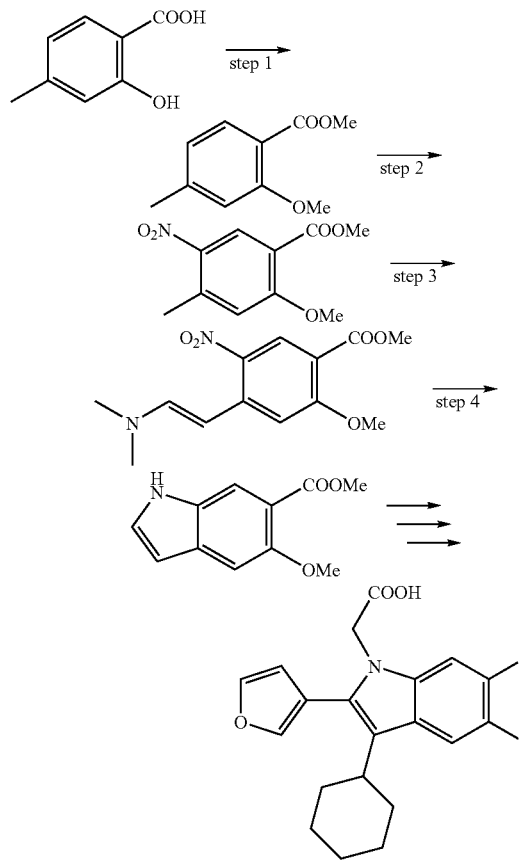

Step 1: 4-methylsalicylic acid (100 g, 0.66 mol) was dissolved in acetone (1 L) and $K_2CO_3$ (227 g, 1.64 mol, 2.5 equiv.) was added in portions. The mixture was heated to reflux and dimethylsulfate (155 mL, 1.64 mol, 2.5 equiv.) was added dropwise over 1 h. The mixture was refluxed overnight. Additional $K_2CO_3$ (90 g) and dimethylsulfate (60 mL) were added and the mixture refluxed for an additional 20 h. $K_2CO_3$ (20 g) and dimethylsulfate (15 mL) were again added and after refluxing for 7 h, the reaction was judged complete by TLC. Solids were removed by filtration using acetone for washings and the filtrate concentrated to a volume of 200 mL. The solution was diluted with MeOH (1 L) and stirred with ammonium hydroxide (300 mL) for 30 min. MeOH was removed under reduced pressure and the residue extracted with EtOAc (2×400 mL). The extract was washed with brine (500 mL) and dried ($Na_2SO_4$). Removal of volatiles gave the desired product as a yellow oil (119 g).

Step 2: the ester from above (117 g, 0.649 mol) was charged in a flask cooled in ice. The ester was dissolved in conc. $H_2SO_4$ (600 mL) and the solution cooled to −3° C. Conc. $HNO_3$ (51 mL) was added dropwise over 1.5 h keeping the internal temperature around 0° C. The ice bath was removed and the mixture stirred at RT for 3.5 h. The reaction mixture was poured over ice and allowed to stand overnight. The precipitated solid was collected by filtration, washed with water and dried. The material was purified by trituration from hot methanol and flash chromatography on silica gel to separate the desired product from a dinitro side product.

Step 3: The nitro ester from above (75.7 g, 0.336 mol) was dissolved in DMF (322 mL) and DMF dimethylacetal (120.1 g, 1.01 mol) was added dropwise over 10 min. The mixture was heated to 115° C. for 3 h (complete by TLC). The reaction mixture was cooled to RT and volatiles removed under vacuum. The residue was co-evaporated twice with DCM and triturated with ether to give a total of 90.02 g (95% yield) of the desired enamine derivative.

Step 4: The enamine from step 3 (90.02 g, 0.321 mol) was dissolved in 1:1 THF-MeOH (1.48 L) and the mixture heated to 35° C. in a water bath. Raney nickel (washed with THF, 6.3 g) was added followed by dropwise addition of hydrazine (18.5 g, 0.369 mol) over 15 min. After stirring for 1 h (internal temperature: 49° C.), a second portion of hydrazine (18.5 g) was added dropwise and the mixture stirred overnight at 49° C. Evaporated solvent was replenished and Raney-nickel (6.3 g) and hydrazine (18.5 g) were again added followed by another portion of hydrazine (18.5 g) after stirring for an additional 3 h. After stirring at 54° C. overnight, the reaction was completed by addition of a last portion of Raney-nickel (6.3 g) and hydrazine (36 mL) and stirring 20 h. The reaction mixture was then brought back to RT and filtered using DCM for washings. The filtrate was evaporated to dryness under reduced pressure and the residue purified by flash chromatography on silica gel using 2-30% EtOAc in DCM as eluent. The desired indole was obtained (41.1 g).

The indole from step 4 was elaborated to the title compound of example 40 using procedures similar to those described in the previous example.

Example 41

3-Cyclohexyl-2-furan-3-yl-5-hydroxy-1-[2-oxo-2-(4-pyrrolidin-1-yl-piperidin-1-yl)-ethyl]-1H-indole-6-carboxylic acid

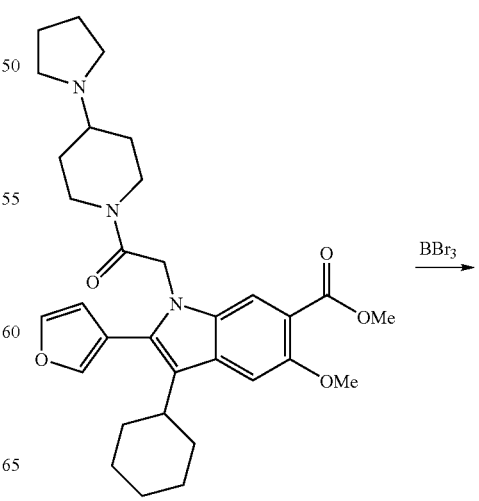

-continued

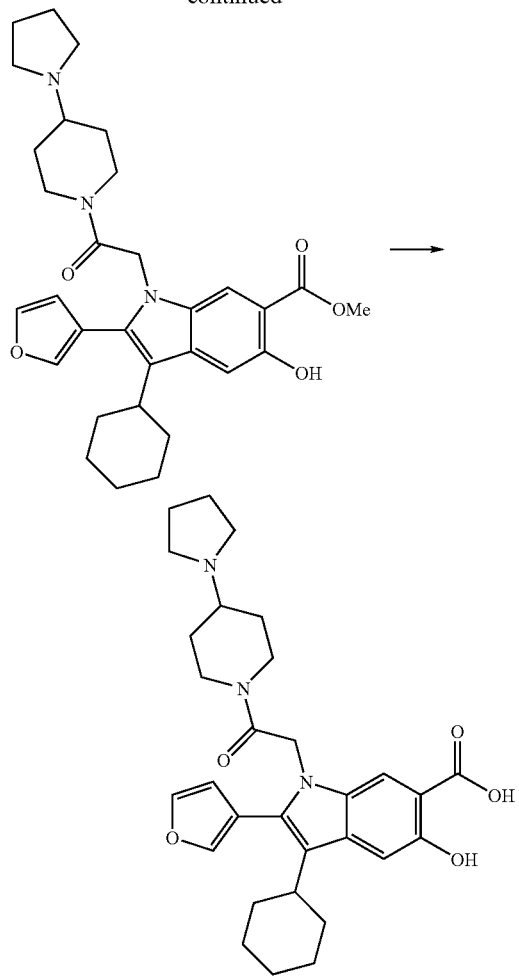

This is a representative procedure that can be applied to analogs with other amide substituents: the methoxyindole (30 mg) was dissolved in DCM (1 mL) and the solution was cooled in ice under a nitrogen atmosphere. Boron tribromide (1M in DCM, 0.3 mL) was added dropwise and the mixture was stirred for 40 min at 0° C. and then 30 min at RT. The reaction was then quenched by addition of ice, diluted with DCM and neutralized by addition of solid NaHCO$_3$. The organic phase was separated and dried (MgSO$_4$). Evaporation of the solvent under reduced pressure gave the desired phenol derivative as a yellow solid (21 mg) that was saponified to give the title compound of example 41 under standard conditions. Alternatively, the intermediate phenolic ester can be alkylated under standard conditions (e.g. NaH in DMF) to produce various ether derivatives (e.g. with tert-butyl bromoacetate)

Example 42

1-(2-Methyl-thiazol-4-yl)-cyclobutylamine hydrochloride

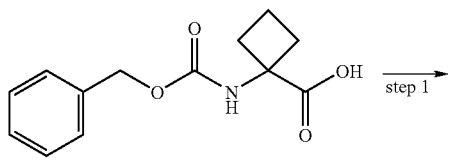

-continued

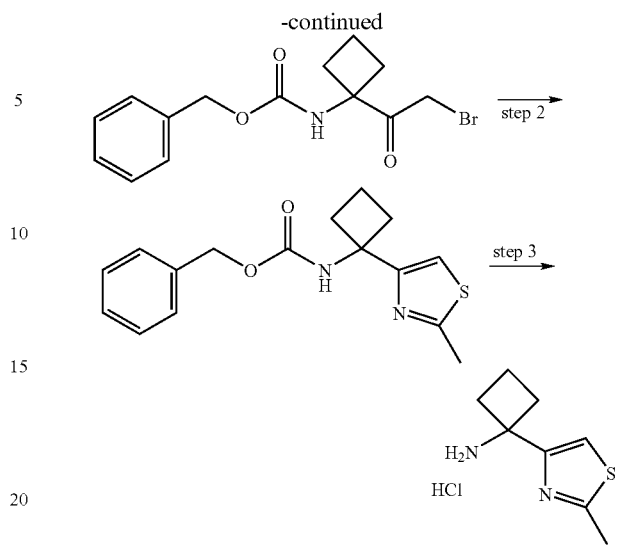

Step 1: The starting protected amino acid was obtained using a similar procedure to that described in example 21 but using benzyl alcohol instead of trimethylsilyl ethanol in the curtius rearrangement. The acid (7.48 g, 30 mmol) was dissolved in THF (50 mL) and the solution cooled to −8° C. under a nitrogen atmosphere. N-Methylmorpholine (3.63 mL, 33 mmol) was added dropwise followed by isobutylchloroformate (3.89 mL, 30 mmol). The suspension was stirred for 10 min and filtered under nitrogen, keeping the filtrate at −8° C. The solution was then added to an excess ethereal diazomethane solution and the mixture stirred for 30 min (TLC shows complete conversion to the diazomethylketone). 48% HBr in water (3.50 mL, 31 mmol) was then added dropwise over 5 min to the cold solution. A second portion of HBr (3.5 mL) was added after 5 min, the cooling bath was removed and the mixture stirred at RT overnight. Ether (250 mL) was added and the solution washed with water (2×50 mL), saturated NaHCO$_3$ (50 mL) and brine (50 mL). After drying (MgSO$_4$), volatiles were removed under reduced pressure and the residue triturated with 1:4 ether/hexanes. The white solid was filtered, washed with hexane and dried in vacuum. The desired bromomethylketone (7.35 g, 75% yield) was obtained as a white solid.

Step 2: The bromomethylketone from above (228 mg, 0.7 mmol) and thioacetamide (56.3 mg, 0.75 mmol) were heated to reflux in isopropanol (5 mL). After 1 h, the reaction mixture was evaporated to dryness and the oily residue triturated with water to give a white precipitate that was collected, washed with water and dried in vacuum (185 mg, 87% yield).

Step 3: 10% Pd on charcoal (70 mg) was suspended in EtOH (5 mL) and the protected thiazole derivative from above (180 mg) was added. Hydrochloric acid was added to acidify the reaction mixture which was then stirred under 1 atm of H$_2$ gas for 20 h. The catalyst was removed by filtration and the filtrate evaporated to dryness under reduced pressure to give the desired amine hydrochloride as a white solid (104 mg) after trituration with ether. The amine hydrochloride was coupled to indole derivatives under standard conditions.

Note: Analogous thiazole derivatives can be prepared in a similar way by using differently substituted thioamide, thiourea or acylthiourea derivatives. In addition, other protected amino acids can be used as starting materials in this sequence and converted to their respective bromo or chloromethylketones to be used in turn to prepare various substituted thiazole derivatives.

Example 43

(Z)-3-[2-(1-Amino-cyclobutyl)-6-ethoxy-1-methyl-1H-benzimidazol-5-yl]-acrylic acid methyl ester

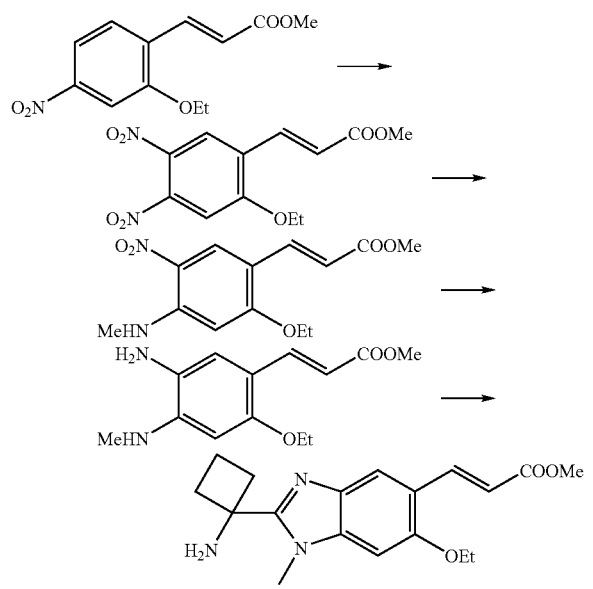

The 4-nitro-2-ethoxycinnamate (303 mg, 1.206 mmol), prepared as described in example 36 was dissolved in concentrated sulfuric acid (3 mL) and the solution cooled to 0° C. Potassium nitrate (128 mg, 1.27 mmol) was added and the mixture stirred for 3.5 h at room temperature. After completion, the reaction mixture was poured over ice and the precipitated solid was collected by filtration. The crude product was washed with water, dried under vacuum and used without purification in the next step (390 mg).

The dinitro derivative from above (390 mg) was dissolved in THF (3 mL) and methylamine in THF (3.02 mL of a 2M solution in THF) was added. After stirring for 30 min, volatiles were removed under reduced pressure and the orange solid used as such in the next step.

The nitro arene from above was suspended in a mixture of EtOH (12 mL) and water (12 mL) and $K_2CO_3$ (1.00 g, 6 equivalents) was added followed by sodium hydrosulfite (1.26 g, 6 equivalents). The mixture was stirred for 4 h at room temperature and EtOH was removed under reduced pressure. The residue was extracted with EtOAc and the organic phase washed with brine and dried ($MgSO_4$). Removal of the solvent and purification of the residue by flash chromatography (50 to 75% EtOAc in hexane) gave the desired diamine (162 mg). The dianiline from above (162 mg) was dissolved in acetonitrile (6 mL) and aminocyclobutanecarboxyl chloride hydrochloride prepared as in example 20 (116 mg) was added. The mixture was stirred overnight at room temperature, diluted with EtOAc and the solution washed with aqueous $NaHCO_3$ and brine. After drying ($MgSO_4$), volatiles were removed under reduced pressure. The residue was dissolved in AcOH (3 mL) and the solution heated to 80° C. for 1 h. After cooling to room temperature, the reaction mixture was poured into water and basified to pH 9 by addition of solid $K_2CO_3$. The organic phase was then extracted with EtOAc, washed with brine and dried ($MgSO_4$). Removal of the solvent gave a residue that was purified by flash chromatography on silica gel using 0 to 5% MeOH in EtOAc to give the title compound of example 43 (68 mg).

Example 44

7-Methoxy-1H-indole-6-carboxylic acid methyl ester

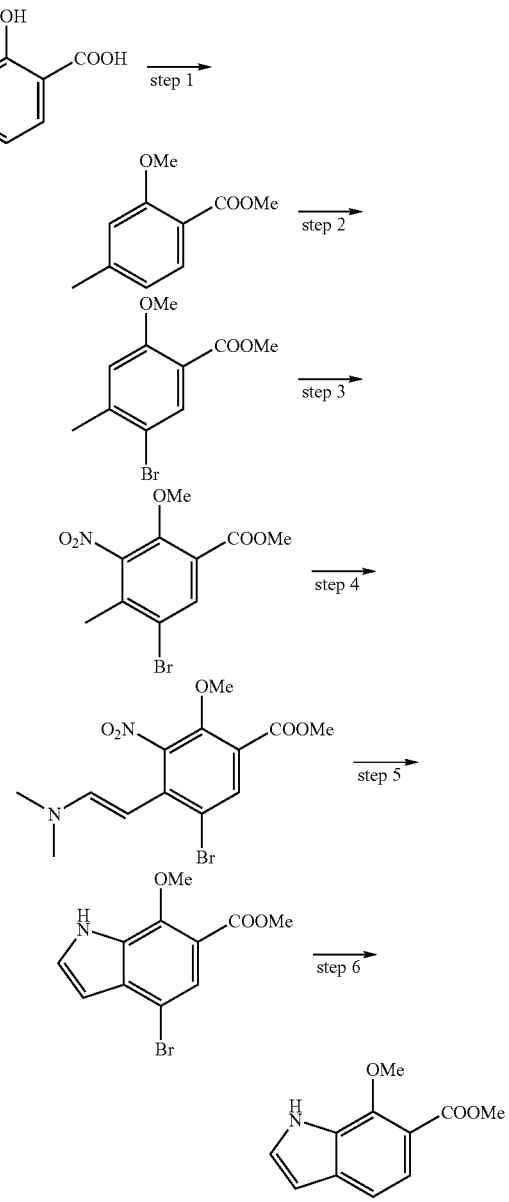

Step 1: 4-methylsalicylic acid (32.1 g, 0.21 mol) and potassium carbonate (61.2 g, 0.44 mol) were suspended in acetone (300 mL) and the mixture brought to reflux temperature. Dimethyl sulfate (66.5 g, 0.53 mol) was added dropwise within 1 h and stirring continued overnight at reflux. Additional dimethylsulfate (30 mL) and potassium carbonate (2×15 g) were added and refluxing for an additional 24 h was required to complete the reaction. The reaction mixture was then cooled to room temperature and inorganic salts removed by filtration using acetone for washings. The filtrate was evaporated under reduced pressure and the oily residue was dissolved in MeOH (300 mL). Concentrated ammonium hydroxide (90 mL) was added and the mixture was stirred for 30 minutes at room temperature. Methanol was removed in vacuo and the residue portioned between ether (300 mL) and water (200 mL). The organic phase was separated and washed with brine and dried (Na$_2$SO$_4$). Evaporation of the ether gave the desired di-methylated product as a yellow oil (38.1 g) that was used directly in the next step.

Step 2: The ester from above (38.0 g, 0.21 mol) was dissolved in AcOH (250 mL) and bromine (37.2 g, 0.23 mol, 1.1 equiv.) was added dropwise over 30 min with stirring at room temperature. After completion, the reaction mixture was stirred for an additional hour, at which point TLC analysis indicated complete conversion. The reaction mixture was poured into water (1 L) and solid Na$_2$CO$_3$ was added cautiously with stirring until the mixture was neutral. The off-white precipitate that formed was collected by filtration, washed with water and dried to give the desired bromo derivative (47.2 g).

Step 3: The bromo derivative from above (44.5 g, 0.17 mol) was added in small portions to conc. H$_2$SO$_4$ (170 mL) and the mixture was stirred in an ice-salt bath until all solids dissolved. Conc. HNO$_3$ (17 mL) was then added dropwise over 20 min and stirring continued for an additional hour in the ice bath. The reaction mixture was then slowly added to ice-water (2 L) and the precipitated yellow solid was collected by filtration. The solid was washed with water, NaHCO$_3$ solution and water again. After drying, the desired nitro derivative was obtained as an orange solid (36.8 g).

Step 4: The product from above (129.0 g, 0.42 mol) was dissolved in DMF (400 mL) and DMF-dimethyl acetal (151.6 g, 1.27 mol. 3 equiv.) was added in one portion. The mixture was heated at 110-120° C. under an argon atmosphere until conversion was judged complete by TLC (24 h). The reaction mixture was cooled to room temperature and volatiles removed under vacuum to give a dark colored residue (~180 g). Trituration from ether-THF gave the desired enamine as red crystals (72 g).

Step 5: The enamine from above (72.0 g, 0.20 mol) was dissolved in a mixture of THF (600 mL) and MeOH (600 mL). The dark red solution was heated to 30° C. and Raney-Nickel (18 g) was added to the solution. Hydrazine hydrate (11.6 g, 0.23 mol, 1.15 equiv.) was then added dropwise over 30 min. The reaction temperature was increased to 50° C. and a second portion of hydrazine hydrate (11.6 g, 0.23 mol, 1.15 equiv.) was added over 30 min. After stirring overnight at 50° C., additional Raney-nickel (20 g) and hydrazine hydrate (11.6 g, 0.23 mol, 1.15 equiv.) were added and after stirring for another 7 h at 50° C., the reaction was judged complete by TLC. After cooling, the catalyst was removed by filtration through a pad of celite and the filtrate was evaporated under reduced pressure. The dark brown residue was dissolved in EtOAc (3 L) and the solution washed with water (1.5 L), 10% HCl (1 L) and brine (700 mL). After drying (Na$_2$SO$_4$), removal of solvents gave the desired bromoindole derivative as a brown solid (35 g).

Step 6: The bromoindole derivative from above (35 g) was dissolved in MeOH (1 L) and triethylamine (16.3 g, 1.2 equiv.) was added followed by 10% Pd/C (1.06 g). The mixture was stirred under hydrogen (35 psi) until completion of the reaction (7 h). The catalyst was then removed by filtration and volatiles removed under reduced pressure. The residue was dissolved in EtOAc (700 mL) and the solution washed with 10% HCl (300 mL), water (350 mL), NaHCO$_3$ (350 mL) and brine. The solution was dried (Na$_2$SO$_4$) and concentrated under reduced pressure to give the desired indole as a light brown solid (25 g).

This indole derivatives was saponified under standard conditions and elaborated to final inhibitors as previously described for analogous derivatives.

Example 45

2-(1-Amino-cyclobutyl)-6-methoxy-3-methyl-3H-benzimidazole-5-carboxylic acid methyl ester

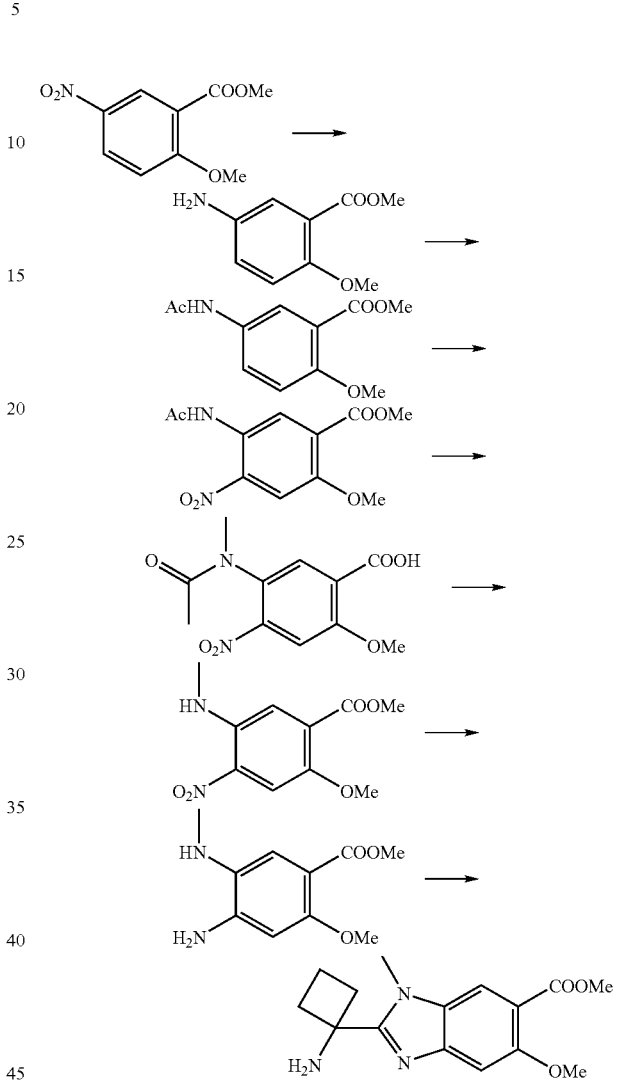

Methyl 2-methoxy-5-nitrobenzoate (6.21 g, 29.4 mmol) was suspended in MeOH (100 mL) and 20% Pd(OH)$_2$/C (500 mg) was added. The mixture was stirred under a hydrogen atmosphere (1 atm) for 18 h. The catalyst was removed by filtration and the solvent evaporated under reduced pressure (5.256 g).

The aniline from above (5.23 g) was dissolved in THF (50 mL) and acetic anhydride (2.984 g) was added. The mixture was stirred overnight at room temperature. The white suspension was concentrated under reduced pressure to a white paste, tert-butylmethyl ether (TBME, 20 mL) was added and while stirring, hexane (100 mL) was added slowly. The suspension was then stirred for an additional 2 h and the solid collected by filtration. The product was washed with hexane and dried in air (6.372 g).

90% Nitric acid (9 mL) was diluted with water (9 mL) and cooled to 0° C. The anilide from above (5.905 g) was added in one portion and the mixture stirred for 30 min in the ice-water bath. The reaction mixture was then added dropwise to ice-water (700 mL) and the precipitated yellow solid was collected by filtration, washed with water and dried in air. The orange solid (5.907 g) was shown by $^1$H NMR to consist of a 2:1 mixture of compounds. Extraction of the aqueous filtrate from above with EtOAc gave an additional 1 g of material that was combined with the first crop and purified by flash chromatography on silica gel using 015% EtOAc in CHCl$_3$ as eluent. An orange solid (4.11 g) was obtained (one isomer). The nitroanilide from above (3.580 g) was dissolved in THF (50 mL) and the solution cooled in ice. Iodomethane (4.155 mL, 66.7 mmol, 5 equivalents) and sodium tert-butoxide (6.414 g, 66.7 mmol, 5 equivalents) were added in two portions at a 3.5 h interval. Stirring at room temperature was continued for an additional 20 h after the second addition. THF was evaporated under reduced pressure and water (100 mL) was added. The deep red solution was washed with TBME (100 mL). The aqueous phase was acidified with conc. HCl and extracted with EtOAc (2×100 mL). The combined organic extracts were dried and concentrated to a dark red powder (3.78 g) that was used directly in the next step.

The free carboxylic acid (3.75 g) was suspended in 8M HCl (100 mL) and the mixture stirred at 100° C. for 8 h. After cooling to room temperature, volatiles were evaporated under vacuum and the residue was co-evaporated 3 times with MeOH. The residue was suspended again in MeoH (100 mL) and cooled in ice-water. Thionyl chloride (5.10 mL, 5 equivalents) was added dropwise and the suspension stirred at 65° C. for 4 h. Volatiles were removed under reduced pressure and the residue co-evaporated twice with MeOH (100 mL) and then toluene (2×100 mL). The residue was then dissolved in MeOH (200 mL), 20% Pd(OH)$_2$/C (500 mg) was added and the mixture stirred overnight under 1 atm of hydrogen gas. The catalyst was then removed by filtration and the solution evaporated to dryness. The residue was dissolved in EtOAc and the solution washed with aqueous NaHCO$_3$ and dried (MgSO$_4$). Removal of solvents gave a solid that was suspended in TBME (50 mL) and heated to 60° C. for 30 min. An equal volume of hexane was then slowly added to the hot solution and the precipitated material was collected by filtration, washed with TBME-hexane and dried (2.00 g).

The diamine from above (1.950 g) was dissolved in DCM (50 mL) and the solution cooled in ice. 1-Aminocyclobutyryl chloride hydrochloride prepared using a similar procedure as in example 20 (1.50 g) was added in 3 portions over a 1.5 h period. The mixture was then warmed to room temperature and stirred overnight. Additional acid chloride (0.50 g) was added and stirring continued for another 2 h. DCM was evaporated under reduced pressure and AcOH (30 mL) was added and the mixture heated to 80° C. for 3 h. The reaction mixture was cooled to room temperature and volatiles evaporated under reduced pressure. The residue was dissolved in water (100 mL) and solid NaHCO$_3$ was added in portions until a pH of 8 was reached. The product was then extracted with EtOAc (3×100 mL), dried (Na$_2$SO$_4$) and concentrated to dryness. The residue was purified by flash chromatography on silica gel using 0 to 15% EtOH in EtOAc as eluent. The title compound of example 45 was obtained as a grey powder (1.05 g).

Example 46

Inhibition of NS5B RNA Dependent RNA Polymerase Activity

The compounds of the invention were tested for inhibitory activity against the hepatitis C virus RNA dependant polymerase (NS5B), according to protocol described in WO 03/010141

Example 47

Specificity of NS5B RNA Dependent RNA Polymerase Inhibition

The compounds of the invention were tested for inhibitory activity against polio virus RNA dependent RNA polymerase and calf thymus DNA dependent RNA polymerase II in the format that is described for the HCV polymerase with the exception that another polymerase was used in place of the HCV NS5B polymerase as is described in WO 03/010141

In Tables 1 to 8 below, the following ranges apply:

IC$_{50}$: A=10 µM–1 µM; B=1 µM–200 nM; and C<200 nM.

TABLE 1

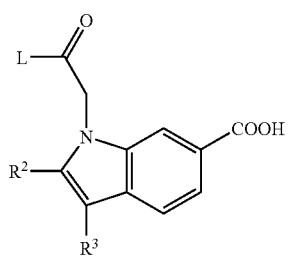

wherein R$^3$ is C$_n$-cycloalkyl and the index n is given in the table:

| Cpd. # | R$^2$ | n | L | IC$_{50}$ | m/z (M + H)$^+$ |
|---|---|---|---|---|---|
| 1001 | (furan) | 6 | (t-butyl) | B | 408.3 |

TABLE 1-continued
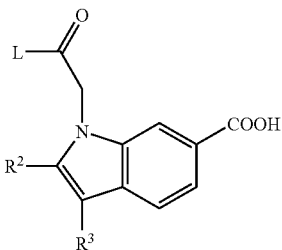
wherein R³ is C_n-cycloalkyl and the index n is given in the table:
| Cpd. # | R² | n | L | IC$_{50}$ | m/z (M + H)⁺ |
|---|---|---|---|---|---|
| 1002 | 3-furyl | 6 | -NH-S(O)₂-phenyl | C | 561.2 |
| 1003 | 3-furyl | 6 | 4-methyl-1,4-diazepan-1-yl | C | 464.3 |
| 1004 | 3-furyl | 6 | -N(CH₃)-CH₂CH₂-(4-pyridyl) | C | 486.2 |
| 1005 | 3-furyl | 6 | -N(Et)-CH₂-(4-pyridyl) | B | 486.3 |
| 1006 | 3-furyl | 6 | -N(CH₃)-CH₂CH(CH₃)₂ | B | 437.2 |
| 1007 | 3-furyl | 6 | -N(Et)-CH₂CH₂-N(Et)₂ | C | 494.3 |
| 1008 | 3-furyl | 6 | -N(CH₃)-CH₂CH₂CH₃ | C | 423.2 |

TABLE 1-continued
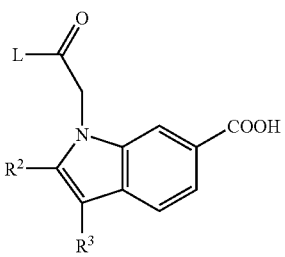
wherein R³ is C_n-cycloalkyl and the index n is given in the table:
| Cpd. # | R² | n | L | IC₅₀ | m/z (M + H)⁺ |
|---|---|---|---|---|---|
| 1009 | 3-furyl | 6 | -NH-CH₂CH₂CH₂-morpholine | B | 494.3 |
| 1010 | 3-furyl | 6 | 4-piperidinopiperidine | C | 518.3 |
| 1011 | 3-furyl | 6 | -N(n-Pr)₂ | B | 451.3 |
| 1012 | 3-furyl | 6 | thiomorpholine | C | 453.2 |
| 1013 | 3-furyl | 6 | -NH-SO₂-CH₃ | B | 445.2 |
| 1014 | 2-furyl | 6 | -N(CH₂CH₂OCH₃)₂ | B | 483.2 |
| 1015 | 3-furyl | 6 | -N(n-Pr)(CH₂CH₂OCH₃) | B | 467.3 |
| 1016 | 3-furyl | 6 | 3-(diethylamino)pyrrolidine | C | 492.3 |

TABLE 1-continued
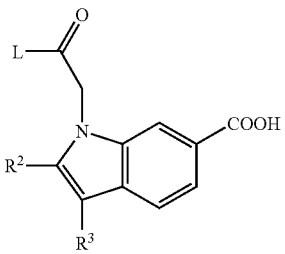
wherein R³ is $C_n$-cycloalkyl and the index n is given in the table:
| Cpd. # | R² | n | L | IC$_{50}$ | m/z (M + H)$^+$ |
|---|---|---|---|---|---|
| 1017 | 3-furyl | 6 | methoxyethyl-ethyl-amino | C | 453.2 |
| 1018 | 3-furyl | 6 | decahydroisoquinolinyl | A | 489.3 |
| 1019 | 3-furyl | 6 | N-methyl-N'-(3-dimethylaminopropyl) | C | 466.3 |
| 1020 | 3-furyl | 6 | 2,6-dimethylmorpholinyl | C | 465.2 |
| 1021 | 3-furyl | 6 | N-methyl-N-(2-diethylaminoethyl) | C | 480.3 |
| 1022 | 3-furyl | 6 | N-ethyl-N-(2-dimethylaminoethyl) | B | 466.2 |
| 1023 | phenyl | 6 | morpholinyl | C | 447.3 |

TABLE 1-continued
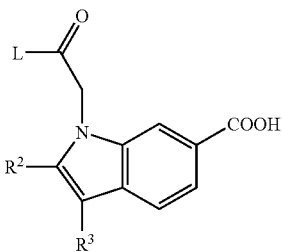
wherein R³ is C_n-cycloalkyl and the index n is given in the table:
| Cpd. # | R² | n | L | IC$_{50}$ | m/z (M + H)$^+$ |
|---|---|---|---|---|---|
| 1024 | phenyl | 6 | pyrrolidinyl-piperidinyl | C | 514.4 |
| 1025 | phenyl | 6 | N,N-dimethylamino | C | 405.3 |
| 1026 | phenyl | 6 | isopropylamino | B | 419.3 |
| 1027 | 3-thienyl | 6 | morpholino | C | 453.2 |
| 1028 | 3-thienyl | 6 | N,N-dimethylamino | C | 411.2 |
| 1029 | 3-thienyl | 6 | isopropylamino | B | 447.2 |
| 1030 | 2-furyl | 6 | morpholino | C | 437.3 |

TABLE 1-continued
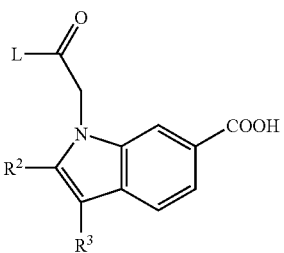
wherein R³ is Cₙ-cycloalkyl and the index n is given in the table:
| Cpd. # | R² | n | L | IC$_{50}$ | m/z (M + H)⁺ |
|---|---|---|---|---|---|
| 1031 | 2-furyl | 6 | N,N-dimethylaminomethyl | C | 395.2 |
| 1032 | 2-furyl | 6 | isopropylaminomethyl | B | 409.3 |
| 1033 | 2-thienyl | 6 | morpholinomethyl | C | 453.2 |
| 1034 | 2-thienyl | 6 | 4-(pyrrolidin-1-yl)piperidin-1-ylmethyl | C | 520.3 |
| 1035 | 2-thienyl | 6 | N,N-dimethylaminomethyl | C | 411.2 |
| 1036 | 2-thienyl | 6 | isopropylaminomethyl | B | 425.2 |
| 1037 | 3-thienyl | 6 | 4-(pyrrolidin-1-yl)piperidin-1-ylmethyl | C | 520.3 |

TABLE 1-continued
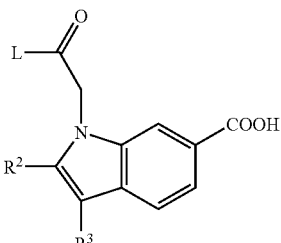
wherein R³ is C$_n$-cycloalkyl and the index n is given in the table:
| Cpd. # | R² | n | L | IC$_{50}$ | m/z (M + H)⁺ |
|---|---|---|---|---|---|
| 1038 | 2-furyl | 6 | pyrrolidinyl-piperidinyl | C | 504.3 |
| 1039 | 1-methylpyrrol-2-yl | 6 | N,N-dimethylamino | B | 408.2 |
| 1040 | 2-(piperidin-1-yl)thiazol-4-yl | 6 | morpholinyl | B | 537.2 |
| 1041 | 2-(tert-butylamino)thiazol-4-yl | 6 | morpholinyl | B | 525.2 |
| 1042 | benzothiophen-2-yl | 6 | morpholinyl | B | 503.2 |
| 1043 | 3-furyl | 5 | morpholinyl | C | 423.2 |

TABLE 1-continued
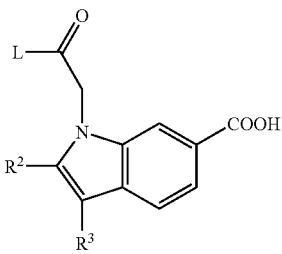
wherein R³ is C$_n$-cycloalkyl and the index n is given in the table:
| Cpd. # | R² | n | L | IC$_{50}$ | m/z (M + H)$^+$ |
|---|---|---|---|---|---|
| 1044 | 3-furyl | 5 | N,N-dimethylaminomethyl | C | 381.1 |
| 1045 | pyrazinyl | 6 | 4-(pyrrolidin-1-yl)piperidin-1-yl-methyl | C | 516.3 |
| 1046 | benzothiophen-2-yl | 6 | N,N-dimethylaminomethyl | A | 461.2 |
| 1047 | benzothiophen-3-yl | 6 | morpholin-4-yl-methyl | A | 503.3 |
| 1048 | benzothiophen-3-yl | 6 | 4-(pyrrolidin-1-yl)piperidin-1-yl-methyl | B | 570.3 |

TABLE 1-continued wherein R³ is C$_n$-cycloalkyl and the index n is given in the table:

| Cpd. # | R² | n | L | IC$_{50}$ | m/z (M + H)$^+$ |
|---|---|---|---|---|---|
| 1049 | benzothiophen-2-yl | 6 | pyrrolidin-1-yl-piperidin-1-yl | B | 570.3 |
| 1050 | 6-amino-pyridin-2-yl | 6 | pyrrolidin-1-yl-piperidin-1-yl | C | 530.3 |
| 1051 | furan-3-yl | 6 | 2-amino-2-methyl-propanamido-phenyl-acrylic acid | C | 598.3 |
| 1052 | furan-3-yl | 6 | 2-amino-2-methyl-propanamido-phenyl-thiazole-COOH | C | 655.3 |
| 1053 | furan-3-yl | 6 | 2-amino-2-methyl-propanamido-phenyl-furan-COOH | C | M-H 636.3 |
| 1054 | furan-3-yl | 6 | 2-amino-2-methyl-propanamido-(1-methyl-indole-2-COOH) | C | 625.3 |

TABLE 1-continued
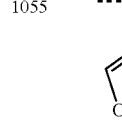
wherein R³ is C_n-cycloalkyl and the index n is given in the table:
| Cpd. # | R² | n | L | IC$_{50}$ | m/z (M + H)$^+$ |
|---|---|---|---|---|---|
| 1055 | 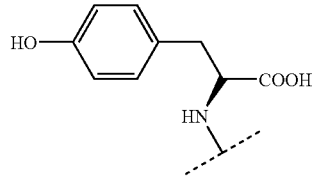 | 6 | 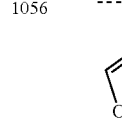 | C | 531.2 |
| 1056 | 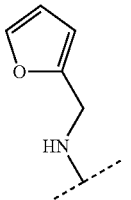 | 6 | 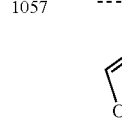 | B | 447.2 |
| 1057 | 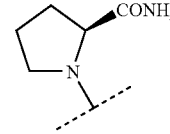 | 6 | 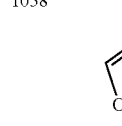 | C | 464.2 |
| 1058 | 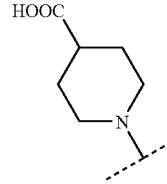 | 6 | 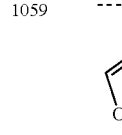 | C | 479.2 |
| 1059 | 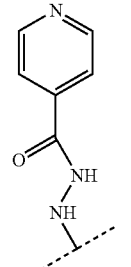 | 6 | 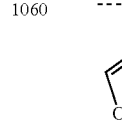 | C | 487.2 |
| 1060 | 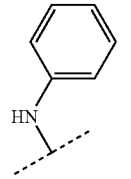 | 6 | | B | 443.2 |

TABLE 1-continued
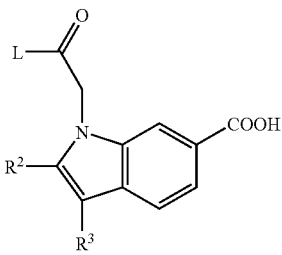
wherein R³ is $C_n$-cycloalkyl and the index n is given in the table:
| Cpd. # | R² | n | L | IC₅₀ | m/z (M + H)⁺ |
|---|---|---|---|---|---|
| 1061 | 3-furyl | 6 | 4-(COOH)phenyl-NH- | B | 487.2 |
| 1062 | 3-furyl | 6 | CH₃-NH- | B | 381.2 |
| 1063 | 3-furyl | 6 | benzyl-NH- | B | 457.2 |
| 1064 | 3-furyl | 6 | 4-methoxybenzyl-NH- | A | 487.3 |
| 1065 | 3-furyl | 6 | H₂N- | B | 367.2 |
| 1066 | 3-furyl | 6 | (S)-prolyl | C | 465.2 |
| 1067 | 3-furyl | 6 | HOOC-CH₂-NH- | C | 425.2 |

TABLE 1-continued
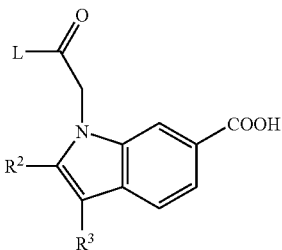
wherein R³ is C_n-cycloalkyl and the index n is given in the table:
| Cpd. # | R² | n | L | IC$_{50}$ | m/z (M + H)$^+$ |
|---|---|---|---|---|---|
| 1068 | 3-furyl | 6 | HOOC-CH₂-NH-NH- | C | 440.2 |
| 1069 | 3-furyl | 6 | 4-(SO₂NH₂)-benzyl-NH- | B | 536.2 |
| 1070 | 3-furyl | 6 | 3-(COOH)-phenyl-NH- | B | 487.2 |
| 1071 | 3-furyl | 6 | 4-(CH=CH-COOH)-phenyl-NH- | B | 513.2 |
| 1072 | 3-furyl | 6 | HOOC-CH₂-N(CH₃)- | C | 439.2 |
| 1073 | 3-furyl | 6 | HOOC-CH₂-CH₂-NH- | C | 439.2 |

TABLE 1-continued
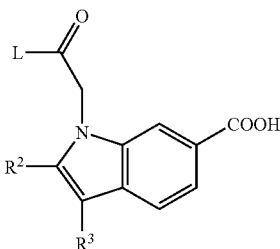
wherein R³ is C_n-cycloalkyl and the index n is given in the table:
| Cpd. # | R² | n | L | IC₅₀ | m/z (M + H)⁺ |
|---|---|---|---|---|---|
| 1074 | 3-furyl | 6 | HOOC-CH₂-piperazinyl | C | 494.3 |
| 1075 | 3-furyl | 6 | -NH-CH₂-C₆H₄-COOH | C | 501.2 |
| 1076 | 3-furyl | 6 | semicarbazide-CH₂-cyclohexyl-COOH (trans) | C | 565.3 |
| 1077 | 3-furyl | 6 | diaminopyrrolidine-C(O)NH-C₆H₄-CH=CH-COOH | C | 625.3 |
| 1078 | 3-furyl | 6 | α,α-dimethyl-aminoacyl-NH-C₆H₄-NO₂ | B | 573.3 |
| 1079 | 3-furyl | 6 | diaminopyrrolidine-C(O)NH-C₆H₄-CH=CH-COOH | C | 625.3 |

TABLE 1-continued
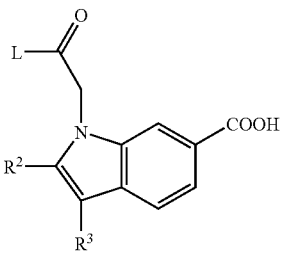
wherein R³ is C_n-cycloalkyl and the index n is given in the table:
| Cpd. # | R² | n | L | IC$_{50}$ | m/z (M + H)⁺ |
|---|---|---|---|---|---|
| 1080 | 3-furyl | 6 | piperidine-carboxamide-phenyl-acrylic acid | C | 639.3 |
| 1081 | 3-furyl | 6 | 5-hydroxytryptophan | C | 570.3 |
| 1082 | 2-pyridyl | 6 | 4-methylpiperazine | C | 461.4 |
| 1083 | 2-pyridyl | 6 | aminoisobutyramide-phenyl-acrylic acid | B | 609.4 |
| 1084 | 2-pyridyl | 6 | pyrrolidine | B | 432.3 |
| 1085 | 2-pyridyl | 6 | piperidine | B | 446.3 |

TABLE 1-continued
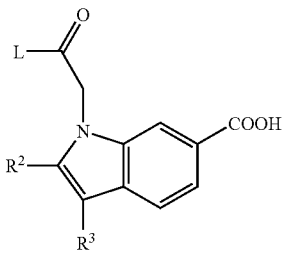
wherein R³ is C$_n$-cycloalkyl and the index n is given in the table:
| Cpd. # | R² | n | L | IC$_{50}$ | m/z (M + H)⁺ |
|---|---|---|---|---|---|
| 1086 | 2-pyridyl | 5 | pyrrolidinyl | B | 418.3 |
| 1087 | 2-pyridyl | 5 | piperidinyl | B | 432.3 |
| 1088 | 3-furyl | 6 | cyclohexyl-NH- | B | 449.3 |
| 1089 | 3-furyl | 6 | cyclohexyl-CH₂-NH- | B | 463.3 |
| 1090 | 3-furyl | 6 | -N(CH₃)CH₂CH₂OH | C | 425.3 |
| 1091 | 3-furyl | 6 | -N(iPr)(cyclohexyl) | B | 491.4 |
| 1092 | 3-furyl | 6 | -N(CH₃)(cyclohexyl) | C | 463.3 |

TABLE 1-continued
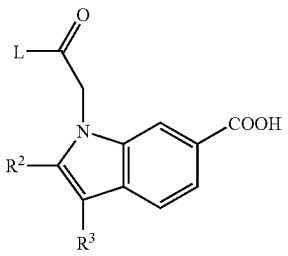
wherein R³ is C$_n$-cycloalkyl and the index n is given in the table:
| Cpd. # | R² | n | L | IC$_{50}$ | m/z (M + H)⁺ |
|---|---|---|---|---|---|
| 1093 | 3-furyl | 6 | N-ethyl-N-cyclohexyl | B | 477.4 |
| 1094 | 3-furyl | 6 | pyrrolidinyl | C | 421.3 |
| 1095 | 3-furyl | 6 | 4-phenylpiperazinyl | B | 512.3 |
| 1096 | 3-furyl | 6 | 4-(2-hydroxyethyl)piperazinyl | C | 480.3 |
| 1097 | 3-furyl | 6 | morpholinyl | C | 437.3 |
| 1098 | 3-furyl | 6 | piperidinyl | C | 435.3 |

TABLE 1-continued
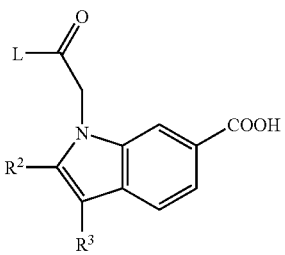
wherein R³ is C$_n$-cycloalkyl and the index n is given in the table:
| Cpd. # | R² | n | L | IC$_{50}$ | m/z (M + H)$^+$ |
|---|---|---|---|---|---|
| 1099 | 3-furyl | 6 | piperidin-3-yl-COOH | C | 479.3 |
| 1100 | 3-furyl | 6 | 4-hydroxypiperidin-1-yl | C | 451.3 |
| 1101 | 3-furyl | 6 | 4-methylpiperidin-1-yl | B | 449.3 |
| 1102 | 3-furyl | 6 | 4-(2-hydroxyethyl)piperidin-1-yl | C | 479.4 |
| 1103 | 3-furyl | 6 | N-methyl-N-(2-(pyridin-2-yl)ethyl)amino | C | 486.3 |
| 1104 | 3-furyl | 6 | N-methyl-N-(1-methylpiperidin-4-yl)amino | C | 478.4 |

TABLE 1-continued
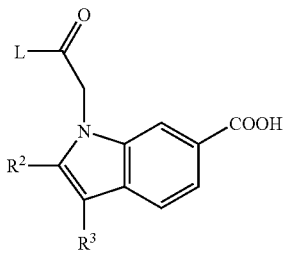
wherein R³ is C$_n$-cycloalkyl and the index n is given in the table:
| Cpd. # | R² | n | L | IC$_{50}$ | m/z (M + H)⁺ |
|---|---|---|---|---|---|
| 1105 | 3-furyl | 6 | 4-(dimethylamino)phenylamino | B | 486.3 |
| 1106 | 3-furyl | 6 | isopropylamino | B | 409.3 |
| 1107 | 3-furyl | 6 | 2-methoxyethylamino | B | 425.3 |
| 1108 | 3-furyl | 6 | diisopropylamino | B | 451.4 |
| 1109 | 3-furyl | 6 | N-benzyl-N-(carboxymethyl)amino | B | 515.3 |
| 1110 | 3-furyl | 6 | acetylhydrazino | C | 424.3 |
| 1111 | 3-furyl | 6 | dimethylamino | C | 395.3 |

TABLE 1-continued
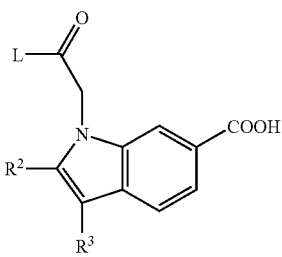
wherein R³ is Cₙ-cycloalkyl and the index n is given in the table:
| Cpd. # | R² | n | L | IC₅₀ | m/z (M + H)⁺ |
|---|---|---|---|---|---|
| 1112 | 3-furyl | 6 | -N(CH₃)CH₂CH₂N(CH₃)₂ | C | 452.4 |
| 1113 | 3-furyl | 6 | -NH-CH₂-(tetrahydrofuran-2-yl) | B | 451.3 |
| 1114 | 3-furyl | 6 | -N(CH₃)-CH₂-(pyridin-3-yl) | B | 472.3 |
| 1115 | 3-furyl | 6 | -N(CH₃)-(2-methylphenyl) | A | 471.3 |
| 1116 | 3-furyl | 6 | 4-(pyrrolidin-1-yl)piperidin-1-yl | C | 504.4 |
| 1117 | 3-furyl | 6 | -NH-NH-C(O)-CH₂-phenyl | B | 500.3 |

TABLE 1-continued

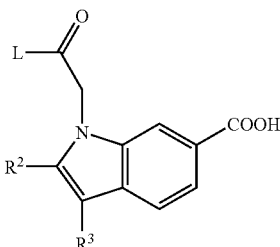

wherein R³ is C_n-cycloalkyl and the index n is given in the table:

| Cpd. # | R² | n | L | IC$_{50}$ | m/z (M + H)$^+$ |
|---|---|---|---|---|---|
| 1118 | furan-3-yl | 6 | N-methyl-N-isopropylamino | C | 423.3 |
| 1119 | furan-3-yl | 6 | 2-(methylamino)butanoic acid | C | 453.3 |
| 1120 | furan-3-yl | 6 | 4-ethylpiperazin-1-yl | C | 464.4 |
| 1121 | furan-3-yl | 6 | N-methyl-N-(2-(dimethylamino)-2-oxoethyl)amino | C | 466.3 |
| 1122 | furan-3-yl | 6 | (S)-2-(dimethylcarbamoyl)pyrrolidin-1-yl | C | 492.4 |
| 1123 | furan-3-yl | 6 | (S)-2-carboxypyrrolidin-1-yl | B | 465.3 |
| 1124 | furan-3-yl | 6 | N-methyl-N-(2-methoxyethyl)amino | B | 439.3 |

TABLE 1-continued
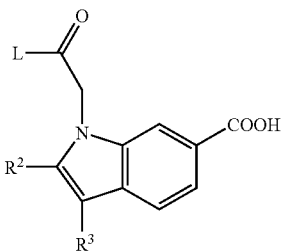
wherein R³ is C$_n$-cycloalkyl and the index n is given in the table:
| Cpd. # | R² | n | L | IC$_{50}$ | m/z (M + H)$^+$ |
|---|---|---|---|---|---|
| 1125 | furan-3-yl | 6 | 1-isopropylpiperazinyl | C | 478.4 |
| 1126 | furan-3-yl | 6 | 4-(2-methoxyethyl)piperazinyl | C | 494.4 |
| 1127 | furan-3-yl | 6 | 4-(methylsulfonyl)benzylamino | C | 535.3 |
| 1128 | furan-3-yl | 6 | 4-hydroxyproline | C | 481.3 |
| 1129 | furan-3-yl | 6 | N-methyl-valine | C | 481.3 |

TABLE 1-continued
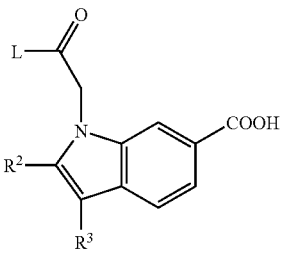
wherein R³ is C_n-cycloalkyl and the index n is given in the table:
| Cpd. # | R² | n | L | IC$_{50}$ | m/z (M + H)⁺ |
|---|---|---|---|---|---|
| 1130 | 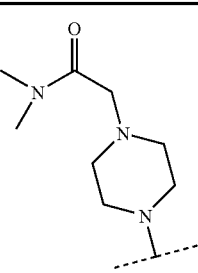 | 6 | 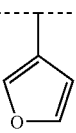 | C | 521.4 |
| 1131 | 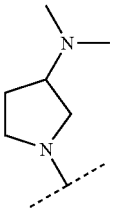 | 6 | 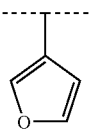 | C | 464.4 |
| 1132 | 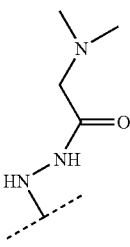 | 6 | 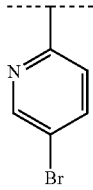 | C | 467.3 |
| 1133 | 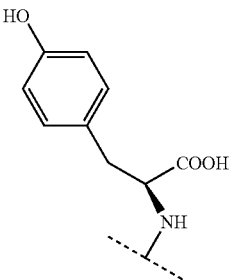 | 6 | 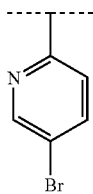 | B | 620.2 |
| 1134 | 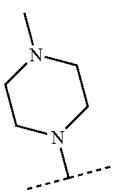 | 6 | | B | 539.3 |

TABLE 1-continued
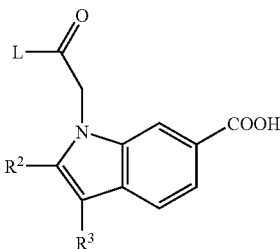
wherein R³ is C_n-cycloalkyl and the index n is given in the table:
| Cpd. # | R² | n | L | IC₅₀ | m/z (M + H)⁺ |
|---|---|---|---|---|---|
| 1135 | 5-Br-pyridin-2-yl | 6 | 1-(piperidin-4-yl-COOH) | B | 568.3 |
| 1136 | 5-Br-pyridin-2-yl | 6 | N,N-dimethylaminomethyl | B | 484.3 |
| 1137 | 5-Br-pyridin-2-yl | 6 | (S)-prolinyl | B | 554.3 |
| 1138 | 5-Br-pyridin-2-yl | 6 | N-methyl-N-(carboxymethyl)amino | B | 528.3 |
| 1139 | 5-Br-pyridin-2-yl | 6 | 4-(carboxymethyl)piperazin-1-yl | C | 583.3 |
| 1140 | 5-Br-pyridin-2-yl | 6 | 6-hydroxy-tryptophanyl | B | 659.3 |

TABLE 1-continued
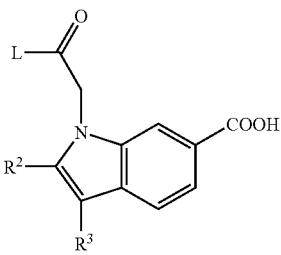
wherein R³ is C_n-cycloalkyl and the index n is given in the table:
| Cpd. # | R² | n | L | IC_{50} | m/z (M + H)⁺ |
|---|---|---|---|---|---|
| 1141 | 5-bromopyridin-2-yl | 6 | trans-4-(HOOC)cyclohexylmethyl-NH-C(O)-NH-NH- | B | 654.3 |
| 1142 | pyridin-2-yl | 6 | (CH₃)₂N-CH< | B | 406.3 |
| 1143 | pyridin-2-yl | 6 | CH₃-NH-CH< | A | 392.2 |
| 1144 | furan-3-yl | 5 | hexahydropyridazin-1-yl | | |
| 1145 | furan-3-yl | 5 | CH₃-NH-N(CH₃)- | | |
| 1146 | furan-3-yl | 5 | CH₃-C(O)-NH-N(CH₃)- | | |
| 1147 | pyrimidin-2-yl | 6 | morpholin-4-yl | | |

TABLE 1-continued
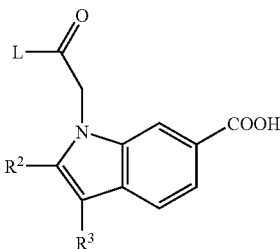
wherein R³ is C_n-cycloalkyl and the index n is given in the table:
| Cpd. # | R² | n | L | IC$_{50}$ | m/z (M + H)$^+$ |
|---|---|---|---|---|---|
| 1148 | pyrazinyl | 6 | N,N-dimethylamino | | |
| 1149 | 6-aminopyridin-2-yl | | morpholino | | |
| 1150 | 6-aminopyridin-2-yl | | N,N-dimethylamino | | |
TABLE 2
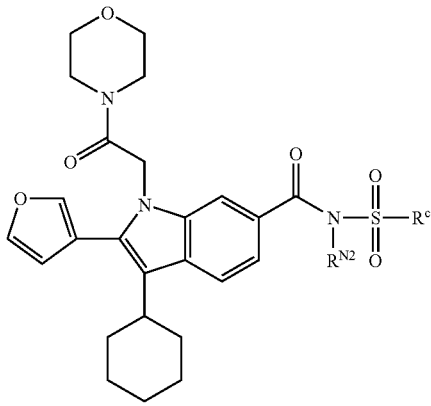
| Cpd. # | R$^{N2}$ | R$^C$ | IC$_{50}$ | m/z (M + H)$^+$ |
|---|---|---|---|---|
| 2001 | H | phenyl | C | 576.3 |
| 2002 | H | CH$_3$ | C | 514.3 |
TABLE 2-continued
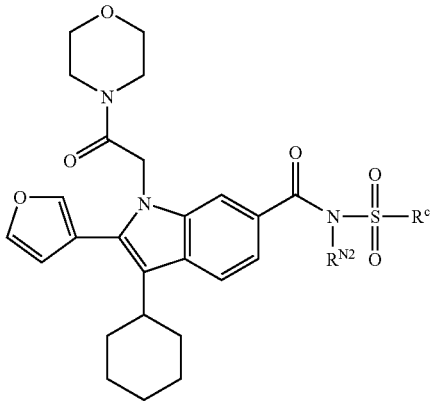
| Cpd. # | R$^{N2}$ | R$^C$ | IC$_{50}$ | m/z (M + H)$^+$ |
|---|---|---|---|---|
| 2003 | H | benzyl | C | 590.3 |

TABLE 2-continued
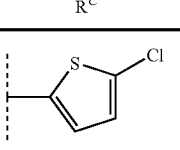
| Cpd. # | R$^{N2}$ | R$^C$ | IC$_{50}$ | m/z (M + H)$^+$ |
|---|---|---|---|---|
| 2004 | H | 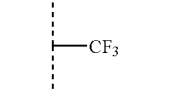 | C | 616.2 |
| 2005 | H | —CF$_3$ | C | 568.2 |
| 2006 | H | 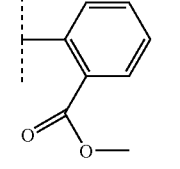 | C | 634.3 |
| 2007 | H | 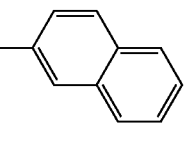 | C | 626.3 |
| 2008 | H | 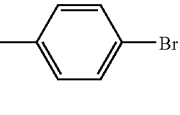 | C | 656.2 |
| 2009 | H | 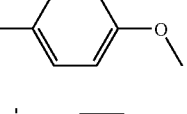 | C | 606.3 |
| 2010 | H | 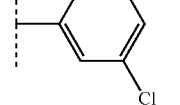 | C | 610.2 |
| 2011 | H | 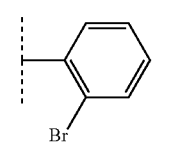 | C | 656.2 |
TABLE 2-continued
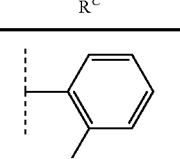
| Cpd. # | R$^{N2}$ | R$^C$ | IC$_{50}$ | m/z (M + H)$^+$ |
|---|---|---|---|---|
| 2012 | H | 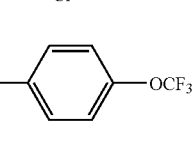 | C | 610.2 |
| 2013 | H | 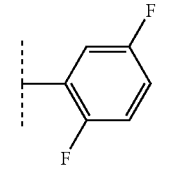 | C | 660.3 |
| 2014 | H | 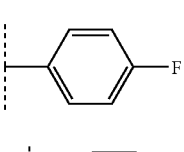 | C | 612.3 |
| 2015 | H | 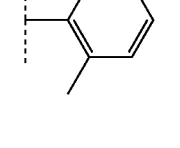 | C | 594.3 |
| 2016 | H | 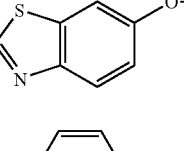 | C | 590.3 |
| 2017 | H | 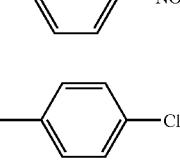 | C | 677.3 |
| 2018 | H |  | C | 621.3 |
| 2019 | H |  | C | 610.2 |

TABLE 2-continued

| Cpd. # | $R^{N2}$ | $R^C$ | IC$_{50}$ | m/z (M + H)$^+$ |
|---|---|---|---|---|
| 2020 | H | 2,3-dimethyl-5-fluorobenzothiophene | C | 664.3 |
| 2021 | H | 4-acetamidophenyl | C | 655.3 |
| 2022 | H | 4-methylphenyl | C | 590.3 |
| 2023 | CH$_3$ | phenyl | A | 590.3 |
| 2024 | H | 8-quinolinyl | C | 627.3 |
| 2025 | H | 4-tert-butylphenyl | C | 632.3 |
| 2026 | H | cyclopropyl | C | 540.2 |
| 2027 | H | CH$_2$CF$_3$ | C | 582.2 |
| 2028 | H | 2,5-dimethoxyphenyl | C | 636.3 |
| 2029 | H | 3-bromo-2,5-dichlorothiophene | C | 728.0 |
| 2030 | H | 2,5-dichlorothiophene | C | 650.1 |
| 2031 | H | 2,6-dichlorophenyl | C | 644.2 |
| 2032 | H | 2-cyanophenyl | B | 601.2 |
| 2033 | H | 5-chloro-1,3-dimethylpyrazol-4-yl | C | 628.2 |

TABLE 2-continued
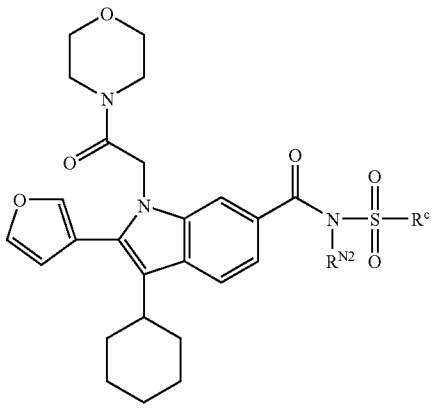
| Cpd. # | R^N2 | R^C | IC50 | m/z (M + H)+ |
|---|---|---|---|---|
| 2034 | H | 3,5-dimethylisoxazol-4-yl | C | 595.3 |
| 2035 | H | benzo[1,2,5]thiadiazol-4-yl | C | 634.2 |
| 2036 | H | 2,6-difluorophenyl | C | 612.2 |
| 2037 | H | 6-chloroimidazo[2,1-b]thiazol-5-yl | C | 656.2 |
| 2038 | H | 2-(methylsulfonyl)phenyl | C | 654.3 |
| 2039 | H | isoquinolin-5-yl | C | 627.3 |
TABLE 2-continued
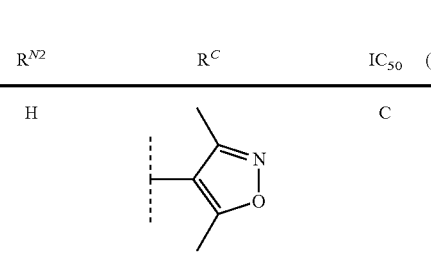
| Cpd. # | R^N2 | R^C | IC50 | m/z (M + H)+ |
|---|---|---|---|---|
| 2040 | H | 2-methoxy-5-methylphenyl | C | 620.3 |
| 2041 | H | 1,3,5-trimethyl-1H-pyrazol-4-yl | C | 608.3 |
| 2042 | H | 5-methyl-1-phenyl-1H-pyrazol-4-yl | C | 656.3 |
| 2043 | H | 2,4,6-triisopropylphenyl | B | 702.4 |
| 2044 | H | mesityl | C | 618.3 |
| 2045 | H | CCl3 | C | 616.1 |

TABLE 3
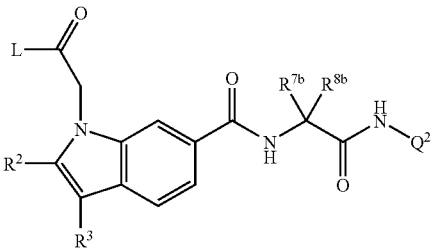
wherein R³ is C$_n$-cycloalkyl and the index n is given in the table:
| Cpd. # | R² | n | L | R⁷ᵇ R⁸ᵇ | Q² | IC$_{50}$ | m/z (M + H)⁺ |
|---|---|---|---|---|---|---|---|
| 3001 | 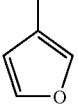 | 5 | 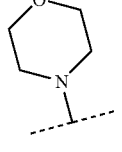 | 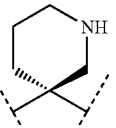 | 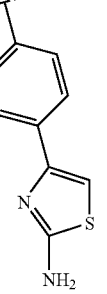 | C | 722.3 |
| 3002 | 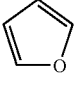 | 6 | 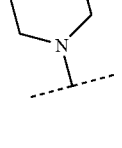 |  | 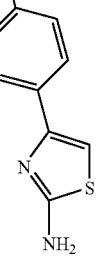 | C | 736.4 |
| 3003 | 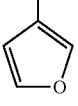 | 6 | 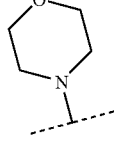 |  | 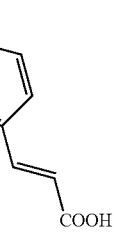 | C | 677.4 |
| 3004 | 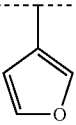 | 6 | 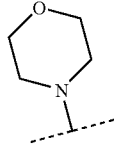 | 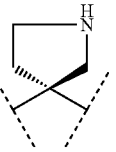 |  | C | 548.3 |

TABLE 3-continued
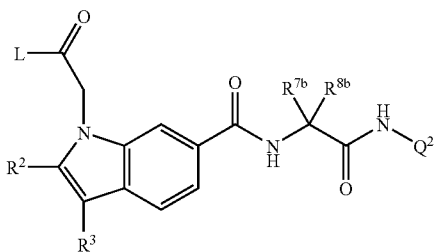
wherein R³ is C$_n$-cycloalkyl and the index n is given in the table:
| Cpd. # | R² | n | L | R⁷ᵇ R⁸ᵇ | Q² | IC$_{50}$ | m/z (M + H)⁺ |
|---|---|---|---|---|---|---|---|
| 3005 | 3-furyl | 6 | COOH-cinnamoyl-NH-C(CH₃)₂-NH- | gem-dimethyl | 4-(COOH-vinyl)phenyl | C | 828.4 |
| 3006 | 2-pyridyl | 6 | N-methylpiperazinyl | gem-dimethyl | 4-(COOH-vinyl)phenyl | C | 691.5 |
| 3007 | 2-pyridyl | 6 | N-methylpiperazinyl | cyclobutyl | 4-(COOH-vinyl)phenyl | C | 703.5 |
| 3008 | 2-pyridyl | 6 | pyrrolidinyl | cyclobutyl | 4-(COOH-vinyl)phenyl | C | 674.4 |

TABLE 3-continued
wherein R³ is C$_n$-cycloalkyl and the index n is given in the table:
| Cpd. # | R² | n | L | R⁷ᵇ R⁸ᵇ | Q² | IC$_{50}$ | m/z (M + H)⁺ |
|---|---|---|---|---|---|---|---|
| 3009 |  | 6 | 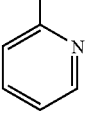 | 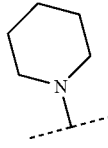 | 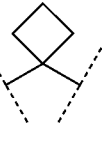 | C | 688.5 |
| 3010 |  | 5 |  | 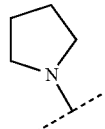 | 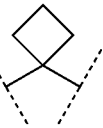 | C | 660.4 |
| 3011 |  | 5 |  | 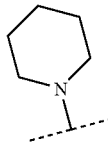 | 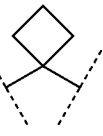 | C | 674.4 |
| 3012 |  | 6 | 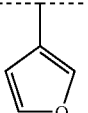 | 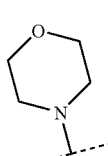 | 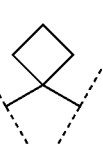 | | |

TABLE 3-continued
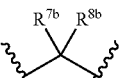
wherein R³ is C$_n$-cycloalkyl and the index n is given in the table:
| Cpd. # | R² | n | L | R$^{7b}$ R$^{8b}$ | Q² | IC$_{50}$ | m/z (M + H)⁺ |
|---|---|---|---|---|---|---|---|
| 3013 |  | 6 | 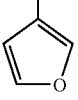 | 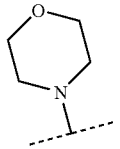 |  | | |
| 3014 | 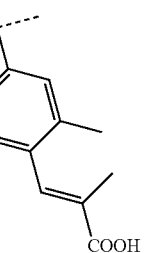 | 6 |  | 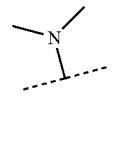 |  | | |
| 3015 | 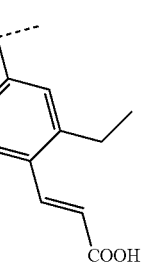 | 6 |  | 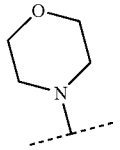 |  | | |
| 3016 | 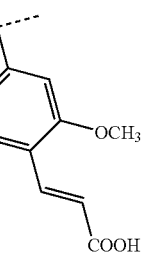 | 6 | 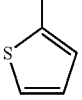 | 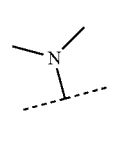 |  | | |

TABLE 3-continued
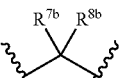
wherein R³ is C_n-cycloalkyl and the index n is given in the table:
| Cpd. # | R² | n | L | R⁷ᵇ R⁸ᵇ | Q² | IC₅₀ | m/z (M + H)⁺ |
|---|---|---|---|---|---|---|---|
| 3017 |  | 6 |  | 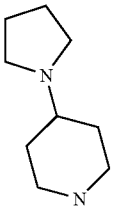 |  | | |
| 3018 | 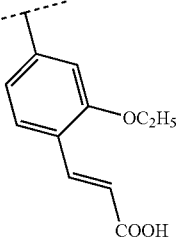 | 6 |  | 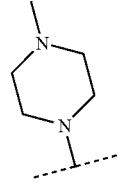 |  | | |
| 3019 | 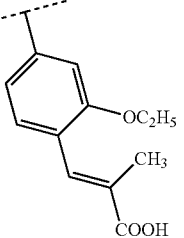 | 6 |  | 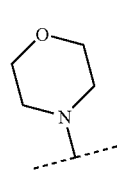 |  | | |
| 3020 | 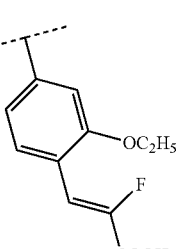 | 6 | 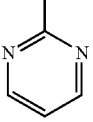 | 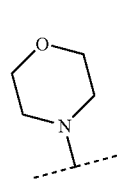 |  | | |

TABLE 4
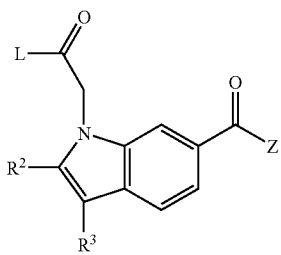
wherein R³ is C$_n$-cycloalkyl and the index n is specified in the table:
| Cpd. # | R² | n | L | Z | IC$_{50}$ | m/z (M + H)⁺ |
|---|---|---|---|---|---|---|
| 4001 | 2-pyridyl | 6 | 4-methylpiperazinyl | NH₂ | A | 460.4 |
| 4002 | 2-pyridyl | 6 | 4-methylpiperazinyl | HN-CH₂-(3,4-dimethoxyphenyl) | B | 610.5 |
| 4003 | 3-furyl | 6 | 4-methylpiperazinyl | HN-CH₂-(3,4-dimethoxyphenyl) | C | 599.4 |
| 4004 | 3-furyl | 6 | 4-pyrrolidin-1-yl-piperidinyl | HN-CH₂-(3,4-dimethoxyphenyl) | C | 653.5 |

TABLE 4-continued
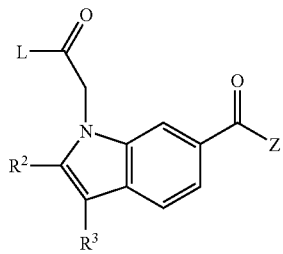
wherein R³ is $C_n$-cycloalkyl and the index n is specified in the table:
| Cpd. # | R² | n | L | Z | IC$_{50}$ | m/z (M + H)⁺ |
|---|---|---|---|---|---|---|
| 4005 | 3-furyl | 6 | 4-(pyrrolidin-1-yl)piperidine | (R)-1-phenylethylamine | C | 607.5 |
| 4006 | 3-furyl | 6 | morpholine | 3,4-dimethoxybenzylamine | C | 586.5 |
| 4007 | 3-furyl | 6 | morpholine | (R)-1-phenylethylamine | B | 540.5 |
| 4008 | 3-furyl | 6 | 4-methylpiperazine | cyclopentylamine | B | 517.4 |
| 4009 | 3-furyl | 6 | 4-methylpiperazine | 2-(1-methylpyrrolidin-2-yl)ethylamine | B | 560.4 |

TABLE 4-continued

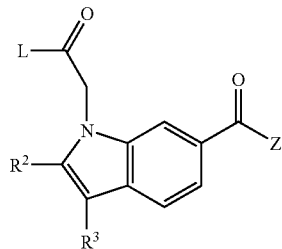

wherein R³ is C_n-cycloalkyl and the index n is specified in the table:

| Cpd. # | R² | n | L | Z | IC₅₀ | m/z (M + H)⁺ |
|---|---|---|---|---|---|---|
| 4010 | 3-furyl | 6 | N-methylpiperazinyl | (1-ethylpyrrolidin-2-yl)methylamino | B | 560.4 |
| 4011 | 3-furyl | 6 | N-methylpiperazinyl | furan-2-ylmethylamino | B | 529.3 |
| 4012 | 3-furyl | 6 | N-methylpiperazinyl | (1-hydroxy-3-methylbutan-2-yl)amino | B | 535.4 |
| 4013 | 3-furyl | 6 | N-methylpiperazinyl | benzo[d][1,3]dioxol-5-ylmethylamino | B | 583.4 |
| 4014 | 3-furyl | 6 | N-methylpiperazinyl | 2-morpholinoethylamino | B | 562.4 |
| 4015 | 3-furyl | 6 | N-methylpiperazinyl | pyridin-2-ylmethylamino | B | 540.4 |

TABLE 4-continued

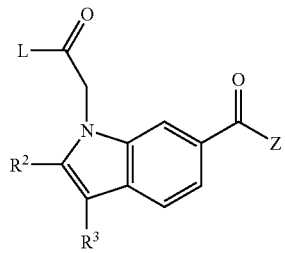

wherein R³ is C_n-cycloalkyl and the index n is specified in the table:

| Cpd. # | R² | n | L | Z | IC$_{50}$ | m/z (M + H)⁺ |
|---|---|---|---|---|---|---|
| 4016 | 3-furyl | 6 | 4-methylpiperazinyl | HN-CH₂CH₂-(2-pyridyl) | B | 554.4 |
| 4017 | 3-furyl | 6 | 4-methylpiperazinyl | HN-CH₂-(3-pyridyl) | B | 540.4 |
| 4018 | 3-furyl | 6 | 4-methylpiperazinyl | HN-CH₂-(4-pyridyl) | B | 540.4 |
| 4019 | 3-furyl | 6 | 4-methylpiperazinyl | HN-C(CH₃)₂-CH₂OH | B | 521.4 |
| 4020 | 3-furyl | 6 | 4-methylpiperazinyl | HN-CH(CH₃)-CH₂OCH₃ | B | 521.4 |
| 4021 | 3-furyl | 6 | 4-methylpiperazinyl | HN-CH₂-phenyl | B | 539.4 |

TABLE 4-continued

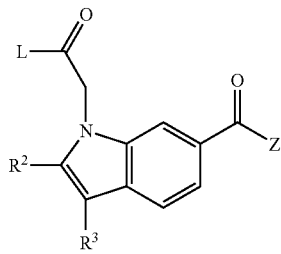

wherein R³ is C$_n$-cycloalkyl and the index n is specified in the table:

| Cpd. # | R² | n | L | Z | IC$_{50}$ | m/z (M + H)⁺ |
|---|---|---|---|---|---|---|
| 4022 | 3-furyl | 6 | N-methylpiperazine | 4-fluorobenzylamino | B | 557.3 |
| 4023 | 3-furyl | 6 | N-methylpiperazine | 2-hydroxy-2-phenylethylamino | B | 569.4 |
| 4024 | 3-furyl | 6 | N-methylpiperazine | 2-phenylpropylamino | A | 567.4 |
| 4025 | 3-furyl | 6 | N-methylpiperazine | 2-(dimethylamino)ethylamino | B | 520.4 |
| 4026 | 3-furyl | 6 | N-methylpiperazine | 2-phenylethylamino | A | 553.4 |
| 4027 | 3-furyl | 6 | N-methylpiperazine | (1-hydroxymethyl)cyclopentylamino | B | 547.4 |

TABLE 4-continued wherein R³ is Cₙ-cycloalkyl and the index n is specified in the table:

| Cpd. # | R² | n | L | Z | IC₅₀ | m/z (M + H)⁺ |
|---|---|---|---|---|---|---|
| 4028 | 3-furyl | 6 | N-methylpiperazinyl | HN-methyl | B | 463.3 |
| 4029 | 3-furyl | 6 | N-methylpiperazinyl | HN-CH₂-(3,4-dihydroxyphenyl) | C | 571.4 |
| 4030 | 3-furyl | 6 | N-methylpiperazinyl | HN-CH₂-(3-methoxy-4-hydroxyphenyl) | C | 585.4 |
| 4031 | 3-furyl | 6 | N-methylpiperazinyl | HN-CH₂-C(O)-phenyl | B | 567.4 |
| 4032 | 3-furyl | 6 | N-methylpiperazinyl | HN-CH₂-(4-sulfamoylphenyl) | C | 618.3 |

TABLE 4-continued

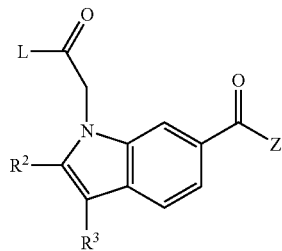

wherein R³ is C_n-cycloalkyl and the index n is specified in the table:

| Cpd. # | R² | n | L | Z | IC$_{50}$ | m/z (M + H)⁺ |
|---|---|---|---|---|---|---|
| 4033 | 3-furyl | 6 | 4-methylpiperazinyl | 1,1-dioxo-tetrahydrothiophen-3-ylamino | A | 567.3 |
| 4034 | 3-furyl | 6 | 4-methylpiperazinyl | cyclopropylmethylamino | B | 503.3 |
| 4035 | 3-furyl | 6 | 4-methylpiperazinyl | 2-(pyridin-4-yl)ethylamino | B | 554.4 |
| 4036 | 3-furyl | 6 | 4-methylpiperazinyl | 1-benzylpyrrolidin-3-ylamino | B | 608.4 |
| 4037 | 3-furyl | 6 | 4-methylpiperazinyl | (2-methyl-1-phenylpropan-2-yl)amino | A | 581.4 |
| 4038 | 3-furyl | 6 | 4-methylpiperazinyl | 2-phenylcyclopropylamino (racemate) | B | 565.4 |

TABLE 4-continued

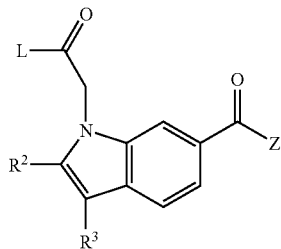

wherein $R^3$ is $C_n$-cycloalkyl and the index n is specified in the table:

| Cpd. # | $R^2$ | n | L | Z | $IC_{50}$ | m/z $(M + H)^+$ |
|---|---|---|---|---|---|---|
| 4039 | 3-furyl | 6 | N-methylpiperazine | (R)-1-phenylethylamino | B | 553.4 |
| 4040 | 3-furyl | 6 | N-methylpiperazine | 2-(pyridin-3-yl)ethylamino | B | 554.4 |
| 4041 | 3-furyl | 6 | N-methylpiperazine | 4-(methylsulfonyl)benzylamino | C | 617.4 |
| 4042 | 3-furyl | 6 | N-methylpiperazine | (S)-1-(3-methoxyphenyl)ethylamino | C | 583.4 |
| 4043 | 3-furyl | 6 | N-methylpiperazine | (S)-1-(4-methoxyphenyl)ethylamino | C | 583.4 |

TABLE 4-continued

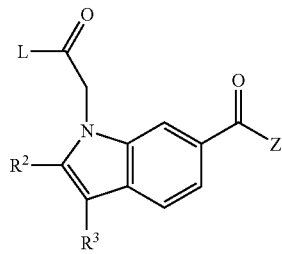

wherein R³ is Cₙ-cycloalkyl and the index n is specified in the table:

| Cpd. # | R² | n | L | Z | IC₅₀ | m/z (M + H)⁺ |
|---|---|---|---|---|---|---|
| 4044 | 3-furyl | 6 | N-methylpiperazinyl | (5-methylpyrazin-2-yl)methylamino | B | 555.4 |
| 4045 | 3-furyl | 6 | morpholinyl | (benzo[1,3]dioxol-5-yl)methylamino | B | 570.3 |
| 4046 | 3-furyl | 6 | morpholinyl | (pyridin-2-yl)methylamino | B | 527.3 |
| 4047 | 3-furyl | 6 | morpholinyl | benzylamino | B | 526.3 |
| 4048 | 3-furyl | 6 | morpholinyl | phenethylamino | A | 540.3 |
| 4049 | 3-furyl | 6 | morpholinyl | methylamino | B | 450.3 |

TABLE 4-continued
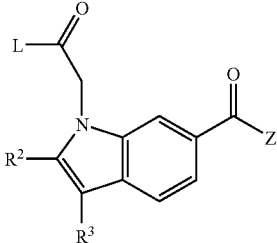
wherein R³ is C$_n$-cycloalkyl and the index n is specified in the table:
| Cpd. # | R² | n | L | Z | IC$_{50}$ | m/z (M + H)$^+$ |
|---|---|---|---|---|---|---|
| 4050 | 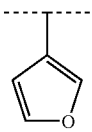 | 6 | 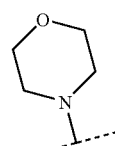 | 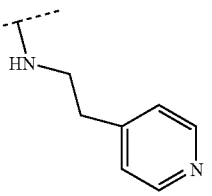 | B | 541.3 |
| 4051 | 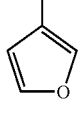 | 6 | 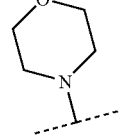 | 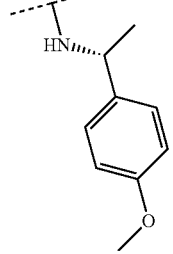 | B | 570.4 |
| 4052 | 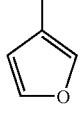 | 6 | 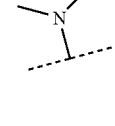 | 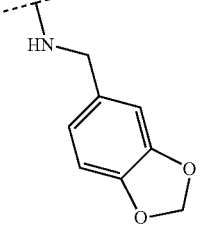 | B | 528.3 |
| 4053 | 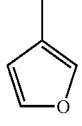 | 6 | 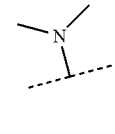 | 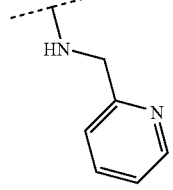 | B | 485.3 |
| 4054 | 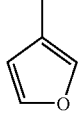 | 6 | 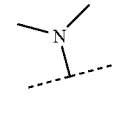 | 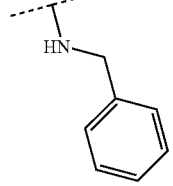 | B | 484.3 |

TABLE 4-continued
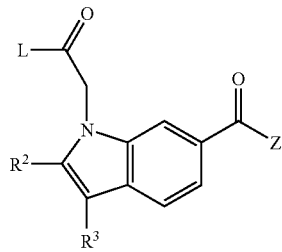
wherein R³ is C_n-cycloalkyl and the index n is specified in the table:
| Cpd. # | R² | n | L | Z | IC_{50} | m/z (M + H)⁺ |
|---|---|---|---|---|---|---|
| 4055 | 3-furyl | 6 | N(CH₃)CH₂- (dimethylaminomethyl) | -NH-CH₂CH₂-phenyl | B | 498.3 |
| 4056 | 3-furyl | 6 | N(CH₃)CH₂- | -NH-CH₃ | B | 408.2 |
| 4057 | 3-furyl | 6 | N(CH₃)CH₂- | -NH-CH₂CH₂-(4-pyridyl) | B | 499.3 |
| 4058 | 3-furyl | 6 | N(CH₃)CH₂- | -NH-CH(CH₃)-phenyl | C | 498.3 |
| 4059 | 3-furyl | 6 | N(CH₃)CH₂- | -NH-CH(CH₃)-(4-methoxyphenyl) | C | 528.3 |
| 4060 | 3-furyl | 6 | 4-(pyrrolidin-1-yl)piperidin-1-yl | -NH-C(CH₃)₂-phenyl | B | 621.4 |

TABLE 4-continued

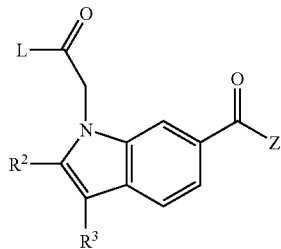

wherein $R^3$ is $C_n$-cycloalkyl and the index n is specified in the table:

| Cpd. # | $R^2$ | n | L | Z | $IC_{50}$ | m/z $(M + H)^+$ |
|---|---|---|---|---|---|---|
| 4061 | 3-furyl | 6 | 4-(pyrrolidin-1-yl)piperidin-1-yl | methyl 3-aminopyrrolidine-3-carboxylate | B | 563.3 |
| 4062 | 3-furyl | 6 | morpholino | 3,4-dihydroxybenzylamino | C | 558.3 |
| 4063 | 3-furyl | 6 | morpholino | (1-(3,4-dimethoxyphenyl)ethyl)amino | B | 600.3 |
| 4064 | 3-furyl | 6 | morpholino | 4-hydroxy-3-methoxybenzylamino | B | 572.3 |
| 4065 | 3-furyl | 6 | morpholino | benzamidomethyl | A | 540.2 |

TABLE 4-continued
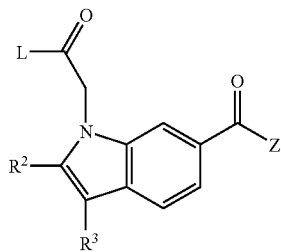
wherein R³ is C_n-cycloalkyl and the index n is specified in the table:
| Cpd. # | R² | n | L | Z | IC$_{50}$ | m/z (M + H)$^+$ |
|---|---|---|---|---|---|---|
| 4066 | 3-furyl | 6 | morpholinyl-CH₂ | -NH-C(O)CH₃ | B | 478.3 |
| 4067 | 3-furyl | 6 | morpholinyl-CH₂ | cyclobutyl-NH-benzimidazole-CH=CH-COOH | C | 676.3 |
| 4068 | 3-furyl | 5 | morpholinyl-CH₂ | (N-methylpyrrolidinyl)-NH-benzimidazole-CH=CH-COOH | C | 691.4 |
| 4069 | 3-furyl | 6 | morpholinyl-CH₂ | (N-methylpyrrolidinyl)-NH-benzimidazole-CH=CH-COOH | C | 705.4 |

TABLE 4-continued

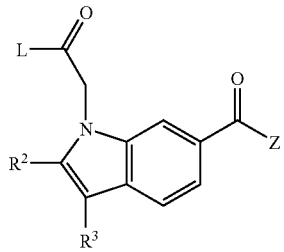

wherein R³ is C_n-cycloalkyl and the index n is specified in the table:

| Cpd. # | R² | n | L | Z | IC₅₀ | m/z (M + H)⁺ |
|---|---|---|---|---|---|---|
| 4070 | 3-furyl | 5 | morpholine | cyclobutyl-NH-benzimidazole-CH=CH-COOH | C | 662.3 |
| 4071 | 3-furyl | 6 | morpholine | 1-ethynylcyclohexyl-NH | B | 542.2 |
| 4072 | 3-furyl | 6 | morpholine | 1-carbamoylcyclopentyl-NH | C | 547.3 |
| 4073 | 3-furyl | 6 | morpholine | 1-(methoxycarbonyl)cyclopentyl-NH | B | 562.2 |
| 4074 | 3-furyl | 6 | morpholine | 1-carboxycyclopentyl-NH | B | 548.2 |
| 4075 | 3-furyl | 6 | morpholine | 2-methoxycarbonyl-propan-2-yl-NH | B | 536.3 |

TABLE 4-continued
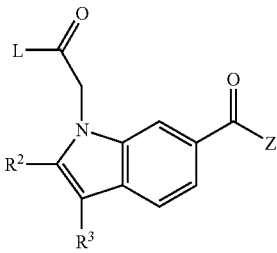
wherein R³ is C$_n$-cycloalkyl and the index n is specified in the table:
| Cpd. # | R² | n | L | Z | IC$_{50}$ | m/z (M + H)⁺ |
|---|---|---|---|---|---|---|
| 4076 | 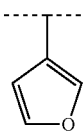 | 6 | 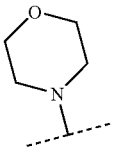 | 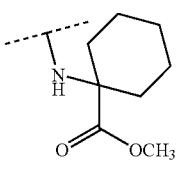 | B | 576.3 |
| 4077 | 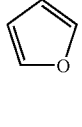 | 6 | 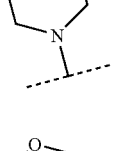 | 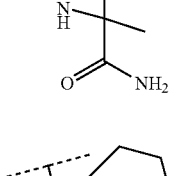 | C | 521.3 |
| 4078 | 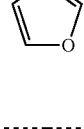 | 6 | 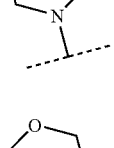 | 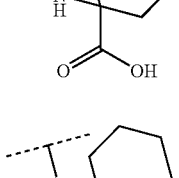 | B | 562.3 |
| 4079 |  | 6 | 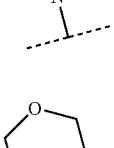 | 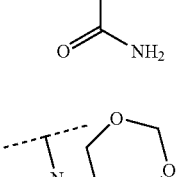 | B | 561.3 |
| 4080 |  | 6 |  | 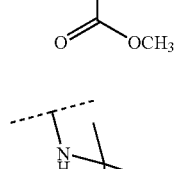 | B | 580.1 |
| 4081 |  | 6 | 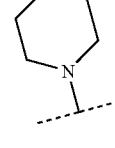 | 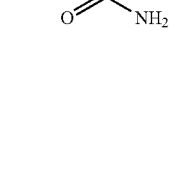 | C | 588.4 |

TABLE 4-continued
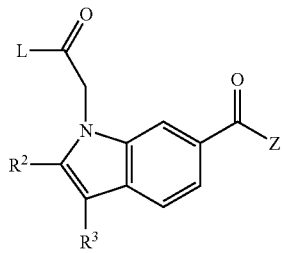
wherein R³ is C_n-cycloalkyl and the index n is specified in the table:
| Cpd. # | R² | n | L | Z | IC$_{50}$ | m/z (M + H)$^+$ |
|---|---|---|---|---|---|---|
| 4082 | 3-furyl | 6 | morpholine | 2-(1-aminocyclobutyl)-1-methyl-6-(2-carboxyvinyl)benzimidazole | C | 690.3 |
| 4083 | 3-furyl | 6 | morpholine | NH-C(COOH)(1,3-dioxane) | C | 566.3 |
| 4084 | 3-furyl | 6 | 4-pyrrolidinyl-piperidine | NH-C(CH₃)₂-C(O)NHCH₃ | C | 602.5 |
| 4085 | 3-furyl | 6 | morpholine | NH-C(C(O)NH₂)(1,3-dioxane) | C | 565.1 |
| 4086 | 3-furyl | 6 | 4-pyrrolidinyl-piperidine | NH-C(CH₃)₂-C(O)N(CH₃)₂ | C | 616.5 |

TABLE 4-continued
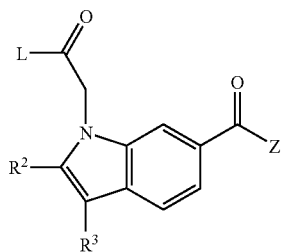
wherein R³ is C$_n$-cycloalkyl and the index n is specified in the table:
| Cpd. # | R² | n | L | Z | IC$_{50}$ | m/z (M + H)⁺ |
|---|---|---|---|---|---|---|
| 4087 | 3-furyl | 6 | morpholine | NH-C(CH₃)₂-COOH | C | 522.2 |
| 4088 | 3-furyl | 6 | morpholine | NH-cyclobutyl-(3-methylbenzofuran-6-COOH) | C | 664.3 |
| 4089 | 3-furyl | 6 | pyrrolidinyl-piperidine | NH-cyclobutyl-C(O)NHCH₃ | C | 614.3 |
| 4090 | 3-furyl | 6 | pyrrolidinyl-piperidine | NH-cyclobutyl-CN | C | 582.3 |
| 4091 | 3-furyl | 6 | morpholine | NH-cyclobutyl-C(O)NHCH₃ | B | 547.3 |

TABLE 4-continued

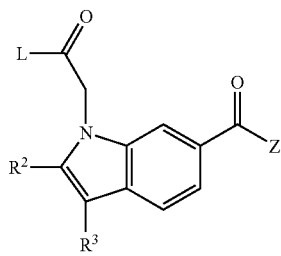

wherein R³ is C$_n$-cycloalkyl and the index n is specified in the table:

| Cpd. # | R² | n | L | Z | IC$_{50}$ | m/z (M + H)$^+$ |
|---|---|---|---|---|---|---|
| 4092 | 3-furyl | 6 | morpholine | 1-carbamoylcyclobutylamino | C | 533.3 |
| 4093 | 3-furyl | 6 | morpholine | 1-(N-methylcarbamoyl)cyclobutylamino | C | 561.3 |
| 4094 | 3-furyl | 6 | 4-(pyrrolidin-1-yl)piperidine | 1-(N-methylcarbamoyl)cyclopentylamino | C | 628.5 |
| 4095 | 3-furyl | 6 | 4-(pyrrolidin-1-yl)piperidine | 1-(N,N-dimethylcarbamoyl)cyclopentylamino | C | 642.5 |
| 4096 | 3-furyl | 6 | morpholine | 1-(N-methylcarbamoyl)cyclopentylamino | C | 561.2 |
| 4097 | 3-furyl | 6 | morpholine | 1-(N,N-dimethylcarbamoyl)cyclopentylamino | C | 573.4 (M − H)$^-$ |

TABLE 4-continued

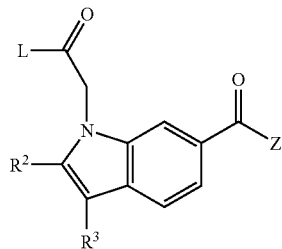

wherein R³ is $C_n$-cycloalkyl and the index n is specified in the table:

| Cpd. # | R² | n | L | Z | IC$_{50}$ | m/z (M + H)⁺ |
|---|---|---|---|---|---|---|
| 4098 | 3-furyl | 6 | morpholine | 1-(2-methylthiazol-4-yl)cyclobutylamino | B | 587.3 |
| 4099 | 3-furyl | 6 | 4-(piperidin-1-yl)pyrrolidine | 1-(2-methylthiazol-4-yl)cyclobutylamino | C | 654.3 |
| 4100 | 3-furyl | 6 | H₂N– | 1-(1-methyl-6-(acrylate)benzimidazol-2-yl)cyclobutylamino | C | 620.4 |
| 4101 | 3-furyl | 6 | 4-(piperidin-1-yl)pyrrolidine | 1-(2-phenylaminothiazol-4-yl)cyclobutylamino | B | 731.4 |

TABLE 4-continued

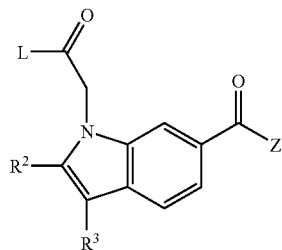

wherein R³ is C_n-cycloalkyl and the index n is specified in the table:

| Cpd. # | R² | n | L | Z | IC₅₀ | m/z (M + H)⁺ |
|---|---|---|---|---|---|---|
| 4102 | 3-furyl | 6 | 4-pyrrolidinylpiperidinyl | 1-(2-acetamido-thiazol-4-yl)cyclobutylamino | C | 697.4 |
| 4103 | 3-furyl | 6 | 4-pyrrolidinylpiperidinyl | 1-(2-methylamino-thiazol-4-yl)cyclobutylamino | C | 669.4 |
| 4104 | 3-furyl | 6 | 4-pyrrolidinylpiperidinyl | 1-(2-benzyl-thiazol-4-yl)cyclobutylamino | A | 730.4 |
| 4105 | 3-furyl | 6 | 4-pyrrolidinylpiperidinyl | 1-(2-isopropylamino-thiazol-4-yl)cyclobutylamino | B | 697.4 |

TABLE 4-continued
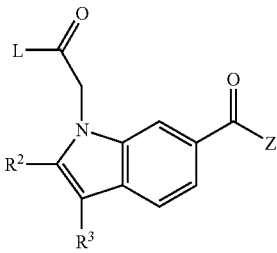
wherein R³ is C_n-cycloalkyl and the index n is specified in the table:
| Cpd. # | R² | n | L | Z | IC$_{50}$ | m/z (M + H)⁺ |
|---|---|---|---|---|---|---|
| 4106 | 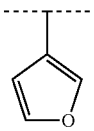 | 6 | 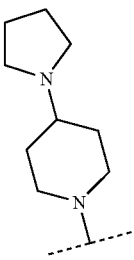 | 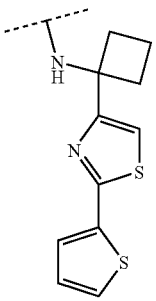 | B | 722.4 |
| 4107 | 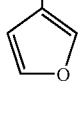 | 6 | 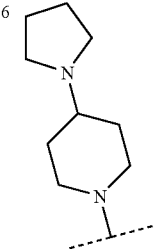 | 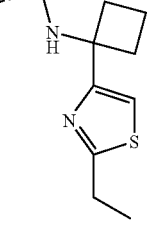 | C | 668.4 |
| 4108 | 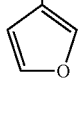 | 6 | 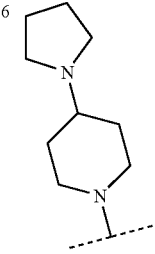 | 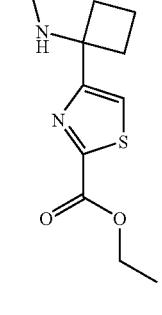 | B | 712.4 |
| 4109 | 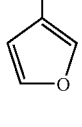 | 6 | 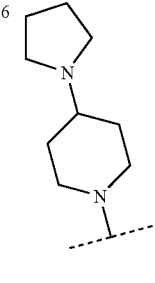 | 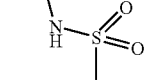 | C | 581.2 |

TABLE 4-continued

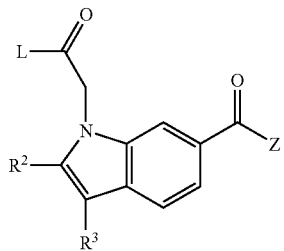

wherein R³ is C$_n$-cycloalkyl and the index n is specified in the table:

| Cpd. # | R² | n | L | Z | IC$_{50}$ | m/z (M + H)$^+$ |
|---|---|---|---|---|---|---|
| 4110 | 3-furyl | 6 | 4-(pyrrolidin-1-yl)piperidin-1-yl | NHSO₂Ph | C | 643.3 |
| 4111 | 3-furyl | 6 | morpholin-4-yl | NH-(1-(4-methylthiazol-2-yl)cyclobutyl) | B | 587.3 |
| 4112 | 3-furyl | 6 | hexahydropyridazin-1-yl | NHSO₂Ph | | |
| 4113 | 3-furyl | 6 | 2-methylhydrazinyl | NHSO₂Ph | | |
| 4114 | 3-furyl | 6 | 1-acetylhydrazinyl | NHSO₂Ph | | |
| 4115 | 6-amino-pyridin-2-yl | 6 | 4-(pyrrolidin-1-yl)piperidin-1-yl | NHSO₂Ph | | |

TABLE 4-continued
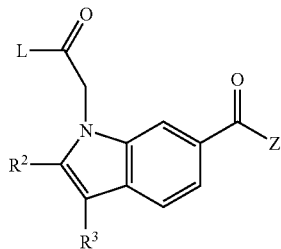
wherein R³ is Cₙ-cycloalkyl and the index n is specified in the table:
| Cpd. # | R² | n | L | Z | IC₅₀ | m/z (M + H)⁺ |
|---|---|---|---|---|---|---|
| 4116 | 6-amino-pyridin-2-yl | 6 | morpholinyl | NHSO₂Ph | | |
| 4117 | 6-amino-pyridin-2-yl | 6 | N(CH₃)₂ | NHSO₂Ph | | |
| 4118 | 6-amino-pyridin-2-yl | 6 | 4-piperidinyl(N-linked) | NHSO₂CH₃ | | |
| 4119 | 6-amino-pyridin-2-yl | 6 | morpholinyl | NHSO₂CH₃ | | |
| 4120 | 6-amino-pyridin-2-yl | 6 | N(CH₃)₂ | NHSO₂CH₃ | | |
| 4121 | pyrazin-2-yl | 6 | 4-piperidinyl(N-linked) | NHSO₂Ph | | |

TABLE 4-continued wherein R³ is Cₙ-cycloalkyl and the index n is specified in the table:

| Cpd. # | R² | n | L | Z | IC₅₀ | m/z (M + H)⁺ |
|---|---|---|---|---|---|---|
| 4122 | pyrazin-2-yl | 6 | morpholino | NHS(O)₂-phenyl | | |
| 4123 | pyrazin-2-yl | 6 | N,N-dimethylamino | NHS(O)₂-phenyl | | |
| 4124 | pyrazin-2-yl | 6 | pyrrolidin-1-yl-piperidin-4-yl | NHS(O)₂CH₃ | | |
| 4125 | pyrazin-2-yl | 6 | morpholino | NHS(O)₂CH₃ | | |
| 4126 | pyrazin-2-yl | 6 | N,N-dimethylamino | NHS(O)₂CH₃ | | |
| 4127 | pyrazin-2-yl | 6 | N,N-dimethylamino | NHS(O)₂-cyclopropyl | | |

TABLE 4-continued

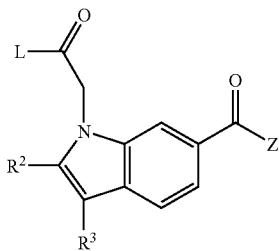

wherein R³ is C_n-cycloalkyl and the index n is specified in the table:

| Cpd. # | R² | n | L | Z | IC$_{50}$ | m/z (M + H)⁺ |
|---|---|---|---|---|---|---|
| 4128 | 3-thienyl | 6 | morpholinomethyl | 1-methyl-2-(cyclobutylamino)-benzimidazol-6-yl methyl acrylate | | |
| 4129 | 3-furyl | 6 | 4-(pyrrolidin-1-yl)piperidinomethyl | 1-methyl-2-(cyclobutylamino)-benzimidazol-6-yl 2-methylacrylic acid | | |
| 4130 | 3-furyl | 6 | dimethylaminomethyl | 1-methyl-2-(cyclobutylamino)-benzimidazol-6-yl acrylic acid | | |

TABLE 4-continued
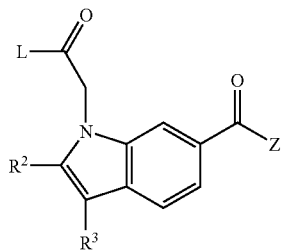
wherein R³ is C_n-cycloalkyl and the index n is specified in the table:
| Cpd. # | R² | n | L | Z | IC$_{50}$ | m/z (M + H)⁺ |
|---|---|---|---|---|---|---|
| 4131 | 3-furyl | 6 | dimethylamino | 1-(1-methylbenzimidazol-6-yl-CH=CH-COOH)cyclobutylamino | | |
| 4132 | 3-furyl | 6 | morpholino | 1-(1-methylbenzimidazol-6-yl-CH=CH-COOH)cyclobutylamino | | |
| 4133 | 2-thienyl | 6 | morpholino | 1-(1-methylbenzimidazol-6-yl-CH=C(CH₃)-COOH)cyclobutyl-N | | |

TABLE 4-continued
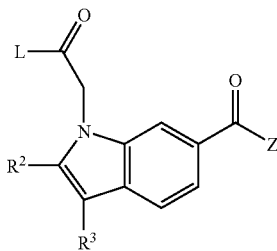
wherein R³ is C_n-cycloalkyl and the index n is specified in the table:
| Cpd. # | R² | n | L | Z | IC_{50} | m/z (M + H)⁺ |
|---|---|---|---|---|---|---|
| 4134 | 3-furyl | 6 | CH₂-N(CH₃)₂ | benzimidazole-cyclobutyl-NH with OCH₃ and CH=CH-COOH | | |
| 4135 | 3-furyl | 6 | CH₂-N(CH₃)₂ | benzimidazole-cyclobutyl-NH with CH₃ and CH=CH-COOH | | |
| 4136 | 3-furyl | 6 | morpholinyl-CH₂ | benzimidazole-cyclobutyl-NH with OCH₂CH₃ and CH=CH-COOH | | |

TABLE 4-continued
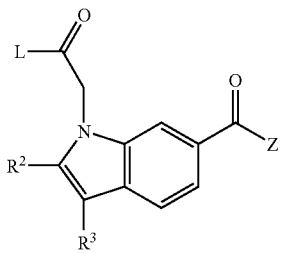
wherein R³ is C_n-cycloalkyl and the index n is specified in the table:
| Cpd. # | R² | n | L | Z | IC$_{50}$ | m/z (M + H)$^+$ |
|---|---|---|---|---|---|---|
| 4137 | 3-furyl | 6 | pyrrolidinyl-piperidinyl | methoxy-benzimidazole-methylacrylic acid cyclobutyl-NH | | |
| 4138 | 3-furyl | 6 | dimethylamino | methoxy-benzimidazole-acrylic acid cyclobutyl-NH | | |
| 4139 | 3-furyl | 6 | dimethylamino | ethyl-benzimidazole-acrylic acid cyclobutyl-NH | | |

TABLE 4-continued
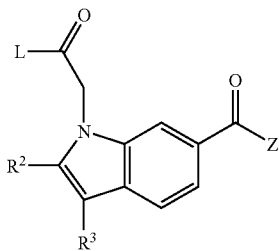
wherein R³ is C_n-cycloalkyl and the index n is specified in the table:
| Cpd. # | R² | n | L | Z | IC$_{50}$ | m/z (M + H)$^+$ |
|---|---|---|---|---|---|---|
| 4140 | 3-furyl | 6 | N,N-dimethylamino | (1-methyl-2-(1-aminocyclobutyl)-6-methyl-5-benzimidazolyl)-CH=C(CH₃)-COOH | | |
| 4141 | 2-thienyl | 6 | morpholino | (1-methyl-2-(1-aminocyclobutyl)-6-ethoxy-5-benzimidazolyl)-CH=CH-COOH | | |
| 4142 | 3-furyl | 6 | morpholino | (1-methyl-2-(1-aminocyclobutyl)-6-indolyl)-CH=CH-COOH | | |

TABLE 4-continued
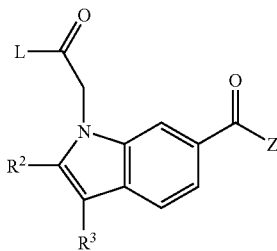
wherein R³ is C$_n$-cycloalkyl and the index n is specified in the table:
| Cpd. # | R² | n | L | Z | IC$_{50}$ | m/z (M + H)⁺ |
|---|---|---|---|---|---|---|
| 4143 | 3-furyl | 5 | dimethylaminomethyl | cyclobutyl-NH-(2-(1-methylindol-6-yl)acrylic acid) | | |
| 4144 | 3-furyl | 6 | pyrrolidinyl-piperidinyl | cyclobutyl-NH-(2-(1-methylindol-6-yl)-2-methylacrylic acid) | | |
| 4145 | 3-furyl | 6 | dimethylaminomethyl | cyclobutyl-NH-(3-methylbenzofuran-5-yl)acrylic acid | | |

TABLE 4-continued
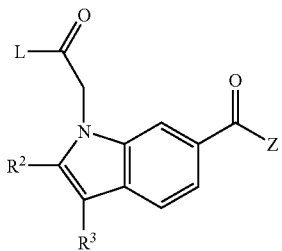
wherein $R^3$ is $C_n$-cycloalkyl and the index n is specified in the table:
| Cpd. # | $R^2$ | n | L | Z | IC$_{50}$ | m/z (M + H)$^+$ |
|---|---|---|---|---|---|---|
| 4146 | 3-furyl | 6 | morpholine | | | |
| 4147 | 2-thienyl | 5 | morpholine | | | |
| 4148 | 3-furyl | 6 | pyrrolidinyl-piperidine | | | |

TABLE 4-continued

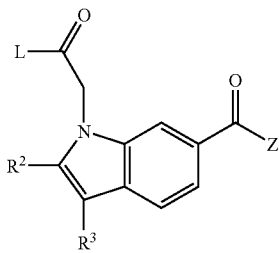

wherein R³ is C$_n$-cycloalkyl and the index n is specified in the table:

| Cpd. # | R² | n | L | Z | IC$_{50}$ | m/z (M + H)$^+$ |
|---|---|---|---|---|---|---|
| 4149 | 3-furyl | 6 | N-methylpiperazine | 1-methylbenzimidazol-2-yl-cyclobutyl-NH with 2-methylacrylic acid | | |
| 4150 | 3-furyl | 6 | morpholine | 1-methylbenzimidazol-2-yl-cyclobutyl-NH with 2-fluoroacrylic acid | | |
| 4151 | 3-furyl | 6 | N-methylpiperazine | 1-methylbenzimidazol-2-yl-cyclobutyl-NH with acrylic acid | | |

TABLE 4-continued
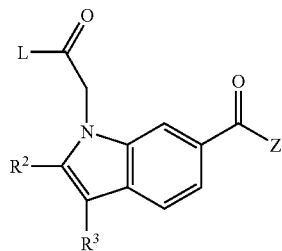
wherein R³ is C_n-cycloalkyl and the index n is specified in the table:
| Cpd. # | R² | n | L | Z | IC$_{50}$ | m/z (M + H)$^+$ |
|---|---|---|---|---|---|---|
| 4152 | 3-furyl | 6 | morpholinyl | (benzimidazole-cyclobutyl-NH, 2-methylacrylic acid) | | |
| 4153 | 3-furyl | 6 | 4-methylpiperazinyl | (benzimidazole-cyclobutyl-NH, 2-fluoroacrylic acid) | | |
| 4154 | 2-pyrimidinyl | 6 | morpholinyl | (benzimidazole-cyclobutyl-NH, acrylic acid) | | |

TABLE 5

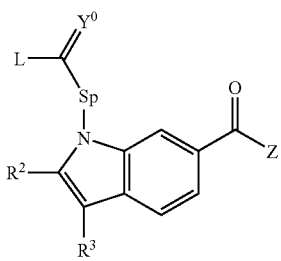

wherein R³ is $C_n$-cycloalkyl and the index n is given in the table:

| Cpd. # | R² | n | [group] | Z | IC$_{50}$ | m/z (M + H)⁺ |
|---|---|---|---|---|---|---|
| 5001 | 3-furyl | 6 | morpholine-thiocarbonyl-propyl | OH | B | 453.2 |
| 5002 | 3-furyl | 6 | morpholine-carbonyl-propyl | OH | B | 451.2 |
| 5003 | 3-furyl | 6 | N,N-dimethylamide-butyl | OH | A | 409.2 |
| 5004 | 3-furyl | 6 | butenyl | OH | B | 350.2 |
| 5005 | 3-furyl | 6 | pentenyl | OH | A | 364.2 |
| 5006 | 3-furyl | 6 | methyl-pentenyl | OH | A | 378.2 |

TABLE 5-continued

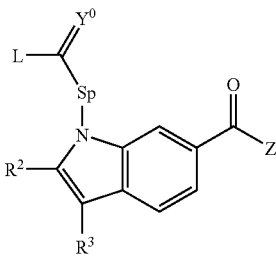

wherein R³ is $C_n$-cycloalkyl and the index n is given in the table:

| Cpd. # | R² | n | [group] | Z | IC$_{50}$ | m/z (M + H)⁺ |
|---|---|---|---|---|---|---|
| 5007 | 3-furyl | 6 | methyl-butenyl | OH | B | 364.2 |
| 5008 | 3-furyl | 6 | morpholine-carbonyl-methylethyl | OH | A | 451.2 |
| 5009 | 3-furyl | 6 | N,N-dimethylamide-methylethyl | OH | A | 409.2 |

TABLE 6

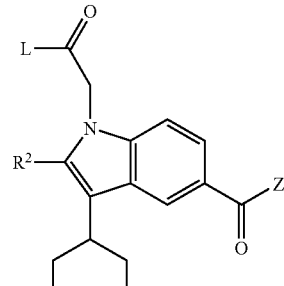

| Cpd. # | R² | L | Z | IC$_{50}$ | m/z (M + H)⁺ |
|---|---|---|---|---|---|
| 6001 | 3-furyl | morpholinylmethyl | OH | B | 437.2 |

TABLE 6-continued

[Structure: indole with N-CH2-C(=O)-L, R² at 2-position, cyclohexyl at 3-position, C(=O)Z at 5-position]

| Cpd. # | R² | L | Z | IC50 | m/z (M + H)+ |
|---|---|---|---|---|---|
| 6002 | 3-furyl | pyrrolidinyl-piperidinyl | OH | C | 504.3 |
| 6003 | 3-furyl | N(Me)2 | OH | B | 395.2 |
| 6004 | pyrazinyl | N(Me)2 | OH | | |

TABLE 6-continued

[Same core structure]

| Cpd. # | R² | L | Z | IC50 | m/z (M + H)+ |
|---|---|---|---|---|---|
| 6005 | 3-furyl | morpholinyl | NHSO2CH3 | | |
| 6006 | 3-furyl | pyrrolidinyl-piperidinyl | NHSO2Ph | | |
| 6007 | 3-furyl | N(Me)2 | NHSO2CH3 | | |

TABLE 7

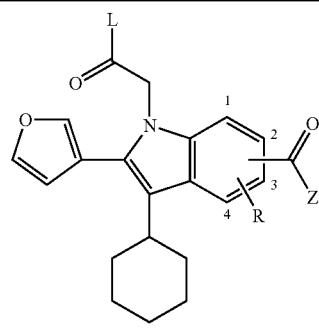

in the following table the index i indicates the position of the group —CO—Z and the index j indicates the position of the group R within the phenyl-ring.
The term Me denotes methyl and Ph denotes phenyl.

| Cpd. # | L | i | Z | j | R | IC50 | m/z (M + H)+ |
|---|---|---|---|---|---|---|---|
| 7001 | N(Me)2 | 2 | OH | 1 | Me | C | 409.1 |

TABLE 7-continued

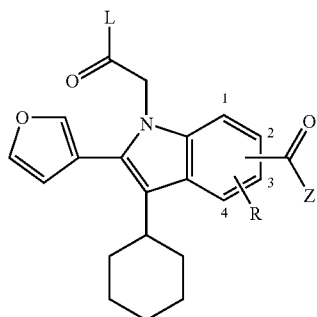

in the following table the index i indicates the position of the group —CO—Z and the index j indicates the position of the group R within the phenyl-ring.

The term Me denotes methyl and Ph denotes phenyl.

| Cpd. # | L | i | Z | j | R | $IC_{50}$ | m/z $(M + H)^+$ |
|---|---|---|---|---|---|---|---|
| 7002 | morpholine-N-yl | 2 | OH | 3 | OMe | B | 467.2 |
| 7003 | 4-(pyrrolidin-1-yl)piperidin-1-yl | 2 | OH | 3 | OMe | B | 534.2 |
| 7004 | 4-(pyrrolidin-1-yl)piperidin-1-yl | 2 | OH | 1 | Me | C | 518.2 |
| 7005 | morpholine-N-yl | 2 | OH | 1 | Me | C | 451.2 |
| 7006 | N,N-dimethylamino | 2 | OH | 3 | OMe | B | 425.1 |

TABLE 7-continued

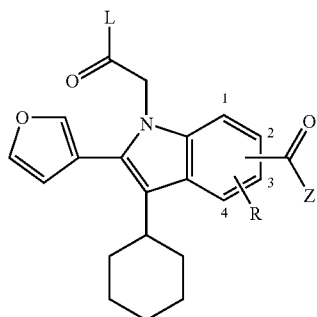

in the following table the index i indicates the position of the group —CO—Z and the index j indicates the position of the group R within the phenyl-ring.

The term Me denotes methyl and Ph denotes phenyl.

| Cpd. # | L | i | Z | j | R | $IC_{50}$ | m/z $(M + H)^+$ |
|---|---|---|---|---|---|---|---|
| 7007 | pyrrolidinyl-piperidinyl | 2 | OH | 3 | OH | A | 520.2 |
| 7008 | morpholinyl | 2 | OH | 3 | OH | A | 453.2 |
| 7009 | N,N-dimethylamino | 2 | OH | 3 | OH | A | 411.1 |
| 7010 | pyrrolidinyl-piperidinyl | 2 | OMe | 3 | OH | A | 534.3 |
| 7011 | morpholinyl | 2 | OH | 3 | $OCH_2COOH$ | A | 511.2 |

TABLE 7-continued
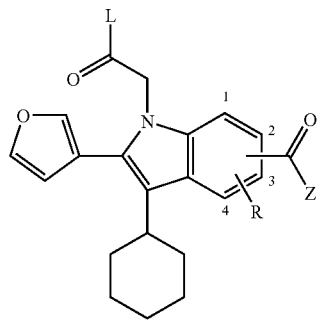
in the following table the index i indicates the position of the group —CO—Z and the
index j indicates the position of the group R within the phenyl-ring.
The term Me denotes methyl and Ph denotes phenyl.
| Cpd. # | L | i | Z | j | R | IC$_{50}$ | m/z (M + H)$^+$ |
|---|---|---|---|---|---|---|---|
| 7012 | | 3 | | — | — | A | 633.4 |
| 7013 | | 3 | | — | — | A | 614.5 |
| 7014 | | 3 | | — | — | A | 600.5 |
| 7015 | | 3 | | — | — | A | 597.4 |

TABLE 7-continued

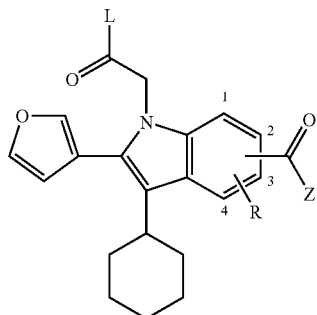

in the following table the index i indicates the position of the group —CO—Z and the index j indicates the position of the group R within the phenyl-ring.
The term Me denotes methyl and Ph denotes phenyl.

| Cpd. # | L | i | Z | j | R | IC$_{50}$ | m/z (M + H)$^+$ |
|---|---|---|---|---|---|---|---|
| 7016 | pyrrolidinyl-piperidinyl | 3 | HN-CH$_2$-tetrahydrofuranyl | — | — | A | 587.4 |
| 7017 | pyrrolidinyl-piperidinyl | 3 | piperidinyl-3-carboxamide | — | — | A | 614.5 |
| 7018 | pyrrolidinyl-piperidinyl | 3 | HN-(4-morpholinophenyl) | — | — | A | 664.5 |
| 7019 | pyrrolidinyl-piperidinyl | 3 | HN-CH$_2$-pyridyl | — | — | A | 594.4 |

TABLE 7-continued

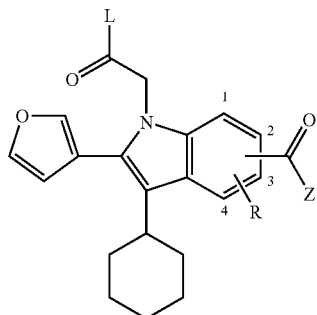

in the following table the index i indicates the position of the group —CO—Z and the index j indicates the position of the group R within the phenyl-ring.
The term Me denotes methyl and Ph denotes phenyl.

| Cpd. # | L | i | Z | j | R | IC$_{50}$ | m/z (M + H)$^+$ |
|---|---|---|---|---|---|---|---|
| 7020 | 4-pyrrolidin-1-yl-piperidin-1-yl | 3 | N-methyl-N-(2-pyridin-2-yl-ethyl)amino | — | — | A | 622.5 |
| 7021 | 4-pyrrolidin-1-yl-piperidin-1-yl | 3 | (pyridin-3-ylmethyl)amino | — | — | A | 594.4 |
| 7022 | 4-pyrrolidin-1-yl-piperidin-1-yl | 3 | (4-ethoxycarbonyl-cyclohexyl)amino | — | — | A | 658.5 |
| 7023 | 4-pyrrolidin-1-yl-piperidin-1-yl | 3 | phenylamino | — | — | A | 579.4 |

TABLE 7-continued

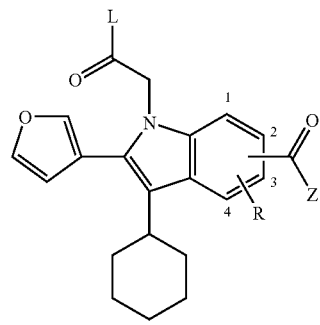

in the following table the index i indicates the position of the group —CO—Z and the index j indicates the position of the group R within the phenyl-ring.
The term Me denotes methyl and Ph denotes phenyl.

| Cpd. # | L | i | Z | j | R | IC$_{50}$ | m/z (M + H)$^+$ |
|---|---|---|---|---|---|---|---|
| 7024 | pyrrolidin-1-yl-piperidin-4-yl | 3 | HN-(4-(2-hydroxyethyl)phenyl) | — | — | A | 623.5 |
| 7025 | pyrrolidin-1-yl-piperidin-4-yl | 3 | HN-CH(Ph)CH$_2$Ph | — | — | A | 683.5 |
| 7026 | pyrrolidin-1-yl-piperidin-4-yl | 3 | HN-CH(Me)Ph | — | — | A | 607.5 |
| 7027 | pyrrolidin-1-yl-piperidin-4-yl | 3 | HN-CH$_2$Ph | — | — | A | 593.4 |

TABLE 7-continued

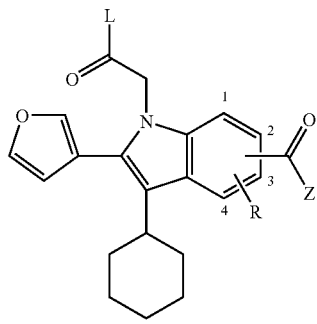

in the following table the index i indicates the position of the group —CO—Z and the index j indicates the position of the group R within the phenyl-ring.
The term Me denotes methyl and Ph denotes phenyl.

| Cpd. # | L | i | Z | j | R | IC$_{50}$ | m/z (M + H)$^+$ |
|---|---|---|---|---|---|---|---|
| 7028 | pyrrolidine-piperidine | 3 | HN-CH$_2$-(3,4-dimethoxyphenyl) | — | — | A | 653.5 |
| 7029 | pyrrolidine-piperidine | 3 | HN-CH$_2$-(3-methylphenyl) | — | — | A | 607.5 |
| 7030 | pyrrolidine-piperidine | 3 | HN-CH$_2$-CH(CH$_3$)-phenyl | — | — | A | 621.5 |
| 7031 | pyrrolidine-piperidine | 3 | HN-CH$_2$-CH$_2$-NH-C(O)-CH$_3$ | — | — | A | 588.5 |

TABLE 7-continued

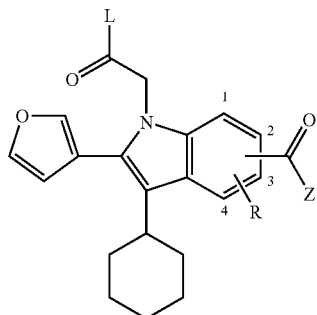

in the following table the index i indicates the position of the group —CO—Z and the
index j indicates the position of the group R within the phenyl-ring.
The term Me denotes methyl and Ph denotes phenyl.

| Cpd. # | L | i | Z | j | R | IC₅₀ | m/z (M + H)⁺ |
|---|---|---|---|---|---|---|---|
| 7032 | pyrrolidine-piperidine | 3 | HN-CH₂-CH₂-phenyl-SO₂NH₂ | — | — | A | 686.5 |
| 7033 | pyrrolidine-piperidine | 3 | N(Me)₂ | — | — | A | 531.4 |
| 7034 | pyrrolidine-piperidine | 3 | NHMe | — | — | A | 517.4 |
| 7035 | pyrrolidine-piperidine | 3 | piperidine-C(O)NH₂ | — | — | A | 614.5 |

TABLE 7-continued

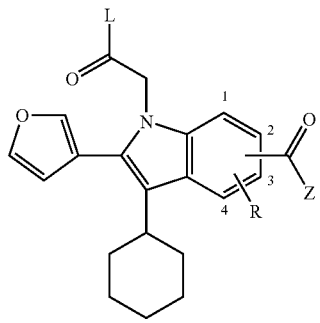

in the following table the index i indicates the position of the group —CO—Z and the
index j indicates the position of the group R within the phenyl-ring.
The term Me denotes methyl and Ph denotes phenyl.

| Cpd. # | L | i | Z | j | R | IC$_{50}$ | m/z (M + H)$^+$ |
|---|---|---|---|---|---|---|---|
| 7036 | (1-(pyrrolidin-1-yl)piperidin-4-yl) | 3 | (2-chloro-6-fluorobenzyl)amino | — | — | A | 645.4 |
| 7037 | (1-(pyrrolidin-1-yl)piperidin-4-yl) | 3 | (biphenyl-3-yl)amino | — | — | A | 655.5 |
| 7038 | (1-(pyrrolidin-1-yl)piperidin-4-yl) | 3 | (2-((2-chloro-6-fluorobenzyl)thio)ethyl)amino | — | — | A | 705.4 |
| 7039 | (1-(pyrrolidin-1-yl)piperidin-4-yl) | 3 | (3-acetamidopyrrolidin-1-yl) | — | — | A | 614.5 |

TABLE 7-continued

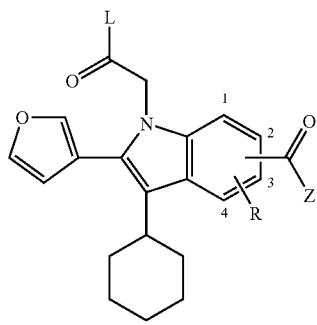

in the following table the index i indicates the position of the group —CO—Z and the index j indicates the position of the group R within the phenyl-ring.

The term Me denotes methyl and Ph denotes phenyl.

| Cpd. # | L | i | Z | j | R | IC$_{50}$ | m/z (M + H)$^+$ |
|---|---|---|---|---|---|---|---|
| 7040 | pyrrolidinyl-piperidine | 3 | N-benzylpyrrolidin-3-ylamino | — | — | A | 662.5 |
| 7041 | pyrrolidinyl-piperidine | 3 | 4-hydroxycyclohexylamino | — | — | A | 601.5 |
| 7042 | pyrrolidinyl-piperidine | 3 | 4-fluoro-3-(trifluoromethyl)benzylamino | — | — | A | 679.4 |

TABLE 7-continued

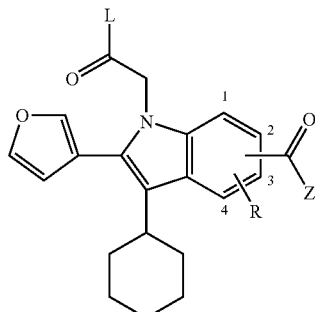

in the following table the index i indicates the position of the group —CO—Z and the index j indicates the position of the group R within the phenyl-ring.
The term Me denotes methyl and Ph denotes phenyl.

| Cpd. # | L | i | Z | j | R | IC$_{50}$ | m/z (M + H)$^+$ |
|---|---|---|---|---|---|---|---|
| 7043 | 4-(pyrrolidin-1-yl)piperidine | 3 | 2-((2-(hydroxymethyl)phenylthio)phenyl)methylamino | — | — | A | 731.5 |
| 7044 | 4-(pyrrolidin-1-yl)piperidine | 3 | 2-(2-oxoimidazolidin-1-yl)ethylamino | — | — | A | 615.5 |
| 7045 | 4-(pyrrolidin-1-yl)piperidine | 3 | 4-(carboxy)benzylamino | — | — | A | 637.5 |
| 7046 | 4-(pyrrolidin-1-yl)piperidine | 3 | (S)-1-carbamoyl-3-methylbutylamino | — | — | A | 616.5 |

TABLE 7-continued

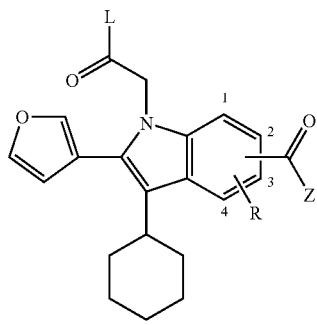

in the following table the index i indicates the position of the group —CO—Z and the
index j indicates the position of the group R within the phenyl-ring.
The term Me denotes methyl and Ph denotes phenyl.

| Cpd. # | L | i | Z | j | R | $IC_{50}$ | m/z $(M + H)^+$ |
|---|---|---|---|---|---|---|---|
| 7047 | (pyrrolidin-1-yl-piperidin-4-yl) | 3 | (HN-C(Me)₂-C(O)-O-tBu) | — | — | A | 645.5 |
| 7048 | (pyrrolidin-1-yl-piperidin-4-yl) | 3 | (HN-phenyl-furan-CO-OH, Me) | — | — | A | 703.5 |
| 7049 | (pyrrolidin-1-yl-piperidin-4-yl) | 3 | (NH-CH(Ph)-CH₂-OH) | — | — | A | 637.5 |

TABLE 7-continued

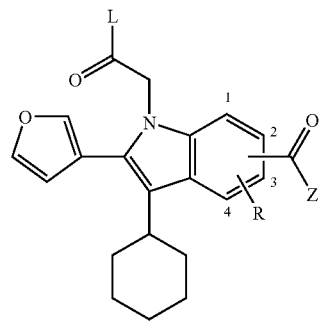

in the following table the index i indicates the position of the group —CO—Z and the
index j indicates the position of the group R within the phenyl-ring.
The term Me denotes methyl and Ph denotes phenyl.

| Cpd. # | L | i | Z | j | R | IC$_{50}$ | m/z (M + H)$^+$ |
|---|---|---|---|---|---|---|---|
| 7050 | (pyrrolidinyl-piperidinyl) | 3 | (cyclopentyl with NH and OBn) | — | — | A | 677.5 |
| 7051 | (pyrrolidinyl-piperidinyl) | 3 | (NH-CH(CF$_3$)-COOH) | — | — | A | 643.4 |
| 7052 | (pyrrolidinyl-piperidinyl) | 3 | (NH-CH$_2$-methylpyrazine) | — | — | A | 609.5 |
| 7053 | (pyrrolidinyl-piperidinyl) | 3 | (NH-tetramethylpiperidinyl) | — | — | B | 656.6 |

TABLE 7-continued

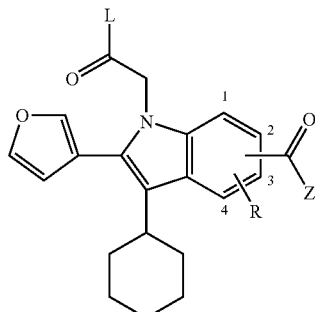

in the following table the index i indicates the position of the group —CO—Z and the
index j indicates the position of the group R within the phenyl-ring.
The term Me denotes methyl and Ph denotes phenyl.

| Cpd. # | L | i | Z | j | R | IC$_{50}$ | m/z (M + H)$^+$ |
|---|---|---|---|---|---|---|---|
| 7054 | pyrrolidine-piperidine | 3 | NH-CH₂-cyclohexyl-COOH | — | — | A | 643.5 |
| 7055 | pyrrolidine-piperidine | 3 | NH-phenyl-COOH | — | — | A | 637.5 |
| 7056 | pyrrolidine-piperidine | 3 | NH-phenyl-CH₂-COOH | — | — | A | 651.5 |
| 7057 | pyrrolidine-piperidine | 3 | NH-CH(CO₂Me)-CH₂-phenyl-OH | — | — | A | 681.5 |

TABLE 7-continued

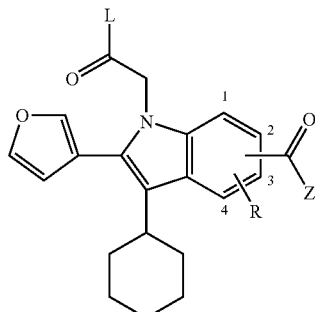

in the following table the index i indicates the position of the group —CO—Z and the index j indicates the position of the group R within the phenyl-ring.
The term Me denotes methyl and Ph denotes phenyl.

| Cpd. # | L | i | Z | j | R | IC$_{50}$ | m/z (M + H)$^+$ |
|---|---|---|---|---|---|---|---|
| 7058 | pyrrolidine-piperidine | 3 | —NH$_2$ | — | — | A | 503.3 |
| 7059 | pyrrolidine-piperidine | 3 | —NH-CH$_2$CH$_2$-O-CH$_2$CH$_2$-OH | — | — | A | 591.4 |
| 7060 | pyrrolidine-piperidine | 3 | methyl ester of 4-chlorophenylalanine | — | — | A | 699.4 |
| 7061 | pyrrolidine-piperidine | 3 | tert-butyl tetrahydroisoquinoline carboxamide | — | — | A | 718.5 |

TABLE 7-continued

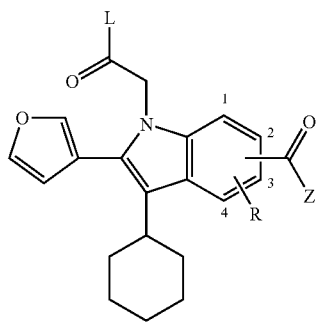

in the following table the index i indicates the position of the group —CO—Z and the
index j indicates the position of the group R within the phenyl-ring.
The term Me denotes methyl and Ph denotes phenyl.

| Cpd. # | L | i | Z | j | R | IC$_{50}$ | m/z (M + H)$^+$ |
|---|---|---|---|---|---|---|---|
| 7062 | pyrrolidine-piperidine | 3 | 1-(cyclobutyl)carboxamide-phenyl-CH=CH-COOH | — | — | A | 746.5 |
| 7063 | pyrrolidine-piperidine | 3 | NHSO$_2$Ph | — | — | A | 643.3 |
| 7064 | morpholine | 3 | OH | — | — | | |
| 7065 | morpholine | 3 | NHSO$_2$Ph | — | — | | |
| 7066 | morpholine | 2 | OH | 3 | OH | | |

TABLE 7-continued

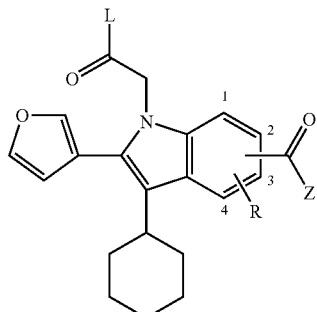

in the following table the index i indicates the position of the group —CO—Z and the index j indicates the position of the group R within the phenyl-ring.
The term Me denotes methyl and Ph denotes phenyl.

| Cpd. # | L | i | Z | j | R | $IC_{50}$ | m/z $(M + H)^+$ |
|---|---|---|---|---|---|---|---|
| 7067 | morpholine | 2 | OH | 3 | OMe | | |
| 7068 | morpholine | 2 | OH | 3 | O—CH$_2$-Ph | | |
| 7069 | morpholine | 2 | NHSO$_2$Ph | 3 | OH | | |
| 7070 | morpholine | 2 | NHSO$_2$Ph | 3 | OMe | | |
| 7071 | morpholine | 2 | NHSO$_2$Ph | 3 | O—CH$_2$-Ph | | |
| 7072 | morpholine | 2 | OH | 4 | OH | | |
| 7073 | morpholine | 2 | OH | 4 | OMe | | |

TABLE 7-continued

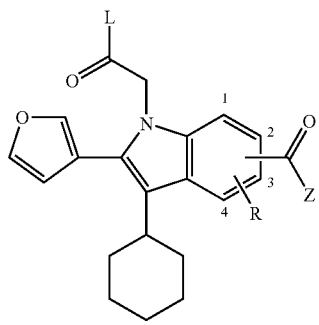

in the following table the index i indicates the position of the group —CO—Z and the index j indicates the position of the group R within the phenyl-ring.
The term Me denotes methyl and Ph denotes phenyl.

| Cpd. # | L | i | Z | j | R | IC$_{50}$ | m/z (M + H)$^+$ |
|---|---|---|---|---|---|---|---|
| 7074 | morpholine-N-CH< | 2 | OH | 4 | NH$_2$ | | |
| 7075 | morpholine-N-CH< | 2 | OH | 4 | NHCOMe | | |
| 7076 | morpholine-N-CH< | 2 | OH | 4 | Cl | | |
| 7077 | morpholine-N-CH< | 2 | OH | 4 | F | | |
| 7078 | morpholine-N-CH< | 2 | OH | 4 | Me | | |
| 7079 | morpholine-N-CH< | 2 | NHSO$_2$Ph | 4 | OH | | |
| 7080 | morpholine-N-CH< | 2 | NHSO$_2$Ph | 4 | OMe | | |

TABLE 7-continued

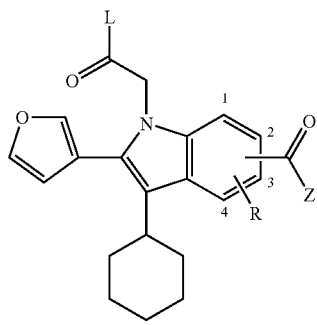

in the following table the index i indicates the position of the group —CO—Z and the index j indicates the position of the group R within the phenyl-ring.
The term Me denotes methyl and Ph denotes phenyl.

| Cpd. # | L | i | Z | j | R | IC$_{50}$ | m/z (M + H)$^+$ |
|---|---|---|---|---|---|---|---|
| 7081 | morpholine | 2 | NHSO$_2$Ph | 4 | NH$_2$ | | |
| 7082 | morpholine | 2 | NHSO$_2$Ph | 4 | NHCOMe | | |
| 7083 | morpholine | 2 | NHSO$_2$Ph | 4 | Cl | | |
| 7084 | morpholine | 2 | NHSO$_2$Ph | 4 | F | | |
| 7085 | morpholine | 2 | NHSO$_2$Ph | 4 | Me | | |
| 7086 | morpholine | 2 | OH | 1 | Me | | |
| 7087 | morpholine | 2 | OH | 1 | OH | | |

TABLE 7-continued

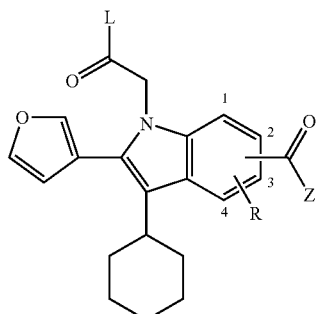

in the following table the index i indicates the position of the group —CO—Z and the index j indicates the position of the group R within the phenyl-ring.
The term Me denotes methyl and Ph denotes phenyl.

| Cpd. # | L | i | Z | j | R | IC$_{50}$ | m/z (M + H)$^+$ |
|---|---|---|---|---|---|---|---|
| 7088 | morpholine-N-CH< | 2 | OH | 1 | OMe | | |
| 7089 | morpholine-N-CH< | 2 | OH | 1 | Cl | | |
| 7090 | morpholine-N-CH< | 2 | OH | 1 | F | | |
| 7091 | morpholine-N-CH< | 2 | OH | 1 | COOH | | |
| 7092 | morpholine-N-CH< | 2 | OH | 1 | CONH$_2$ | | |
| 7093 | morpholine-N-CH< | 2 | OH | 1 | CONHMe | | |
| 7094 | morpholine-N-CH< | 2 | OH | 1 | CONHCH$_2$Ph | | |

TABLE 7-continued

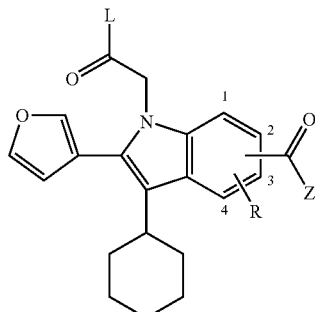

in the following table the index i indicates the position of the group —CO—Z and the
index j indicates the position of the group R within the phenyl-ring.
The term Me denotes methyl and Ph denotes phenyl.

| Cpd. # | L | i | Z | j | R | IC$_{50}$ | m/z (M + H)$^+$ |
|---|---|---|---|---|---|---|---|
| 7095 | morpholine | 2 | OH | 1 | NH$_2$ | | |
| 7096 | morpholine | 2 | OH | 1 | NHCONHMe | | |
| 7097 | morpholine | 2 | OH | 1 | NMe$_2$ | | |
| 7098 | morpholine | 2 | OH | 1 | NHCOMe | | |
| 7099 | morpholine | 2 | OH | 1 | NHCOCH$_2$Ph | | |
| 7100 | morpholine | 2 | OH | 1 | NHCONH$_2$ | | |
| 7101 | morpholine | 2 | NHSO$_2$Ph | 1 | Me | | |

TABLE 7-continued

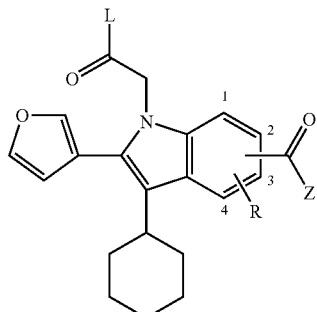

in the following table the index i indicates the position of the group —CO—Z and the index j indicates the position of the group R within the phenyl-ring.
The term Me denotes methyl and Ph denotes phenyl.

| Cpd. # | L | i | Z | j | R | $IC_{50}$ | m/z $(M + H)^+$ |
|---|---|---|---|---|---|---|---|
| 7102 | morpholine | 2 | NHSO₂Ph | 1 | OH | | |
| 7103 | morpholine | 2 | NHSO₂Ph | 1 | OMe | | |
| 7104 | morpholine | 2 | NHSO₂Ph | 1 | Cl | | |
| 7105 | morpholine | 2 | NHSO₂Ph | 1 | F | | |
| 7106 | morpholine | 2 | NHSO₂Ph | 1 | COOH | | |
| 7107 | morpholine | 2 | NHSO₂Ph | 1 | CONH₂ | | |
| 7108 | morpholine | 2 | NHSO₂Ph | 1 | CONHMe | | |

TABLE 7-continued

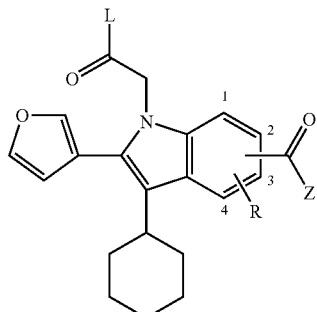

in the following table the index i indicates the position of the group —CO—Z and the
index j indicates the position of the group R within the phenyl-ring.
The term Me denotes methyl and Ph denotes phenyl.

| Cpd. # | L | i | Z | j | R | IC$_{50}$ | m/z (M + H)$^+$ |
|---|---|---|---|---|---|---|---|
| 7109 | morpholine | 2 | NHSO$_2$Ph | 1 | CONHCH$_2$Ph | | |
| 7110 | morpholine | 2 | NHSO$_2$Ph | 1 | NH$_2$ | | |
| 7111 | morpholine | 2 | NHSO$_2$Ph | 1 | NHCONHMe | | |
| 7112 | morpholine | 2 | NHSO$_2$Ph | 1 | NMe$_2$ | | |
| 7113 | morpholine | 2 | NHSO$_2$Ph | 1 | NHCOMe | | |
| 7114 | morpholine | 2 | NHSO$_2$Ph | 1 | NHCOCH$_2$Ph | | |
| 7115 | morpholine | 2 | NHSO$_2$Ph | 1 | NHCONH$_2$ | | |

TABLE 8

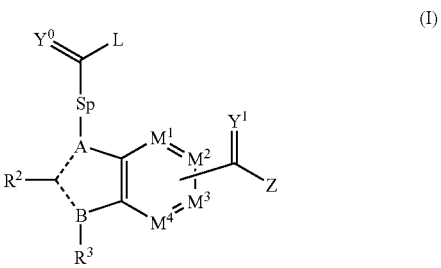

| Cpd. # | L | Z |
|---|---|---|
| 8001 | -N(CH3)2 (dimethylamino) | -OH |
| 8002 | morpholino | -OH |
| 8003 | 4-pyrrolidin-1-yl-piperidin-1-yl | -OH |
| 8004 | -N(CH3)2 (dimethylamino) | -NHSO2Ph |
| 8005 | morpholino | -NHSO2Ph |
| 8006 | 4-pyrrolidin-1-yl-piperidin-1-yl | -NHSO2Ph |

The invention claimed is:

1. An enantiomer, diastereoisomer or tautomer of a compound, represented by formula I:

(I)

wherein:
either A or B is N and the other B or A is C, wherein ----- between two C-atoms represents a double bond and ----- between a C-atom and a N-atom represents a single bond,
the group —C(=$Y^1$)—Z is covalently linked to either $M^2$ or $M^3$,
$M^1$ is $CR^{4a}$,
$M^2$ or $M^3$, when not linked to —C(=$Y^1$)—Z, is $CR^5$,
$M^4$ is $CR^{4b}$,
and in addition one or two of the groups selected from $M^1$, $M^2$, $M^3$ and $M^4$ may also be N, with the proviso that the group $M^2$ or $M^3$ to which —C(=$Y^1$)—Z is linked is an C-atom,
Sp is a spacer group selected from —$(CR^{51}R^{52})_{k1}$—, wherein
k1 is 1, 2 or 3;
$R^{51}$, $R^{52}$ are independently H, $(C_{1-6})$alkyl, $(C_{3-7})$cycloalkyl or $(C_{1-3})$alkyl-$(C_{3-7})$cycloalkyl, or
$R^{51}$ and $R^{52}$ are covalently bonded together and to the carbon-atom to which they are attached to form a 3, 4, 5, 6 or 7-membered saturated or 5, 6 or 7-membered unsaturated cyclic system whereby the 5, 6 or 7-membered saturated or unsaturated cyclic system may contain 1 to 3 heteroatoms selected from N, O or S;
said alkyl, cycloalkyl, alkyl-cycloalkyl or cyclic system being optionally substituted by halogen, hydroxy, $(C_{1-6})$alkoxy, cyano, amino, —NH$(C_{1-4}$-alkyl) and/or —N$(C_{1-4}$-alkyl)$_2$;
$Y^0$ is O, S, $NR^{11}$ or $CR^{12}R^{13}$, wherein
$R^{11}$, $R^{12}$, $R^{13}$ are each independently defined as $R^O$;
$R^{13}$ may also be $COOR^O$ or $SO_2R^C$;
wherein $R^C$ and each $R^O$ is optionally substituted with $R^{150}$;
or both $R^{12}$ and $R^{13}$ are covalently bonded together and to the carbon-atom to which they are attached to form a 3, 4, 5, 6 or 7-membered saturated or 5, 6 or 7-membered unsaturated cyclic system whereby the 5, 6 or 7-membered saturated or unsaturated cyclic system may contain 1 to 3 heteroatoms selected from N, O or S; said cyclic systems being optionally substituted with $R^{150}$;
L is Het, $(C_{1-6})$alkyl-Het, all of which being optionally substituted with $R^{60}$;
$Y^1$ is O, S or $NR^{14}$, wherein $R^{14}$ is H or $(C_{1-6})$ alkyl;
Z is defined as
a) $OR^O$;
b) $SO_2R^C$;
c) $N(R^{N2})R^{N1}$;
d) $NR^{N3}$—$N(R^{N2})R^{N1}$;

e) $NR^{N3}-NR^{N2}-CO-R^C$;

f) $NR^{N4}-NR^{N3}-CO-N(R^{N2})R^{N1}$;

g) $NR^{N2}-SO_2-R^C$ or h) $NR^{N3}-SO_2-N(R^{N2})R^{N1}$;

i) $NR^{N2}-CO-R^C$;

j) $COOR^O$;

k) $N(R^{N1})OR^O$;

wherein $R^O$ and $R^C$ are optionally substituted with $R^{60}$; and said $R^{N1}$, including any heterocycle or heterobicycle formed by $R^{N1}$, $R^{N2}$, and/or $R^{N3}$, being optionally substituted with $R^{60}$;

or Z is $OR^{6b}$ or $N(R^{5b})R^{6b}$ wherein $R^{5b}$ is defined as $R^{N2}$ and $R^{6b}$ is:

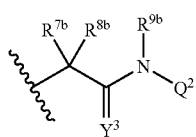

or $R^{6b}$ is:

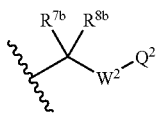

wherein $R^{7b}$, $R^{8b}$ are each independently defined as $R^O$, $COOR^O$ or $CON(R^{N2})R^{N1}$, wherein said $R^O$ is optionally substituted with $R^{60}$ or $R^{7b}$ and $R^{8b}$ are covalently bonded together to form a $(C_{3-7})$cycloalkyl or a 4, 5- or 6-membered heterocycle having from 1 to 3 heteroatom selected from O, N, and S; wherein said cycloalkyl or heterocycle being optionally substituted by $R^{150}$; and $W^2$ is selected from a) a single bond;

b) $-CH_2-$;

c) $-CH_2-CH_2-$; and d) $-CH=CH-$;

wherein the alkylene and alkenylene groups according to b), c) and d) may be substituted with $(C_{1-3})$ alkyl;

$Y^3$ is O or S;

$R^{9b}$ is defined as $R^O$, wherein said $R^O$ is optionally substituted with $R^{60}$; and $Q^2$ is aryl, Het, $(C_{1-6})$ alkyl-aryl, $(C_{1-6})$ alkyl-Het, $(C_{1-6})$ alkyl-CONH-aryl or $(C_{1-6})$ alkyl-CONH-Het, all of which being or $Q^2$ is $R^{160}$ or $Q^2$ is selected from the group consisting of $O-C_{1-4}$-alkyl, $S-C_{1-4}$-alkyl, $C_{1-4}$-alkyl, $C_{2-4}$-alkenyl and $C_{2-4}$-alkynyl, all of which being optionally substituted with $R^{160}$; and $R^2$ is selected from:

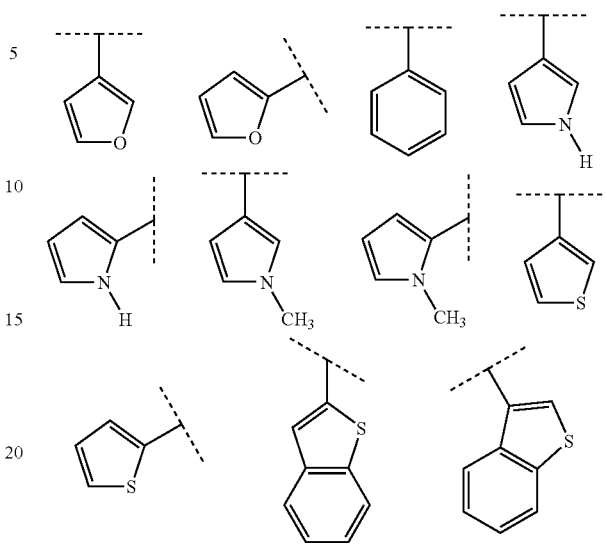

optionally substituted with $R^{150}$;

$R^3$ is selected from $(C_{1-6})$alkyl, $(C_{3-7})$cycloalkyl, $(C_{1-3})$alkyl-$(C_{3-7})$cycloalkyl, $(C_{5-7})$cycloalkenyl, $(C_{1-3})$alkyl-$(C_{5-7})$cycloalkenyl, $(C_{6-10})$bicycloalkyl, $(C_{1-3})$alkyl-$(C_{6-10})$bicycloalkyl, $(C_{6-10})$bicycloalkenyl, $(C_{1-3})$alkyl-$(C_{6-10})$bicycloalkenyl, HCy or $(C_{1-3})$alkyl-HCy, wherein HCy is a saturated or unsaturated 4 to 7-membered heterocyclic group with 1 to 3 heteroatoms selected from O, S and N;

said alkyl, cycloalkyl, cycloalkenyl, bicycloalkyl, bicycloalkenyl, HCy and alkyl-HCy being optionally substituted with from 1 to 4 substituents selected from: a) halogen;

b) $(C_{1-6})$alkyl optionally substituted with:

1 to 3 substituents selected from halogen;

$OR^{31}$ or $SR^{31}$ wherein $R^{31}$ is H, $(C_{1-6}$alkyl$)$, $(C_{3-7})$cycloalkyl or $(C_{1-3})$alkyl-$(C_{3-7})$cycloalkyl; or $N(R^{32})_2$ wherein each $R^{32}$ is independently H, $(C_{1-6})$alkyl, $(C_{3-7})$cycloalkyl or $(C_{1-3})$alkyl-$(C_{3-7})$cycloalkyl; or both $R^{32}$ are covalently bonded together and to the nitrogen to which they are attached to form a 5, 6 or 7-membered saturated heterocycle;

c) $OR^{33}$ or $SR^{33}$ wherein $R^{33}$ is H, $(C_{1-6})$alkyl, $(C_{3-7})$cycloalkyl or $(C_{1-3})$alkyl-$(C_{3-7})$cycloalkyl;

d) $N(R^{35})_2$ wherein each $R^{35}$ is independently H, $(C_{1-6})$alkyl, $(C_{3-7})$cycloalkyl or $(C_{1-3})$alkyl-$(C_{3-7})$cycloalkyl; or both $R^{35}$ are covalently bonded together and to the nitrogen to which they are attached to form a 5, 6 or 7-membered saturated heterocycle;

$R^{4a}$, $R^{4b}$, $R^5$ each are independently H or defined as $R^{150}$;

$R^{60}$ is each defined as 1 to 4 substituents independently selected from:

1 to 3 substituents selected from halogen;

one of each substituent selected from: $OPO_3H$, $NO_2$, cyano, azido, $C(=NH)NH_2$, $C(=NH)NH(C_{1-6})$alkyl or $C(=NH)NHCO(C_{1-6})$alkyl, $SO_3H$; and 1 to 3 substituents selected from:
a) $(C_{1-6})$ alkyl, $(C_{3-7})$cycloalkyl, $C_{3-7}$ spirocycloalkyl optionally containing 1 or 2 heteroatoms selected from N, O and S; $(C_{2-6})$alkenyl, $(C_{2-8})$alkynyl, $(C_{1-6})$ alkyl-$(C_{3-7})$cycloalkyl, all of which optionally being substituted with $R^{150}$;
b) $OR^O$;
c) $OC(O)R^O$;
d) $SR^O$, $SO_2R^C$, $SO_2N(R^{N2})R^{N1}$, $SO_2N(R^{N2})C(O)R^C$, $CONR^{N3}SO_2N(R^{N2})R^{N1}$, or $CONR^{N2}SO_2R^C$;
e) $N(R^{N2})R^{N1}$, $N(R^{N2})COOR^C$, $N(R^{N2})SO_2R^C$ or $N(R^{N1})R^O$;
f) $N(R^{N2})COR^C$;
g) $N(R^{N3})CON(R^{N2})R^{N1}$;
h) $N(R^{N3})COCOR^C$, $N(R^{N3})COCOOR^O$ or $N(R^{N3})CO\text{-}CON(R^{N2})R^{N1}$;
i) $COR^O$;
j) $COOR^O$;
k) $CON(R^{N2})R^{N1}$;
l) aryl, Het, $(C_{1-4}\text{alkyl})$aryl or $(C_{1-4}\text{alkyl})$Het, all of which optionally being substituted with $R^{150}$;
wherein said $R^{N1}$, $R^C$ and $R^O$ are each independently optionally substituted with $R^{150}$ as defined,
$R^{150}$ is each defined as 1 to 4 substituents independently selected from:
1 to 3 substituents selected from halogen;
one of each substituent selected from: $OPO_3H$, $NO_2$, cyano, azido, $C(=NH)NH_2$, $C(=NH)NH(C_{1-6})$alkyl or $C(=NH)NHCO(C_{1-6})$alkyl; and
1 to 3 substituents selected from:
a) $(C_{1-6})$ alkyl, $(C_{3-7})$cycloalkyl, $C_{3-7}$ spirocycloalkyl optionally containing 1 or 2 heteroatoms selected from N, O and S; $(C_{2-6})$alkenyl, $(C_{2-8})$alkynyl, $(C_{1-3})$ alkyl-$(C_{3-7})$cycloalkyl, all of which optionally substituted with $R^{160}$;
b) $OR^O$;
c) $OC(O)R^O$;
d) $SR^O$, $SO_2R^C$, $SO_2N(R^{N2})R^{N1}$, $SO_2N(R^{N2})C(O)R^C$ or $CON(R^{N2})SO_2R^C$;
e) $N(R^{N2})R^{N1}$, $N(R^{N2})COOR^C$, $N(R^{N2})SO_2R^C$, or $N(R^{N1})R^O$;
f) $N(R^{N2})COR^C$;
g) $N(R^{N3})CON(R^{N2})R^{N1}$;
h) $N(R^{N3})COCOR^C$, $N(R^{N3})COCOOR^O$, $N(R^{N3})CO\text{-}CON(R^{N2})OH$, $N(R^{N3})COCON(R^{N2})OC_{1-4}$-alkyl or $N(R^{N3})COCON(R^{N2})R^{N1}$;
i) $COR^O$;
j) $COOR^O$;
k) tetrazole, triazole, $CONR^{N3}\text{-}SO_2N(R^{N2})R^{N1}$; or $CON(R^{N2})R^{N1}$;
wherein said $R^{N1}$, $R^C$ and/or $R^O$ are optionally substituted with $R^{160}$ as defined;
$R^{160}$ is each defined as 1, 2 or 3 substituents independently selected from:
1, 2 or 3 fluorine substituents; and
one of each substituent selected from tetrazole, triazole, chlorine, bromine, iodine, CN, nitro, $C_{1-4}$alkyl, $CF_3$, $COOR^{161}$, $SO_3H$, $SR^{161}$, $SCF_3$, $SO_2R^{163}$, $OR^{161}$, $OCF_3$, $N(R^{162})_2$, $SO_2N(R^{162})_2$, $NR^{162}SO_2R^C$, $NR^{162}COR^{162}$, $CON(R^{162})_2$, $-NR^{161}\text{-}CO\text{-}COOR^{161}$, $-NR^{161}\text{-}CO\text{-}CO(NR^{162})_2$, $-CONR^{161}SO_2R^C$, $CONR^{161}\text{-}SO_2N(R^{162})_2$ or $-SO_2\text{-}NR^{161}\text{-}COR^C$, wherein $R^{161}$, $R^{163}$ and each $R^{162}$ is independently $(C_{1-4})$alkyl, $(C_{3-7})$cycloalkyl or $(C_{1-3})$alkyl-$(C_{3-7})$cycloalkyl; and $R^{161}$ and each $R^{162}$ may each independently also be H; or both $R^{162}$ are covalently bonded together and to the nitrogen to which they are attached to form a 5, 6 or 7-membered saturated heterocycle;

$R^O$, $R^C$ are independently defined as $(C_{1-6})$alkyl, $(C_{3-6})$ cycloalkyl, $(C_{1-4})$alkyl-$(C_{3-6})$cycloalkyl, $(C_{2-6})$alkenyl, aryl, Het, $(C_{1-4})$alkyl-aryl and $(C_{1-4})$alkyl-Het; and $R^O$ may also be H;

$R^{N1}$ is independently selected from H, $(C_{1-6})$alkyl, $(C_{3-7})$ cycloalkyl, $(C_{1-4})$alkyl-$(C_{3-6})$cycloalkyl, $(C_{2-6})$alkenyl, aryl, Het, $(C_{1-4})$alkyl-aryl, $(C_{1-4})$alkyl-Het; or $R^{N2}$, $R^{N3}$, $R^{N4}$ are independently H, $CH_3$, $(C_{2-6})$alkyl, $(C_{3-6})$cycloalkyl, $(C_{1-4})$alkyl-$(C_{3-6})$cycloalkyl; wherein said alkyl, cycloalkyl or alkylcycloalkyl is optionally substituted with hydroxy, halogen, carboxy, $C_{1-6}$-alkoxycarbonyl, $C_{1-6}$-alkyl, $C_{1-6}$-alkoxy, amino, $-NH(C_{1-4}\text{-alkyl})$ and/or $-N(C_{1-4}\text{-alkyl})_2$; and wherein said $CH_3$ is optionally substituted with halogen, carboxy or $C_{1-6}$-alkoxycarbonyl; and in the case
a) of a group $N(R^{N2})R^{N1}$ the substituents $R^{N2}$ and $R^{N1}$; or
b) of a group $NR^{N3}\text{-}N(R^{N2})R^{N1}$ the substituents $R^{N3}$ and $R^{N1}$, or $R^{N2}$ and $R^{N1}$;

may be covalently bonded together to form a 4-, 5-, 6- or 7-membered saturated or unsaturated N-containing heterocycle or a 8-, 9-, 10- or 11-membered N-containing heterobicycle each may have additionally from 1 to 3 heteroatoms selected from O, N, and S;

wherein Het is defined as a 4-, 5-, 6- or 7-membered heterocycle having 1 to 4 heteroatoms selected from O, N and S, or a 8-, 9-, 10- or 11-membered heterobicycle having 1 to 5 heteroatoms selected from O, N and S;

or a salt thereof.

2. The compound according to claim 1 wherein:
either A or B is N and the other B or A is C, wherein ----- between two C-atoms represents a double bond and ----- between a C-atom and a N-atom represents a single bond,
the group $-C(=Y^1)-Z$ is covalently linked to either $M^2$ or $M^3$,
$M^1$ is $CR^{4a}$,
$M^2$ or $M^3$ is $CR^5$,
$M^4$ is $CR^{4b}$,
and in addition one or two of the groups selected from $M^1$, $M^2$, $M^3$ and $M^4$ may also be N, with the proviso that the group $M^2$ or $M^3$ to which $-C(=Y^1)-Z$ is linked is an C-atom,
Sp is a spacer group selected from $-(CR^{51}R^{52})_{k1}-$, wherein
k1 is 1, 2 or 3;
$R^{51}$, $R^{52}$ are independently H, $(C_{1-6})$alkyl, $(C_{3-7})$cycloalkyl or $(C_{1-3})$alkyl-$(C_{3-7})$cycloalkyl, or
$R^{51}$ and $R^{52}$ are covalently bonded together and to the carbon-atom to which they are attached to form a $(C_{3-6})$cycloalkyl group,
said alkyl, cycloalkyls or alkyl-cycloalkyl being optionally substituted by halogen, hydroxy, $(C_{1-6})$alkoxy, cyano, amino, $-NH(C_{1-4}\text{-alkyl})$ and/or $-N(C_{1-4}\text{-alkyl})_2$;
$Y^0$ is O, S, $NR^{11}$ or $CR^{12}R^{13}$, wherein
$R^{11}$, $R^{12}$, $R^{13}$ are each independently defined as $R^O$;
$R^{13}$ may also be $COOR^O$ or $SO_2R^C$;
wherein $R^C$ and each $R^O$ is optionally substituted with $R^{150}$;
or both $R^{12}$ and $R^{13}$ are covalently bonded together and to the carbon-atom to which they are attached to form a 3, 4, 5, 6 or 7-membered saturated or 5, 6 or 7-membered unsaturated cyclic system whereby the 5, 6 or 7-membered saturated or unsaturated cyclic system may contain 1 to 3 heteroatoms selected from N, O or S; said cyclic systems being optionally substituted with $R^{150}$;

L is Het or $(C_{1-6})$alkyl-Het, all of which being optionally substituted with $R^{60}$;

$Y^1$ is O, S or $NR^{14}$, wherein $R^{14}$ is H or $(C_{1-6})$ alkyl;

Z is defined as
- a) $OR^O$;
- b) $SO_2R^C$;
- c) $N(R^{N2})R^{N1}$;
- d) $NR^{N3}$—$N(R^{N2})R^{N1}$;
- e) $NR^{N3}$—$NR^{N2}$—CO—$R^O$;
- f) $NR^{N4}$—$NR^{N3}$—CO—$N(R^{N2})R^{N1}$;
- g) $NR^{N2}$—$SO_2$—$R^O$ or
- h) $NR^{N2}$—CO—$R^O$;
- i) $COOR^O$;
- j) $N(R^{N1})OR^O$;

wherein $R^O$ and $R^C$ are optionally substituted with $R^{60}$; and said $R^{N1}$, including any heterocycle or heterobicycle formed by $R^{N1}$, $R^{N2}$, and/or $R^{N3}$, being optionally substituted with $R^{60}$;

or Z is $OR^{6b}$ or $N(R^{5b})R^{6b}$ wherein $R^{5b}$ is defined as $R^{N2}$ and $R^{6b}$ is:

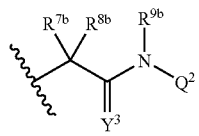

wherein $R^{7b}$, $R^{8b}$ are each independently defined as $R^O$, wherein said $R^O$ is optionally substituted with $R^{60}$; or $R^{7b}$ and $R^{8b}$ are covalently bonded together to form a $(C_{3-7})$cycloalkyl; wherein said cycloalkyl being optionally substituted by $R^{150}$; and $Y^3$ is O or S;

$R^{9b}$ is defined as $R^O$, wherein said $R^O$ is optionally substituted with $R^{60}$; and $Q^2$ is aryl, $(C_{1-6})$ alkyl-aryl or $(C_{1-6})$ alkyl-CONH-aryl, all of which being optionally substituted with $R^{60}$;

$R^2$ is selected from

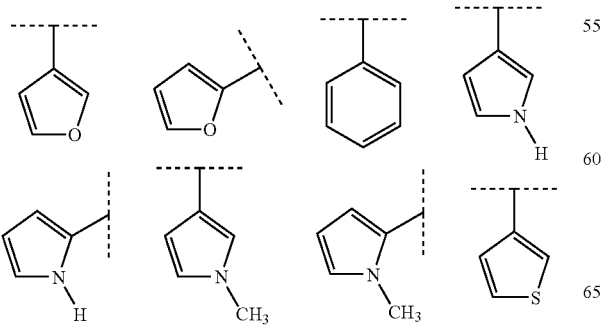

optionally substituted by $R^{150}$;

$R^3$ is selected from $(C_{1-6})$alkyl, $(C_{3-7})$cycloalkyl, $(C_{1-3})$ alkyl-$(C_{3-7})$cycloalkyl, $(C_{5-7})$cycloalkenyl, $(C_{1-3})$alkyl-$(C_{5-7})$cycloalkenyl, $(C_{6-10})$bicycloalkyl, $(C_{1-3})$alkyl-$(C_{6-10})$bicycloalkyl, $(C_{6-10})$bicycloalkenyl, $(C_{1-3})$alkyl-$(C_{6-10})$bicycloalkenyl, HCy or $(C_{1-3})$alkyl-HCy, wherein HCy is a saturated or unsaturated 4 to 7-membered heterocyclic group with 1 to 3 heteroatoms selected from O, S and N;

said alkyl, cycloalkyl, cycloalkenyl, bicycloalkyl, bicycloalkenyl, HCy and alkyl-HCy being optionally substituted with from 1 to 4 substituents selected from: a) halogen;

b) $(C_{1-6})$alkyl optionally substituted with:
  $OR^{31}$ or $SR^{31}$ wherein $R^{31}$ is H, $(C_{1-6}$alkyl), $(C_{3-7})$cycloalkyl or $(C_{1-3})$alkyl-$(C_{3-7})$cycloalkyl; or
  $N(R^{32})_2$ wherein each $R^{32}$ is independently H, $(C_{1-6})$alkyl, $(C_{3-7})$cycloalkyl or $(C_{1-3})$alkyl-$(C_{3-7})$cycloalkyl; or both $R^{32}$ are covalently bonded together and to the nitrogen to which they are attached to form a 5, 6 or 7-membered saturated heterocycle;

c) $OR^{33}$ or $SR^{33}$ wherein $R^{33}$ is H, $(C_{1-6})$alkyl, $(C_{3-7})$cycloalkyl or $(C_{1-3})$alkyl-$(C_{3-7})$cycloalkyl;

d) $N(R^{35})_2$ wherein each $R^{35}$ is independently H, $(C_{1-6})$alkyl, $(C_{3-7})$cycloalkyl or $(C_{1-3})$alkyl-$(C_{3-7})$cycloalkyl; or both $R^{35}$ are covalently bonded together and to the nitrogen to which they are attached to form a 5, 6 or 7-membered saturated heterocycle;

$R^{4a}$, $R^{4b}$, $R^5$ each are independently H or defined as $R^{150}$;

$R^{60}$ is each defined as 1 to 4 substituents independently selected from:
  1 to 3 substituents selected from halogen;
  one of each substituent selected from: $OPO_3H$, $NO_2$, cyano, azido, C(=NH)$NH_2$, C(=NH)NH$(C_{1-6})$alkyl or C(=NH)NHCO$(C_{1-6})$alkyl, $SO_3H$; and
  1 to 3 substituents selected from:
  a) $(C_{1-6})$ alkyl, $(C_{3-7})$cycloalkyl, $C_{3-7}$ spirocycloalkyl optionally containing 1 or 2 heteroatoms selected from N, O and S; $(C_{2-6})$alkenyl, $(C_{2-8})$alkynyl, $(C_{1-6})$alkyl-$(C_{3-7})$cycloalkyl, all of which optionally being substituted with $R^{150}$;
  b) $OR^O$;
  c) $OC(O)R^O$;
  d) $SR^O$, $SO_2R^C$, $SO_2N(R^{N2})R^{N1}$, $SO_2N(R^{N2})C(O)R^C$ or $CONR^{N2}SO_2R^C$;
  e) $N(R^{N2})R^{N1}$, $N(R^{N2})COOR^C$, or $N(R^{N2})SO_2R^C$;
  f) $N(R^{N2})COR^C$;
  g) $N(R^{N3})CON(R^{N2})R^{N1}$;
  h) $N(R^{N3})COCOR^C$, $N(R^{N3})COCOOR^O$ or $N(R^{N3})CO-CON(R^{N2})R^{N1}$;
  i) $COR^O$;
  j) $COOR^O$;

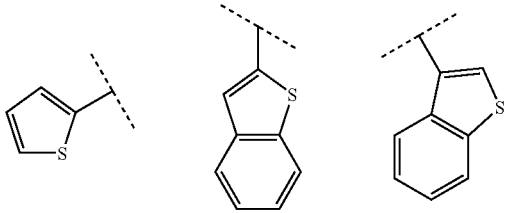

k) CON(R^{N2})R^{N1};

l) aryl, Het, (C_{1-4}alkyl)aryl or (C_{1-4}alkyl)Het, all of which optionally being substituted with R^{150};

wherein said R^{N1}, R^{C} and R^{O} are each independently optionally substituted with R^{150} as defined, R^{150} is each defined as 1 to 4 substituents independently selected from:
1 to 3 substituents selected from halogen;
one of each substituent selected from: OPO_{3}H, NO_{2}, cyano, azido, C(=NH)NH_{2}, C(=NH)NH(C_{1-6})alkyl or C(=NH)NHCO(C_{1-6})alkyl; and
1 to 3 substituents selected from:
a) (C_{1-6}) alkyl, (C_{3-7})cycloalkyl, C_{3-7} spirocycloalkyl optionally containing 1 or 2 heteroatoms selected from N, O and S; (C_{2-6})alkenyl, (C_{2-8})alkynyl, (C_{1-3}) alkyl-(C_{3-7})cycloalkyl, all of which optionally substituted with R^{160};
b) OR^{O};
c) OC(O)R^{O};
d) SR^{O}, SO_{2}R^{C}, SO_{2}N(R^{N2})R^{N1}, SO_{2}N(R^{N2})C(O)R^{C} or CON(R^{N2})SO_{2}R^{C};
e) N(R^{N2})R^{N1}, N(R^{N2})COOR^{C}, or N(R^{N2})SO_{2}R^{C};
f) N(R^{N2})COR^{C};
g) N(R^{N3})CON(R^{N2})R^{N1};
h) N(R^{N3})COCOR^{C}, N(R^{N3})COCOOR^{O} or N(R^{N3})CO-CON(R^{N2})R^{N1}; wherein R^{N1} is as defined or OH, O—C_{1-4}-alkyl;
i) COR^{O};
j) COOR^{O};
k) tetrazole or CON(R^{N2})R^{N1};
wherein said R^{N1}, R^{C} and/or R^{O} are optionally substituted with R^{160} as defined;

R^{160} is each defined as 1, 2 or 3 substituents independently selected from:
1, 2 or 3 fluorine substituents; and
one of each substituent selected from tetrazole, chlorine, bromine, iodine, CN, nitro, C_{1-4}alkyl, CF_{3}, COOR^{161}, SO_{3}H, SR^{161}, SO_{2}R^{163}, OR^{161}, N(R^{162})_{2}, SO_{2}N(R^{162})_{2}, SO_{2}NR^{162}COR^{162}, NR^{162}SO_{2}R^{163}, NR^{162}COR^{162}, or CON(R^{162})_{2}, wherein R^{161}, R^{163} and each R^{162} is independently (C_{1-4})alkyl, (C_{3-7}) cycloalkyl or (C_{1-3})alkyl-(C_{3-7})cycloalkyl; and R^{161} and each R^{162} may each independently also be H; or both R^{162} are covalently bonded together and to the nitrogen to which they are attached to form a 5, 6 or 7-membered saturated heterocycle;

R^{O}, R^{C} are independently defined as (C_{1-6})alkyl, (C_{3-6}) cycloalkyl, (C_{1-4})alkyl-(C_{3-6})cycloalkyl, (C_{2-6})alkenyl, aryl, Het, (C_{1-4})alkyl-aryl and (C_{1-4})alkyl-Het; and R^{O} may also be H;

R^{N1} is independently selected from H, (C_{1-6})alkyl, (C_{3-7}) cycloalkyl, (C_{1-4})alkyl-(C_{3-6})cycloalkyl, (C_{2-6})alkenyl, aryl, Het, (C_{1-4})alkyl-aryl, (C_{1-4})alkyl-Het; or R^{N2}, R^{N3}, R^{N4} are independently H, CH_{3}, (C_{2-6}alkyl), (C_{3-6})cycloalkyl, (C_{1-4})alkyl-(C_{3-6})cycloalkyl; wherein said alkyl, cycloalkyl or alkylcycloalkyl is optionally substituted with hydroxy, halogen, carboxy, C_{1-6}-alkoxycarbonyl, C_{1-6}-alkyl, C_{1-6}-alkoxy, amino, —NH(C_{1-4}-alkyl) and/or —N(C_{1-4}-alkyl)_{2}; and wherein said CH_{3} is optionally substituted with halogen, carboxy or C_{1-6}-alkoxycarbonyl; and
in the case
a) of a group N(R^{N2})R^{N1} the substituents R^{N2} and R^{N1}; or
b) of a group NR^{N3}—N(R^{N2})R^{N1} the substituents R^{N3} and R^{N1}, or R^{N2} and R^{N1};
may be covalently bonded together to form a 4-, 5-, 6- or 7-membered saturated or unsaturated N-containing heterocycle or a 8-, 9-, 10- or 11-membered N-containing heterobicycle each may have additionally from 1 to 3 heteroatoms selected from O, N, and S;

wherein Het is defined as a 4-, 5-, 6- or 7-membered heterocycle having 1 to 4 heteroatoms selected from O, N and S, or a 8-, 9-, 10- or 11-membered heterobicycle having 1 to 5 heteroatoms selected from O, N and S;

or a salt thereof.

3. The compound according to claim 1 of formula (Ia)

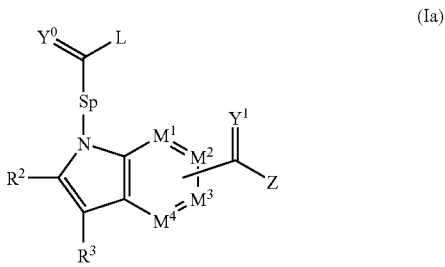

(Ia)

wherein R^{2}, R^{3}, L, M^{1}, M^{2}, M^{3}, M^{4}, Y^{1}, Y^{0}, Z and Sp are as defined in claim 1.

4. The compound according to claim 1 of formula (Ic):

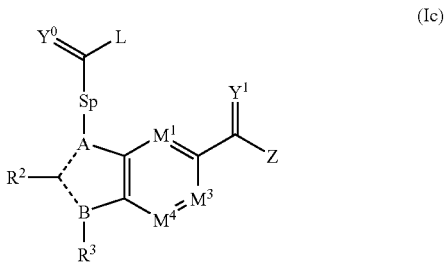

(Ic)

wherein A, B, R^{2}, R^{3}, L, M^{1}, M^{3}, M^{4}, Y^{1}, Y^{0}, Z and Sp are as defined in claim 1.

5. The compound according to claim 1 selected from the group of formulas I.1 to I.4

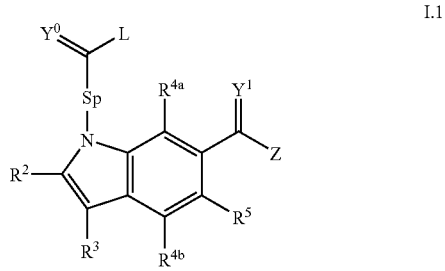

I.1

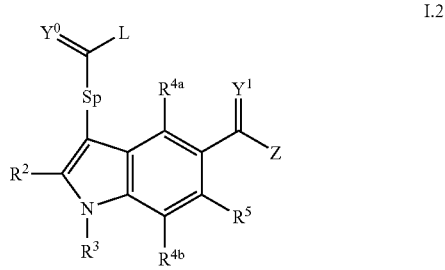

I.2

-continued

I.3

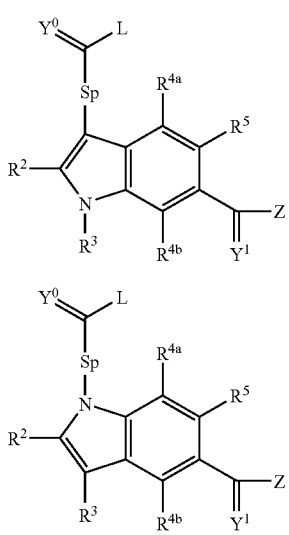

I.4 wherein $R^2$, $R^3$, $R^{4a}$, $R^{4b}$, $R^5$, L, $Y^0$, $Y^1$, Z and Sp are defined as in claim 1.

6. The compound according to claim 1, wherein
Sp is a spacer group selected from $-(CR^{51}R^{52})_{k1}-$, wherein
k1 is 1, 2 or 3; and
$R^{51}$, $R^{52}$ are independently H or $(C_{1-3})$alkyl; and/or
$R^{51}$, $R^{52}$ are covalently bonded together and to the carbon-atom to which they are attached to form a cyclopropyl, cyclobutyl or cyclopentyl group.

7. The compound according to claim 6, wherein Sp is a spacer group selected
From $-CH_2-$, $-CH(CH_3)-$, $-C(CH_3)_2$, $-CH_2-CH_2-$ and

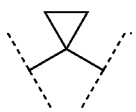

8. The compound according to claim 7, wherein Sp is $-CH_2-$.

9. The compound according to claim 1, wherein $Y^0$ is O or S.

10. The compound according to claim 1, wherein $Y^1$ is O.

11. The compound according to claim 1, wherein
Z is defined as
a) $OR^O$;
c) $N(R^{N2})R^{N1}$;
g) $NR^{N2}-SO_2-R^C$;
h) $NR^{N3}-SO_2-N(R^{N2})R^{N1}$; or
i) $NR^{N2}-CO-R^C$;
wherein $R^O$ and $R^C$ are optionally substituted with $R^{60}$; and
said $R^{N1}$, including any heterocycle or heterobicycle formed by $R^{N1}$ and $R^{N2}$,
being optionally substituted with $R^{60}$;

or Z is $OR^{6b}$ or $N(R^{5b})R^{6b}$ wherein $R^{5b}$ is defined as $R^{N2}$ and $R^{6b}$ is:

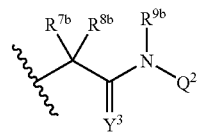

or $R^{6b}$ is:

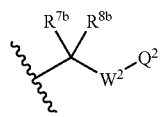

wherein $R^{7b}$, $R^{8b}$, $Y^3$, $R^{9b}$, $W^2$, $Q^2$, $R^{60}$, $R^O$, $R^C$, $R^{N1}$, $R^{N2}$ and $R^{N3}$ are defined as in claim 1.

12. The compound according to claim 1, wherein
Sp is a spacer group selected from $-CH_2-$, $-CH(CH_3)-$, $-C(CH_3)_2-$, $-CH_2-CH_2-$ and

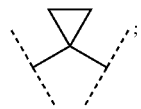

and
$Y^0$ is O or S;
L is Het, $(C_{1-6})$alkyl-Het, all of which being optionally substituted with $R^{60}$;
$Y^1$ is O or S;
Z is defined as
a) $OR^O$;
c) $N(R^{N2})R^{N1}$; or
g) $NR^{N2}-SO_2-R^C$;
j) $COOR^O$;
wherein $R^O$ and $R^C$ are optionally substituted with $R^{60}$; and
said $R^{N1}$, including any heterocycle or heterobicycle formed by $R^{N1}$ and $R^{N2}$, being optionally substituted with $R^{60}$; or
Z is $N(R^{5b})R^{6b}$ wherein $R^{5b}$ is defined as $R^{N2}$ and $R^{6b}$ is:

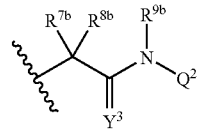

or $R^{6b}$ is:

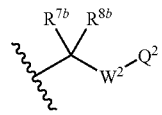

wherein $R^{7b}$, $R^{8b}$, $R^{9b}$, $R^{60}$, $R^O$, $R^C$, $R^{N1}$, $R^{N2}$, $Q^2$, $W^2$, Het and $Y^3$ are defined as in claim 1.

13. The compound according to claim 1 of the formula I.1a

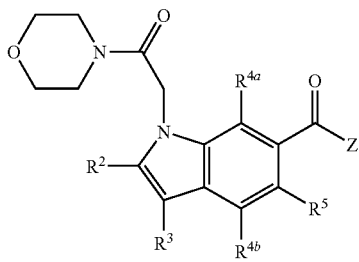

I.1a wherein the morpholinyl ring is optionally substituted with $R^{60}$;
Z is defined as
  a) $OR^O$;
  c) $N(R^{N2})R^{N1}$;
  g) $NR^{N2}$—$SO_2$—$R^C$; or
  j) $COOR^0$
  wherein $R^O$, $R^{N1}$ and $R^C$ are optionally substituted with $R^{60}$; or
Z is $N(R^{5b})R^{6b}$ wherein $R^{5b}$ is defined as $R^{N2}$ and $R^{6b}$ is:

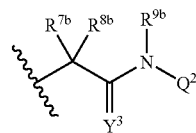

or $R^{6b}$ is:

wherein $R^2$, $R^3$, $R^{4a}$, $R^{4b}$, $R^5$, $R^{7b}$, $R^{8b}$, $R^{9b}$, $R^{60}$, $R^O$, $R^C$, $R^{N1}$, $R^{N2}$, $R^{N3}$, $R^{N4}$, $Q^2$, $W^2$ and $Y^3$ are defined as in claim 1.

14. The compound according to claim 1 of the formula I.1b

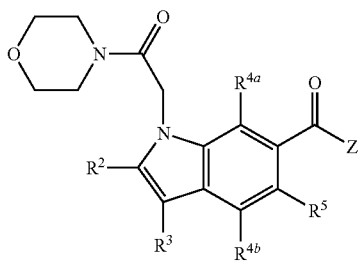

I.1b wherein the piperazinyl ring is optionally substituted with $R^{60}$;
Z is defined as
  a) $OR^O$;
  c) $N(R^{N2})R^{N1}$;
  g) $NR^{N2}$—$SO_2$—$R^C$; or
  j) $COOR^0$
  wherein $R^O$, $R^{N1}$ and $R^C$ is optionally substituted with $R^{60}$; or
Z is $N(R^{5b})R^{6b}$ wherein $R^{5b}$ is defined as $R^{N2}$ and $R^{6b}$ is:

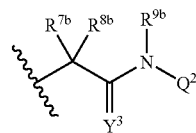

or $R^{6b}$ is:

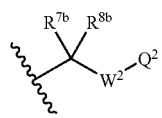

wherein $R^2$, $R^3$, $R^{4a}$, $R^{4b}$, $R^5$, $R^{7b}$, $R^{8b}$, $R^{9b}$, $R^{60}$, $R^O$, $R^C$, $R^{N1}$, $R^{N2}$, and $Y^3$ are defined as in claim 1.

15. The compound according to claim 1 of the formula I.1c

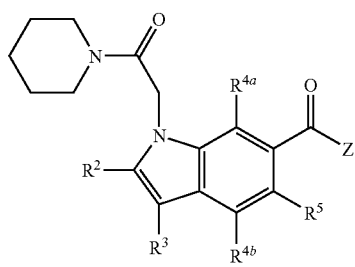

I.1c

Wherein the piperidinyl ring is optionally substituted with $R^{60}$ or pyrrolidine;
Z is defined as
  a) $OR^O$;
  c) $N(R^{N2})R^{N1}$;
  g) $NR^{N2}$—$SO_2$—$R^C$; or
  j) $COOR^0$
  wherein $R^O$, $R^{N1}$ and $R^C$ are optionally substituted with $R^{60}$;
Z is $N(R^{5b})R^{6b}$ wherein $R^{5b}$ is defined as $R^{N2}$ and $R^{6b}$ is:

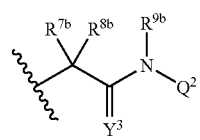

or $R^{6b}$ is:

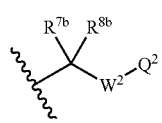

wherein $R^2$, $R^3$, $R^{4a}$, $R^{4b}$, $R^5$, $R^{7b}$, $R^{8b}$, $R^{9b}$, $R^{60}$, $R^O$, $R^C$, $R^{N1}$, $R^{N2}$, $Q^2$; $W^2$ and $Y^3$ are defined as in claim 1.

16. The compound according to claim 1 of the formula I.1d

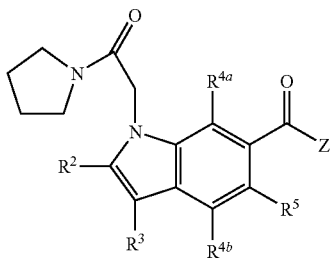

wherein
Z is defined as
  a) $OR^O$;
  c) $N(R^{N2})R^{N1}$;
  g) $NR^{N2}—SO_2—R^C$; or
  j) $COOR^O$;
  wherein $R^O$, $R^{N1}$ and $R^C$ are optionally substituted with $R^{60}$; or
Z is $N(R^{5b})R^{6b}$ wherein $R^{5b}$ is defined as $R^{N2}$ and $R^{6b}$ is:

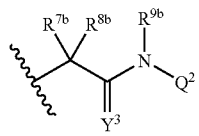

or $R^{6b}$ is:

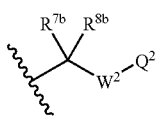

wherein $R^2$, $R^3$, $R^{4a}$, $R^{4b}$, $R^5$, $R^{7b}$, $R^{8b}$, $R^{9b}$, $R^{60}$, $R^O$, $R^C$, $R^{N1}$, $R^{N2}$, $Q^2$, $W^2$ and $Y^3$ are defined as in claim 1.

17. The compound according to claim 1, wherein Z is $OR^O$ wherein
$R^O$ is H, $C_{1-4}$alkyl, $(C_{3-6})$cycloalkyl, $C_{1-3}$alkyl-$(C_{3-6})$cycloalkyl, $(C_{2-6})$alkenyl, $(C_{1-3}$alkyl)phenyl, $(C_{1-3})$alkyl-pyridinyl, wherein said alkyl, alkyl-cycloalkyl, cycloalkyl, alkenyl, alkyl-phenyl, or alkyl-pyridinyl is optionally substituted with 1 to 3 substituents independently selected from:
  1, 2 or 3 fluorine substituents; and
  one of each substituent selected from chlorine, bromine, iodine, CN, nitro, $C_{1-4}$alkyl, $CF_3$, $COOR^{161}$, $SO_2R^{161}$, $OR^{161}$, $N(R^{162})_2$, $SO_2N(R^{162})_2$, $NR^{162}COR^{162}$ or $CON(R^{162})_2$, wherein $R^{161}$ and each $R^{162}$ is independently H, $(C_{1-4}$alkyl, $(C_{3-7})$cycloalkyl or $(C_{1-3})$alkyl-$(C_{3-7})$cycloalkyl; or both $R^{162}$ are covalently bonded together and to the nitrogen to which they are attached to form a 5, 6 or 7-membered saturated heterocycle.

18. The compound according to claim 17, wherein Z is OH.

19. The compound according to claim 11, wherein Z is defined as $N(R^{N2})R^{N1}$; said $R^{N1}$, including any heterocycle or heterobicycle formed by $R^{N1}$ and $R^{N2}$, being optionally substituted with $R^{60}$; and wherein $R^{60}$, $R^{N1}$ and $R^{N2}$ are defined as in claim 11.

20. The compound according to claim 19, wherein Z is defined as $N(R^{N2})R^{N1}$ wherein
$R^{N2}$ is H, methyl, $(C_{2-4})$alkyl, $(C_{3-6})$cycloalkyl or $(C_{1-3})$alkyl-$(C_{3-6})$cycloalkyl, all of which being optionally substituted with halogen, carboxy or $(C_{1-4}$alkoxycarbonyl; and/or wherein said alkyl, cycloalkyl or alkyl-cycloalkyl is optionally substituted with hydroxy, $C_{1-3}$-alkyl, amino, —$NH(C_{1-4}$-alkyl), —$N(C_{1-4}$-alkyl$)_2$ and/or —O—$(C_{1-4}$-alkyl);
$R^{N1}$ is methyl, $(C_{2-6})$alkyl, $(C_{1-4}$alkyl-phenyl or $(C_{1-4})$alkyl-Het; wherein the methyl and alkyl groups are optionally substituted with $C_{1-3}$-alkyl, halogen, carboxy or $(C_{1-4})$alkoxycarbonyl, $CONH_2$, $CONH(C_{1-4}$-alkyl), $CON(C_{1-4}$-alkyl$)_2$; and/or wherein said alkyl is optionally substituted with hydroxy, amino, —$NH(C_{1-4}$-alkyl), —$N(C_{1-4}$-alkyl$)_2$ and/or —O—$(C_{1-4}$-alkyl); and
wherein Het is a 4-, 5-, 6- or 7-membered monocyclic group which contains 1 or 2 heteroatoms selected from N, O and S, wherein a benzene ring may be fused to the monocyclic group; and
wherein said phenyl group, heterocycle, heterobicycle or Het is optionally substituted by 1 to 4 substituents independently selected from:
  1 to 3 substituents selected from halogen;
  one of each substituent selected from: $NO_2$, cyano, azido; and
  1 to 3 substituents selected from: $(C_{1-4})$alkyl, hydroxy, O—$(C_{1-4})$alkyl, amino, —COOH, —$COO(C_{1-4})$alkyl, $CONH_2$, $CONH(C_{1-4}$-alkyl), $CON(C_{1-4}$-alkyl$)_2$, —$NH(C_{1-4}$-alkyl), —$N(C_{1-4}$-alkyl$)_2$, N-pyrrolidinyl, N-piperidinyl, N-morpholinyl, N-thiomorpholinyl, N-piperazinyl, —$(C_{1-4})$alkyl-OH, —$(C_{1-4})$alkyl-O—$(C_{1-4})$alkyl, —$(C_{1-4})$alkyl-COOH, —$(C_{1-4})$alkyl-COO$(C_{1-4})$alkyl, —$(C_{1-4})$alkyl-$CONH_2$, —$(C_{1-4})$alkyl-CONH$(C_{1-4}$-alkyl), —$(C_{1-4})$alkyl-CON$(C_{1-4}$-alkyl$)_2$, —$(C_{1-4})$alkyl-amino, —$(C_{1-4})$alkyl-NH$(C_{1-4}$-alkyl), —$(C_{1-4})$alkyl-N$(C_{1-4}$-alkyl$)_2$,
wherein the alkyl-groups may be substituted with halogen; and
wherein the N-piperazinyl-group may be N-substituted with $(C_{1-4})$alkyl, $(C_{3-6})$cycloalkyl or $(C_{1-3})$alkyl-$(C_{3-6})$cycloalkyl.

21. The compound according to claim 20, wherein Z is defined as $N(R^{N2})R^{N1}$ wherein
$R^{N2}$ is H, methyl, ethyl, n-propyl, i-propyl, all of which being optionally substituted with methyl, fluorine, chlorine, carboxyl or methoxycarbonyl; and/or wherein said ethyl, n-propyl or i-propyl is optionally substituted with hydroxy, amino, —$NH(CH_3)$, —$N(CH_3)_2$ and/or —O—$(CH_3)$;
$R^{N1}$ is methyl, ethyl, n-propyl, i-propyl, benzyl, phenylethyl, pyridinylmethyl or pyridinylethyl; wherein all of said methyl, ethyl, n-propyl, and i-propyl, groups are optionally substituted with fluorine, chlorine, methyl, ethyl, carboxy, methoxycarbonyl, $CONH_2$, $CONH(CH_3)$, $CON(CH_3)_2$; and/or wherein said ethyl, n-propyl or i-propyl is optionally substituted with hydroxy, amino, —$NH(CH_3)$, —$N(CH_3)_2$ and/or —O—$CH_3$; and
wherein said phenyl and pyridinyl group is optionally substituted by 1, 2 or 3 substituents independently selected from:
  1, 2 or 3 substituents selected from halogen;
  one of each substituent selected from: $NO_2$, cyano, azido; and
  1, 2 or 3 substituents selected from: methyl, trifluoromethyl, ethyl, n-propyl, i-propyl, hydroxy, methoxy, ethoxy, —COOH, —$COOCH_3$, $CONH_2$, $CONH(CH_3)$, $CON(CH_3)_2$, amino, —$NH(CH_3)$, —$N(CH_3)_2$, —$CH_2$—OH, —$CH_2$—O—$CH_3$, —$CH_2$—$NH_2$, —$CH_2$—$N(CH_3)_2$ and —$(CH_2)_2$—OH.

22. The compound according to claim 1, wherein
Z is $NR^{N2}—SO_2—R^C$ or $NR^{N2}—CO—R^C$ wherein
$R^{N2}$ is H, $(C_{1-4})$alkyl, $(C_{3-6})$cycloalkyl or $(C_{1-3})$alkyl-$(C_{3-6})$cycloalkyl, and $R^C$ is $(C_{1-6})$alkyl, $(C_{3-6})$cycloalkyl, $(C_{1-3})$alkyl-$(C_{3-6})$cycloalkyl, $(C_{2-6})$alkenyl, phenyl, naphthyl, Het, $(C_{1-3})$alkyl-phenyl, $(C_{1-3})$alkyl-naphthyl, $(C_{1-3})$alkyl-Het, wherein said alkyl, cycloalkyl, alkyl-cycloalkyl, alkenyl, phenyl, Het, alkyl-phenyl, alkyl-naphthyl or alkyl-Het, are all optionally substituted with 1 to 4 substituents selected from $R^{60}$; wherein Het and $R^{60}$ are defined as in claim 1.

23. The compound according to claim 1, wherein Z is OR$^{6b}$ or N(R$^{5b}$)R$^{6b}$ wherein R$^{5b}$ is defined as R$^{N2}$ and R$^{6b}$ is defined as:

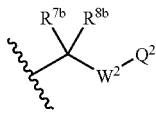

wherein
R$^{7b}$ is defined as H, COOH, CONH$_2$, (C$_{1-6}$)alkyl, (C$_{3-6}$) cycloalkyl, (C$_{1-4}$)alkyl-(C$_{3-6}$)cycloalkyl, (C$_{2-6}$)alkenyl, aryl, Het, (C$_{1-4}$)alkyl-aryl, (C$_{1-4}$)alkyl-Het; all of which are optionally substituted with R$^{60}$; and
R$^{8b}$ is H or (C$_{1-4}$)alkyl; or
R$^{7b}$ and R$^{8b}$ are covalently bonded together to form a second (C$_{3-7}$)cycloalkyl or a 4, 5- or 6-membered heterocycle having from 1 to 3 heteroatom selected from O, N, and S; and
when Z is N(R$^{5b}$)R$^{6b}$, either of R$^{7b}$ or R$^{8b}$ may be covalently bonded to R$^{5b}$ to form a nitrogen-containing 5- or 6-membered heterocycle, wherein said cycloalkyl or heterocycle being optionally substituted by R$^{150}$; and
W$^2$ is selected from
a single bond;
—CH$_2$—;
—CH$_2$—CH$_2$—; and
—CH=CH—;
wherein the alkylene and alkenylene groups according to b), c) and d) may be substituted with (C$_{1-3}$) alkyl;
Q$^2$ is a group of the subformula IIIb

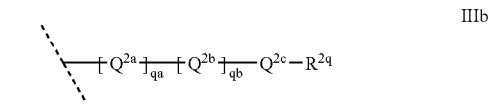

IIIb wherein
Q$^{2a}$ is aryl, Hetaryl, (C$_{1-3}$)alkyl-aryl or (C$_{1-3}$)alkyl-Hetaryl;
Q$^{2b}$ is a phenyl or Hetaryl;
Q$^{2c}$ is a bond, O—C$_{1-4}$-alkyl, S—C$_{1-4}$-alkyl, C$_{1-4}$-alkyl, C$_{2-4}$-alkenyl or C$_{2-4}$-alkynyl, wherein said O—C$_{1-4}$-alkyl, S—C$_{1-4}$-alkyl, C$_{1-4}$-alkyl, C$_{2-4}$-alkenyl or C$_{2-4}$-alkynyl are optionally substituted with R$^{170}$;
wherein R$^{170}$ is defined as H or as 1, 2 or 3 substituents independently selected from:
1, 2, or 3 substituents selected from halogen;
one or two of each substituent selected from (C$_{1-4}$) alkyl, (C$_{1-4}$) alkoxy, (C$_{3-5}$) cycloalkyl, or cyano; wherein (C$_{1-4}$) alkyl may optionally be substituted with 1 to 3 halogen atoms; and
R$^{2q}$ is selected from H, CN, COOR$^{161}$, CON(R$^{162}$)$_2$, SO$_2$N(R$^{162}$)$_2$, —N(R$^{162}$)$_2$, OR$^{161}$, SR$^{161}$, —NHCOR$^{162}$, —NH—CO—COOR$^{161}$, —NH—CO—CON(R$^{162}$)$_2$, NHSO$_2$R$^O$, CONHSO$_2$R$^C$, SO$_2$NHCOR$^O$, tetrazole, triazole and CONHSO$_2$N(R$^{162}$)$_2$;
qa is 0 or 1;
qb is 0 or 1;
wherein each aryl, phenyl, Hetaryl, alkyl, alkenyl and/or alkynyl-groups is optionally substituted with R$^{160}$; and
wherein Hetaryl is an aromatic 5- or 6-membered heterocycle having 1 or 2 heteroatoms selected from O, N, and S, or a 9- or 10-membered aromatic heterobicycle having 1 to 4 heteroatoms selected from O, N, and S; and
wherein Het, R$^O$, R$^C$, R$^{N2}$, R$^{60}$, R$^{150}$, R$^{160}$, R$^{161}$ and R$^{162}$ are defined as in claim 1.

24. The compound according to claim 1, wherein Z is OR$^{6b}$ or N(R$^{5b}$)R$^{6b}$ wherein R$^{5b}$ is defined as R$^{N2}$ and R$^{6b}$ is:

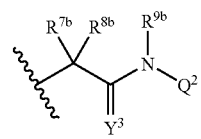

wherein R$^{7b}$ and R$^{8b}$ are each independently defined as R$^O$, wherein said R$^O$ is optionally substituted with R$^{60}$; or
R$^{7b}$ and R$^{8b}$ are covalently bonded together to form a (C$_{3-7}$)cycloalkyl or a 4,5- or 6-membered heterocycle having from 1 to 3 heteroatom selected from O, N, and S; or
when Z is N(R$^{5b}$)R$^{6b}$, either of R$^{7b}$ or R$^{7b}$ may be covalently bonded to R$^{5b}$ to form a nitrogen-containing 5- or 6-membered heterocycle, wherein said cycloalkyl or heterocycle being optionally substituted by R$^{60}$; and
Y$^3$ is O or S;
R$^{9b}$ is defined as R$^O$, wherein said R$^O$ is optionally substituted with R$^{150}$; or
R$^{9b}$ is covalently bonded to either of R$^{7b}$ or R$^{8b}$ to form a 5- or 6-membered heterocycle;
Q$^2$ is a group of the subformula IIIb

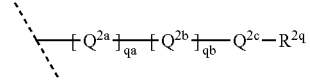

IIIb wherein
Q$^{2a}$ is aryl, Hetaryl, (C$_{1-3}$) alkyl-aryl or (C$_{1-3}$)alkyl-Hetaryl;
Q$^{2b}$ is a phenyl or Hetaryl;
Q$^{2c}$ is a bond, O—C$_{1-4}$-alkyl, S—C$_{1-4}$-alkyl, C$_{1-4}$-alkyl, C$_{2-4}$-alkenyl or C$_{2-4}$-alkynyl, wherein said O—C$_{1-4}$-alkyl, S—C$_{1-4}$-alkyl, C$_{1-4}$-alkyl, C$_{2-4}$-alkenyl or C$_{2-4}$-alkynyl are optionally substituted with R$^{170}$;
wherein R$^{170}$ is defined as H or as 1, 2 or 3 substituents independently selected from:
1, 2, or 3 substituents selected from halogen;
one or two of each substituent selected from (C$_{1-4}$) alkyl, (C$_{1-4}$) alkoxy, (C$_{3-5}$) cycloalkyl, or cyano; wherein (C$_{1-4}$) alkyl may optionally be substituted with 1 to 3 halogen atoms; and
R$^{2q}$ is selected from H, CN; COOR$^{161}$, CON(R$^{162}$)$_2$, SO$_2$N(R$^{162}$)$_2$, —N(R$^{162}$)$_2$, OR$^{161}$, SR$^{161}$, —NHCOR$^{162}$, —NH—CO—COOR$^{161}$, —NH—CO—CON(R$^{162}$)$_2$, CONHSO$_2$R$^C$, tetrazole, triazole and CONHSO$_2$N(R$^{162}$)$_2$;
qa is 0 or 1;
qb is 0 or 1;
wherein each aryl, phenyl, Hetaryl, alkyl, alkenyl and/or alkynyl-groups is optionally substituted with R$^{160}$; and
wherein Hetaryl is an aromatic 5- or 6-membered heterocycle having 1 or 2 heteroatoms selected from O, N, and S, or a 9- or 10-membered aromatic heterobicycle having 1 to 4 heteroatoms selected from O, N, and S; and
wherein R$^O$, R$^C$, R$^{N2}$, R$^{60}$, R$^{150}$, R$^{160}$, R$^{161}$ and R$^{162}$ are defined as in claim 1.

25. The compound according to claim 23 or 24, wherein
a) qa is 1, Q$^{2a}$ is phenyl, qb is 1 and Q$^{2c}$ is a bond;
b) qa is 1, Q$^{2a}$ is phenyl, qb is 0 and Q$^{2c}$ is —CH=C(R$^{170}$)—,
wherein R$^{170}$ is selected from H, F, —CH$_3$ or —CH$_2$CH$_3$; or
c) qa is 1, Q$^{2a}$ is a 9- or 10-membered aromatic heterobicycle having 1 or 2 heteroatoms selected from O, N, and S, said heterobicycle optionally being substituted with $R^{160}$; qb is 0 and $Q^{2c}$ is a bond, —$CH_2$—$CH_2$— or —CH=C($R^{170}$)—, wherein $R^{170}$ is selected from H, F, —$CH_3$ or —$CH_2CH_3$.

26. The compound according to claim 23 or 24, wherein the group $Q^{2c}$-$R^{2q}$ is —CH=C($R^{170}$)—COOH, wherein $R^{170}$ is selected from H, F, —$CH_3$ or —$CH_2CH_3$.

27. The compound according to claim 1, wherein $R^2$ is $R^{21}$, wherein $R^{21}$ is defined as in claim 1, and wherein $R^{21}$ is optionally substituted with 1, 2 or 3 substituents selected from:
   1 to 3 substituents selected from halogen;
   one of each substituent selected from: $NO_2$, cyano, azido; and
   1 to 2 substituents selected from:
   a) $(C_{1-4})$alkyl or $(C_{1-4})$alkoxy, both optionally substituted with OH, O$(C_{1-4})$alkyl, $SO_2(C_{1-4}$ alkyl), 1 to 3 halogen atoms, amino, NH($CH_3$) or N($CH_3$)$_2$);
   b) $NR^{111}R^{112}$ wherein both $R^{111}$ and $R^{112}$ are independently H, $(C_{1-4})$alkyl, or $R^{112}$ is $(C_{3-7})$cycloalkyl, $(C_{1-3})$alkyl$(C_{3-7})$cycloalkyl, phenyl, benzyl; or both $R^{111}$ and $R^{112}$ are covalently bonded together and to the nitrogen to which they are attached to form a nitrogen-containing heterocycle, each of said alkyl, cycloalkyl, alkylcycloalkyl, phenyl and benzyl, being optionally substituted with halogen or:
   —$OR^{2h}$ or N($R^{2h}$)$_2$, wherein each $R^{2h}$ is independently H, $(C_{1-4})$alkyl, or both $R^{2h}$ are covalently bonded together and to the nitrogen to which they are attached to form a nitrogen-containing heterocycle;
   c) $NHCOR^{117}$ wherein $R^{117}$ is $(C_{1-4})$alkyl, O$(C_{1-4})$alkyl or O$(C_{3-7})$cycloalkyl; and
   e) $CONH_2$, $CONH(C_{1-4}$alkyl), $CON(C_{1-4}$alkyl)$_2$.

28. The compound according to claim 1, wherein $R^3$ is selected from $(C_{3-7})$cycloalkyl, $(C_{5-7})$cycloalkenyl, $(C_{6-10})$bicycloalkyl, $(C_{6-10})$bicycloalkenyl, or HCy, wherein said groups are unsubstituted or mono- or disubstituted by halogen, hydroxy, $C_{1-4}$alkyl and/or O—$C_{1-4}$alkyl, wherein the alkyl groups may be fluorinated; wherein HCy is defined as in claim 1.

29. The compound according to claim 28, wherein $R^3$ is cyclopropyl, cyclobutyl, cyclopentyl, cyclohexyl or cycloheptyl, or a group selected from

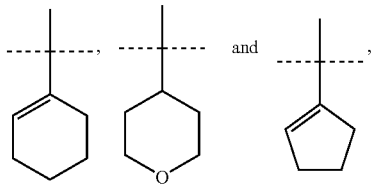

wherein all said groups are unsubstituted or substituted by fluorine, $C_{1-3}$alkyl or $CF_3$.

30. The compound according to claim 29, wherein $R^3$ is cyclopentyl or cyclohexyl.

31. The compound according to claim 1, wherein $R^{60}$ is each defined as 1 to 4 substituents independently selected from:
   1 to 3 substituents selected from halogen;
   one of each substituent selected from: $NO_2$, cyano, azido; and
   1 to 3 substituents selected from:
   a) $(C_{1-4})$ alkyl, $(C_{3-7})$cycloalkyl, $(C_{2-4}$alkenyl, $(C_{2-4}$alkynyl, $(C_{1-3})$alkyl-$(C_{3-7})$cycloalkyl, all of which optionally being substituted with $R^{150}$;
   b) $OR^O$;
   e) N($R^{N2}$)$R^{N1}$;
   f) N($R^{N2}$)$COR^C$;
   j) $COOR^O$;
   k) CON($R^{N2}$)$R^{N1}$;
   l) phenyl, Het, $(C_{1-3}$alkyl)phenyl or $(C_{1-3}$alkyl)Het; wherein
   Het is selected from furan, tetrahydrofuran, thiophene, tetrahydrothiophene, tetrahydropyran, pyridinyl, azetidine, pyrrolidine, piperidine, piperazine, morpholine, thiomorpholine, homopiperidine and homopiperazine, all of which optionally being substituted with $R^{150}$;
   wherein said $R^{N1}$, $R^C$ and/or $R^O$ are optionally substituted with $R^{150}$ as defined, and $R^{150}$, $R^{N1}$, $R^{N2}$, $R^C$ and $R^O$ are defined as in claim 1.

32. The compound according to claim 1, wherein $R^{150}$ is defined as 1 to 4 substituents independently selected from:
   1 to 3 fluorine-substituents;
   one of each substituent selected from: chlorine, bromine, iodine, $NO_2$, cyano, azido; and
   1 to 3 substituents selected from:
   a) $(C_{1-3})$ alkyl, $CF_3$, $(C_{3-6})$cycloalkyl, $(C_{1-3})$ alkyl-$(C_{3-6})$ cycloalkyl, all of which optionally substituted with $R^{160}$;
   b) $OR^O$;
   e) N($R^{N2}$)$R^{N1}$;
   f) N($R^{N2}$)$COR^C$;
   j) $COOR^O$;
   k) CON($R^{N2}$)$R^{N1}$;
   wherein said $R^{N1}$, $R^C$ and/or $R^O$ are optionally substituted with $R^{160}$ as defined; and $R^{160}$, $R^{N1}$, $R^{N2}$, $R^C$ and $R^O$ are defined as in claim 1.

33. The compound according to claim 1, wherein $R^{160}$ is defined as 1, 2 or 3 substituents independently selected from:
   1, 2 or 3 fluorine substituents; and
   one of each substituent selected from chlorine, bromine, iodine, CN, nitro, methyl, trifluoromethyl, ethyl, n-propyl, i-propyl, COOH, $COOCH_3$, OH, $OCH_3$, $OCF_3$, $NH_2$, $NHCH_3$, N($CH_3$)$_2$, $SO_2NH_2$, $SO_2NHCOCH_3$, $NHCOCH_3$ or $CONH_2$, $CONHCH_3$ and CON($CH_3$)$_2$.

34. The compound according to claim 1, wherein $R^O$ and $R^C$ are each defined as $(C_{1-4})$alkyl, $(C_{3-6})$cycloalkyl, $(C_{1-3})$alkyl-$(C_{3-6})$cycloalkyl, phenyl, benzyl, Het, $(C_{1-3})$alkyl-Het; all of which are optionally substituted as defined; and $R^O$ may also be H;
   $R^{N1}$ is H, $(C_{1-4})$alkyl, $(C_{3-6})$cycloalkyl, $(C_{1-3})$alkyl-$(C_{3-6})$ cycloalkyl, phenyl, benzyl, phenylethyl, Het, $(C_{1-3})$ alkyl-Het; wherein said alkyl, cycloalkyl, alkyl-cycloalkyl, phenyl, benzyl, phenylethyl, Het and alkyl-Het are optionally substituted as defined; or
   $R^{N2}$, $R^{N3}$, $R^{N4}$ are independently H, methyl, ethyl, n-propyl, i-propyl, cyclopropyl, cyclopropylmethyl; all of which being optionally substituted with fluorine, carboxy or methoxycarbonyl; and/or wherein said ethyl, n-propyl or i-propyl is optionally substituted with hydroxy, methyl, methoxy, amino, —NH($CH_3$) and/or —N($CH_3$)$_2$; and
   in the case
   a) of a group N($R^{N2}$)$R^{N1}$ the substituents $R^{N2}$ and $R^{N1}$ or
   b) of a group $NR^{N3}$—N($R^{N2}$)$R^{N1}$ the substituents $R^{N3}$ and $R^{N1}$ or $R^{N2}$ and $R^{N1}$ may be covalently bonded together to form a 5-, 6- or 7-membered saturated heterocycle which may have additionally one heteroatom selected from O, N, and S, wherein said heterocycle is optionally substituted as defined;
   wherein Het is defined as in claim 1.

35. The compound according to claim 1 wherein $R^{4a}$, $R^{4b}$, $R^5$ each are independently H, hydroxy, halogen, cyano, nitro, carboxyl, $(C_{1-4})$alkyl, $CF_3$, $(C_{1-4})$alkoxy, —O—$(C_{3-7})$cycloalkyl, —O—$(C_{1-3})$alkyl-$(C_{3-7})$cycloalkyl, —O-aryl, —O—$(C_{1-3})$alkyl-aryl, —O-Het, —O—$(C_{1-3})$alkyl-Het, $NR^{N1}R^{N2}$, $COR^O$, $NR^{N2}COR^C$, $CONR^{N2}R^{N1}$, or $NR^{N3}CONR^{N1}R^{N2}$, wherein all said alkyl and alkoxy groups may be mono-, di- or trisubstituted with fluorine or mono-substituted with chlorine or bromine; and wherein $R^O$, $R^{N1}$, $R^{N2}$, $R^{N3}$, $R^{160}$, and Het are as defined in claim 1.

36. The compound according to claim 35 wherein $R^O$ and $R^{N1}$ are independently H, $(C_{1-4})$alkyl, aryl, or $(C_{1-3})$alkyl-aryl; $R^C$ is $(C_{1-4})$alkyl, aryl, or $(C_{1-3})$alkyl-aryl;

wherein all of said aryl is phenyl optionally substituted with $R^{160}$, wherein $R^{160}$ is defined as in claim 46; and $R^{N2}$ and $R^{N3}$ are each H or methyl;

wherein all said alkyl groups may be mono-, di- or trisubstituted with fluorine or mono-substituted with chlorine or bromine.

37. The compound according to claim 35 wherein $R^{4a}$, $R^{4b}$, $R^5$ each are independently H, hydroxy, halogen, cyano, nitro, methyl, $CF_3$, methoxy, carboxy, amino, —$NMe_2$, —$CONH_2$, —$NHCONH_2$, —CO—NHMe, —NHCONHMe, —CO-$NMe_2$ or —$NHCONMe_2$.

38. The compound according to claim 37 wherein $R^{4a}$, $R^{4b}$, $R^5$ each are independently H, methyl or methoxy.

39. The compound according to claim 1 wherein at least two of $R^{4a}$, $R^{4b}$, $R^5$ are H.

40. The compound according to claim 1 of the formula:

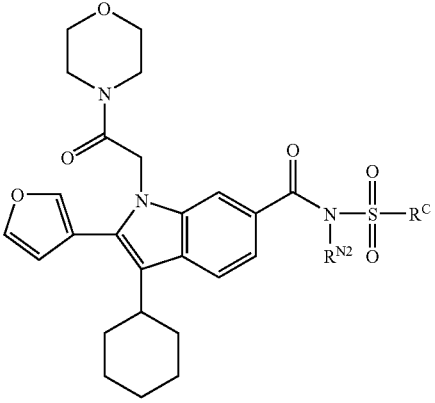

wherein the substituents $R^{N2}$ and $R^C$ are defined according to the following table

| Cpd. # | $R^{N2}$ | $R^C$ |
|---|---|---|
| 2001 | H | phenyl |
| 2002 | H | —CH₃ |
| 2003 | H | benzyl |
| 2004 | H | 5-chloro-thien-2-yl |
| 2005 | H | —CF₃ |
| 2006 | H | 2-(methoxycarbonyl)phenyl |
| 2007 | H | naphth-2-yl |
| 2008 | H | 4-bromophenyl |
| 2009 | H | 4-methoxyphenyl |
| 2010 | H | 3-chlorophenyl |
| 2011 | H | 2-bromophenyl |
| 2012 | H | 2-chlorophenyl |
| 2013 | H | 4-trifluoromethoxyphenyl |

| 371 | | 372 | |
|---|---|---|---|
| -continued | | -continued | |

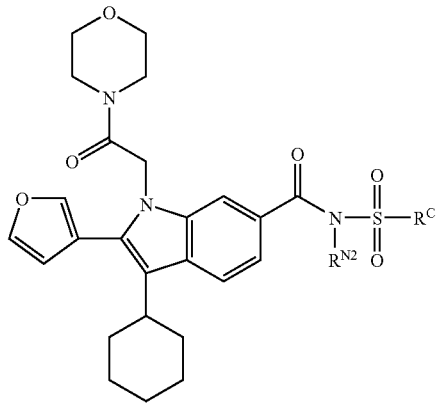

wherein the substituents $R^{N2}$ and $R^C$ are defined according to the following table

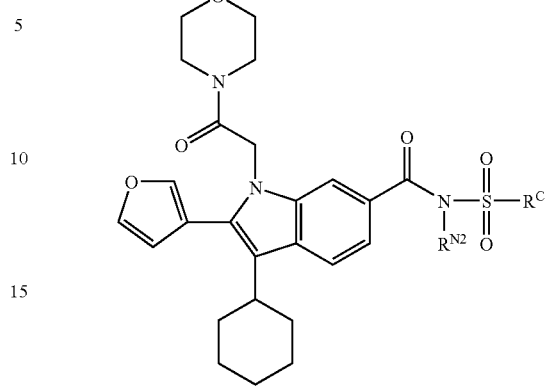

wherein the substituents $R^{N2}$ and $R^C$ are defined according to the following table

| Cpd. # | $R^{N2}$ | $R^C$ |
|---|---|---|
| 2014 | H | 2,5-difluorophenyl |
| 2015 | H | 4-fluorophenyl |
| 2016 | H | 2-methylphenyl |
| 2017 | H | 6-ethoxybenzothiazol-2-yl |
| 2018 | H | 4-nitrophenyl |
| 2019 | H | 4-chlorophenyl |
| 2020 | H | 5-fluoro-3-methylbenzothiophen-2-yl |
| 2021 | H | 4-acetamidophenyl |

| Cpd. # | $R^{N2}$ | $R^C$ |
|---|---|---|
| 2022 | H | 4-methylphenyl |
| 2024 | H | quinolin-8-yl |
| 2025 | H | 4-tert-butylphenyl |
| 2026 | H | cyclopropyl |
| 2027 | H | 2,2,2-trifluoroethyl |
| 2028 | H | 2,5-dimethoxyphenyl |
| 2029 | H | 3-bromo-2,5-dichlorothiophen-4-yl |

373

-continued

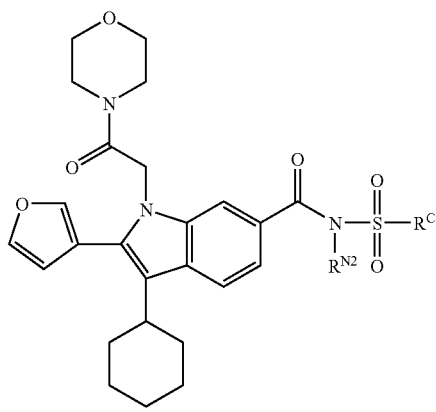

wherein the substituents R$^{N2}$ and R$^C$ are defined according to the following table

| Cpd. # | R$^{N2}$ | R$^C$ |
|---|---|---|
| 2030 | H | 2,5-dichlorothiophen-3-yl |
| 2031 | H | 2,6-dichlorophenyl |
| 2033 | H | 5-chloro-1,3-dimethyl-1H-pyrazol-4-yl |
| 2034 | H | 3,5-dimethylisoxazol-4-yl |
| 2035 | H | 2,1,3-benzothiadiazol-4-yl |
| 2036 | H | 2,6-difluorophenyl |

374

-continued

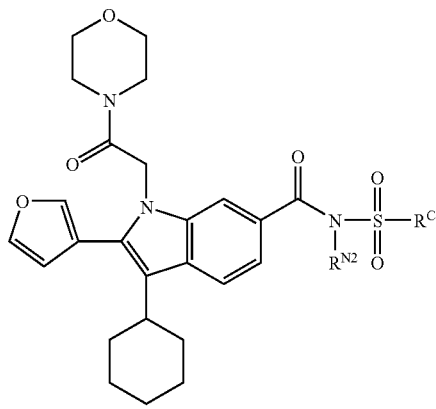

wherein the substituents R$^{N2}$ and R$^C$ are defined according to the following table

| Cpd. # | R$^{N2}$ | R$^C$ |
|---|---|---|
| 2037 | H | 6-chloroimidazo[2,1-b]thiazol-5-yl |
| 2038 | H | 2-(methylsulfonyl)phenyl |
| 2039 | H | isoquinolin-5-yl |
| 2040 | H | 2-methoxy-5-methylphenyl |
| 2041 | H | 1,3,5-trimethyl-1H-pyrazol-4-yl |
| 2042 | H | 5-methyl-1-phenyl-1H-pyrazol-4-yl |

-continued

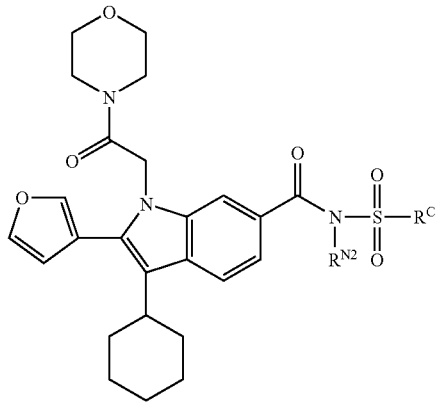

wherein the substituents $R^{N2}$ and $R^C$ are defined according to the following table

| Cpd. # | $R^{N2}$ | $R^C$ |
|---|---|---|
| 2044 | H | (2,4,6-trimethylphenyl) |

-continued

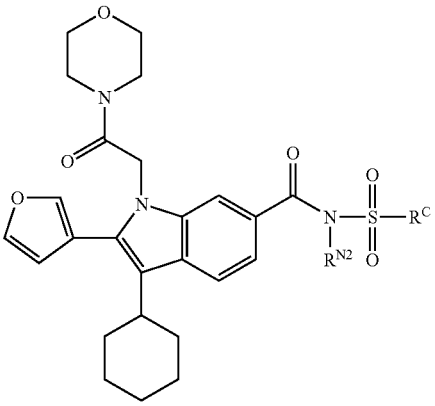

wherein the substituents $R^{N2}$ and $R^C$ are defined according to the following table

| Cpd. # | $R^{N2}$ | $R^C$ |
|---|---|---|
| 2045 | H | —CCl$_3$. |

41. The compound according to claim 1 of the formula:

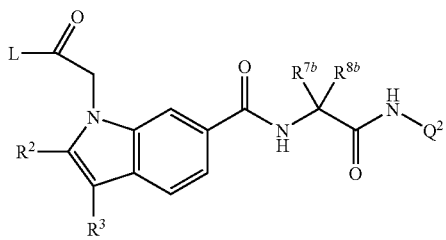

wherein $R^3$ is $C_n$-cycloalkyl and the index n and the substituents L, $R^2$, $R^{7b}$, $R^{8b}$ and $Q^2$ are defined according to the following table

| Cpd. # | $R^2$ | n | L | $R^{7b}\ R^{8b}$ | $Q^2$ |
|---|---|---|---|---|---|
| 3001 | 3-furyl | 5 | morpholinylmethyl | spiro-piperidine | 4-(2-aminothiazol-4-yl)phenyl |

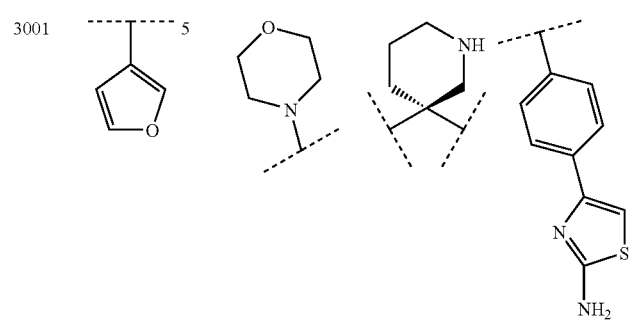

-continued

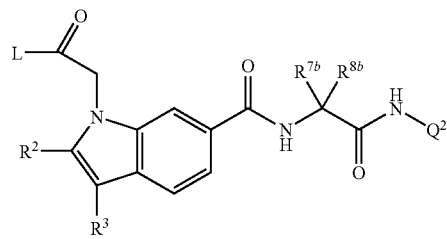

wherein R³ is Cₙ-cycloalkyl and the index n and the substituents L, R², R⁷ᵇ, R⁸ᵇ and Q² are defined according to the following table

| Cpd. # | R² | n | L | R⁷ᵇ R⁸ᵇ | Q² |
|---|---|---|---|---|---|
| 3002 | 3-furyl | 6 | morpholinyl-CH₂- | spiro-piperidine | 4-(2-aminothiazol-4-yl)phenyl |
| 3003 | 3-furyl | 6 | morpholinyl-CH₂- | spiro-cyclobutyl | 4-(2-carboxyvinyl)phenyl |
| 3004 | 3-furyl | 6 | morpholinyl-CH₂- | spiro-pyrrolidine | H |
| 3012 | 3-furyl | 6 | morpholinyl-CH₂- | spiro-cyclobutyl | 2-methyl-4-(2-carboxyvinyl)phenyl |

-continued
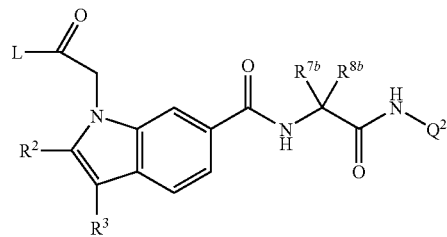
wherein R³ is C_n-cycloalkyl and the index n and the substituents L, R², R⁷ᵇ, R⁸ᵇ and Q² are defined according to the following table
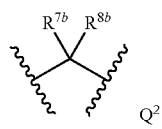
| Cpd. # | R² | n | L | R⁷ᵇ R⁸ᵇ | Q² |
|---|---|---|---|---|---|
| 3013 | 3-furyl | 6 | morpholine | cyclobutyl | 4-(2-methylpropenoic acid)-phenyl |
| 3015 | 3-furyl | 6 | morpholine | cyclobutyl | 2-OCH₃, 4-(acrylic acid)-phenyl |
| 3017 | 3-furyl | 6 | 4-pyrrolidinyl-piperidine | cyclobutyl | 2-OC₂H₅, 4-(acrylic acid)-phenyl |

-continued

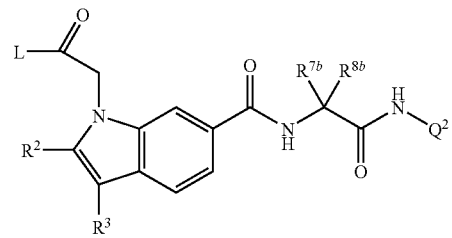

wherein $R^3$ is $C_n$-cycloalkyl and the index n and the substituents L, $R^2$, $R^{7b}$, $R^{8b}$ and $Q^2$ are defined according to the following table

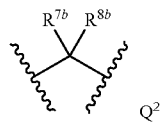

| Cpd. # | $R^2$ | n | L | $R^{7b}\ R^{8b}$ | $Q^2$ |
|---|---|---|---|---|---|
| 3018 | furanyl | 6 | piperazinyl | cyclobutyl | thiomorpholinyl |
| 3019 | furanyl | 6 | morpholinyl | cyclobutyl | phenyl-OC$_2$H$_5$, F, COOH |

42. A pharmaceutical composition, comprising an effective amount of a compound of formula I according to claim 1, or a pharmaceutically acceptable salt thereof, and a pharmaceutically acceptable carrier.

43. The composition according to claim 42 further comprising a therapeutically effective amount of one or more antiviral agents.

44. The composition according to claim 43, wherein said antiviral agent is selected from: ribavirin and amantadine.

45. The pharmaceutical composition according to claim 43, wherein the other antiviral agent is an immunomodulatory agent, selected from α-, β-, δ- γ-, and ω-interferon.

46. The composition according to claim 43, wherein said antiviral agent is another inhibitor of HCV polymerase.

47. The composition according to claim 43, wherein the other antiviral agent is an inhibitor of HCV NS3 protease.

48. The composition according to claim 43, wherein the other anti-HCV agent is an inhibitor of another target in the HCV life cycle.

49. The composition according to claim 48, wherein said inhibitor of another target in the HCV life cycle is an agent that inhibits a target selected from HCV helicase, HCV NS2/3 protease and HCV IRES.

50. The compound according to claim 1 of the formula:

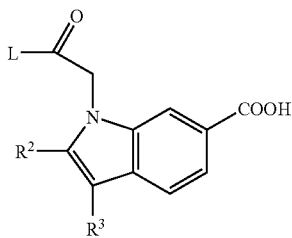

wherein $R_3$ is $C_n$-cycloalkyl and the index n and the substituents L, $R^2$ are defined according to the following table

| Cpd. | $R^2$ | n | L |
|---|---|---|---|
| 1003 | furanyl | 6 | diazepanyl-N-CH$_3$ |

-continued

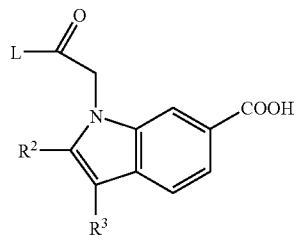

wherein R$_3$ is C$_n$-cycloalkyl and the index n and the substituents L, R$^2$ are defined according to the following table

| Cpd. | R$^2$ | n | L |
|---|---|---|---|
| 1010 | furan-3-yl | 6 | 4-piperidin-1-yl-piperidin-1-yl |
| 1012 | furan-3-yl | 6 | thiomorpholin-4-yl |
| 1016 | furan-3-yl | 6 | 3-(diethylamino)pyrrolidin-1-yl |
| 1020 | furan-3-yl | 6 | 2,6-dimethylmorpholin-4-yl |
| 1023 | phenyl | 6 | morpholin-4-yl |
| 1024 | phenyl | 6 | 4-pyrrolidin-1-yl-piperidin-1-yl |

-continued

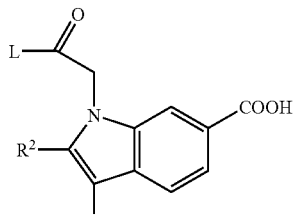

wherein R$_3$ is C$_n$-cycloalkyl and the index n and the substituents L, R$^2$ are defined according to the following table

| Cpd. | R$^2$ | n | L |
|---|---|---|---|
| 1027 | thiophen-3-yl | 6 | morpholin-4-yl |
| 1030 | furan-2-yl | 6 | morpholin-4-yl |
| 1033 | thiophen-2-yl | 6 | morpholin-4-yl |
| 1034 | thiophen-2-yl | 6 | 4-pyrrolidin-1-yl-piperidin-1-yl |
| 1037 | thiophen-3-yl | 6 | 4-pyrrolidin-1-yl-piperidin-1-yl |
| 1038 | furan-2-yl | 6 | 4-pyrrolidin-1-yl-piperidin-1-yl |

-continued

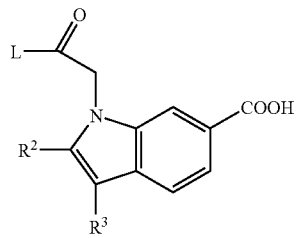

wherein R₃ is $C_n$-cycloalkyl and the index n and the substituents L, $R^2$ are defined according to the following table

| Cpd. | $R^2$ | n | L |
|---|---|---|---|
| 1043 | 3-furyl | 6 | morpholine |
| 1057 | 3-furyl | 6 | pyrrolidine-2-CONH₂ |
| 1058 | 3-furyl | 6 | piperidine-4-COOH |
| 1059 | 3-furyl | 6 | isonicotinoyl hydrazide |
| 1066 | 3-furyl | 6 | pyrrolidine-2-COOH |
| 1074 | 3-furyl | 6 | piperazine-CH₂COOH |

-continued

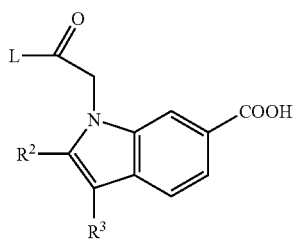

wherein R₃ is $C_n$-cycloalkyl and the index n and the substituents L, $R^2$ are defined according to the following table

| Cpd. | $R^2$ | n | L |
|---|---|---|---|
| 1094 | 3-furyl | 6 | pyrrolidine |
| 1096 | 3-furyl | 6 | 4-(2-hydroxyethyl)piperazine |
| 1097 | 3-furyl | 6 | morpholine |
| 1098 | 3-furyl | 6 | morpholine |
| 1099 | 3-furyl | 6 | piperidine-3-COOH |
| 1100 | 3-furyl | 6 | 4-hydroxypiperidine |

-continued

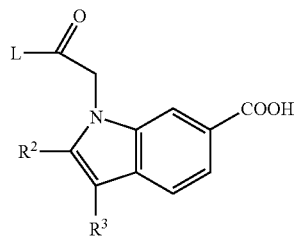

wherein R₃ is $C_n$-cycloalkyl and the index n and the substituents L, $R^2$ are defined according to the following table

| Cpd. | $R^2$ | n | L |
|---|---|---|---|
| 1102 | furan-3-yl | 6 | 2-(piperidin-4-yl)ethanol, N-linked |
| 1116 | furan-3-yl | 6 | 4-(pyrrolidin-1-yl)piperidine, N-linked |
| 1120 | furan-3-yl | 6 | 1-ethylpiperazine, N-linked |
| 1122 | furan-3-yl | 6 | N,N-dimethylpyrrolidine-2-carboxamide, N-linked |
| 1125 | furan-3-yl | 6 | 1-isopropylpiperazine, N-linked |

-continued

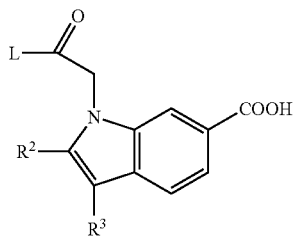

wherein R₃ is $C_n$-cycloalkyl and the index n and the substituents L, $R^2$ are defined according to the following table

| Cpd. | $R^2$ | n | L |
|---|---|---|---|
| 1126 | furan-3-yl | 6 | 1-(2-methoxyethyl)piperazine, N-linked |
| 1128 | furan-3-yl | 6 | 4-hydroxyproline, N-linked |
| 1130 | furan-3-yl | 6 | 2-(piperazin-1-yl)-N,N-dimethylacetamide, N-linked |
| 1131 | furan-3-yl | 6 | 3-(dimethylamino)pyrrolidine, N-linked |

51. The compound according to claim 1 of the formula:

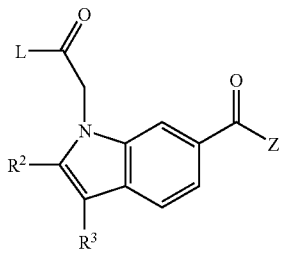

wherein R³ is C_n-cycloalkyl and the index n and the substituents L, R² and Z are defined according to the following table

| Cpd. # | R² | n | L | Z |
|---|---|---|---|---|
| 4003 | 3-furyl | 6 | 4-methylpiperazin-1-yl | (3,4-dimethoxybenzyl)amino |
| 4004 | 3-furyl | 6 | 4-(pyrrolidin-1-yl)piperidin-1-yl | (3,4-dimethoxybenzyl)amino |
| 4005 | 3-furyl | 6 | 4-(pyrrolidin-1-yl)piperidin-1-yl | ((S)-1-phenylethyl)amino |
| 4006 | 3-furyl | 6 | morpholin-4-yl | (3,4-dimethoxybenzyl)amino |

-continued
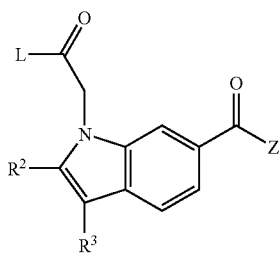
wherein R³ is C$_n$-cycloalkyl and the index n and the substituents L, R² and Z are defined according to the following table
| Cpd. # | R² | n | L | Z |
|---|---|---|---|---|
| 4029 | 3-furyl | 6 | 4-methylpiperazin-1-yl | NH-CH₂-(3,4-dihydroxyphenyl) |
| 4030 | 3-furyl | 6 | 4-methylpiperazin-1-yl | NH-CH₂-(3-methoxy-4-hydroxyphenyl) |
| 4032 | 3-furyl | 6 | 4-methylpiperazin-1-yl | NH-CH₂-(4-sulfamoylphenyl) |
| 4041 | 3-furyl | 6 | 4-methylpiperazin-1-yl | NH-CH₂-(4-methanesulfonylphenyl) |

-continued

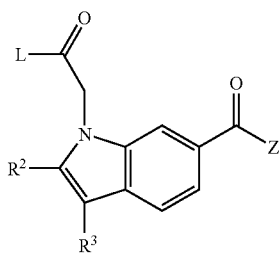

wherein R³ is C_n-cycloalkyl and the index n and the substituents L, R² and Z are defined according to the following table

| Cpd. # | R² | n | L | Z |
|---|---|---|---|---|
| 4042 | 3-furyl | 6 | 4-methylpiperazin-1-yl | (S)-1-(3-methoxyphenyl)ethylamino |
| 4043 | 3-furyl | 6 | 4-methylpiperazin-1-yl | (S)-1-(4-methoxyphenyl)ethylamino |
| 4062 | 3-furyl | 6 | morpholin-4-yl | 3,4-dihydroxybenzylamino |
| 4067 | 3-furyl | 6 | morpholin-4-yl | 1-(1H-benzimidazol-2-yl)cyclobutylamino with (E)-CH=CH-COOH on benzimidazole |

-continued

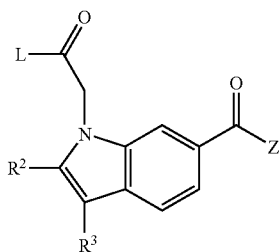

wherein R³ is Cₙ-cycloalkyl and the index n and the substituents L, R² and Z are defined according to the following table

| Cpd. # | R² | n | L | Z |
|---|---|---|---|---|
| 4068 | 3-furyl | 5 | morpholinomethyl | (3S)-3-amino-1-methylpyrrolidin-3-yl linked to benzimidazole-2-yl with 6-(E-CH=CH-COOH) |
| 4069 | 3-furyl | 6 | morpholinomethyl | (3S)-3-amino-1-methylpyrrolidin-3-yl linked to benzimidazole-2-yl with 6-(E-CH=CH-COOH) |
| 4070 | 3-furyl | 5 | morpholinomethyl | 1-aminocyclobutyl linked to benzimidazole-2-yl with 6-(E-CH=CH-COOH) |
| 4072 | 3-furyl | 6 | morpholinomethyl | 1-amino-1-(carbamoyl)cyclopentyl |

-continued

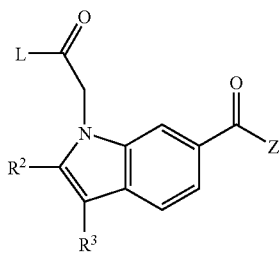

wherein R³ is C_n-cycloalkyl and the index n and the substituents L, R² and Z are defined according to the following table

| Cpd. # | R² | n | L | Z |
|---|---|---|---|---|
| 4077 | 3-furyl | 6 | morpholin-4-yl | -NH-C(CH₃)₂-C(O)NH₂ |
| 4081 | 3-furyl | 6 | 4-(pyrrolidin-1-yl)piperidin-1-yl | -NH-C(CH₃)₂-C(O)NH₂ |
| 4082 | 3-furyl | 6 | morpholin-4-yl | -NH-cyclobutyl(1-methylbenzimidazol-2-yl)- with CH=CH-COOH |
| 4083 | 3-furyl | 6 | morpholin-4-yl | -NH-C(1,3-dioxan-5-yl)-COOH |
| 4084 | 3-furyl | 6 | 4-(pyrrolidin-1-yl)piperidin-1-yl | -NH-C(CH₃)₂-C(O)NHCH₃ |

-continued

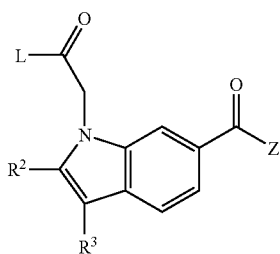

wherein R³ is C_n-cycloalkyl and the index n and the substituents L, R² and Z are defined according to the following table

| Cpd. # | R² | n | L | Z |
|---|---|---|---|---|
| 4085 | 3-furyl | 6 | morpholinylmethyl | NH-(4-carbamoyl-tetrahydropyran-4-yl) |
| 4086 | 3-furyl | 6 | 4-(pyrrolidin-1-yl)piperidin-1-ylmethyl | NH-C(CH₃)₂-C(O)N(CH₃)₂ |
| 4087 | 3-furyl | 6 | morpholinylmethyl | NH-C(CH₃)₂-COOH |
| 4088 | 3-furyl | 6 | morpholinylmethyl | NH-[1-(3-methyl-6-carboxybenzofuran-2-yl)cyclobutyl] |
| 4089 | 3-furyl | 6 | 4-(pyrrolidin-1-yl)piperidin-1-ylmethyl | NH-[1-(N-methylcarbamoyl)cyclobutyl] |

-continued

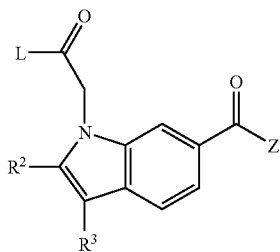

wherein R³ is C$_n$-cycloalkyl and the index n and the substituents L, R² and Z are defined according to the following table

| Cpd. # | R² | n | L | Z |
|---|---|---|---|---|
| 4090 | 3-furyl | 6 | 4-(pyrrolidin-1-yl)piperidin-1-yl | NH-(1-cyanocyclobutyl) |
| 4092 | 3-furyl | 6 | morpholin-4-yl | NH-(1-carbamoylcyclobutyl) |
| 4093 | 3-furyl | 6 | morpholin-4-yl | NH-(1-(N,N-dimethylcarbamoyl)cyclobutyl) |
| 4094 | 3-furyl | 6 | 4-(pyrrolidin-1-yl)piperidin-1-yl | NH-(1-(N-methylcarbamoyl)cyclopentyl) |
| 4095 | 3-furyl | 6 | 4-(pyrrolidin-1-yl)piperidin-1-yl | NH-(1-(N,N-dimethylcarbamoyl)cyclopentyl) |

-continued

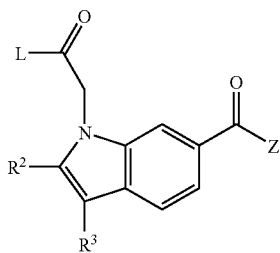

wherein R³ is Cₙ-cycloalkyl and the index n and the substituents L, R² and Z are defined according to the following table

| Cpd. # | R² | n | L | Z |
|---|---|---|---|---|
| 4096 | 3-furyl | 6 | morpholin-4-ylmethyl | 1-(N-methylcarbamoyl)cyclopentylamino |
| 4097 | 3-furyl | 6 | morpholin-4-ylmethyl | 1-(N,N-dimethylcarbamoyl)cyclopentylamino |
| 4099 | 3-furyl | 6 | 4-(pyrrolidin-1-yl)piperidin-1-yl | 1-(2-methylthiazol-4-yl)cyclobutylamino |
| 4102 | 3-furyl | 6 | 4-(pyrrolidin-1-yl)piperidin-1-yl | 1-(2-acetamidothiazol-4-yl)cyclobutylamino |

-continued

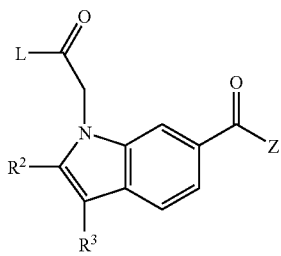

wherein R³ is C_n-cycloalkyl and the index n and the substituents L, R² and Z are defined according to the following table

| Cpd. # | R² | n | L | Z |
|---|---|---|---|---|
| 4103 | 3-furyl | 6 | 4-(pyrrolidin-1-yl)piperidin-1-yl | NH-(1-(2-(methylamino)thiazol-4-yl)cyclobutyl) |
| 4107 | 3-furyl | 6 | 4-(pyrrolidin-1-yl)piperidin-1-yl | NH-(1-(2-ethylthiazol-4-yl)cyclobutyl) |
| 4109 | 3-furyl | 6 | 4-(pyrrolidin-1-yl)piperidin-1-yl | NH-S(O)₂-CH₃ |
| 4110 | 3-furyl | 6 | 4-(pyrrolidin-1-yl)piperidin-1-yl | NH-S(O)₂-phenyl |

52. The compound according to claim 1 chosen from one of the following formulas:
| Cpd. # | Formula |
|---|---|
| 6002 | 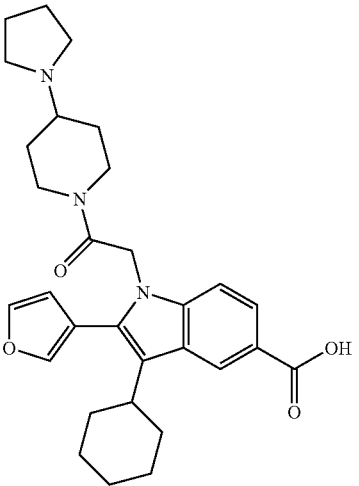 |
-continued
| Cpd. # | Formula |
|---|---|
| 7004 | 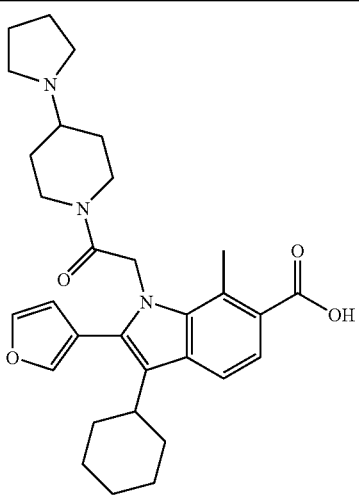 |
| 7005 | 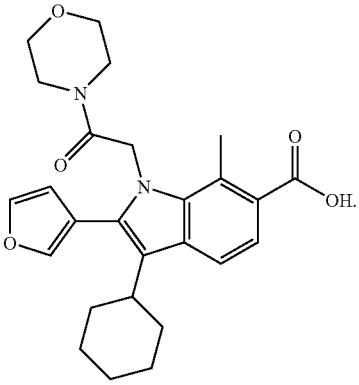 |
\* \* \* \* \*